(12) United States Patent
Habashita et al.

(10) Patent No.: US 7,053,090 B2
(45) Date of Patent: May 30, 2006

(54) TRIAZASPIRO[5.5]UNDECANE DERIVATIVES AND DRUGS CONTAINING THE SAME AS THE ACTIVE INGREDIENT

(75) Inventors: Hiromu Habashita, Mishima-gun (JP); Shin-ichi Hamano, Mishima-gun (JP); Shiro Shibayama, Mishima-gun (JP); Yoshikazu Takaoka, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 223 days.

(21) Appl. No.: 10/472,555

(22) PCT Filed: Mar. 18, 2002

(86) PCT No.: PCT/JP02/02554

§ 371 (c)(1),
(2), (4) Date: Sep. 22, 2003

(87) PCT Pub. No.: WO02/074770

PCT Pub. Date: Sep. 26, 2002

(65) Prior Publication Data

US 2004/0082584 A1    Apr. 29, 2004

(30) Foreign Application Priority Data

Mar. 19, 2001 (JP) ............................ P 2001-79610
May 29, 2001 (JP) ............................ P 2001-160251

(51) Int. Cl.
  *A61K 31/497*   (2006.01)
  *C07D 237/00*   (2006.01)
  *C07D 239/00*   (2006.01)
  *C07D 241/00*   (2006.01)

(52) U.S. Cl. .................................. 514/253.01; 544/231
(58) Field of Classification Search ........... 514/253.01; 544/231
See application file for complete search history.

(56) References Cited

U.S. PATENT DOCUMENTS 6,288,084 B1 * 9/2001 Luly et al. ................ 514/318

FOREIGN PATENT DOCUMENTS

| EP | 1 236 726 A1 | 9/2002 |
| WO | WO 97/11940 A1 | 4/1997 |
| WO | WO 98/25605 * | 6/1998 |
| WO | WO 98/25605 A1 | 6/1998 |
| WO | WO 98/31364 1 | 7/1998 |
| WO | WO 00/14086 A1 | 3/2000 |
| WO | WO 01/40227 A1 | 6/2001 |
| WO | WO 02/074769 A1 | 9/2002 |

OTHER PUBLICATIONS

Maeda et al, "Novel Low Molecular Weight Spirodiketopiperazine Derivatives Potently Inhibit R5 HIV-1 Infection through Antagonistic Effects on CCR5" Journal of Biological Chemistry, vol. 276(37), pp. 35194-35200 (2001).*

Cascieri and Springer, "The chemokine/chemokine-receptor family: potential and progess for therapeutic intervention" Current Opinion in Chemical Biology, vol. 4(4), pp. 420-427 (2000).*

Horuk and Ng, "Chemokine Receptor Antagonists" Medicinal Research Reviews, vol. 20(2), pp. 155-168 (2000).*

Supplementary European Search Report dated Aug. 18, 2004.

Kenji Maeda et al., Novel low molecular weight spirodiketopiperazine derivatives potently inhibit R5 HIV-1 infection through their antagonistic effects on CCR5, The Journal of Biological Chemistry, 2001, vol. 276, No. 37, pp. 35194 to 35200.

* cited by examiner

Primary Examiner—James O. Wilson
Assistant Examiner—Zachary C. Tucker
(74) Attorney, Agent, or Firm—Sughrue Mion, PLLC

(57) ABSTRACT

Triazaspiro[5.5]undecane derivatives of the formula (I), quaternary ammonium salts thereof, N-oxides thereof, non-toxic salts thereof, or pharmaceutical compositions comprising them, as active ingredients (wherein $R^1$ is formula (II) or formula (III); $R^2$ is alkyl or alkynyl etc.; $R^3$, $R^4$ is H, (substituted) alkyl etc., or $R^3$ and $R^4$ together to form formula (IV); $R^5$ is H or alkyl).

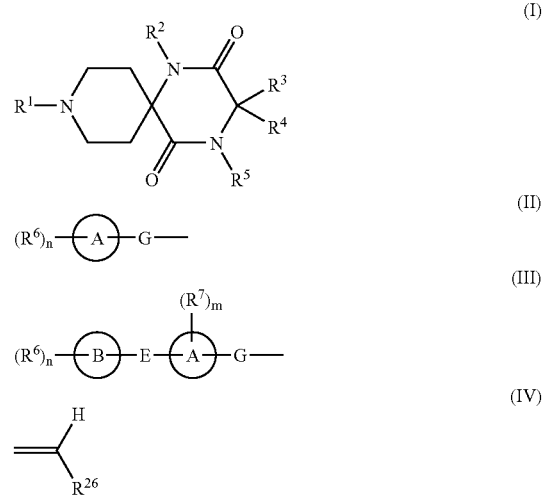

Therefore the compounds of the formula (I) regulate the effect of chemokine/chemokine receptor, they are used for prevention and treatment of various inflammatory diseases, asthma, atopic dermatitis, urticaria, allergic diseases, nephritis, nephropathy, hepatitis, arthritis or rheumatoid arthritis etc.

4 Claims, No Drawings

TRIAZASPIRO[5.5]UNDECANE DERIVATIVES AND DRUGS CONTAINING THE SAME AS THE ACTIVE INGREDIENT

This application was filed under 35 U.S.C. 371, and is the U.S. National Stage of PCT/JP02/02554, filed 18 Mar. 2002.

TECHNICAL FIELD

The present invention relates to triazaspiro[5.5]undecane derivatives and pharmaceutical compositions comprising the same, as an active ingredients.

More particularly, it relates to triazaspiro[5.5]undecane derivatives of the formula (I)

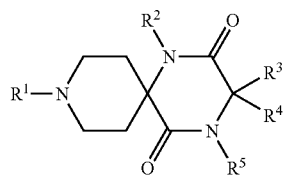

(wherein all the symbols have the same meanings as defined hereinafter), quaternary ammonium salts thereof, N-oxides thereof, non-toxic salts thereof, the methods for preparation thereof and pharmaceutical compositions comprising thereof, as active ingredients.

BACKGROUND ART

Chemokine is known as a basic protein having endogeneous leukocyte chemotactic and activating abilities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine is deeply related to the migration of these various cells. For example, MIP3β, SLC and its receptor CCR7 play an important role in the migration and homing of naive T cell, memory T cell and the mature dendritic cell which captured an antigen into a topical lymphoid tissue for the dendritic cells to encounter efficiently with the T cells. The T cell and dendritic cell necessary for controlling antigen-specific immune responses are hardly observed in the secondary lymph node of a PLT mouse having deficiency in the expression of SLC (*J. Exp. Med.*, 189(3), 451 (1999)).

MDC, TARC and its receptor CCR4 play an important role in the migration of Th2 cell into topical sites in immune and inflammatory responses in which the Th2 cell is related. In a rat fluminant hepatitis model (*P. acnes*+LPS), an anti-TARC antibody suppressed increase of the amount of ALT in blood and increase of the expressing amounts of TNFα and FasL in the liver and also improved lethality of the rats (*J. Clin. Invest.*, 102, 1933 (1998)). Also, an anti-MDC antibody decreased the number of eosinophils accumulated in the lung interstitium and suppressed airway hypersensitivity in a mouse OVA-induced airway hypersensitivity model (*J. Immunology*, 163, 403 (1999)).

MCP-1 and its receptor CCR2 are related to the infiltration of macrophage into inflammation sites. An anti-MCP-1 antibody showed an effect to suppress infiltration of monocyte and macrophage into glomerulus in a rat anti-Thy1.1 antibody glomerular nephritis model (*Kidney Int.*, 51, 770 (1997)).

Thus, chemokine receptors are greatly related to the control of inflammation and immune responses through a mechanism in which they are expressed at certain specified periods in variously specific cells and the effector cells are accumulated in a region where chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with *pneumocystis carinii* pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell*, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

In 1996, a cell membrane protein called Fusin was identified as a factor other than the CD4 molecule, which is related to the HIV infection (*Science*, 272, 872 (1996)). It was confirmed that this Fusin molecule is a receptor (namely, CXCR4) of stromal derived factor-1 (hereinafter referred to as "SDF-1"). In addition, it was confirmed also in vitro that the SDF-1 specifically inhibits infection of T cell tropic (X4) HIV (*Nature*, 382, 829 (1996), *Nature*, 382, 833 (1996)). That is, it is considered that the HIV infection was inhibited by the binding of SDF-1 to CXCR4 preceding HIV, thereby depriving HIV of a foothold for infecting cells.

Also at that time, it was discovered that another chemokine receptor CCR5, which is a receptor of RANTES, MIP-1α and MIP-1β, is also used at the time of the infection with a macrophage tropic (R5) HIV (*Science*, 272, 1955 (1996)).

Accordingly, substances which can compete with CXCR4 and CCR5 for HIV, or which can bind to HIV virus thus causing the virus unable to bind to CXCR4 and CCR5, could become HIV infection inhibitors. Also, there is a case in which a low molecular compound initially discovered as an HIV infection inhibitor was actually a CXCR4 antagonist (*Nature Medicine*, 4, 72 (1998)).

Based on the above, it is considered that the chemokine/chemokine receptors are deeply related to the inflammation, immune disease or HIV infection. For example, it is considered that they are related to the inhibition of various inflammatory diseases, asthma, atopic dermatitis, nettle rash, allergic diseases (allergic bronchopulmonary aspergillosis, allergic eosinophilic gastroenteritis and the like), glomerular nephritis, nephropathy, hepatitis, arthritis, chronic rheumatoid arthritis, psoriasis, rhinitis, conjunctivitis and ischemia-reperfusion injury, in the treatment of multiple sclerosis, ulcerative colitis, acute respiratory distress syndrome, shock accompanied by bacterial infection, diabetes mellitus and autoimmune diseases, and transplant rejection, immunosuppression, metastasis prevention and acquired immunodeficiency syndrome.

On the other hand, in specification of WO97/11940, it is described that the compounds of the formula (Z)

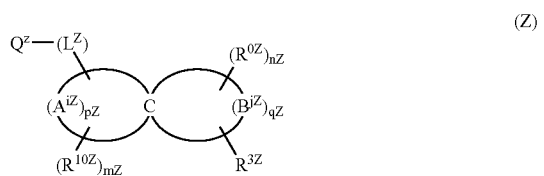

(wherein the atoms $A^{iZ}$ and $B^{iZ}$ are independently selected from carbon, nitrogen, oxygen and sulfur (provided that at least one atom of $A^{iZ}$ is carbon, and at least one atom $B^{jZ}$ is carbon);

the rings of the spirobicycle formed by $A^{iZ}$ and $B^{iZ}$, respectively, may optionally be partly unsaturated, pZ and qZ are independently numbers from 2 to 6, mZ is a number from 0 to pZ, $R^{10Z}$ is the same or different and is a non-interfering substituent independently selected from hydrogen, alkyl, halosubstituted alkyl, alkenyl, alkynyl, cycloalkyl, =O and =S etc., nZ is a number from 0 to qZ, $R^{0Z}$ is the same or different and is a non-interfering substituent independently selected from hydrogen, alkyl, halosubstituted alkyl, alkenyl, alkynyl, cycloalkyl, =O, and =S etc., the linking group -($L^Z$)- is a single bond or a divalent substituted or unsubstituted chain of from 1 to 10 atoms selected from the group consisting of carbon, nitrogen, sulfur, and oxygen, $Q^Z$ is a basic group containing one or more basic radicals, and $R^{3Z}$ is an acidic group containing one or more acid radicals) are useful for inhibiting platelet aggregation.

In specification of WO98/25605, it is described that compounds of the formula (Y)

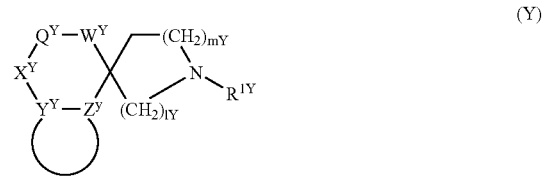

(wherein, mY or lY are each independently 0, 1, 2, 3, 4 or 5, $R^{1Y}$ is hydrogen, C1–8 alkyl, C2–8 alkenyl, C2–8 alkynyl etc., $W^Y$ is a single bond, C1–3 alkyl or C1–3 alkyl substituted with oxo etc., $Q^Y$ is —$NR^2$—, —O—, —S—, —S(O)— or —$SO_2$—, $X^Y$ is a single bond, C1–3 alkyl or C1–3 alkyl substituted with oxo etc., $Y^Y$-$Z^Y$ ring is phenyl, naphthyl or hetero aryl, with the proviso that the definition of each symbol is an excerpt partially.) are useful as modulators of the chemokine receptors.

DISCLOSURE OF THE INVENTION

The present inventors have investigated to find compounds regulating chemokine/chemokine receptors, so that the present inventors have found that the purpose has been achieved by triazaspiro[5.5]undecane derivatives of the formula (I).

The present invention relates to i) a triazaspiro[5.5]undecane derivative of the formula (I)

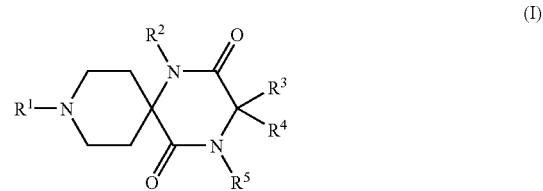

[wherein $R^1$ is formula (1) or (2):

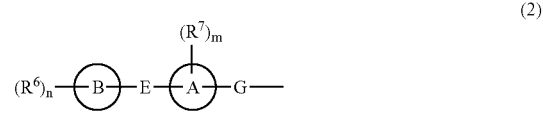

(wherein G is a bond, C1–4 alkylene, C2–4 alkenylene, or —CO—,

A ring is (1) C5–10 membered mono- or bi-carbocyclic ring or (2) 5–10 membered mono- or bi-cyclic hetero ring containing 1–2 nitrogen atoms and/or 1–2 oxygen atoms)

$R^6$ is
(1) C1–4 alkyl,
(2) halogen,
(3) nitrile,
(4) trifluoromethyl,
(5) —$OR^8$,
(6) —$SR^9$,
(7) —$NR^{10}R^{11}$,
(8) —$COOR^{12}$,
(9) —$CONR^{13}R^{14}$,
(10) —$SO_2NR^{15}R^{16}$,
(11) —$NR^{17}SO_2R^{18}$,
(12) —$S(O)R^{19}$,
(13) —$SO_2R^{20}$,
(14) —$N(SO_2R^{21})_2$,
(15) C1–4 alkyl substituted by a substituent selected from (a) —$OR^8$, (b) —$NR^{10}R^{11}$, and (c) Cyc 1, or
(16) —$NR^{27}COR^{28}$, wherein $R^8$—$R^{17}$ are each independently (1) hydrogen, (2) C1–4 alkyl, (3) Cyc 1, (4) —$OR^{22}$, and (5) C1–4 alkyl substituted by a substituent selected from (a) —$OR^{22}$, (b) —$NR^{23}R^{24}$, (c) —$COOR^{25}$, and (d) Cyc 1, or $R^{10}$ and $R^{11}$, $R^{13}$ and $R^4$, or $R^{15}$ and $R^{16}$, are each independently, together with the nitrogen atom to which they are attached form a 5–6 membered mono-cyclic hetero ring containing 1–2 nitrogen atoms and/or an oxygen atom (wherein 5–6 membered mono-cyclic hetero ring may be optionally substituted by C1–4 alkyl or hydroxy), $R^{22}$–$R^{25}$ are each independently (1) hydrogen, (2) C1–4 alkyl or (3) C1–4 alkyl substituted by C1–4 alkoxy, or $R^{23}$ and $R^{24}$ together with the nitrogen atom to which they are attached form a 5–6 membered mono-cyclic hetero ring containing 1–2 nitrogen atoms and/or an oxygen atom (wherein 5–6 membered mono-cyclic hetero ring may be optionally substituted by C1–4 alkyl or hydroxy), $R^{18}$–$R^{21}$ are each independently C1–4 alkyl, $R^{27}$ is (1) hydrogen, (2) C1–4 alkyl, (3) Cyc 1 or (4) C1–4 alkyl substituted by a substituent optionally selected from (a) —$OR^{22}$, (b) —$NR^{23}R^{24}$, (c) —$COOR^{25}$, and (d) Cyc 1, $R^{28}$ is (1) C1–4 alkyl, (2) Cyc 1 or (3) C1–4 alkyl substituted by a substituent optionally selected from (a) —$OR^{22}$, (b) —$NR^{23}R^{24}$, (c) —$COOR^{25}$, and (d) Cyc 1, Cyc 1 is (1) C5–6 membered mono-carbocyclic ring or (2) 5–6 membered mono-cyclic hetero ring containing 1–2 nitrogen atoms and/or an oxygen atom (wherein carbocyclic ring or hetero ring may be optionally substituted by C1–4 alkoxy, halogen, or —$COOR^{29}$ (wherein $R^{29}$ is (1) hydrogen, (2) C1–4 alkyl, (3) Cyc 1, or (4) C1–4 alkyl substituted by a substituent selected from (a) —$OR^{22}$, (b) —$NR^{23}R^{24}$, (c) —$COOR^{25}$, and (d) Cyc 1).), E is a bond, —O—, —S—, —CO—, or —CHOH—, B ring is (1) C5–6 membered mono-carbocyclic ring or (2) 5–6 membered mono-cyclic hetero ring containing 1–2 nitrogen atoms and/or an oxygen atom, $R^7$ is C1–4 alkyl or halogen, n is a number from 0 or 1 to 4 and m is a number from 0 or 1 to 4), $R^2$ is (1) C1–4 alkyl, (2) C2–4 alkynyl, or (3) C1–4 alkyl substituted by a substituent optionally selected from (a) —$OR^{30}$, (b) —$NR^{31}$—$R^{32}$ and (c) Cyc 3 (wherein $R^{30}$–$R^{32}$ are each independently (1) hydrogen, (2) C1–4 alkyl, (3) Cyc 3 or (4) C1–4 alkyl substituted by Cyc 3, Cyc 3 is (1) C5–6 membered mono-carbocyclic ring or (2) 5–6 membered mono-cyclic hetero ring containing 1–2 nitrogen atoms and/or an oxygen atom (wherein C5–6 membered mono-carbocyclic ring or 5–6 membered mono-cyclic hetero ring may be optionally substituted by C1–4 alkoxy)), $R^3$ and $R^4$ are each independently (1) hydrogen, (2) C1–4 alkyl, or (3) C1–4 alkyl substituted by 1–2 substituent selected from (a) Cyc 2, and (b) hydroxy (wherein Cyc 2 is (1) C5–6 membered mono-carbocyclic ring or (2) 5–6 membered mono-cyclic hetero ring containing 1–2 nitrogen atoms and/or an oxygen atom), or $R^3$ and $R^4$ together to form

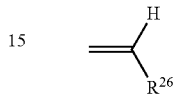

(wherein $R^{26}$ is C1–4 alkyl or Cyc 2), and $R^5$ is hydrogen or C1–4 alkyl], a quaternary ammonium salt thereof, an N-oxide thereof, or a non-toxic salt thereof, ii) a compound of the formula (I) according to the above i) wherein $R^3$ and $R^4$ are hydrogen, iii) a compound of the formula (I) according to the above i) wherein $R^3$ is hydrogen and $R^4$ is (1) C1–4 alkyl or (2) C1–4 alkyl substituted by 1–2 substituent optionally selected from (a) Cyc 2, and (b) hydroxy, iv) a compound of the formula (I) according to the above i) wherein $R^3$ and $R^4$ are each independently (1) C1–4 alkyl, or (2) C1–4 alkyl substituted optionally selected from (a) Cyc 2 and (b) hydroxy, v) a compound of the formula (I) described in above i) which $R^3$ and $R^4$ together to form

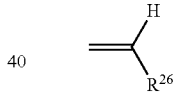

(wherein $R^{26}$ has the same meaning as defined according to the above i)), vi) a compound (1) (3R)-1-butyl-2,5-dioxo-3-((1R)-1-hydroxy-2-methyl-propyl)-9-benzyl-1,4,9-triazaspiro[5.5]undecane, (2) (3R)-1-butyl-2,5-dioxo-3-((1R)-1-hydroxy-2-methyl-propyl)-9-(6-phenyloxypyridin-3-ylmethyl)-1,4,9-triazaspiro[5.5]undecane, (3) (3R)-1-butyl-2,5-dioxo-3-((1R)-1-hydroxy-2-methyl-propyl)-9-(4-(4-methoxyphenyloxy)phenylmethyl)-1,4,9-triazaspiro[5.5]undecane, (4) (3R)-1-butyl-2,5-dioxo-3-((1R)-1-hydroxy-2-methyl-propyl)-9-(4-(3-methoxyphenyloxy)phenylmethyl)-1,4,9-triazaspiro[5.5]undecane, (5) (3R)-1-butyl-2,5-dioxo-3-((1R)-1-hydroxy-2-methyl-propyl)-9-(4-(4-fluorophenyloxy)phenylmethyl)-1,4,9-triazaspiro[5.5]undecane, (6) (3R)-1-butyl-2,5-dioxo-3-((1R)-1-hydroxy-2-methyl-propyl)-9-(4-(4-chlorophenyloxy)phenylmethyl)-1,4,9-triazaspiro[5.5]undecane, (7) (3R)-1-butyl-2,5-dioxo-3-((1R)-1-hydroxy-2-methyl-propyl)-9-(4-(phenylcarbonyl)phenylmethyl)-1,4,9-triazaspiro[5.5]undecane, (8) (3R)-1-butyl-2,5-dioxo-3-((1R)-1-hydroxy-2-methylpropyl)-9-(4-(1-phenyl-1-hydroxymethyl)phenylmethyl)-1,4,9-triazaspiro[5.5]undecane, (9) (3R)-1-butyl-2,5-dioxo-3-((1R)-1-hydroxy-2-methylpropyl)-9-(4-(morpholin-4-ylcarbonyl)phenyloxy)phenylmethyl)-1,4,9-triazaspiro[5.5]undecane,

(10) (3R)-1-butyl-2,5-dioxo-3-((1R)-1-hydroxy-2-methylpropyl)-9-(4-(6-methylpyridin-3-yloxy)phenylmethyl)-1,4,9-triazaspiro[5.5]undecane,

(11) (3R)-1-butyl-2,5-dioxo-3-((1R)-1-hydroxy-2-methylpropyl)-9-(4-(pyridin-1-oxido-3-yloxy)phenylmethyl)-1,4,9-triazaspiro[5.5]undecane,

(12) (3R)-1-butyl-2,5-dioxo-3-((1R)-1-hydroxy-2-methylpropyl)-9-(4-(4-hydroxypiperidin-1-ylmethyl)phenylmethyl)-1,4,9-triazaspiro[5.5]undecane,

(13) (3R)-1-butyl-2,5-dioxo-3-((1R)-1-hydroxy-2-methylpropyl)-9-(3,5-dimethyl-1-cyclohexylpyrazol-4-ylmethyl)-1,4,9-triazaspiro[5.5]undecane,

(14) (3R)-1-butyl-2,5-dioxo-3-((1R)-1-hydroxy-2-methylpropyl)-9-(1,3,5-trimethylpyrazol-4-ylmethyl)-1,4,9-triazaspiro[5.5]undecane,

(15) (3R)-1-butyl-2,5-dioxo-3-((1R)-1-hydroxy-2-methylpropyl)-9-(4-(4-aminosulfonylphenyloxy)phenylmethyl)-1,4,9-triazaspiro[5.5]undecane,

(16) (3R)-1-butyl-2,5-dioxo-3-((1R)-1-hydroxy-2-methylpropyl)-9-(4-(4-methylthiophenyloxy)phenylmethyl)-1,4,9-triazaspiro[5.5]undecane,

(17) (3R)-1-butyl-2,5-dioxo-3-((1R)-1-hydroxy-2-methylpropyl)-9-(4-(4-methylsulfonylphenyloxy)phenylmethyl)-1,4,9-triazaspiro[5.5]undecane,

(18) (3R)-1-butyl-2,5-dioxo-3-((1R)-1-hydroxy-2-methylpropyl)-9-(4-(4-cyanophenyloxy)phenylmethyl)-1,4,9-triazaspiro[5.5]undecane,

(19) (3R)-1-butyl-2,5-dioxo-3-((1R)-1-hydroxy-2-methylpropyl)-9-(4-(phenylthio)phenylmethyl)-1,4,9-triazaspiro[5.5]undecane,

(20) (3R)-1-butyl-2,5-dioxo-3-((1R)-1-hydroxy-2-methylpropyl)-9-(3,5-dimethyl-1-(4-hydroxyphenyl)pyrazol-4-ylmethyl)-1,4,9-triazaspiro[5.5]undecane,

(21) (3R)-1-butyl-2,5-dioxo-3-((1R)-1-hydroxy-2-methylpropyl)-9-(3,5-dimethyl-1-(4-methylsulfonylaminophenyl)pyrazol-4-ylmethyl)-1,4,9-triazaspiro[5.5]undecane,

(22) (3R)-1-butyl-2,5-dioxo-3-((1R)-1-hydroxy-2-methylpropyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane,

(23) (3R)-1-butyl-2,5-dioxo-3-((1R)-1-hydroxy-2-methylpropyl)-9-(3,5-dimethyl-1-(4-(pyrrolidin-1-ylsulfonyl)phenyl)pyrazol-4-ylmethyl)-1,4,9-triazaspiro[5.5]undecane,

(24) (3R)-1-butyl-2,5-dioxo-3-((1R)-1-hydroxy-2-methylpropyl)-9-(4-(6-methylpyridin-1-oxido-3-yloxy)phenylmethyl)-1,4,9-triazaspiro[5.5]undecane,

(25) (3R)-1-butyl-2,5-dioxo-3-((1R)-1-hydroxy-2-methylpropyl)-9-(4-(4-hydroxyphenyloxy)phenylmethyl)-1,4,9-triazaspiro[5.5]undecane,

(26) (3R)-1-butyl-2,5-dioxo-3-((1R)-1-hydroxy-2-methylpropyl)-9-(6-(4-methoxyphenyloxy)pyridin-3-ylmethyl)-1,4,9-triazaspiro[5.5]undecane,

(27) (3R)-1-butyl-2,5-dioxo-3-((1R)-1-hydroxy-2-methylpropyl)-9-(3,5-dimethyl-1-(4-(methylaminosulfonyl)phenyl)pyrazol-4-ylmethyl)-1,4,9-triazaspiro[5.5]undecane,

(28) (3R)-1-butyl-2,5-dioxo-3-((1R)-1-hydroxy-2-methylpropyl)-9-(3,5-dimethyl-1-(4-(N-methyl-N-(2-hydroxyethyl)aminosulfonyl)phenyl)pyrazol-4-ylmethyl)-1,4,9-triazaspiro[5.5]undecane,

(29) (3R)-1-butyl-2,5-dioxo-3-((1R)-1-hydroxy-2-methylpropyl)-9-(3,5-dimethyl-1-(4-(2-hydroxyethylaminosulfonyl)phenyl)pyrazol-4-ylmethyl)-1,4,9-triazaspiro[5.5]undecane,

(30) (3R)-1-butyl-2,5-dioxo-3-((1R)-1-hydroxy-2-methylpropyl)-9-(3,5-dimethyl-1-(4-(N,N-dimethylaminocarbonyl)phenyl)pyrazol-4-ylmethyl)-1,4,9-triazaspiro[5.5]undecane,

(31) (3R)-1-butyl-2,5-dioxo-3-((1R)-1-hydroxy-2-methylpropyl)-9-(3,5-dimethyl-1-(4-(2-(morpholin-4-yl)ethylaminosulfonyl)phenyl)pyrazol-4-ylmethyl)-1,4,9-triazaspiro[5.5]undecane,

(32) (3R)-1-butyl-2,5-dioxo-3-((1R)-1-hydroxy-2-methylpropyl)-9-(3,5-dimethyl-1-(4-(pyrrolidin-1-ylcarbonyl)phenyl)pyrazol-4-ylmethyl)-1,4,9-triazaspiro[5.5]undecane,

(33) (3R)-1-butyl-2,5-dioxo-3-((1R)-1-hydroxy-2-methylpropyl)-9-(4-(4-methylsulfinylphenyloxy)phenylmethyl)-1,4,9-triazaspiro[5.5]undecane,

(34) (3R)-1-butyl-2,5-dioxo-3-((1R)-1-hydroxy-2-methylpropyl)-9-(3,5-dimethyl-1-(4-(N,N-dimethylaminosulfonyl)phenyl)pyrazol-4-ylmethyl)-1,4,9-triazaspiro[5.5]undecane,

(35) (3R)-1-butyl-2,5-dioxo-3-((1R)-1-hydroxy-2-methylpropyl)-9-(3,5-dimethyl-1-(4-(morpholin-4-ylsulfonyl)phenyl)pyrazol-4-ylmethyl)-1,4,9-triazaspiro[5.5]undecane,

(36) (3R)-1-butyl-2,5-dioxo-3-((1R)-1-hydroxy-2-methylpropyl)-9-(4-(4-aminocarbonylphenyloxy)phenylmethyl)-1,4,9-triazaspiro[5.5]undecane,

(37) (3R)-1-butyl-2,5-dioxo-3-((1R)-1-hydroxy-2-methylpropyl)-9-(4-(4-methylaminocarbonylphenyloxy)phenylmethyl)-1,4,9-triazaspiro[5.5]undecane,

(38) (3R)-1-butyl-2,5-dioxo-3-((1R)-1-hydroxy-2-methylpropyl)-9-(3,5-dimethyl-1-(4-methylphenyl)pyrazol-4-ylmethyl)-1,4,9-triazaspiro[5.5]undecane,

(39) (3R)-1-butyl-2,5-dioxo-3-((1R)-1-hydroxy-2-methylpropyl)-9-(3,5-dimethyl-1-(4-(N,N-diethylaminosulfonyl)phenyl)pyrazol-4-ylmethyl)-1,4,9-triazaspiro[5.5]undecane,

(40) (3R)-1-butyl-2,5-dioxo-3-((1R)-1-hydroxy-2-methylpropyl)-9-(3,5-dimethyl-1-(4-(4-methylpiperazin-1-ylsulfonyl)phenyl)pyrazol-4-ylmethyl)-1,4,9-triazaspiro[5.5]undecane,

(41) (3R)-1-butyl-2,5-dioxo-3-((1R)-1-hydroxy-2-methylpropyl)-9-(5-chloro-3-methyl1-phenylpyrazol-4-ylmethyl)-1,4,9-triazaspiro[5.5]undecane,

(42) (3R)-1-butyl-2,5-dioxo-3-((1R)-1-hydroxy-2-methylpropyl)-9-(3,5-dimethyl-1-(4-(morpholin-4-ylcarbonyl)phenyl)pyrazol-4-ylmethyl)-1,4,9-triazaspiro[5.5]undecane,

(43) (3R)-1-butyl-2,5-dioxo-3-((1R)-1-hydroxy-2-methylpropyl)-9-(3,5-dimethyl-1-(4-(2-hydroxyethylaminocarbonyl)phenyl)pyrazol-4-ylmethyl)-1,4,9-triazaspiro[5.5]undecane,

(44) (3R)-1-butyl-2,5-dioxo-3-((1R)-1-hydroxy-2-methylpropyl)-9-(4-(4-(2-(N,N-dimethylamino)ethylaminocarbonyl)phenyloxy)phenylmethyl)-1,4,9-triazaspiro[5.5]undecane,

(45) (3R)-1-butyl-2,5-dioxo-3-((1R)-1-hydroxy-2-methylpropyl)-9-(4-(pyridin-3-yloxy)phenylmethyl)-1,4,9-triazaspiro[5.5]undecane,

(46) (3R)-1-butyl-2,5-dioxo-3-((1R)-1-hydroxy-2-methylpropyl)-9-(4-(4-carboxyphenyloxy)phenylmethyl)-1,4,9-triazaspiro[5.5]undecane,

(47) (3R)-1-butyl-2,5-dioxo-3-((1R)-1-hydroxy-2-methylpropyl)-9-(4-(4-methylphenyloxy)phenylmethyl)-1,4,9-triazaspiro[5.5]undecane,
(48) (3R)-1-butyl-2,5-dioxo-3-((1R)-1-hydroxy-2-methylpropyl)-9-(3,5-dimethyl-1-(2,4-difluorophenyl)pyrazol-4-ylmethyl)-1,4,9-triazaspiro[5.5]undecane,
(49) (3R)-1-butyl-2,5-dioxo-3-((1R)-1-hydroxy-2-methylpropyl)-9-(3,5-dimethyl-1-(pyridin-2-yl)pyrazol-4-ylmethyl)-1,4,9-triazaspiro[5.5]undecane,
(50) (3R)-1-butyl-2,5-dioxo-3-((1R)-1-hydroxy-2-methylpropyl)-9-(3,5-dimethyl-1-(4-methylaminocarbonylphenyl)pyrazol-4-ylmethyl)-1,4,9-triazaspiro[5.5]undecane,
(51) (3R)-1-butyl-2,5-dioxo-3-((1R)-1-hydroxy-2-methylpropyl)-9-(4-cyclohexyloxyphenylmethyl)-1,4,9-triazaspiro[5.5]undecane,
(52) (3R)-1-butyl-2,5-dioxo-3-((1R)-1-hydroxy-2-methylpropyl)-9-(4-(3,4,5,6-tetrahydropyran-4-yloxy)phenylmethyl)-1,4,9-triazaspiro[5.5]undecane,
(53) (3R)-1-butyl-2,5-dioxo-3-((1R)-1-hydroxy-2-methylpropyl)-9-(4-(4-methoxyphenylmethylaminocarbonyl)phenylmethyl)-1,4,9-triazaspiro[5.5]undecane,
(54) (3R)-1-butyl-2,5-dioxo-3-((1R)-1-hydroxy-2-methylpropyl)-9-(4-(cyclohexylaminocarbonyl)phenylmethyl)-1,4,9-triazaspiro[5.5]undecane,
(55) (3R)-1-butyl-2,5-dioxo-3-((1R)-1-hydroxy-2-methylpropyl)-9-(4-(4-(pyrrolidin-1-ylcarbonyl)phenyloxy)phenylmethyl)-1,4,9-triazaspiro[5.5]undecane,
(56) (3R)-1-butyl-2,5-dioxo-3-((1R)-1-hydroxy-2-methylpropyl)-9-(3,5-dimethyl-1-(4-fluorophenyl)pyrazol-4-ylmethyl)-1,4,9-triazaspiro[5.5]undecane,
(57) (3R)-1-butyl-2,5-dioxo-3-((1R)-1-hydroxy-2-methylpropyl)-9-(3,5-dimethyl-1-(4-(2-phenylethyl)phenyl)pyrazol-4-ylmethyl)-1,4,9-triazaspiro[5.5]undecane,
(58) (3R)-1-butyl-2,5-dioxo-3-((1R)-1-hydroxy-2-methylpropyl)-9-(3,5-dimethyl-1-(1-benzyloxycarbonylpiperidin-4-yl)pyrazol-4-ylmethyl)-1,4,9-triazaspiro[5.5]undecane,
(59) (3R)-1-butyl-2,5-dioxo-3-((1R)-1-hydroxy-2-methylpropyl)-9-(4-(4-(2-hydroxyethylaminocarbonyl)phenyloxy)phenylmethyl)-1,4,9-triazaspiro[5.5]undecane,
(60) (3R)-1-butyl-2,5-dioxo-3-((1R)-1-hydroxy-2-methylpropyl)-9-(3,5-dimethyl-1-(1-methylsulfonylpiperidin-4-yl)pyrazol-4-ylmethyl)-1,4,9-triazaspiro[5.5]undecane,
(61) (3R)-1-butyl-2,5-dioxo-3-((1R)-1-hydroxy-2-methylpropyl)-9-(4-(4-hydroxymethylphenyloxy)phenylmethyl)-1,4,9-triazaspiro[5.5]undecane,
(62) (3S)-1-butyl-2,5-dioxo-3-((1S)-1-hydroxy-2-methylpropyl)-9-(6-phenyloxypyridin-3-ylmethyl)-1,4,9-triazaspiro[5.5]undecane,
(63) (3S)-1-butyl-2,5-dioxo-3-(2-methylpropyl)-9-(3,5-dimethyl-1-(4-(N,N-dimethylaminocarbonyl)phenyl)pyrazol-4-ylmethyl)-1,4,9-triazaspiro[5.5]undecane,
(64) (3S)-1-butyl-2,5-dioxo-3-(2-methylpropyl)-9-(3,5-dimethyl-1-(4-(pyrrolidin-1-ylcarbonyl)phenyl)pyrazol-4-ylmethyl)-1,4,9-triazaspiro[5.5]undecane,
(65) (3S)-1-butyl-2,5-dioxo-3-(2-methylpropyl)-9-(3,5-dimethyl-1-(4-(morpholin-4-ylcarbonyl)phenyl)pyrazol-4-ylmethyl)-1,4,9-triazaspiro[5.5]undecane,
(66) (3S)-1-butyl-2,5-dioxo-3-(2-methylpropyl)-9-(4-methylsulfonylphenylmethyl)-1,4,9-triazaspiro[5.5]undecane,
(67) (3S)-1-butyl-2,5-dioxo-3-(2-methylpropyl)-9-(4-(4-methylsulfonylphenyloxy)phenylmethyl)-1,4,9-triazaspiro[5.5]undecane,
(68) (3S)-1-butyl-2,5-dioxo-3-(2-methylpropyl)-9-(3,5-dimethyl-1-(4-(2-(morpholin-4-yl)ethylaminosulfonyl)phenyl)pyrazol-4-ylmethyl)-1,4,9-triazaspiro[5.5]undecane,
(69) (3S)-1-butyl-2,5-dioxo-3-(2-methylpropyl)-9-(3,5-dimethyl-1-(4-(4-methylpiperazin-1-ylsulfonyl)phenyl)pyrazol-4-ylmethyl)-1,4,9-triazaspiro[5.5]undecane,
(70) (3S)-1-butyl-2,5-dioxo-3-(2-methylpropyl)-9-(4-(4-methylsulfinylphenyloxy)phenylmethyl)-1,4,9-triazaspiro[5.5]undecane,
(71) (3S)-1-butyl-2,5-dioxo-3-(2-methylpropyl)-9-(4-(pyridin-1-oxido-3-yloxy)phenylmethyl)-1,4,9-triazaspiro[5.5]undecane,
(72) (3S)-1-butyl-2,5-dioxo-3-(2-methylpropyl)-9-(3,5-dimethyl-1-(4-(2-hydroxyethylaminocarbonyl)phenyl)pyrazol-4-ylmethyl)-1,4,9-triazaspiro[5.5]undecane,
(73) (3S)-1-butyl-2,5-dioxo-3-(2-methylpropyl)-9-(4-(4-(morpholin-4-ylcarbonyl)phenyloxy)phenylmethyl)-1,4,9-triazaspiro[5.5]undecane,
(74) (3S)-1-butyl-2,5-dioxo-3-(2-methylpropyl)-9-(3,5-dimethyl-1-(4-(N,N-diethylaminosulfonyl)phenyl)pyrazol-4-ylmethyl)-1,4,9-triazaspiro[5.5]undecane,
(75) (3S)-1-butyl-2,5-dioxo-3-(2-methylpropyl)-9-(4-(4-(2-hydroxyethylaminocarbonyl)phenyloxy)phenylmethyl)-1,4,9-triazaspiro[5.5]undecane,
(76) (3S)-1-butyl-2,5-dioxo-3-(2-methylpropyl)-9-(4-(4-(pyrrolidin-1-ylcarbonyl)phenyloxy)phenylmethyl)-1,4,9-triazaspiro[5.5]undecane,
(77) (3S)-1-butyl-2,5-dioxo-3-(2-methylpropyl)-9-(3,5-dimethyl-1-(4-(cyclohexylaminosulfonyl)phenyl)pyrazol-4-ylmethyl)-1,4,9-triazaspiro[5.5]undecane,
(78) (3S)-1-butyl-2,5-dioxo-3-(2-methylpropyl)-9-(3,5-dimethyl-1-(4-(3-methoxypropylaminosulfonyl)phenyl)pyrazol-4-ylmethyl)-1,4,9-triazaspiro[5.5]undecane,
(79) (3S)-1-butyl-2,5-dioxo-3-(2-methylpropyl)-9-(4-methylsulfinylphenylmethyl)-1,4,9-triazaspiro[5.5]undecane,
(80) (3S)-1-butyl-2,5-dioxo-3-(2-methylpropyl)-9-(3,5-dimethyl-1-propylpyrazol-4-ylmethyl)-1,4,9-triazaspiro[5.5]undecane,
(81) (3S)-1-butyl-2,5-dioxo-3-(2-methylpropyl)-9-(3,5-dimethyl-1-ethylpyrazol-4-ylmethyl)-1,4,9-triazaspiro[5.5]undecane,
(82) (3S)-1-butyl-2,5-dioxo-3-(2-methylpropyl)-9-(3,5-dimethyl-1-cyclopentylpyrazol-4-ylmethyl)-1,4,9-triazaspiro[5.5]undecane,
(83) (3S)-1-butyl-2,5-dioxo-3-(2-methylpropyl)-9-(3,5-dimethyl-1-(1,1-dimethylethyl)pyrazol-4-ylmethyl)-1,4,9-triazaspiro[5.5]undecane,
(84) (3S)-1-butyl-2,5-dioxo-3-(2-methylpropyl)-9-(3,5-dimethyl-1-(1-benzyloxycarbonylpiperidin-4-yl)pyrazol-4-ylmethyl)-1,4,9-triazaspiro[5.5]undecane,
(85) (3S)-1-butyl-2,5-dioxo-3-(2-methylpropyl)-9-(4-((4-methoxyphenyl)methylaminocarbonyl)phenylmethyl)-1,4,9-triazaspiro[5.5]undecane,
(86) (3S)-1-butyl-2,5-dioxo-3-(2-methylpropyl)-9-(4-(3-methoxypropylaminocarbonyl)phenylmethyl)-1,4,9-triazaspiro[5.5]undecane,
(87) (3S)-1-butyl-2,5-dioxo-3-(2-methylpropyl)-9-(3,5-dimethyl-1-(4-methoxycarbonylphenyl)pyrazol-4-ylmethyl)-1,4,9-triazaspiro[5.5]undecane,
(88) (3S)-1-butyl-2,5-dioxo-3-(2-methylpropyl)-9-(3,5-dimethyl-1-(4-methoxyphenyl)pyrazol-4-ylmethyl)-1,4,9-triazaspiro[5.5]undecane,
(89) (3S)-1-butyl-2,5-dioxo-3-(2-methylpropyl)-9-(3,5-dimethyl-1-(4-(3-(morpholin-4-yl)propylaminosulfonyl)phenyl)pyrazol-4-ylmethyl)-1,4,9-triazaspiro[5.5]undecane,
(90) (3S)-1-butyl-2,5-dioxo-3-(2-methylpropyl)-9-(4-(pyrrolidin-1-ylcarbonyl)phenylmethyl)-1,4,9-triazaspiro[5.5]undecane,

(91) (3S)-1-butyl-2,5-dioxo-3-(2-methylpropyl)-9-(4-(piperidin-1-ylcarbonyl)phenylmethyl)-1,4,9-triazaspiro[5.5]undecane,

(92) (3S)-1-butyl-2,5-dioxo-3-(2-methylpropyl)-9-(4-(morpholin-4-ylcarbonyl)phenylmethyl)-1,4,9-triazaspiro[5.5]undecane,

(93) (3S)-1-butyl-2,5-dioxo-3-(2-methylpropyl)-9-(4-(N-methylN-(2-(pyridin-2-yl)ethyl)aminocarbonyl)phenylmethyl)-1,4,9-triazaspiro[5.5]undecane,

(94) (3S)-1-butyl-2,5-dioxo-3-(2-methylpropyl)-9-(4-(cyclohexylaminocarbonyl)phenylmethyl)-1,4,9-triazaspiro[5.5]undecane,

(95) (3S)-1-butyl-2,5-dioxo-3-(2-methylpropyl)-9-(4-(N,N-dimethylaminosulfonyl)phenylmethyl)-1,4,9-triazaspiro[5.5]undecane,

(96) (3S)-1-butyl-2,5-dioxo-3-(2-methylpropyl)-9-(4-(4-methoxycarbonylphenyloxy)phenylmethyl)-1,4,9-triazaspiro[5.5]undecane,

(97) (3S)-1-butyl-2,5-dioxo-3-(2-methylpropyl)-9-(3,5-dimethyl-1-(1-methylpiperidin-4-yl)pyrazol-4-ylmethyl)-1,4,9-triazaspiro[5.5]undecane,

(98) (3S)-1-butyl-2,5-dioxo-3-(2-methylpropyl)-9-(3,5-dimethyl-1-(1-methylsulfonylpiperidin-4-yl)pyrazol-4-ylmethyl)-1,4,9-triazaspiro[5.5]undecane,

(99) (3S)-1-butyl-2,5-dioxo-3-(2-methylpropyl)-9-(3,5-dimethyl-1-(4-(3-(N,N-dimethylamino)propylaminosulfonyl)phenyl)pyrazol-4-ylmethyl)-1,4,9-triazaspiro[5.5]undecane, (100) (3S)-1-butyl-2,5-dioxo-3-(2-methylpropyl)-9-(4-(4-(N,N-dimethylamino)phenyloxy)phenylmethyl)-1,4,9-triazaspiro[5.5]undecane, (101) (3S)-1-butyl-2,5-dioxo-3-(2-methylpropyl)-9-(3,5-dimethyl-1-(4-(N-methyl-N-(2-(N',N'-dimethylamino)ethyl)aminosulfonylphenyl)pyrazol-4-ylmethyl)-1,4,9-triazaspiro[5.5]undecane, (102) (3S)-1-butyl-2,5-dioxo-3-(2-methylpropyl)-9-(4-(4-((N,N-dimethylamino)methyl)phenyloxy)phenylmethyl)-1,4,9-triazaspiro[5.5]undecane, (103) (3S)-1-butyl-2,5-dioxo-3-(2-methylpropyl)-9-(4-(4-carboxyphenyloxy)phenylmethyl)-1,4,9-triazaspiro[5.5]undecane, (104) (3S)-1-butyl-2,5-dioxo-3-(2-methylpropyl)-9-(3,5-dimethyl-1-(4-methylaminocarbonylphenyl)pyrazol-4-ylmethyl)-1,4,9-triazaspiro[5.5]undecane, (105) (3S)-1-butyl-2,5-dioxo-3-(2-methylpropyl)-9-(4-((methoxycarbonyl)methylaminocarbonyl)phenylmethyl)-1,4,9-triazaspiro[5.5]undecane, (106) (3S)-1-butyl-2,5-dioxo-3-(2-methylpropyl)-9-(3-(3,5-dimethyl-1-phenylpyrazol-4-yl)-2E-propenyl)-1,4,9-triazaspiro[5.5]undecane, (107) (3S)-1-butyl-2,5-dioxo-3-(2-methylpropyl)-9-(4-(carboxymethylaminocarbonyl)phenylmethyl)-1,4,9-triazaspiro[5.5]undecane, (108) (3S)-1-butyl-2,5-dioxo-3-(2-methylpropyl)-9-(3-(3,5-dimethyl-1-phenylpyrazol-4-yl)propyl)-1,4,9-triazaspiro[5.5]undecane, (109) (3S)-1-butyl-2,5-dioxo-3-cyclohexylmethyl-9-(3,5-dimethyl-1-(4-(N,N-dimethylaminocarbonyl)phenyl)pyrazol-4-ylmethyl)-1,4,9-triazaspiro[5.5]undecane, (110) (3S)-1-butyl-2,5-dioxo-3-cyclohexylmethyl-9-(3,5-dimethyl-1-(4-(pyrrolidin-1-ylcarbonyl)phenyl)pyrazol-4-ylmethyl)-1,4,9-triazaspiro[5.5]undecane, (111) (3S)-1-butyl-2,5-dioxo-3-cyclohexylmethyl-9-(3,5-dimethyl-1-(4-(morpholin-4-ylcarbonyl)phenyl)pyrazol-4-ylmethyl)-1,4,9-triazaspiro[5.5]undecane, (112) (3S)-1-butyl-2,5-dioxo-3-cyclohexylmethyl-9-(3,5-dimethyl-1-(4-(2-(N,N-dimethylamino)ethylaminocarbonyl)phenyl)pyrazol-4-ylmethyl)-1,4,9-triazaspiro[5.5]undecane, (113) (3S)-1-butyl-2,5-dioxo-3-cyclohexylmethyl-9-(4-(4-(morpholin-4-ylcarbonyl)phenyloxy)phenylmethyl)-1,4,9-triazaspiro[5.5]undecane, (114) (3S)-1-butyl-2,5-dioxo-3-cyclohexylmethyl-9-(4-methylsulfonylphenylmethyl)-1,4,9-triazaspiro[5.5]undecane, (115) (3S)-1-butyl-2,5-dioxo-3-cyclohexylmethyl-9-(4-(4-methylsulfonylphenyloxy)phenylmethyl)-1,4,9-triazaspiro[5.5]undecane, (116) (3S)-1-butyl-2,5-dioxo-3-cyclohexylmethyl-9-(3,5-dimethyl-1-(4-(2-(morpholin-4-yl)ethylaminosulfonyl)phenyl)pyrazol-4-ylmethyl)-1,4,9-triazaspiro[5.5]undecane, (117) (3S)-1-butyl-2,5-dioxo-3-cyclohexylmethyl-9-(3,5-dimethyl-1-(4-(4-methylpiperazin-1-ylsulfonyl)phenyl)pyrazol-4-ylmethyl)-1,4,9-triazaspiro[5.5]undecane, (118) (3S)-1-butyl-2,5-dioxo-3-cyclohexylmethyl-9-(4-(4-methylsulfinylphenyloxy)phenylmethyl)-1,4,9-triazaspiro[5.5]undecane, (119) (3S)-1-butyl-2,5-dioxo-3-cyclohexylmethyl-9-(3,5-dimethyl-1-(4-(2-hydroxyethylaminocarbonyl)phenyl)pyrazol-4-ylmethyl)-1,4,9-triazaspiro[5.5]undecane, (120) (3S)-1-butyl-2,5-dioxo-3-cyclohexylmethyl-9-(4-(4-(2-hydroxyethylaminocarbonyl)phenyloxy)phenylmethyl)-1,4,9-triazaspiro[5.5]undecane, (121) (3S)-1-butyl-2,5-dioxo-3-cyclohexylmethyl-9-(4-(4-(pyrrolidin-1-ylcarbonyl)phenyloxy)phenylmethyl)-1,4,9-triazaspiro[5.5]undecane, (122) (3S)-1-butyl-2,5-dioxo-3-cyclohexylmethyl-9-(3,5-dimethyl-1-(4-(cyclohexylaminosulfonyl)phenyl)pyrazol-4-ylmethyl)-1,4,9-triazaspiro[5.5]undecane, (123) (3S)-1-butyl-2,5-dioxo-3-cyclohexylmethyl-9-(3,5-dimethyl-1-(4-(3-methoxypropylaminosulfonyl)phenyl)pyrazol-4-ylmethyl)-1,4,9-triazaspiro[5.5]undecane, (124) (3S)-1-butyl-2,5-dioxo-3-cyclohexylmethyl-9-(4-methylsulfinylphenylmethyl)-1,4,9-triazaspiro[5.5]undecane, (125) (3S)-1-butyl-2,5-dioxo-3-cyclohexylmethyl-9-(3,5-dimethyl-1-propylpyrazol-4-ylmethyl)-1,4,9-triazaspiro[5.5]undecane, (126) (3S)-1-butyl-2,5-dioxo-3-cyclohexylmethyl-9-(3,5-dimethyl-1-ethylpyrazol-4-ylmethyl)-1,4,9-triazaspiro[5.5]undecane, (127) (3S)-1-butyl-2,5-dioxo-3-cyclohexylmethyl-9-(3,5-dimethyl-1-cyclopentylpyrazol-4-ylmethyl)-1,4,9-triazaspiro[5.5]undecane, (128) (3S)-1-butyl-2,5-dioxo-3-cyclohexylmethyl-9-(3,5-dimethyl-1-(4-(3-(morpholin-4-yl)propylaminosulfonyl)phenyl)pyrazol-4-ylmethyl)-1,4,9-triazaspiro[5.5]undecane, (129) (3S)-1-butyl-2,5-dioxo-3-cyclohexylmethyl-9-(4-(N,N-dimethylaminosulfonyl)phenylmethyl)-1,4,9-triazaspiro[5.5]undecane, (130) (3S)-1-butyl-2,5-dioxo-3-cyclohexylmethyl-9-(4-(pyrrolidin-1-ylcarbonyl)phenylmethyl)-1,4,9-triazaspiro[5.5]undecane, (131) (3S)-1-butyl-2,5-dioxo-3-cyclohexylmethyl-9-(4-(4-(N,N-dimethylamino)phenyloxy)phenylmethyl)-1,4,9-triazaspiro[5.5]undecane, (132) (3S)-1-butyl-2,5-dioxo-3-cyclohexylmethyl-9-(4-(cyclohexylaminocarbonyl)phenylmethyl)-1,4,9-triazaspiro[5.5]undecane, (133) (3S)-1-butyl-2,5-dioxo-3-cyclohexylmethyl-9-(3,5-dimethyl-1-(4-methoxycarbonylphenyl)pyrazol-4-ylmethyl)-1,4,9-triazaspiro[5.5]undecane, (134) (3S)-1-butyl-2,5-dioxo-3-cyclohexylmethyl-9-(4-(3-methoxypropylaminocarbonyl)phenylmethyl)-1,4,9-triazaspiro[5.5]undecane, (135) (3S)-1-butyl-2,5-dioxo-3-cyclohexylmethyl-9-(4-(N-methyl-N-(2-(pyridin-2-yl)ethyl)aminocarbonyl)phenylmethyl)-1,4,9-triazaspiro[5.5]undecane, (136) (3S)-1-butyl-2,5-dioxo-3-cyclohexylmethyl-9-(4-((4-methoxyphenyl)methylaminocarbonyl)phenylmethyl)-1,4,9-triazaspiro[5.5]undecane, (137) (3S)-1-butyl-2,5-dioxo-3-cyclohexylmethyl-9-(4-(4-methoxycarbonylphenyloxy)phenylmethyl)-1,4,9-triazaspiro[5.5]undecane, (138) (3S)-1-butyl-2,5-dioxo-3-cyclohexylmethyl-9-(3,5-dimethyl-1-(4-methoxyphenyl)pyrazol-4-ylmethyl)-1,4,9-triazaspiro[5.5]undecane, (139) (3S)-1-butyl-2,5-dioxo-3-cyclohexylmethyl-9-(3,5-dimethyl-1-(1-methylpiperidin-4-yl)pyrazol-4-ylmethyl)-1,4,9-triazaspiro[5.5]undecane, (140) (3S)-1-butyl-2,5-dioxo-3-cyclohexylmethyl-9-(3,5-dimethyl-1-(1-methylsulfonylpiperidin-4-yl)pyrazol-4-ylmethyl)-1,4,9-triazaspiro[5.5]undecane, (141) (3S)-1-butyl-2,5-dioxo-3-cyclohexylmethyl-9-(3,5-dimethyl-1-(4-(3-(N,N-dimethylamino)propylaminosulfonyl)phenyl)pyrazol-4-ylmethyl)-1,4,9-triazaspiro[5.5]undecane, (142) (3S)-1-butyl-2,5-dioxo-3-cyclohexylmethyl-9-(3,5-dimethyl-1-(4-(N-methyl-N-(2-(N',N'-dimethylamino)ethyl)aminosulfonylphenyl)pyrazol-4-ylmethyl)-1,4,9-triazaspiro[5.5]undecane, (143) (3S)-1-butyl-2,5-dioxo-3-cyclohexylmethyl-9-(4-(piperidin-1-ylcarbonyl)phenylmethyl)-1,4,9-triazaspiro[5.5]undecane, (144) (3S)-1-butyl-2,5-dioxo-3-cyclohexylmethyl-9-(4-(morpholin-4-ylcarbonyl)phenylmethyl)-1,4,9-triazaspiro[5.5]undecane, (145) (3S)-1-butyl-2,5-dioxo-3-cyclohexylmethyl-9-(4-(4-((N,N-dimethylamino)methyl)phenyloxy)phenylmethyl)-1,4,9-triazaspiro[5.5]undecane, (146) (3S)-1-butyl-2,5-dioxo-3-cyclohexylmethyl-9-(3,5-dimethyl-1-(4-methylaminocarbonylphenyl)pyrazol-4-ylmethyl)-1,4,9-triazaspiro[5.5]undecane, (147) (3S)-1-butyl-2,5-dioxo-3-cyclohexylmethyl-9-(3,5-dimethyl-1-(1,1-dimethylethyl)pyrazol-4-ylmethyl)-1,4,9-triazaspiro[5.5]undecane, (148) (3S)-1-butyl-2,5-dioxo-3-cyclohexylmethyl-9-(3,5-dimethyl-1-(1-benzyloxycarbonylpiperidin-4-yl)pyrazol-4-ylmethyl)-1,4,9-triazaspiro[5.5]undecane, (149) (3S)-1-butyl-2,5-dioxo-3-cyclohexylmethyl-9-(4-(4-hydroxymethylphenyloxy)phenylmethyl)-1,4,9-triazaspiro[5.5]undecane, (150) (3S)-1-butyl-2,5-dioxo-3-cyclohexylmethyl-9-(4-((methoxycarbonyl)methylaminocarbonyl)phenylmethyl)-1,4,9-triazaspiro[5.5]undecane, (151) (3S)-1-butyl-2,5-dioxo-3-cyclohexylmethyl-9-(4-(carboxymethylaminocarbonyl)phenylmethyl)-1,4,9-triazaspiro[5.5]undecane, (152) (3R)-1-butyl-2,5-dioxo-3-((1R)-1-hydroxy-1-cyclohexylmethyl)-9-(4-phenyloxyphenylmethyl)-1,4,9-triazaspiro[5.5]undecane, (153) (3R)-1-butyl-2,5-dioxo-3-((1R)-1-hydroxy-1-cyclohexylmethyl)-9-(6-phenyloxypyridin-3-ylmethyl)-1,4,9-triazaspiro[5.5]undecane, (154) (3R)-1-butyl-2,5-dioxo-3-((1R)-1-hydroxy-1-cyclohexylmethyl)-9-(4-(4-fluorophenyloxy)phenylmethyl)-1,4,9-triazaspiro[5.5]undecane, (155) (3R)-1-butyl-2,5-dioxo-3-((1R)-1-hydroxy-1-cyclohexylmethyl)-9-(4-(4-chlorophenyloxy)phenylmethyl)-1,4,9-triazaspiro[5.5]undecane, (156) (3R)-1-butyl-2,5-dioxo-3-((1R)-1-hydroxy-1-cyclohexylmethyl)-9-(4-(4-cyanophenyloxy)phenylmethyl)-1,4,9-triazaspiro[5.5]undecane, (157) (3R)-1-butyl-2,5-dioxo-3-((1R)-1-hydroxy-1-cyclohexylmethyl)-9-(4-(4-methylsulfonylaminophenyloxy)phenylmethyl)-1,4,9-triazaspiro[5.5]undecane, (158) (3R)-1-butyl-2,5-dioxo-3-((1R)-1-hydroxy-1-cyclohexylmethyl)-9-(4-(6-methylpyridin-3-yloxy)phenylmethyl)-1,4,9-triazaspiro[5.5]undecane, (159) (3R)-1-butyl-2,5-dioxo-3-((1R)-1-hydroxy-1-cyclohexylmethyl)-9-(4-(1-methylethyl)phenylmethyl)-1,4,9-triazaspiro[5.5]undecane, (160) (3R)-1-butyl-2,5-dioxo-3-((1R)-1-hydroxy-1-cyclohexylmethyl)-9-(4-(4-methylsulfylphenyloxy)phenylmethyl)-1,4,9-triazaspiro[5.5]undecane, (161) (3R)-1-butyl-2,5-dioxo-3-((1R)-1-hydroxy-1-cyclohexylmethyl)-9-(4-(3,4,5,6-tetrahydropyran-4-yloxy)phenylmethyl)-1,4,9-triazaspiro[5.5]undecane, (162) (3R)-1-butyl-2,5-dioxo-3-((1R)-1-hydroxy-1-cyclohexylmethyl)-9-(4-phenylcarbonylphenylmethyl)-1,4,9-triazaspiro[5.5]undecane, (163) (3R)-1-butyl-2,5-dioxo-3-((1R)-1-hydroxy-1-cyclohexylmethyl)-9-(4-(1-phenyl-1-hydroxymethyl)phenylmethyl)-1,4,9-triazaspiro[5.5]undecane, (164) (3R)-1-butyl-2,5-dioxo-3-((1R)-1-hydroxy-1-cyclohexylmethyl)-9-(3,5-dimethyl-1-(4-(morpholin-4-ylsulfonyl)phenyl)pyrazol-4-ylmethyl)-1,4,9-triazaspiro[5.5]undecane, (165) (3R)-1-butyl-2,5-dioxo-3-((1R)-1-hydroxy-1-cyclohexylmethyl)-9-(3,5-dimethyl-1-(4-methylaminosulfonylphenyl)pyrazol-4-ylmethyl)-1,4,9-triazaspiro[5.5]undecane, (166) (3R)-1-butyl-2,5-dioxo-3-((1R)-1-hydroxy-1-cyclohexylmethyl)-9-(3,5-dimethyl-1-(4-(N-methyl-N-(2-hydroxyethyl)aminosulfonyl)phenyl)pyrazol-4-ylmethyl)-1,4,9-triazaspiro[5.5]undecane, (167) (3R)-1-butyl-2,5-dioxo-3-((1R)-1-hydroxy-1-cyclohexylmethyl)-9-(3,5-dimethyl-1-(pyridin-2-yl)pyrazol-4-ylmethyl)-1,4,9-triazaspiro[5.5]undecane, (168) (3R)-1-butyl-2,5-dioxo-3-((1R)-1-hydroxy-1-cyclohexylmethyl)-9-(3,5-dimethyl-1-cyclohexylpyrazol-4-ylmethyl)-1,4,9-triazaspiro[5.5]undecane, (169) (3R)-1-butyl-2,5-dioxo-3-((1R)-1-hydroxy-1-cyclohexylmethyl)-9-(1,3,5-trimethylpyrazol-4-ylmethyl)-1,4,9-triazaspiro[5.5]undecane, (170) (3R)-1-butyl-2,5-dioxo-3-((1R)-1-hydroxy-1-cyclohexylmethyl)-9-(3,5-dimethyl-1-(4-(N,N-dimethylaminocarbonyl)phenyl)pyrazol-4-ylmethyl)-1,4,9-triazaspiro[5.5]undecane, (171) (3R)-1-butyl-2,5-dioxo-3-((1R)-1-hydroxy-1-cyclohexylmethyl)-9-(4-(N,N-bismethylsulfonyl)phenylmethyl)-1,4,9-triazaspiro[5.5]undecane, (172) (3R)-1-butyl-2,5-dioxo-3-((1R)-1-hydroxy-1-cyclohexylmethyl)-9-(3,5-dimethyl-1-(4-methylsulfonylaminophenyl)pyrazol-4-ylmethyl)-1,4,9-triazaspiro[5.5]undecane, (173) (3R)-1-butyl-2,5-dioxo-3-((1R)-1-hydroxy-1-cyclohexylmethyl)-9-(3,5-dimethyl-1-(4-(N,N-dimethylsulfonyl)phenyl)pyrazol-4-ylmethyl)-1,4,9-triazaspiro[5.5]undecane, (174) (3R)-1-butyl-2,5-dioxo-3-((1R)-1-hydroxy-1-cyclohexylmethyl)-9-(3,5-dimethyl-1-(4-(pyrrolidin-1-ylcarbonyl)phenyl)pyrazol-4-ylmethyl)-1,4,9-triazaspiro[5.5]undecane, (175) (3R)-1-butyl-2,5-dioxo-3-((1R)-1-hydroxy-1-cyclohexylmethyl)-9-(3,5-dimethyl-1-(4-(morpholin-4-ylcarbonyl)phenyl)pyrazol-4-ylmethyl)-1,4,9-triazaspiro[5.5]undecane, (176) (3R)-1-butyl-2,5-dioxo-3-((1R)-1-hydroxy-1-cyclohexylmethyl)-9-(4-aminocarbonylphenylmethyl)-1,4,9-triazaspiro[5.5]undecane, (177) (3R)-1-butyl-2,5-dioxo-3-((1R)-1-hydroxy-1-cyclohexylmethyl)-9-(4-(4-aminocarbonylphenyloxy)phenylmethyl)-1,4,9-triazaspiro[5.5]undecane, (178) (3R)-1-butyl-2,5-dioxo-3-((1R)-1-hydroxy-1-cyclohexylmethyl)-9-(4-(4-aminosulfonylphenyloxy)phenylmethyl)-1,4,9-triazaspiro[5.5]undecane, (179) (3R)-1-butyl-2,5-dioxo-3-((1R)-1-hydroxy-1-cyclohexylmethyl)-9-(4-(6-methylpyridin-1-oxido-3-yloxy)phenylmethyl)-1,4,9-triazaspiro[5.5]undecane, (180) (3R)-1-butyl-2,5-dioxo-3-((1R)-1-hydroxy-1-cyclohexylmethyl)-9-(4-(4-hydroxyphenyloxy)phenylmethyl)-1,4,9-triazaspiro[5.5]undecane, (181) (3R)-1-butyl-2,5-dioxo-3-((1R)-1-hydroxy-1-cyclohexylmethyl)-9-(3,5-dimethyl-1-(4-hydroxyphenyl)pyrazol-4-ylmethyl)-1,4,9-triazaspiro[5.5]undecane, (182) (3R)-1-butyl-2,5-dioxo-3-((1R)-1-hydroxy-1-cyclohexylmethyl)-9-(3,5-dimethyl-1-(4-(2-hydroxyethylaminosulfonyl)phenyl)pyrazol-4-ylmethyl)-1,4,9-triazaspiro[5.5]undecane, (183) (3R)-1-butyl-2,5-dioxo-3-((1R)-1-hydroxy-1-cyclohexylmethyl)-9-(3,5-dimethyl-1-(4-(pyrrolidin-1-ylsulfonyl)phenyl)pyrazol-4-ylmethyl)-1±4,9-triazaspiro[5.5]undecane, (184) (3R)-1-butyl-2,5-dioxo-3-((1R)-1-hydroxy-1-cyclohexylmethyl)-9-(5-chloro-3-methyl-1-phenylpyrazol-4-ylmethyl)-1,4,9-triazaspiro[5.5]undecane, (185) (3R)-1-butyl-2,5-dioxo-3-((1R)-1-hydroxy-1-cyclohexylmethyl)-9-(4-(4-methoxyphenyloxy)phenylmethyl)-1,4,9-triazaspiro[5.5]undecane, (186) (3R)-1-butyl-2,5-dioxo-3-((1R)-1-hydroxy-1-cyclohexylmethyl)-9-(4-(3-methoxyphenyloxy)phenylmethyl)-1,4,9-triazaspiro[5.5]undecane, (187) (3R)-1-butyl-2,5-dioxo-3-((1R)-1-hydroxy-1-cyclohexylmethyl)-9-(4-(N,N-dimethylaminocarbonyl)phenylmethyl)-1,4,9-triazaspiro[5.5]undecane, (188) (3R)-1-butyl-2,5-dioxo-3-((1R)-1-hydroxy-1-cyclohexylmethyl)-9-(3,5-dimethyl-1-phenylpyrazol-4-ylmethyl)-1,4,9-triazaspiro[5.5]undecane, (189) (3R)-1-butyl-2,5-dioxo-3-((1R)-1-hydroxy-1-cyclohexylmethyl)-9-(3,5-dimethyl-1-(4-methylphenyl)pyrazol-4-ylmethyl)-1,4,9-triazaspiro[5.5]undecane, (190) (3R)-1-butyl-2,5-dioxo-3-((1R)-1-hydroxy-1-cyclohexylmethyl)-9-(3,5-dimethyl-1-(4-fluorophenyl)pyrazol-4-ylmethyl)-1,4,9-triazaspiro[5.5]undecane, (191) (3R)-1-butyl-2,5-dioxo-3-((1R)-1-hydroxy-1-cyclohexylmethyl)-9-(6-(4-methoxyphenyloxy)pyridin-3-ylmethyl)-1,4,9-triazaspiro[5.5]undecane, (192) (3R)-1-butyl-2,5-dioxo-3-((1R)-1-hydroxy-1-cyclohexylmethyl)-9-(4-(4-methylsulfonylphenyloxy)phenylmethyl)-1,4,9-triazaspiro[5.5]undecane, (193) (3R)-1-butyl-2,5-dioxo-3-((1R)-1-hydroxy-1-cyclohexylmethyl)-9-(4-(4-(2-(N,N-dimethylamino)ethylaminocarbonyl)phenyloxy)phenylmethyl)-1,4,9-triazaspiro[5.5]undecane, (194) (3R)-1-butyl-2,5-dioxo-3-((1R)-1-hydroxy-1-cyclohexylmethyl)-9-(3,5-dimethyl-1-(4-(2-hydroxyethylaminocarbonyl)phenyl)pyrazol-4-ylmethyl)-1,4,9-triazaspiro[5.5]undecane, (195) (3R)-1-butyl-2,5-dioxo-3-((1R)-1-hydroxy-1-cyclohexylmethyl)-9-(3,5-dimethyl-1-(4-(2-(N,N-dimethylamino)ethylaminocarbonyl)phenyl)pyrazol-4-ylmethyl)-1,4,9-triazaspiro[5.5]undecane, (196) (3R)-1-butyl-2,5-dioxo-3-((1R)-1-hydroxy-1-cyclohexylmethyl)-9-(3,5-dimethyl-1-(4-(2-(morpholin-4-yl)ethylaminosulfonyl)phenyl)pyrazol-4-ylmethyl)-1,4,9-triazaspiro[5.5]undecane, (197) (3R)-1-butyl-2,5-dioxo-3-((1R)-1-hydroxy-1-cyclohexylmethyl)-9-(4-(4-(morpholin-4-ylcarbonyl)phenyloxy)phenylmethyl)-1,4,9-triazaspiro[5.5]undecane, (198) (3R)-1-butyl-2,5-dioxo-3-((1R)-1-hydroxy-1-cyclohexylmethyl)-9-(1,4-benzodioxan-6-ylmethyl)-1,4,9-triazaspiro[5.5]undecane, (199) (3R)-1-butyl-2,5-dioxo-3-((1R)-1-hydroxy-1-cyclohexylmethyl)-9-(3,5-dimethyl-1-(4-(N,N-diethylaminosulfonyl)phenyl)pyrazol-4-ylmethyl)-1,4,9-triazaspiro[5.5]undecane, (200) (3R)-1-butyl-2,5-dioxo-3-((1R)-1-hydroxy-1-cyclohexylmethyl)-9-(4-(pyridin-1-oxido-3-yloxy)phenylmethyl)-1,4,9-triazaspiro[5.5]undecane, (201) (3R)-1-butyl-2,5-dioxo-3-((1R)-1-hydroxy-1-cyclohexylmethyl)-9-(3,5-dimethyl-1-(4-(4-methylpiperazin-1-ylsulfonyl)phenyl)pyrazol-4-ylmethyl)-1,4,9-triazaspiro[5.5]undecane, (202) (3R)-1-butyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane, (203) (3R)-1-butyl-2,5-dioxo-3-((1R)-1-hydroxy-1-cyclohexylmethyl)-9-(3,5-dimethyl-1-(2,4-difluorophenyl)pyrazol-4-ylmethyl)-1,4,9-triazaspiro[5.5]undecane, (204) (3R)-1-butyl-2,5-dioxo-3-((1R)-1-hydroxy-1-cyclohexylmethyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane, (205) (3R)-1-butyl-2,5-dioxo-3-((1R)-1-hydroxy-1-cyclohexylmethyl)-9-(3,5-dimethyl-1-(4-methylaminocarbonylphenyl)pyrazol-4-ylmethyl)-1,4,9-triazaspiro[5.5]undecane, (206) (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane, (207) (3R)-1-butyl-2,5-dioxo-3-((1R)-1-hydroxy-1-cyclohexylmethyl)-9-(4-((4-methoxyphenyl)methylaminocarbonyl)phenylmethyl)-1,4,9-triazaspiro[5.5]undecane, (208) (3R)-1-butyl-2,5-dioxo-3-((1R)-1-hydroxy-1-cyclohexylmethyl)-9-(4-(3-methoxypropylaminocarbonyl)phenylmethyl)-1,4,9-triazaspiro[5.5]undecane, (209) (3R)-1-butyl-2,5-dioxo-3-((1R)-1-hydroxy-1-cyclohexylmethyl)-9-(4-(N-methyl-N-(2-(pyridin-2-yl)ethyl)aminocarbonyl)phenylmethyl)-1,4,9-triazaspiro[5.5]undecane, (210) (3R)-1-butyl-2,5-dioxo-3-((1R)-1-hydroxy-1-cyclohexylmethyl)-9-(4-(4-(pyrrolidin-1-ylcarbonyl)phenyloxy)phenylmethyl)-1,4,9-triazaspiro[5.5]undecane, (211) (3R)-1-butyl-2,5-dioxo-3-((1R)-1-hydroxy-1-cyclohexylmethyl)-9-(3,5-dimethyl-1-(4-chlorophenyl)pyrazol-4-ylmethyl)-1,4,9-triazaspiro[5.5]undecane, (212) (3R)-1-butyl-2,5-dioxo-3-((1R)-1-hydroxy-1-cyclohexylmethyl)-9-(3,5-dimethyl-1-(4-trifluoromethylphenyl)pyrazol-4-ylmethyl)-1,4,9-triazaspiro[5.5]undecane, (213) (3R)-1-butyl-2,5-dioxo-3-((1R)-1-hydroxy-1-cyclohexylmethyl)-9-(3,5-dimethyl-1-(4-methoxyphenyl)pyrazol-4-ylmethyl)-1,4,9-triazaspiro[5.5]undecane, (214) (3R)-1-butyl-2,5-dioxo-3-((1R)-1-hydroxy-1-cyclohexylmethyl)-9-(3,5-dimethyl-1-ethylpyrazol-4-ylmethyl)-1,4,9-triazaspiro[5.5]undecane, (215) (3R)-1-butyl-2,5-dioxo-3-((1R)-1-hydroxy-1-cyclohexylmethyl)-9-(3,5-dimethyl-1-propylpyrazol-4-ylmethyl)-1,4,9-triazaspiro[5.5]undecane, (216) (3R)-1-butyl-2,5-dioxo-3-((1R)-1-hydroxy-1-cyclohexylmethyl)-9-(3,5-dimethyl-1-(1,1-dimethylethyl)pyrazol-4-ylmethyl)-1,4,9-triazaspiro[5.5]undecane, (217) (3R)-1-butyl-2,5-dioxo-3-((1R)-1-hydroxy-1-cyclohexylmethyl)-9-(3,5-dimethyl-1-cyclopentylpyrazol-4-ylmethyl)-1,4,9-triazaspiro[5.5]undecane, (218) (3R)-1-butyl-2,5-dioxo-3-((1R)-1-hydroxy-1-cyclohexylmethyl)-9-(3,5-dimethyl-1-(2-phenylethyl)pyrazol-4-ylmethyl)-1,4,9-triazaspiro[5.5]undecane, (219) (3R)-1-butyl-2,5-dioxo-3-((1R)-1-hydroxy-1-cyclohexylmethyl)-9-(3,5-dimethyl-1-(1-benzyloxycarbonylpiperidin-4-yl)pyrazol-4-ylmethyl)-1,4,9-triazaspiro[5.5]undecane, (220) (3R)-1-butyl-2,5-dioxo-3-((1R)-1-hydroxy-1-cyclohexylmethyl)-9-(4-(cyclohexylaminocarbonyl)phenylmethyl)-1,4,9-triazaspiro[5.5]undecane, (221) (3R)-1-butyl-2,5-dioxo-3-((1R)-1-hydroxy-1-cyclohexylmethyl)-9-(3,5-dimethyl-1-(1-methylsulfonylpiperidin-4-yl)pyrazol-4-ylmethyl)-1,4,9-triazaspiro[5.5]undecane, (222) (3R)-1-butyl-2,5-dioxo-3-((1R)-1-hydroxy-1-cyclohexylmethyl)-9-(4-(4-(2-hydroxyethylaminocarbonyl)phenyloxy)phenylmethyl)-1,4,9-triazaspiro[5.5]undecane, (223) (3R)-1-butyl-2,5-dioxo-3-((1R)-1-hydroxy-1-cyclohexylmethyl)-9-(4-(4-hydroxymethylphenyloxy)phenylmethyl)-1,4,9-triazaspiro[5.5]undecane, (224) (3S)-1-butyl-2,5-dioxo-3-((1S)-1-hydroxy-1-cyclohexylmethyl)-9-(4-(4-methylsulfonylaminophenyloxy)phenylmethyl)-1,4,9-triazaspiro[5.5]undecane, (225) (3R)-1-butyl-2,5-dioxo-3-((1R)-1-hydroxy-1-(3,4,5,6-tetrahydropyran-4-yl)methyl)-9-(3,5-dimethyl-1-phenylpyrazol-4-ylmethyl)-1,4,9-triazaspiro[5.5]undecane, (226) (3R)-1-butyl-2,5-dioxo-3-((1R)-1-hydroxy-1-(3,4,5,6-tetrahydropyran-4-yl)methyl)-9-(4-(4-methylaminocarbonylphenyloxy)phenylmethyl)-1,4,9-triazaspiro[5.5]undecane, (227) (3R)-1-butyl-2,5-dioxo-3-((1R)-1-hydroxy-1-(3,4,5,6-tetrahydropyran-4-yl)methyl)-9-(4-(4-methoxyphenylmethylaminocarbonyl)phenylmethyl) 1,4,9-triazaspiro[5.5]undecane, (228) (3R)-1-butyl-2,5-dioxo-3-((1R)-1-hydroxy-1-(3,4,5,6-tetrahydropyran-4-yl)methyl)-9-(3,5-dimethyl-1-(4-(N,N-dimethylaminocarbonyl)phenylpyrazol-4-ylmethyl)-1,4,9-triazaspiro[5.5]undecane, (229) (3R)-1-butyl-2,5-dioxo-3-((1R)-1-hydroxy-1-(3,4,5,6-tetrahydropyran-4-yl)methyl)-9-(4-(4-carboxyphenyloxy)phenylmethyl)-1,4,9-triazaspiro[5.5]undecane, (230) (3R)-1-butyl-2,5-dioxo-3-((1R)-1-hydroxy-1-(3,4,5,6-tetrahydropyran-4-yl)methyl)-9-(4-(4-methylsulfonylaminophenyloxy)phenylmethyl)-1,4,9-triazaspiro[5.5]undecane, (231) (3R)-1-butyl-2,5-dioxo-3-((1R)-1-hydroxy-1-cyclopentylmethyl)-9-(3,5-dimethyl-1-phenylpyrazol-4-ylmethyl)-1,4,9-triazaspiro[5.5]undecane, (232) (3R)-1-butyl-2,5-dioxo-3-((1R)-1-hydroxy-1-cyclopentylmethyl)-9-(4-(4-(4-methoxyphenylmethylaminocarbonyl)phenylmethyl)-1,4,9-triazaspiro[5.5]undecane, (233) (3R)-1-butyl-2,5-dioxo-3-((1R)-1-hydroxy-1-cyclopentylmethyl)-9-(4-(4-methylaminocarbonylphenyloxy)phenylmethyl)-1,4,9-triazaspiro[5.5]undecane, (234) (3R)-1-butyl-2,5-dioxo-3-((1R)-1-hydroxy-1-cyclopentylmethyl)-9-(4-(4-carboxyphenyloxy)phenylmethyl)-1,4,9-triazaspiro[5.5]undecane, (235) (3R)-1-propyl-2,5-dioxo-3-((1R)-1-hydroxy-2-methylpropyl)-9-(4-(4-methylaminocarbonylphenyloxy)phenylmethyl)-1,4,9-triazaspiro[5.5]undecane, (236) (3R)-1-propyl-2,5-dioxo-3-((1R)-1-hydroxy-2-methylpropyl)-9-(3,5-dimethyl-1-cyclohexylpyrazol-4-ylmethyl)-1,4,9-triazaspiro[5.5]undecane, (237) (3R)-1-propyl-2,5-dioxo-3-((1R)-1-hydroxy-2-methylpropyl)-9-(4-(4-methoxyphenylmethylaminocarbonyl)phenylmethyl)-1,4,9-triazaspiro[5.5]undecane, (238) (3R)-1-propyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane, (239) (3R)-1-propyl-2,5-dioxo-3-((1R)-1-hydroxy-1-cyclohexylmethyl)-9-(3,5-dimethyl-1-cyclohexylpyrazol-4-ylmethyl)-1,4,9-triazaspiro[5.5]undecane, (240) (3R)-1-propyl-2,5-dioxo-3-((1R)-1-hydroxy-1-cyclohexylmethyl)-9-(4-(4-methoxyphenylmethylaminocarbonyl)phenylmethyl)-1,4,9-triazaspiro[5.5]undecane, (241) (3R)-1-propyl-2,5-dioxo-3-((1R)-1-hydroxy-1-cyclohexylmethyl)-9-(3,5-dimethyl-1-(4-(N,N-dimethylaminocarbonyl)phenyl)pyrazol-4-ylmethyl)-1,4,9-triazaspiro[5.5]undecane, (242) (3R)-1-propyl-2,5-dioxo-3-((1R)-1-hydroxy-1-cyclohexylmethyl)-9-(4-(4-carboxyphenyloxy)phenylmethyl)-1,4,9-triazaspiro[5.5]undecane, (243) (3R)-1-propyl-2,5-dioxo-3-((1R)-1-hydroxy-1-cyclohexylmethyl)-9-(4-(4-methoxycarbonylphenyloxy)phenylmethyl)-1,4,9-triazaspiro[5.5]undecane, (244) (3R)-1-propyl-2,5-dioxo-3-(1-cyclohexylmethylidene)-9-(4-(4-carboxyphenyloxy)phenylmethyl)-1,4,9-triazaspiro[5.5]undecane, (245) (3S)-1-propyl-2,5-dioxo-3-(2-methylpropyl)-9-(3,5-dimethyl-1-cyclohexylpyrazol-4-ylmethyl)-1,4,9-triazaspiro[5.5]undecane, (246) (3S)-1-propyl-2,5-dioxo-3-(2-methylpropyl)-9-(4-(4-methylsulfonylaminophenyloxy)phenylmethyl)-1,4,9-triazaspiro[5.5]undecane, (247) (3S)-1-propyl-2,5-dioxo-3-(2-methylpropyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane, (248) (3S)-1-propyl-2,5-dioxo-3-cyclohexylmethyl-9-(3,5-dimethyl-1-cyclohexylpyrazol-4-ylmethyl)-1,4,9-triazaspiro[5.5]undecane, (249) (3S)-1-propyl-2,5-dioxo-3-cyclohexylmethyl-9-(4-(4-methylsulfonylaminophenyloxy)phenylmethyl)-1,4,9-triazaspiro[5.5]undecane, (250) 1-butyl-2,5-dioxo-9-(4-(4-methylsulfonylaminophenyloxy)phenylmethyl)-1,4,9-triazaspiro[5.5]undecane, (251) 1-butyl-2,5-dioxo-9-(3,5-dimethyl-1-cyclohexylpyrazol-4-ylmethyl)-1,4,9-triazaspiro[5.5]undecane, (252) (3R)-1-(2-butynyl)-2,5-dioxo-3-((1R)-1-hydroxy-1-cyclohexylmethyl)-9-(3,5-dimethyl-1-phenylpyrazol-4-ylmethyl)-1,4,9-triazaspiro[5.5]undecane, (253) (3S)-1-(2-butynyl)-2,5-dioxo-3-((1S)-1-hydroxy-1-cyclohexylmethyl)-9-(3,5-dimethyl-1-phenylpyrazol-4-ylmethyl)-1,4,9-triazaspiro[5.5]undecane, (254) (3S)-1-butyl-2,5-dioxo-3-cyclohexylmethyl-9-(2-(4-phenyloxyphenyl)ethyl)-1,4,9-triazaspiro[5.5]undecane,
(255) (3S)-1-butyl-2,5-dioxo-3-(2-methylpropyl)-9-(2-(4-phenyloxyphenyl)ethyl)-1,4,9-triazaspiro[5.5]undecane,
(256) (3S)-1-butyl-2,5-dioxo-3-(2-methylpropyl)-9-(2-(4-methoxyphenyl)ethyl)-1,4,9-triazaspiro[5.5]undecane,
(257) (3S)-1-butyl-2,5-dioxo-3-cyclohexylmethyl-9-(4-ethoxycarbonylphenyl)-1,4,9-triazaspiro[5.5]undecane,
(258) (3S)-1-butyl-2,5-dioxo-3-cyclohexylmethyl-4-methyl-9-(4-phenyloxyphenylmethyl)-1,4,9-triazaspiro[5.5]undecane,
(259) (3R)-1-butyl-2,5-dioxo-3-((1R)-1-hydroxy-1-cyclohexylmethyl)-9-(4-(2-methylpropanoylamino)phenylmethyl)-1,4,9-triazaspiro[5.5]undecane,
(260) (3R)-1-butyl-2,5-dioxo-3-((1R)-1-hydroxy-1-cyclohexylmethyl)-9-(4-(2-methoxyacetylamino)phenylmethyl)-1,4,9-triazaspiro[5.5]undecane,
(261) (3R)-1-butyl-2,5-dioxo-3-((1R)-1-hydroxy-1-cyclohexylmethyl)-9-(4-(2-phenylacetylamino)phenylmethyl)-1,4,9-triazaspiro[5.5]undecane,
(262) (3R)-1-butyl-2,5-dioxo-3-((1R)-1-hydroxy-1-cyclohexylmethyl)-9-(4-(2-(4-fluorophenyl)acetylamino)phenylmethyl)-1,4,9-triazaspiro[5.5]undecane,
(263) (3R)-1-butyl-2,5-dioxo-3-((1R)-1-hydroxy-1-cyclohexylmethyl)-9-(4-(4-methoxycarbonylphenylaminocarbonyl)phenylmethyl)-1,4,9-triazaspiro[5.5]undecane,
(264) (3R)-1-butyl-2,5-dioxo-3-((1R)-1-hydroxy-1-cyclohexylmethyl)-9-(4-(4-methoxyphenylmethyloxycarbonyl)phenylmethyl)-1,4,9-triazaspiro[5.5]undecane,
(265) (3R)-1-butyl-2,5-dioxo-3-((1R)-1-hydroxy-1-cyclohexylmethyl)-9-(2-(4-methylaminocarbonylphenyloxy)pyridin-5-ylmethyl)-1,4,9-triazaspiro[5.5]undecane,
(266) (3S)-1-butyl-2,5-dioxo-3-((1S)-1-hydroxy-1-cyclohexylmethyl)-9-(4-(4-carboxyphenyloxy)phenylmethyl)-1,4,9-triazaspiro[5.5]undecane,
(267) (3S)-1-butyl-2,5-dioxo-3-(pyridin-3-ylmethyl)-9-(4-(4-methylaminocarbonylphenyloxy)phenylmethyl)-1,4,9-triazaspiro[5.5]undecane,
(268) (3S)-1-butyl-2,5-dioxo-3-phenylmethyl-9-(4-(4-methylaminocarbonylphenyloxy)phenylmethyl)-1,4,9-triazaspiro[5.5]undecane,
(269) (3S)-1-butyl-2,5-dioxo-3-(pyridin-2-ylmethyl)-9-(4-(4-methylaminocarbonylphenyloxy)phenylmethyl)-1,4,9-triazaspiro[5.5]undecane,
(270) (3S)-1-butyl-2,5-dioxo-3-hydroxymethyl-9-(4-(4-methylaminocarbonylphenyloxy)phenylmethyl)-1,4,9-triazaspiro[5.5]undecane,
(271) (3S)-1-butyl-2,5-dioxo-3-(pyridin-1-oxido-2-ylmethyl)-9-(4-(4-methylaminocarbonylphenyloxy)phenylmethyl)-1,4,9-triazaspiro[5.5]undecane,
(272) (3S)-1-butyl-2,5-dioxo-3-(pyridin-1-oxido-3-ylmethyl)-9-(4-(4-methylaminocarbonylphenyloxy)phenylmethyl)-1,4,9-triazaspiro[5.5]undecane,
(273) (3R)-1-(4-methoxyphenylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane,
(274) (3R)-1-phenylmethyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane,
(275) (3R)-1-(2-methoxyethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane,
(276) (3R)-1-(pyridin-2-ylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane,
(277) (3R)-1-(pyridin-3-ylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane,
(278) (3R)-1-butyl-2,5-dioxo-3-cyclohexylmethyl-9-(4-(4-carboxyphenyloxy)phenylmethyl)-1,4,9-triazaspiro[5.5]undecane,
(279) (3S)-1-butyl-2,5-dioxo-3-(pyridin-1-oxido-2-ylmethyl)-9-(4-(4-methylaminocarbonylphenyloxy)phenylmethyl)-1,4,9-triazaspiro[5.5]undecane 9-oxide,
(280) 1-butyl-2,5-dioxo-3-(morpholin-4-ylmethyl)-9-(4-(4-methylaminocarbonylphenyloxy)phenylmethyl)-1,4,9-triazaspiro[5.5]undecane,
(281) (3R)-1-butyl-2,5-dioxo-3-((1R)-1-hydroxy-1-cyclohexylmethyl)-9-(4-(4-(N-hydroxycarbamoyl)phenyloxy)phenylmethyl)-1,4,9-triazaspiro[5.5]undecane,
(282) (3R)-1-butyl-2,5-dioxo-3-((1R)-1-hydroxy-1-cyclohexylmethyl)-9-(4-(4-methylaminocarbonylphenyloxy)phenylcarbonyl)-1,4,9-triazaspiro[5.5]undecane, or
(283) (3R)-1-butyl-2,5-dioxo-3-((1R)-1-hydroxy-1-cyclohexylmethyl)-9-(4-(4-methylaminocarbonylphenyloxy)phenyl)-1,4,9-triazaspiro[5.5]undecane, a quaternary ammonium salt thereof, an N-oxide thereof, or a non-toxic salt thereof, vii) a pharmaceutical composition comprising a triazaspiro[5.5]undecane derivative of the formula (I) described in above i), a quaternary ammonium salt thereof, an N-oxide thereof, or a non-toxic salt thereof, as an active ingredient, viii) a chemokine/chemokine receptor regulator comprising a triazaspiro[5.5]undecane derivative of the formula (I) described in above i), a quaternary ammonium salt thereof, an N-oxide thereof, or a non-toxic salt thereof as an active ingredient, and ix) an agent for prevention and/or treatment of asthma, atopic dermatitis, urticaria, allergic bronchopulmonary aspergillosis, allergic eosinophilic gastroenteritis, nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, transplant rejection, immunosuppression, cancer metastasis or acquired immune deficiency syndrome comprising a triazaspiro[5.5]undecane derivative of the formula (I) described in above i), a quaternary ammonium salt thereof, an N-oxide thereof, or a non-toxic salt thereof, as an active ingredient.

DETAILED DESCRIPTION OF THE INVENTION

In the present invention, C1–4 alkyl means methyl, ethyl, propyl, butyl or isomeric groups thereof.

C1–4 alkoxy means methoxy, ethoxy, propoxy, butoxy or isomeric groups thereof.

Halogen is chlorine, bromine, fluorine or iodine.

C1–4 alkylene means methylene, ethylene, trimethylene, tetramethylene or isomeric groups thereof.

C2–4 alkenylene means vinylene, propenylene, butenylene or isomeric groups thereof.

C2–4 alkynyl means ethynyl, propynyl, butynyl or isomeric groups thereof.

C5–10 membered mono- or bi-carbocyclic ring means cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, indene, naphthalene, indan, tetrahydronaphthalene, bicyclo[3.3.0]octane, bicyclo[4.3.0]nonane or bicyclo[4.4.0]decane etc.

5–10 membered mono- or bi-(fused or spiro)cyclic hetero ring containing 1–2 nitrogen atoms and/or 1–2 oxygen atoms means 5–10 membered mono- or bi-(fused or spiro) cyclic hetero aryl containing 1–2 nitrogen atoms and/or 1–2 oxygen atoms and partially or fully saturated one. For example, in above 5–10 membered mono- or bi-(fused or spiro)cyclic hetero aryl containing 1–2 nitrogen atoms and/or 1–2 oxygen atoms and partially or fully saturated one include pyrrole, imidazole, pyrazole, pyridine, pyrazine, pyrimidine, pyridazine, azepine, diazepine, furan, pyran, oxepine, oxazole, isoxazole, furazan, oxadiazole, oxazine, oxadiazine, oxazepine, oxadiazepine, indole, isoindole, benzofuran, isobenzofuran, indazole, quinoline, isoquinoline, phthalazine, naphthyridine, quinoxaline, quinazoline, cinnoline, benzoxazole, benzimidazole, benzofurazan, benzotriazole, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxazole, tetrahydrooxazole, dihydroisoxazole, tetrahydroisoxazole, dihydrooxadiazole, tetrahydrooxadiazole, tetrahydrooxadiazine, tetrahydrooxazepine, tetrahydrooxadiazepine, perhydrooxazepine, perhydrooxadiazepine, morpholine, indoline, isoindoline, dihydrobenzofuran, perhydrobenzofuran, dihydroisobenzofuran, perhydroisobenzofuran, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzimidazole, perhydrobenzimidazole, dioxolane, dioxane, benzodioxalane or benzodioxane etc.

A 5–6 membered mono-cyclic hetero ring containing 1–2 nitrogen atoms and/or an oxygen atom to which an each substituent together with the nitrogen atom it attaches form, means 5–6 membered mono-cyclic hetero aryl containing 1–2 nitrogen atoms and/or an oxygen atom, and partially or fully saturated one. For example, in above 5–6 membered mono-cyclic hetero aryl containing 1–2 nitrogen atoms and/or an oxygen atom, and partially or fully saturated one include pyrrole, imidazole, pyrazole, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, tetrahydrooxazole, tetrahydroisoxazole, dihydrooxadiazole, tetrahydrooxadiazole, tetrahydrooxadiazine or morpholine etc.

5–6 membered mono-carbocyclic ring is concretely, cyclopentane, cyclohexane, cyclopentene, cyclohexene, cyclopentadiene, cyclohexadiene or benzene etc.

5–6 membered mono-cyclic hetero ring containing 1–2 nitrogen atoms and/or an oxygen atom means 5–6 membered mono-cyclic hetero aryl containing 1–2 nitrogen atoms and/or an oxygen atom, and partially or fully saturated one. For example, in above 5–6 membered mono-cyclic hetero aryl containing 1–2 nitrogen atoms and/or an oxygen atom, and partially or fully saturated one include pyrrole, imidazole, pyrazole, pyridine, pyrazine, pyrimidine, pyridazine, furan, pyran, oxazole, isoxazole, furazan, oxadiazole, oxazine, oxadiazine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrooxazole, tetrahydrooxazole, dihydroisoxazole, tetrahydroisoxazole, dihydrooxadiazole, tetrahydrooxadiazole, tetrahydrooxadiazine or morpholine etc.

In the present invention, each group represented by $R^1$, $R^2$, $R^3$, $R^4$ or $R^5$ is all preferable. Especially, the substituents described in examples are preferable.

Unless otherwise specified, all isomers are included in the present invention. For example, alkyl, alkoxy and alkylene groups include straight or branched ones. In addition, isomers on double bond, ring, fused ring (E-, Z-, cis-, trans-isomer), isomers generated from asymmetric carbon atoms (R—, S—, α-, β-isomer, enantiomer, diastereomer), optically active isomers (D-, L-, d-, I-isomer), polar compounds generated by chromatographic separation (more polar compound, less polar compound), equilibrium compounds, mixtures thereof, at voluntary ratios and racemic mixtures are also included in the present invention.

[Salts]

Non-toxic salts of the present invention include all pharmaceutically acceptable salts, for example, general salts, and acid addition salts.

The compounds of the present invention of the formula (I) may be converted into the corresponding salts by conventional means. Non-toxic and water-soluble salts are preferred. Suitable salts, for example, include: salts of alkali metals (potassium or sodium etc.), salts of alkaline earth metals (calcium or magnesium etc.), ammonium salts, and salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine or N-methyl-D-glucamine etc.).

The compounds of the present invention of the formula (I) may be converted into the corresponding acid addition salts by conventional means. Water-soluble salts are preferred. Suitable salts for example, include: salts of inorganic acids e.g. hydrochloride, hydrobromide, sulfate, phosphate or nitrate; salts of organic acids e.g. acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate or gluconate.

The compounds of the present invention of the formula (I) and salts thereof may be converted into the corresponding hydrates by conventional means.

All of the compounds of the formula (I) or non-toxic salts thereof are preferable, concretely, the compounds described in the examples or non-toxic salts thereof.

Quaternary ammonium salts of the compounds of the formula (I) are the compounds where nitrogen of the compounds of the formula (I) is quarternalized by $R^0$.

$R^0$ is C1–4 alkyl or C1–4 alkyl substituted by phenyl.

N-oxides of the compounds of the formula (I) are the compounds where nitrogen of the compounds of the formula (I) is oxidized.

[Methods for Preparation of the Compounds in the Present Invention]

The compounds of the present invention of the formula (I) may be prepared by the following methods or the methods described in examples.

Among the compounds of the present invention of the formula (I), the compound where nitrogens are not quaternary ammonium salts or N-oxides, i.e., the compound of the formula (I-1)

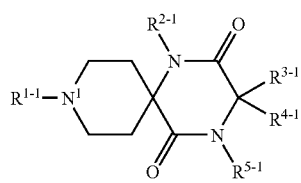

(I-1)

(wherein $R^{1-1}$, $R^{2-1}$, $R^{3-1}$, $R^{4-1}$ and $R^{5-1}$ have the same meanings as $R^1$, $R^2$, $R^3$, $R^4$ and $R^5$ respectively, and $N^1$ is nitrogen, and wherein any nitrogen are not quaternary ammonium salts or N-oxides) may be prepared by the following methods.

Among the compounds of the present invention of the formula (I-1), the compound in which any $R^{1-1}$, $R^{2-1}$, $R^{3-1}$, $R^{4-1}$ and $R^{5-1}$ are not a group containing carboxyl, hydroxy, amino or thiol, i.e., the compound of the formula (I-1A)

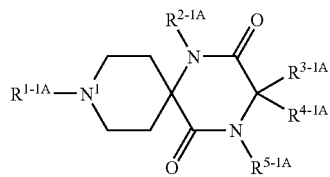

(I-1A)

(wherein $R^{1-1A}$, $R^{2-1A}$, $R^{3-1A}$, $R^{4-1A}$ and $R^{5-1A}$ have the same meanings as $R^{1-1}$, $R^{2-1}$, $R^{3-1}$, $R^{4-1}$ and $R^{5-1}$ respectively, and wherein all of them are not a group containing carboxyl, hydroxy, amino or thiol, and the other symbols have the same meanings as defined hereinbefore.) may be prepared by cyclization of the compound of the formula (II)

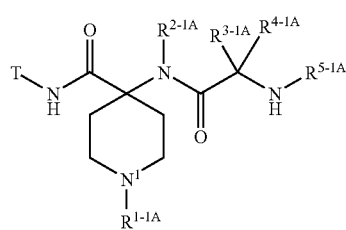

(II)

(wherein T is C1–4 alkyl, C5–6 mono-carbocyclic ring, or C1–4 alkyl substituted by a substituent selected from C5–6 mono-carbocyclic ring and C5–6 mono-cyclic hetero ring containing 1–2 nitrogen and/or an oxygen.).

The cyclization of compound of the formula (II) is well known. For example, it may be carried out by heating in an organic solvent (dichloroethane or toluene etc.) in the presence or absence of a tertiary amine (triethylamine or diisopropylethylamine etc.), or acid (acetic acid or trifluoroacetic acid etc.) at 60–120° C. This cyclization reaction is completed simultaneously with the cleavage of T group.

Moreover, the cyclization may be carried out with the compound in which $R^3$ or $R^4$ is hydroxyl group.

The cyclization may be carried out with the compound in which nitrogen of $R^1$, $R^2$, $R^3$ or $R^4$ is oxidized to N-oxide.

If necessary, the conversion to desired non-toxic salts may be carried out by the conventional means after the cyclization.

Among the compounds of the formula (I-1A), the compound, in which G group in $R^{1-1A}$ is methylene or vinylene, i.e., the compound of the formula (I-1A-1)

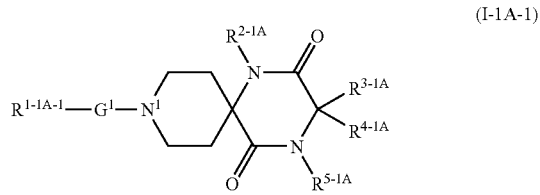

(I-1A-1)

(wherein $G^1$ group is methylene or vinylene, $R^{1-1A-1}$ is

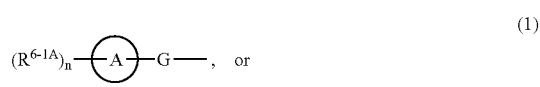

(1)

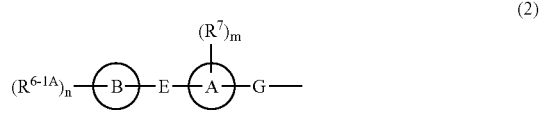

(2)

(wherein $R^{6-1A}$ has the same meaning as $R^6$, and wherein all of them are not a group containing carboxyl, hydroxy, amino or thiol), and the other symbols have the same meanings as defined hereinbefore.) may be prepared by the reductive amination of the compound of the formula (III)

$R^{1-1A-1}$—CHO (III)

wherein all of the symbols have the same meanings as defined hereinbefore.) or the compound of the formula (IV)

(IV)

with the compound the formula (V).

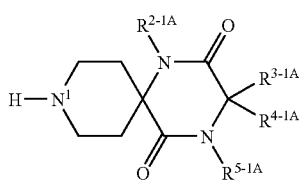
(V)

The reductive amination is well known. For example, it may be carried out in an organic solvent (dichloroethane, dichloromethane, dimethylformamide, acetic acid or a mixture thereof etc.) in the presence of a reducing agent (sodium triacetoxyborohydride or sodium cyanoborohydride etc.) at 0–40° C.

Moreover, the reductive amination may be carried out with the compound in which nitrogen of $R^1$ is oxidized to N-oxide.

Moreover, the reductive amination may be carried out with the compound in which $R^3$ or $R^4$ is hydroxyl group.

Among the compounds of the formula (I-1A), the compound, in which G group in $R^{1-1A}$ is ethylene, i.e., the compound of the formula (I-1A-2)

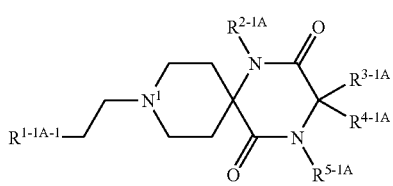
(I-1A-2)

(wherein all of the symbols have the same meanings as defined hereinbefore.) may be prepared by reacting the compound of the formula (VI)

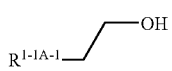
(VI)

(wherein all of the symbols have the same meanings as defined hereinbefore.) with the compound of the formula (V).

This reaction is well known, for example, firstly, PS-TsCl-HL resin (brand name of Argonaut Technologies, catalog number 800366) may be carried out in an organic solvent (e.g. chloroform or dichloromethane etc.) with the compound of the formula (VI) in the presence of a tertiary amine (isopropylethylamine etc.) at 0–40° C., and then the resin may be carried out in an organic solvent (e.g. chloroform or dichloromethane etc.) with the compound of the formula (V) in the presence of a tertiary amine (triethylamine or diisopropylethylamine etc.) at 40–100° C.

This reaction may be carried out with the compound in which nitrogen of $R^1$, $R^2$, $R^3$ or $R^4$ is oxidized to N-oxide.

Among the compounds of the formula (I-1A), the compound, in which G group in $R^{1-1A}$ is a single bond, i.e., the compound of the formula (I-1A-3)

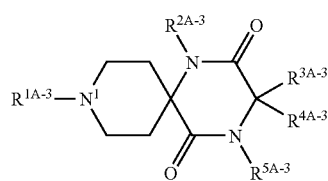
(I-1A-3)

(wherein all of the symbols have the same meanings as defined hereinbefore.) may be prepared by reacting the compound of the formula (VII)

$$R^{1-1A-1}-X \quad (VII)$$

(wherein X is halogen and the other symbols have the same meanings as defined hereinbefore.) with the compound of the formula (V).

The reaction is well known, and it may be carried out, for example, in an organic solvent (dimethylsulfoxide etc.) in the presence of an alkaline (potassium carbonate or sodium carbonate etc.) at 100–150° C.

Moreover, this reaction may be carried out with the compound in which nitrogen of $R^1$, $R^2$, $R^3$ or $R^4$ is oxidized to N-oxide.

Among the compounds of the formula (I-1A), the compound, in which G group in $R^{1-1A}$ is —CO—, i.e., the compound of the formula (I-1A-5)

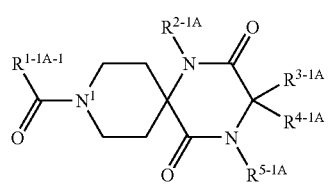
(I-1A-5)

(wherein all of the symbols have the same meanings as defined hereinbefore.) may be prepared by the amidation of the compound of the formula (XIII)

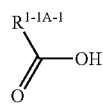
(XIII)

(wherein all of the symbols have the same meanings as defined hereinbefore.) with the compound of the formula (V).

The amidation is well known, and it includes the methods, for example,
(1) via an acyl halide,
(2) via a mixed acid anhydride,
(3) using a condensing agent.

These methods are explained as follows.
(1) The method via an acyl halide may be carried out, for example, by reacting carboxylic acid with an acyl halide (e.g. oxalyl chloride or thionyl chloride etc.) in an organic solvent (e.g. chloroform, methylene chloride, diethyl ether or tetrahydrofuran) or without a solvent at −20° C. to reflux temperature. And then the obtained acyl halide derivative may be reacted with amine in an inert organic solvent (e.g. chloroform, methylene chloride, diethyl ether or tetrahydrofuran), in the presence of a tertiary amine (e.g. pyridine, triethyl amine, dimethyl aniline or dimethylaminopyridine) at 0–40° C. As an alternative, the obtained acyl halide derivative may be reacted with amine in an organic solvent (e.g. dioxane or tetrahydrofuran) using an alkaline aqueous solution (e.g. sodium bicarbonate or sodium hydroxide) at 0–40° C.

(2) The method via a mixed acid anhydride may be carried out, for example, by reacting carboxylic acid with an acyl halide (e.g. pivaloyl chloride, tosyl chloride or mesyl chloride), or an acid derivative (e.g. ethyl chloroformate or isobutyl chloroformate) in an organic solvent (e.g. chloroform, methylene chloride, diethyl ether or tetrahydrofuran) or without a solvent, in the presence of a tertiary amine (e.g. pyridine, triethylamine, dimethylaniline or dimethylaminopyridine), at 0–40° C. And then the obtained mixed acid anhydride derivative may be reacted with amine in an organic solvent (e.g. chloroform, methylene chloride, diethyl ether or tetrahydrofuran), at 0–40° C.

(3) The method using a condensing agent may be carried out, for example, by reacting carboxylic acid with amine in an organic solvent (e.g. chloroform, methylene chloride, dimethylformamide, diethyl ether or tetrahydrofuran) or without a solvent, in the presence or absence of a tertiary amine (e.g. pyridine, triethylamine, dimethylaniline or dimethylaminopyridine), using a condensing agent (e.g. 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide or 1-propanephosphonic acid cyclic anhydride), in the presence or absence of 1-hydroxybenzotiazole (HOBt), at 0–40° C.

The reaction described in (1), (2) and (3) may be carried out under an inert gas (e.g. argon or nitrogen) to avoid water in order to obtain a preferable result.

Moreover, the amidation may be carried out with the compound in which $R^3$ or $R^4$ is hydroxyl group.

Moreover, the amidation may be carried out with the compound in which nitrogen of $R^1$, $R^2$, $R^3$ or $R^4$ is oxidized to N-oxide.

Among the compounds of the formula (I-1), the compound, in which at least one group of $R^1$, $R^2$, $R^3$, $R^4$ or $R^5$ represents a group containing carboxyl, hydroxy, amino or thiol, i.e., the compound of the formula (I-1B)

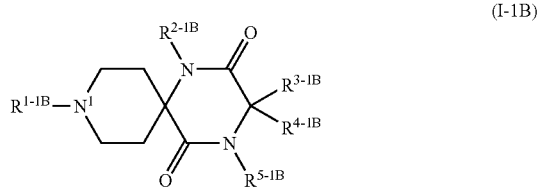

(I-1B)

(wherein $R^{1-1B}$, $R^{2-1B}$, $R^{3-1B}$, $R^{4-1B}$ and $R^{5-1B}$ have the same meanings as $R^{1-1}$, $R^{2-1}$, $R^{3-1}$, $R^{4-1}$ and $R^{5-1}$ respectively, and wherein at least one group represents a group containing carboxyl, hydroxy, amino or thiol, and the other symbols have the same meanings as defined hereinbefore) may be prepared by the removal of protecting groups containing carboxyl, hydroxy, amino and thiol protected by protecting groups, i.e., the compound of the formula (I-1A-4)

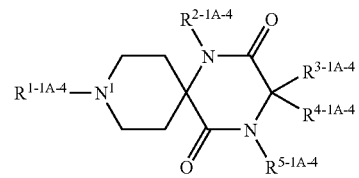

(I-1A-4)

(wherein $R^{1-1A-4}$, $R^{2-1A-4}$, $R^{3-1A-4}$, $R^{4-1A-4}$ and $R^{5-1A-4}$ have the same meanings as $R^{1-1}$, $R^{2-1}$, $R^{3-1}$, $R^{4-1}$ and $R^{5-1}$ respectively, and wherein at least one group represents a group containing carboxyl, hydroxy, amino or thiol, and the other symbols have the same meanings as defined hereinbefore).

A protecting group of carboxyl includes, for example, methyl, ethyl, t-butyl, benzyl or allyl.

A protecting group of hydroxy includes, for example, methoxymethyl, 2-tetrahydropyranyl, t-butyldimethylsilyl, t-butyldiphenylsilyl, acetyl or benzyl.

A protecting group of amino includes, for example, benzyloxycarbonyl, allyloxycarbonyl, t-butoxycarbonyl, trifluoroacetyl or 9-fluorenylmethoxycarbonyl.

A protecting group of thiol includes, for example, benzyl, methoxybenzyl, acetoamidomethyl, triphenylmethyl or acetyl.

The protecting group of carboxyl, hydroxy, amino or thiol includes the above one, and in addition to the other protecting group which is removable selectively and easily, for example, one described in T. W. Greene et. al., Protective Groups in Organic Synthesis, Third Edition, Wiley-Interscience, New York, 1999.

The removal of a protecting group of amino may be carried out by the method described hereinbefore.

The removal of a protecting group of carboxyl, hydroxy or thiol is well known. For example, it is (1) the alkaline hydrolysis,
(2) the removal of a protecting group in an acidic condition,
(3) the removal of a protecting group by hydrogenolysis, or
(4) the removal of a protecting group containing silyl or
(5) the removal of a protecting group using metal complex etc.

The concrete descriptions of these methods are as follows:

(1) The removal of a protecting group by alkaline hydrolysis condition (e.g. trifluoroacethyl group) may be carried out, for example, in an organic solvent (methanol, tetrahydrofuran or dioxane etc.) with hydroxide of alkaline metal (sodium hydroxide, potassium hydroxide or lithium hydroxide etc.), hydroxide of alkaline earth metal (barium hydroxide or calcium hydroxide etc.), carbonate (sodium carbonate or potassium carbonate etc.), or an aqueous solution thereof or a mixture thereof at 0–40° C.

(2) The removal of a protecting group in an acidic condition (e.g. t-butoxycarbonyl group) may be carried out, for example, in an organic solvent (dichloromethane, chloroform, dioxane, ethyl acetate or anisole etc.), organic acid (acetic acid, trifluoroacetic acid or methanesulfonic acid etc.) or inorganic acid (hydrochloric acid or sulfuric acid etc.), or a mixture thereof (hydrogen bromide/acetic acid etc.) at 0–100° C.

(3) The removal of a protecting group by hydrogenolysis (e.g. benzyl, benzyloxycarbonyl or allyloxycarbonyl) may be carried out, for example, in a solvent (ether (tetrahydrofuran, dioxane, dimethoxyethane or diethylether etc.), alcohol (methanol or ethanol etc.), benzene (benzene or toluene etc.), ketone (acetone or methylethylketone etc.), nitrile (acetonitrile etc.), amide (dimethylformamide etc.), water, ethyl acetate, acetic acid or a mixture thereof etc.) in the presence of a catalyst (palladium on carbon, palladium black, palladium hydroxide, platinum oxide, or Raney nickel etc.), at an atmospheric or positive pressure under atmosphere of hydrogen or in the presence of ammonium formate at 0–200° C.

(4) The removal of a protecting group containing silyl may be carried out, for example, in an organic solvent (tetrahydrofuran or acetonitrile etc.), with tetrabutylammoniumfluoride at 0–40° C.

(5) The removal of a protecting group using metal complex may be carried out, for example, in an organic solvent (dichloromethane, dimethylformamide or tetrahydrofuran etc.) in the presence of a trap reagent (tributyltin hydride or dimedone etc.) and/or an organic acid (acetic acid etc.) with metal complex (tetrakis(triphenylphosphine)palladium(0) complex etc.) at 0–40° C.

As well known to the person in the art, the aimed compounds of the present invention may be prepared easily by choice of these methods.

Among the compounds of the formula (I), the compound, in which at least one nitrogen represents quaternary ammonium salt, i.e., the compound of the formula (I-2)

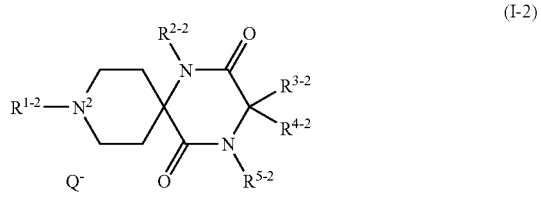

(I-2)

(wherein $R^{1-2}$, $R^{2-2}$, $R^{3-2}$, $R^{4-2}$ and $R^{5-2}$ have the same meanings as $R^1$, $R^2$, $R^3$, $R^4$ and $R^5$ respectively, and wherein at least one nitrogen represents quaternary ammonium salt, and wherein Q is halogen) may be prepared by reacting the compound of the formula (XI)

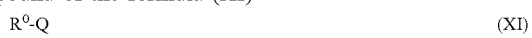

R°-Q  (XI)

(wherein R° is C1–4 alkyl or C1–4 alkyl substituted by phenyl, and Q is halogen.).

The reaction is well known, and it may be carried out, for example, in an organic solvent (acetone, dimethylsulfoxide or methyl ethyl ketone etc.) at 0–40° C.

Among the compounds of the formula (I), the compound, in which at least one nitrogen represents N-oxide, i.e., the compound of the formula (I-3)

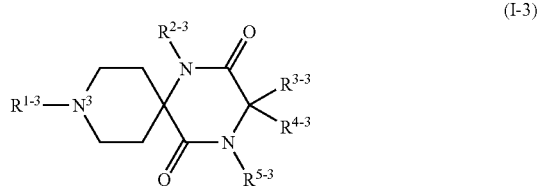

(I-3)

(wherein $R^{1-2}$, $R^{2-2}$, $R^{3-2}$, $R^{4-2}$ and $R^{5-2}$ have the same meanings as $R^1$, $R^2$, $R^3$, $R^4$ and $R^5$ respectively, and wherein at least one nitrogen represents N-oxide, and wherein Q is halogen.) may be prepared by the oxidation of the compound of the formula (I-1).

The oxidation is well known and it may be carried out, for example, in a suitable organic solvent (dichloromethane, chloroform, benzene, hexane or t-butylalcohol etc.) in the presence of an excessive oxidizing reagent (hydrogen peroxide, sodium periodate, acyl nitrite, sodium perborate, peroxidized acid (for example, 3-chloroperbenzoic acid or peracetic acid etc.), OXONE (brand name, OXONE is an abbreviation for potassium peroxymonosulfate.), potassium permanganate or chromic acid etc.) at 20–60° C.

The compounds of the (II) may be prepared according to the following Scheme 1.

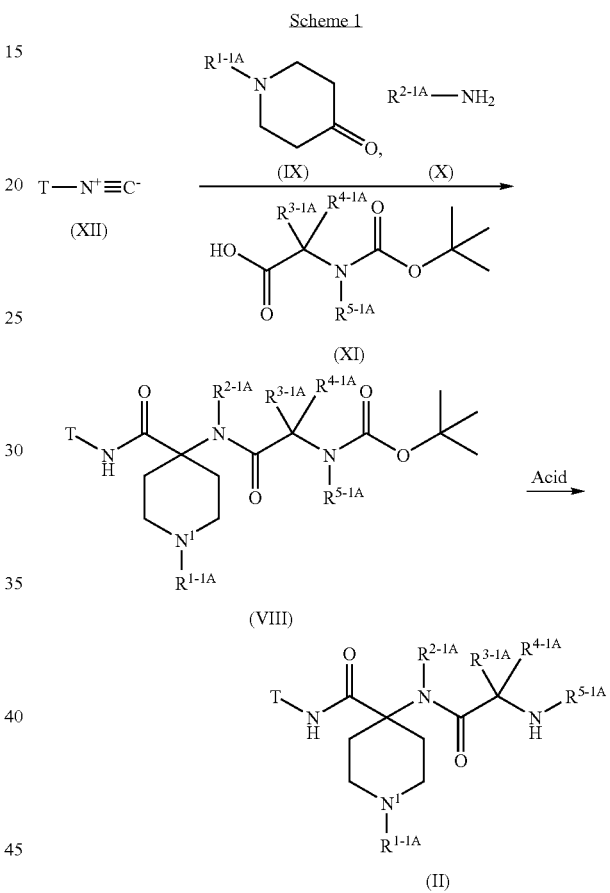

In above Scheme 1 each reaction may be carried out by known methods. Moreover in above Scheme 1, the starting materials of the compounds of the formula (IX), formula (X), formula (XI) or formula (XII) may be known per se or may be prepared by known methods.

In the present invention, in each reaction, the obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. The purification may be done after each reaction or after several reactions.

The other starting materials and each reagent in the present invention may be known per se or may be prepared by known methods.

[Pharmacological Activities]

Efficacy of the compounds of the invention of the formula (I) was confirmed, e.g., by the following tests.

As described in the foregoing, in order to carry out screening of a compound capable of inhibiting binding of HIV to CXCR4 or CCR5 which is a receptor on the CD4-positive cell, it is a more directive method to carry out it in an assay system that uses HIV virus. However, the use of a large amount of HIV virus in the screening is not practical due to a difficulty in handling it. On the other hand, since both the macrophage tropic (R5) HIV-1 and the ligands, that is, RANTES, MIP-1α and MIP-1β, bind to CCR5, it can be presumed that certain common characteristics are present in the CCR5 binding sites of the HIV side and the RANTES, MIP-1α and MIP-1β sides, and in the binding sides of CCR5 to the ligands, that is, RANTES, MIP-1α and MIP-1β, and HIV Accordingly, in order to find a compound capable of inhibiting adsorption of HIV virus to cells, which has an inhibitory mechanism different from the current anti-AIDS drugs (reverse transcriptase inhibitors and protease inhibitors), it is possible to use an assay system that uses an endogeneous CCR5 ligand, RANTES, MIP-1α or MIP-1β instead of HIV.

Concretely, e.g., since CCR5 is a G protein-coupled seven transmembrane type receptor, an assay system in which the effect of RANTES on the transient increase of Ca ion induced via CCR5 can be carried out for screening a compound capable of inhibiting binding of RANTES to CCR5. Since both of the T cell tropic (X4) HIV and SDF-1 bind to CXCR4, similar idea can be considered for screening a compound.

[Test Methods]

(1) Isolation of Human CCR5 Gene

Human placental cDNA was prepared using Marathon cDNA amplification kit (Clontech). PCR primers hCCR5XbaI-F1: 5'-AGCTAGTCTAGATCCGTTCCCCTA-CAAGAAACTCTCC-3' (SEQ ID NO:1) and hCCR5XbaI-R1: 5'-AGCTAGTCTAGAGTGCACAACTCT-GACTGGGTCACCA-3' (SEQ ID NO:2) were designed based on the sequence of GenBank U54994.

Using the human placental cDNA as the template and using Ex Taq (Takara), PCR reaction (2 minutes at 95° C.→(30 seconds at 95° C., 45 seconds at 60° C., 1 minute at 72° C.)×35 times) was carried out. The thus amplified PCR product was subjected to a 1% agarose gel electrophoresis, purified using QIAquick Gel Extraction Kit (QUIAGEN) and then digested with a restriction enzyme XbaI. The digested fragments were ligated to an expression vector pEF-BOS-bsr using DNA Ligation Kit Ver. 2 (Takara) and transformed into *Escherichia coli* DH5a. By preparing the resulting plasmid pEF-BOS-bsr/hCCR5, its DNA sequence was verified.

(2) Culturing of CHO Cell

CHO-dhfr(−) was cultured using Ham's F-12 (containing fetal bovine serum (10%), penicillin (50 U/ml) and streptomycin (50 mg/ml)). Also, the transduced cell was cultured by adding blasticidin (5 mg/ml) to the above medium.

(3) Transduction into CHO Cell

The plasmid pEF-BOS-bsr/hCCR5 was transduced into the CHO-dhfr(−) cell using DMRIE-C reagent (Gibco BRL). After 48 hours, the medium was replaced with a medium containing 5 mg/ml of blasticidin to carry out the selection, thereby establishing a stably over-expressing cell.

(4) Inhibition Test on the Binding of RANTES to CCR5 (Activity of RANTES to Induce Transient Increase of Ca Ion).

The thus established human CCR5 stably over-expressing CHO cell (CCR5/CHO cell) was suspended in Ham's F-12 medium containing FBS (10%) and dispensed in $3.0 \times 10^6$ cells/well portions into a 96 well plate. One day after culturing at 37° C., the culture supernatant was discarded, and Ham's F-12 medium (containing Fura-2AM (5 μM), Probenecid (2.5 mM) and HEPES (20 mM; pH 7.4)) was dispensed in 80 μl/well portions to carry out 1 hour of incubation at 37° C. under shaded condition. After washing twice with 1× Hanks/HEPES (20 mM; pH 7.4) solution, the same solution was dispensed in 100 μl/well portions. Each of the test compounds was added to the thus Fura2AM-incorporated CCR5/CHO cell, and 3 minutes thereafter, a recombinant human RANTES (PeproTach) diluted with 1× Hanks/HEPES (20 mM; pH 7.4) solution was added thereto to a final concentration of 10 nM. Transient increase in the intracellular $Ca^{2+}$ concentration induced by the human RANTES was measured using a $Ca^{2+}$ detector for 96 well use (Hamamatsu Photonics), and inhibition ratio (%) of the test compound was calculated by the following calculation formula.

Inhibition ratio=$(Ec-Ea)/Ec \times 100$

Ec: measured value of $Ca^{2+}$ transient increase by RANTES

Ea: measured value of $Ca^{2+}$ transient increase by RANTES when a test compound was added.

As a result, the compounds of the invention showed an inhibition ratio of 50% or more at 10 μM. For example, the compound of Example 2 showed an $IC_{50}$ value of 0.027 μM, and the compound of Example 3 an $IC_{50}$ value of 0.37 μM.

An assay system for finding a compound having adsorption inhibition effect on CCR5 directional HIV strain was described in the foregoing, and it is possible as a matter of course to find a compound capable of inhibiting the activity of CCR5 or a ligand thereof using this system. In the same manner, it is possible to find a compound capable of inhibiting the activity of other chemokine receptor or a ligand thereof. For example, a system for finding a compound capable of inhibiting the activity of CCR2 or a ligand thereof can be constructed. Since CCR2 is a G protein-coupled seven transmembrane type receptor similar to the case of CCR5, it can be carried out by measuring the effect of a ligand of CCR2, e.g., MCP-1 on the transient increase of Ca ion induced via CCR2.

(5) Inhibition Test on the Binding of MCP-1 to CCR2 (Activity of MCP-1 to Induce Transient Increase of Ca Ion).

A human CCR2-expressing cell, e.g., a human monocyte cell strain THP-1 (ATCC No. TIB-202), was suspended in RPMI 1640 medium containing FBS (10%), Fura-2AM (5 μM), Probenecid (2.5 mM) and HEPES (20 mM, pH 7.4) to a density of $5.0 \times 10^6$ cells/ml and incubated at 37° C. for 30 minutes under shaded condition. This was mixed with 4 to 8 volumes of 1× Hanks/HEPES (20 mM, pH 7.4)/Probenecid (2.5 mM) and further incubated at 37° C. for 30 minutes under shaded condition. After washing with 1× Hanks/HEPES (20 mM, pH 7.4)/Probenecid (2.5 mM) solution, the thus washed cells were resuspended in the same solution to a density of $2.0 \times 10^6$ cells/ml and dispensed in 100 μl/well portions into a 96 well plate. Each of the test compound solutions was added thereto, and 3 minutes thereafter, a recombinant human MCP-1 (PeproTach) diluted with 1× Hanks/HEPES (20 mM, pH 7.4)/Probenecid (2.5 mM) was added thereto to a final concentration of 30 nM. Transient increase in the intracellular $Ca^{2+}$ concentration induced by the human MCP-1 was measured using a Ca²⁺ detector for 96 well use (Hamamatsu Photonics), and inhibition ratio (%) of the test compound was calculated by the following calculation formula.

Inhibition ratio=$(Ec-Ea)/Ec \times 100$

Ec: measured value of $Ca^{2+}$ transient increase by MCP-1
Ea: measured value of $Ca^{2+}$ transient increase by MCP-1 when a test compound was added.

[Toxicity]

The toxicity of the compounds of the present invention is very low and therefore the compounds may be considered safe for pharmaceutical use.

INDUSTRIAL APPLICABILITY

[Application to Pharmaceuticals]

The compounds of the present invention of the formula (I) regulate the effect of chemokine/chemokine receptor in animal included human, especially human, so they are used for prevention and/or treatment of various inflammatory diseases, asthma, atopic dermatitis, urticaria, allergic diseases (allergic bronchopulmonary aspergillosis or allergic eosinophilic gastroenteritis etc.), nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, transplant rejection, immunosuppression, cancer metastasis or acquired immune deficiency syndrome.

For the purpose above described, the compounds of formula (I), non-toxic salts thereof, acid addition salts or hydrates thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compounds may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compounds may be dissolved, suspended or emulized into diluents commonly used in the art (such as purified water, ethanol or a mixture thereof. Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvents for injection immediately before use. In injections, one or more of the active compounds may be dissolved, suspended or emulized into solvents. The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms such as freeze-dried products, which may be dissolved in sterile water or some other sterile diluents for injection immediately before use.

Other forms for parenteral administration include liquids for external use, ointments and endermic liniments, inhalations, sprays, suppositories and pessaries for vaginal administration which comprise one or more of the active compounds and may be prepared by methods known per se.

Sprays may comprise additional substances other than diluents, such as stabilizing agents, such as sodium sulfate, isotonic buffers, such as sodium chloride, sodium citrate or citric acid. For preparation of such sprays, for example, the method described in the U.S. Pat. No. 2,868,691 or 3,095,355 may be used. The compound of the present invention of the formula (I), a quaternary ammonium salt thereof, an N-oxide thereof, or a non-toxic salt thereof may be used together with at least one member of other prevention and/or treatment agents for HIV infection (particularly an agent for prevention and/or treatment agent AIDS). In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection.

The compound of the formula (I), a quaternary ammonium salt thereof, an N-oxide thereof, or a non-toxic salt thereof has an infection inhibiting activity to HIV-1 which acquired resistance to other agent for prevention and/or treatment of HIV infection (particularly, an agent for prevention and/or treatment agent AIDS). Therefore, it is also able to be used for HIV-infected patients to whom other agent for prevention and/or treatment of HIV infection is no longer effective. In that case, although the compound of the present invention may be used solely, it may be also used together with an agent for prevention and/or treatment of HIV infection where infected HIV-1 strain acquired resistance or with other drugs.

The present invention covers the case where the compound of the formula (I), a quaternary ammonium salt thereof, an N-oxide thereof, or a non-toxic salt thereof is combined with a drug which does not inhibit the HIV infection whereby prevention and/or treatment effect for HIV infection is enhanced as compared with a single preparation.

Examples of other agent for prevention and/or treatment of HIV infection used in combination with the compound of the present invention of the formula (I), a quaternary ammonium salt thereof, an N-oxide thereof, or a non-toxic salt thereof are reverse transcriptase inhibitor, protease inhibitor, chemokine antagonist (such as CCR2 antagonist, CCR3 antagonist, CCR4 antagonist, CCR5 antagonist and CXCR4 antagonist), fusion inhibitor, antibody to surface antigen of HIV-1 and vaccine of HIV-1 etc.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir) etc. and (2) normucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivative, non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in Bioorg. Med. Chem. Lett., 10, 1803 (2000) etc.

CCR3 antagonists are concretely written in specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088 etc.

CCR5 antagonists are concretely written in specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO0/59503, WO00/76933, WO98/25605 or WO99/04794, WO99/38514 or in Bioorg. Med. Chem. Lett., 10, 1803 (2000) etc.

CXCR4 antagonists are concretely AMD-3100, T-22, KRH-1120 or the compounds written in specification of WO00/66112 etc.

Fusion Inhibitors are concretely, T-20 (Pentafuside) and T-1249 etc.

The examples of agents for combination therapy written above are intended to illustrate the present invention, but do not limit them.

The typical examples of the usual the dosage level in clinical trials of reverse transcriptase inhibitors or protease inhibitors written below are intended to illustrate the present invention, but do not limit them.

| | |
|---|---|
| Zidovudine: | 100 mg capsule, 200 mg per dose, 3 times per day; 300 mg tablet, 300 mg per dose, twice per day; |
| didanosine: | 25–200 mg tablet, 125–200 mg per dose, twice per day; |
| zalcitabine: | 0.375–0.75 mg tablet, 0.75 mg per dose, 3 times per day; |
| stavudine: | 15–40 mg capsule, 30–40 mg per dose, twice per day; |
| lamivudine: | 150 mg tablet, 150 mg per dose, twice per day; |
| abacavir: | 300 mg tablet, 300 mg per dose, twice per day; |
| nevirapine: | 200 mg tablet, 200 mg per dose, once per day for 14 days and then twice per day; |
| delavirdine: | 100 mg tablet, 400 mg per dose, 3 times per day; |
| efavirenz: | 50–200 mg capsule, 600 mg per dose, once per day; |
| indinavir: | 200–400 mg capsule, 800 mg per dose, 3 times per day; |
| ritonavir: | 100 mg capsule, 600 mg per dose, twice per day; |
| nelfinavir: | 250 mg tablet, 750 mg per dose, 3 times per day; |
| saquinavir: | 200 mg capsule, 100 or 200 mg per dose, 3 times per day; |
| amprenavir: | 50–150 mg tablet, 100 or 200 mg per dose, twice per day. |

The following Reference Examples and Examples are intended to illustrate the present invention, but do not limit them.

In chromatographic separations and TLC, the solvents in parenthesis show the eluting and developing solvents and the ratios of the solvents used are by volume.

The solvents in parenthesis in NMR show the solvents used for measurement.

REFERENCE EXAMPLE 1

(2R,3R)-2-(t-butoxycarbonylamino)-3-hydroxy-4-methyl-N-butyl-N-[4-benzylaminocarbonyl-1-benzylpiperidin-4-yl]pentanamide

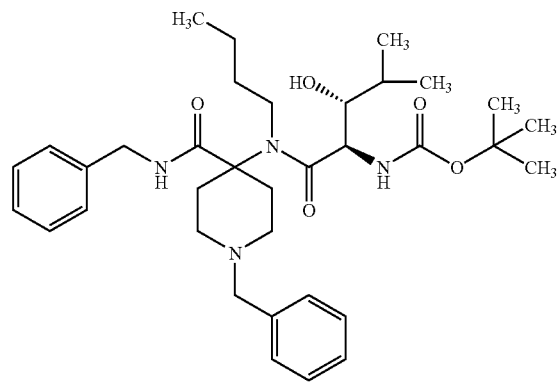

To a solution of (2R,3R)-2-(t-butoxycarbonylamino)-3-hydroxy-4-methylpentanoic acid (10.5 g) in methanol (340 ml) was added n-butylamine (4.2 ml), N-benzyl-4-piperidone (7.9 ml) and benzylisonitrile (5.2 ml). The reaction mixture was stirred overnight at 55° C. The reaction mixture was concentrated. The obtained residue was purified by column chromatography on silica gel (chloroform:methanol=100:1→75:1→50:1) to give the title compound (19.8 g) having the following physical data.

TLC: Rf 0.49 (chloroform:methanol=10:1);

NMR (CD$_3$OD): δ 7.38–7.15 (m, 10H), 4.58 (d, J=9.6 Hz, 1H), 4.39 (d, J=15.0 Hz, 1H), 4.23 (d, J=15.0 Hz, 1H), 3.70–3.30 (m, 3H), 3.50 (s, 2H), 2.79–2.30 (m, 6H), 2.08–1.88 (m, 2H), 1.88–1.70 (m, 3H), 1.50–1.28 (m, 2H), 1.38 (s, 9H), 0.98 (t, J=7.2 Hz, 3H), 0.96 (d, J=6.6 Hz, 3H), 0.91 (d, J=6.6 Hz, 3H).

REFERENCE EXAMPLE 2

(2R,3R)-2-amino-3-hydroxy-4-methyl-N-butyl-N-[4-benzylaminocarbonyl-1-benzyl-piperidin-4-yl]pentanamide

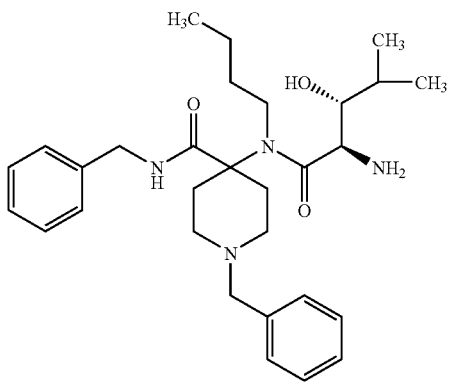

To a solution of the compound (19.8 g) prepared in Reference example 1 in dichloromethane (65 ml) was added trifluoroacetic acid (50 ml) under ice bath. The reaction mixture was stirred for 1 hr at room temperature. To the reaction mixture was added dichloromethane, neutrified with aqueous solution of sodium carbonate and extracted. The extract was washed with water and saturated aqueous solution of sodium chloride, dried over anhydrous sodium sulfate and concentrated to give the title compound having the following physical data. The obtained residue was used in the next reaction without further purification.

TLC: Rf 0.38 (chloroform:methanol=10:1).

EXAMPLE 1

(3R)-1-butyl-2,5-dioxo-3-((1R)-1-hydroxy-2-methylpropyl)-9-benzyl-1,4,9-triazaspiro[5.5]undecane

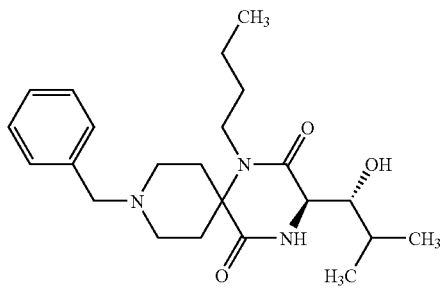

To a solution of the compound prepared in Reference example 2 in toluene (200 ml) was added acetic acid (15 ml). The reaction mixture was stirred for 45 minutes at 80° C. The reaction mixture was diluted with ethyl acetate, neutrified with aqueous solution of sodium carbonate and extracted. The extract was washed with saturated aqueous solution of sodium chloride, dried over anhydrous sodium sulfate and concentrated. The obtained residue purified by column chromatography on silica gel (ethyl acetate:methanol=25:1) to give the title compound (12.9 g) having the following physical data.

TLC: Rf 0.49 (chloroform:methanol=10:1);

NMR (CD$_3$OD): δ 7.36–7.22 (m, 5H), 4.10 (d, J=2.7 Hz, 1H), 3.60 (s, 2H), 3.47 (m, 1H), 3.38–3.25 (m, 2H), 2.96 (m, 1H), 2.87–2.73 (m, 3H), 2.25–1.94 (m, 4H), 1.82 (m, 1H), 1.64 (m, 1H), 1.53–1.27 (m, 3H), 0.96 (d, J=6.6 Hz, 6H), 0.95 (t, J=7.5 Hz, 3H).

REFERENCE EXAMPLE 3

(3R)-1-butyl-2,5-dioxo-3-((1R)-1-hydroxy-2-methylpropyl)-1,4,9-triazaspiro[5.5]undecane.hydrochloride

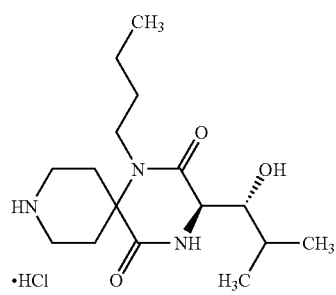

Under an atmosphere of argon, to a solution of the compound (12.67 g) prepared in Example 1 in methanol (160 ml) was added 20% palladium hydroxide on carbon (1.3 g). Under an atmosphere of hydrogen, the reaction mixture was stirred for 12 hours at room temperature. The reaction mixture was filtrated with Celite (brand name) and the filtrate was concentrated. The obtained residue was purified by column chromatography on silica gel (chloroform:hexane=3:1→chloroform:methanol=100:1→50:1→30:1→20:1→10:1). The obtained compound was added 4N hydrogen chloride/ethyl acetate solution and concentrated to give the title compound (8.6 g) having the following physical data.

TLC: Rf 0.16 (chloroform:methanol:acetic acid=20:4:1);

NMR (CD$_3$OD): δ 4.15 (d, J=2.1 Hz, 1H), 3.95 (m, 1H), 3.71 (m, 1H), 3.52 (m, 1H), 3.42–3.31 (m, 2H), 3.21 (m, 1H), 3.21 (dd, J=9.6, 2.1 Hz, 1H), 2.48–2.32 (m, 2H), 2.23 (m, 1H), 2.14–1.96 (m, 2H), 1.72 (m, 1H), 1.55–1.33 (m, 3H), 1.02–0.92 (m, 9H);

Optical rotation: [α]$_D$ +13.9 (c 1.00, methanol, 28° C.).

REFERENCE EXAMPLE 3(1)–3(9)

By the same procedure described in Reference example 1→Reference example 2→Example 1→Reference example 3 using the corresponding amino acid derivatives respectively instead of (2R,3R)-2-(t-butoxycarbonylamino)-3-hydroxy-4-methylpentanoic acid, using the corresponding amine derivatives respectively instead of n-butylamine, the following compounds were obtained.

REFERENCE EXAMPLE 3(1)

(3S)-1-butyl-2,5-dioxo-3-(2-methylpropyl)-1,4,9-triazaspiro[5.5]undecane.hydrochloride

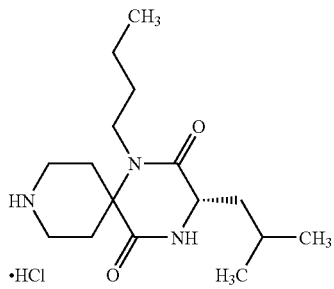

TLC: Rf 0.18 (chloroform:methanol=4:1);
NMR (CD₃OD): δ 4.02 (dd, J=7.8, 4.6 Hz, 1H), 3.82–3.70 (m, 2H), 3.39 (m, 4H), 2.34–2.09 (m, 4H), 1.88–1.50 (m, 5H), 1.37 (m, 2H), 0.97 (t, J=7.5 Hz, 3H), 0.95 (d, J=6.5 Hz, 3H), 0.94 (d, J=6.5 Hz, 3H);
Optical rotation: [α]$_D$ –38.8 (c 1.04, methanol, 23° C.).

REFERENCE EXAMPLE 3(2)

(3S)-1-butyl-2,5-dioxo-3-cyclohexylmethyl-1,4,9-triazaspiro[5.5]undecane.hydrochloride

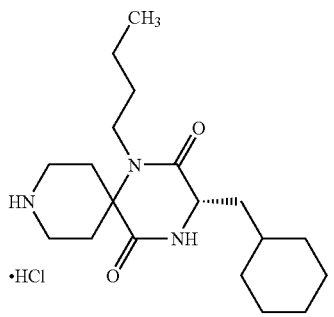

TLC: Rf 0.08 (chloroform:methanol:acetic acid 90:10:1);
NMR (CD₃OD): δ 4.05 (dd, J=7.8, 4.8 Hz, 1H), 3.84–3.68 (m, 2H), 3.46–3.34 (m, 4H), 2.40–2.04 (m, 4H), 1.83–1.46 (m, 10H), 1.39 (sextet, J=7.5 Hz, 2H), 1.05–0.86 (m, 2H), 0.97 (t, J=7.2 Hz, 3H);
Optical rotation: [α]$_D$ –37.5 (c 1.04, methanol, 18° C.).

REFERENCE EXAMPLE 3(3)

(3R)-1-butyl-2,5-dioxo-3-((1R)-1-hydroxy-1-cyclohexyl)-1,4,9-triazaspiro[5.5]undecane.hydrochloride

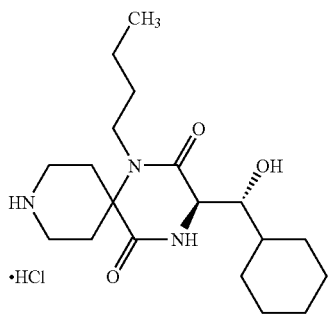

TLC: Rf 0.32 (butanol:acetic acid:water=4:2:1);
NMR (CD₃OD): δ 4.16 (d, J=2.0 Hz, 1H), 3.95 (m, 1H), 3.70 (m, 1H), 3.52 (m, 1H), 3.37 (m, 1H), 3.28 (m, 1H), 3.22–3.13 (m, 2H), 2.46–1.93 (m, 6H), 1.80–1.64 (m, 5H), 1.48–1.15 (m, 6H), 1.02–0.87 (m, 5H);
Optical rotation: [α]$_D$ +1.22 (c 1.04, methanol, 26° C.).

REFERENCE EXAMPLE 3(4)

(3R)-1-butyl-2,5-dioxo-3-((1R)-1-hydroxy-1-(3,4,5,6-tetrahydropyran-4-yl)methyl)-1,4,9-triazaspiro[5.5]undecane.hydrochloride

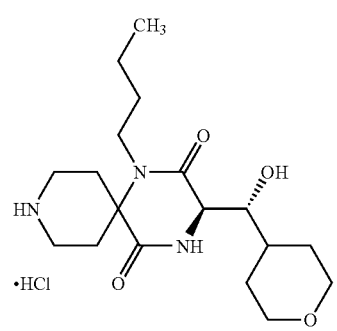

TLC: Rf 0.05 (chloroform:methanol=10:1);
NMR (CD₃OD): δ 4.13 (d, J=2.0 Hz, 1H), 4.01–3.91 (m, 3H), 3.70 (m, 1H), 3.59–3.32 (m, 6H), 3.20 (m, 1H), 2.47–2.19 (m, 3H), 2.11–1.69 (m, 5H), 1.47–1.17 (m, 5H), 0.70 (t, J=7.0 Hz, 3H).

REFERENCE EXAMPLE 3(5)

(3R)-1-butyl-2,5-dioxo-3-((1R)-1-hydroxy-1-cyclopentyl)-1,4,9-triazaspiro[5.5]undecane.hydrochloride

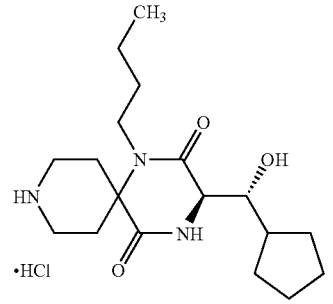

TLC: Rf 0.04 (chloroform:methanol=10:1);
NMR (CD₃OD): δ 4.00 (d, J=2.0 Hz, 1H), 3.95 (m, 1H), 3.70 (m, 1H), 3.53 (m, 1H), 3.40–3.34 (m, 3H), 3.21 (m, 1H), 2.46–2.19 (m, 4H), 2.08 (m, 1H), 1.92–1.83 (m, 2H), 1.70–1.50 (m, 6H), 1.45–1.26 (m, 5H), 0.97 (t, J=7.0 Hz, 3H).

REFERENCE EXAMPLE 3(6)

(3R)-1-propyl-2,5-dioxo-3-((1R)-1-hydroxy-2-methylpropyl)-1,4,9-triazaspiro[5.5]undecane.hydrochloride

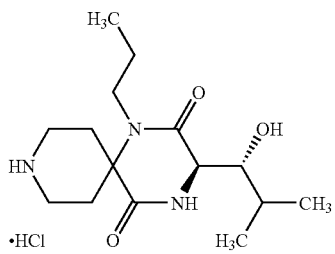

TLC: Rf 0.15 (chloroform:methanol:acetic acid=20:4:1);
NMR (CD$_3$OD): δ 4.15 (d, J=2.1 Hz, 1H), 3.96 (m, 1H), 3.71 (m, 1H), 3.56–3.25 (m, 3H), 3.20 (dd, J=9.6, 2.1 Hz, 1H), 3.13 (m, 1H), 2.51–1.95 (m, 5H), 1.75 (m, 1H), 1.49 (m, 1H), 0.99 (d, J=6.6 Hz, 3H), 0.98 (d, J=6.6 Hz, 3H), 0.95 (t, J=7.5 Hz, 3H).

REFERENCE EXAMPLE 3(7)

(3R)-1-propyl-2,5-dioxo-3-((1R)-1-hydroxy-1-cyclohexyl)-1,4,9-triazaspiro[5.5]undecane.hydrochloride

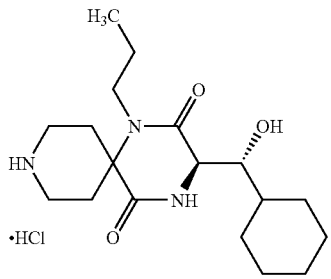

TLC: Rf 0.16 (chloroform:methanol:acetic acid=20:4:1);
NMR (CD$_3$OD): δ 4.16 (d, J=2.1 Hz, 1H), 3.95 (m, 1H), 3.70 (m, 1H), 3.47 (m, 1H), 3.41–3.24 (m, 4H), 3.12 (m, 1H), 2.44 (m, 1H), 2.33 (m, 1H), 2.19 (m, 1H), 2.08 (m, 1H), 2.03–1.89 (m, 2H), 1.84–1.62 (m, 4H), 1.50 (m, 1H), 1.40–1.10 (m, 3H), 1.05–0.80 (m, 2H), 0.95 (t, J=7.5 Hz, 3H);
Optical rotation: [α]$_D$ –2.92 (c 1.06, methanol, 25° C.).

REFERENCE EXAMPLE 3(8)

(3S)-1-butyl-2,5-dioxo-3-((1S)-1-hydroxy-2-methylpropyl)-1,4,9-triazaspiro[5.5]undecane.hydrochloride

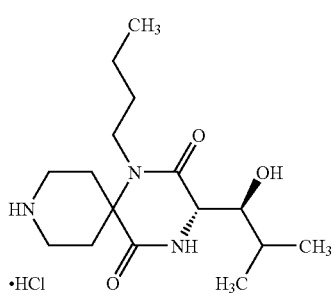

TLC: Rf 0.16 (chloroform:methanol:acetic acid=20:4:1);
NMR (CD$_3$OD): δ 4.15 (d, J=2.1 Hz, 1H), 3.95 (m, 1H), 3.71 (m, 1H), 3.52 (m, 1H), 3.42–3.31 (m, 2H), 3.21 (m, 1H), 3.21 (dd, J=9.6, 2.1 Hz, 1H), 2.48–2.32 (m, 2H), 2.23 (m, 1H), 2.14–1.96 (m, 2H), 1.72 (m, 1H), 1.55–1.33 (m, 3H), 1.02–0.92 (m, 9H);
Optical rotation: [α]$_D$ –13.8 (c 1.00, methanol, 28° C.).

REFERENCE EXAMPLE 3(9)

(3S)-1-butyl-2,5-dioxo-3-((1S)-1-hydroxy-1-cyclohexyl)-1,4,9-triazaspiro[5.5]undecane.hydrochloride

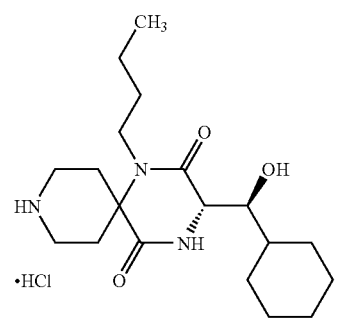

TLC: Rf 0.17 (chloroform:methanol:acetic acid=20:4:1);
NMR (CD$_3$OD): δ 4.16 (d, J=2.1 Hz, 1H), 3.95 (m, 1H), 3.70 (m, 1H), 3.52 (m, 1H), 3.42–3.25 (m, 3H), 3.17 (m, 1H), 2.49–2.38 (m, 2H), 2.21 (m, 1H), 2.14–1.90 (m, 3H), 1.84–1.61 (m, 5H), 1.55–1.13 (m, 6H), 1.04–0.81 (m, 2H), 0.97 (t, J=7.2 Hz, 3H);
Optical rotation: [α]$_D$ –1.29 (c 1.09, methanol, 26° C.).

EXAMPLE 2

(3R)-1-butyl-2,5-dioxo-3-((1R)-1-hydroxy-2-methylpropyl)-9-(6-phenyloxypyridin-3-ylmethyl)-1,4,9-triazaspiro[5.5]undecane.2hydrochloride

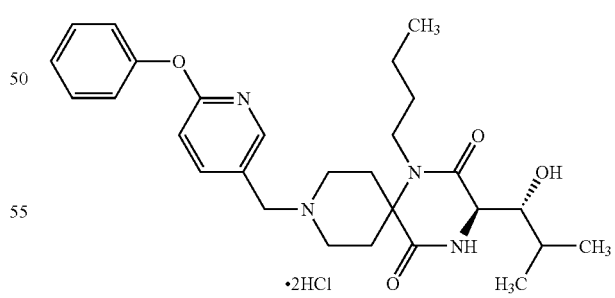

To a solution of the compound prepared in Reference example 3 (120 mg) in dimethylformamide (1 ml) was added acetic acid (59 μl). The reaction mixture was added sodium triacetoxyborohydride (146 mg) and 3-formyl-6-phenyloxypyridine (89 mg). The reaction mixture was stirred overnight at room temperature. The reaction mixture was added methanol and concentrated. The obtained residue was purified by column chromatography on silica gel (ethyl acetate→chloroform:methanol=25:1) and the obtained compound was conversed to hydrochloride salt by using a conventional method to give the title compound (118 mg) having the following physical data.

TLC: Rf 0.48 (chloroform:methanol=10:1);

NMR (CD$_3$OD): δ 8.35 (d, J=2.1 Hz, 1H), 8.12 (dd, J=8.7, 2.1 Hz, 1H), 7.49–7.40 (m, 2H), 7.27 (t, J=7.8 Hz, 1H), 7.15 (d, J=7.8 Hz, 2H), 7.06 (d, J=8.7, 1H), 4.39 (s, 2H), 4.14 (d, J=2.1 Hz, 1H), 4.07–3.93 (m, 1H), 3.82–3.67 (m, 1H), 3.58–3.40 (m, 3H), 3.30–3.15 (m, 1H), 3.19 (dd, J=9.6, 2.1 Hz, 1H), 2.60–2.28 (m, 3H), 2.18–2.05 (m, 1H), 2.05–1.90 (m, 1H), 1.80–1.55 (m, 1H), 1.50–1.25 (m, 3H), 0.99 (d, J=6.6 Hz, 3H), 0.97 (d, J=6.6 Hz, 3H), 0.95 (t, J=7.2 Hz, 3H);

Optical rotation: [α]$_D$ +10.80 (c 1.05, methanol, 24° C.);

HPLC Conditions column: CHIRALCEL OJ-R, 0.46×15 cm, DAICEL, OJROCD-JB026:

flow rate: 0.7 ml/min;

solvent

A solution: 0.1M aqueous solution of potassium dihydrogen phosphate, B solution: acetonitrile (A:B=76:24);

UV: 225 nm;

retention time: 11.53 min.

EXAMPLE 2(1)–2(59)

By the same procedure as described in Example 2 using the corresponding aldehyde derivatives instead of 3-formyl-6-phenyloxypyridine, the following compounds were obtained.

EXAMPLE 2(1)

(3R)-1-butyl-2,5-dioxo-3-((1R)-1-hydroxy-2-methylpropyl)-9-(4-(4-methoxyphenyloxy)phenylmethyl)-1,4,9-triazaspiro[5.5]undecane.hydrochloride

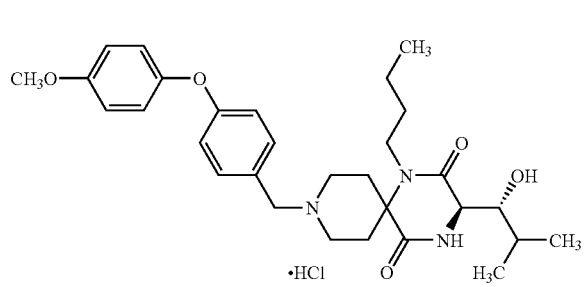

TLC: Rf 0.36 (ethyl acetate:methanol=10:1);

NMR (CD$_3$OD): δ 7.45 (d, J=8.7 Hz, 2H), 7.00–6.96 (m, 6H), 4.27 (s, 2H), 4.14 (d, J=2.1 Hz, 1H), 3.94–3.69 (m, 2H), 3.79 (s, 3H), 3.60–3.05 (m, 5H), 2.50–1.95 (m, 5H), 1.70 (m, 1H), 1.50–1.30 (m, 3H), 1.00–0.93 (m, 9H).

EXAMPLE 2(2)

(3R)-1-butyl-2,5-dioxo-3-((1R)-1-hydroxy-2-methylpropyl)-9-(4-(3-methoxyphenyloxy)phenylmethyl)-1,4,9-triazaspiro[5.5]undecane.hydrochloride

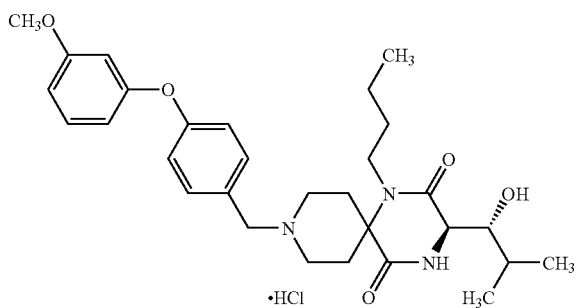

TLC: Rf 0.41 (ethyl acetate:methanol=10:1);

NMR (CD$_3$OD): δ 7.51 (d, J=8.4 Hz, 2H), 7.28 (t, J=8.4 Hz, 1H), 7.08 (d, J=9.0 Hz, 2H), 6.75 (m, 1H), 6.61–6.57 (m, 2H), 4.32 (s, 2H), 4.14 (d J=2.1 Hz, 1H), 3.99–3.73 (m, 2H), 3.77 (s, 3H), 3.60–3.10 (m, 5H), 2.55–1.95 (m, 5H), 1.70 (m, 1H), 1.50–1.30 (m, 3H), 1.00–0.93 (m, 9H).

EXAMPLE 2(3)

(3R)-1-butyl-2,5-dioxo-3-((1R)-1-hydroxy-2-methylpropyl)-9-(4-(4-fluorophenyloxy)phenylmethyl)-1,4,9-triazaspiro[5.5]undecane.hydrochloride

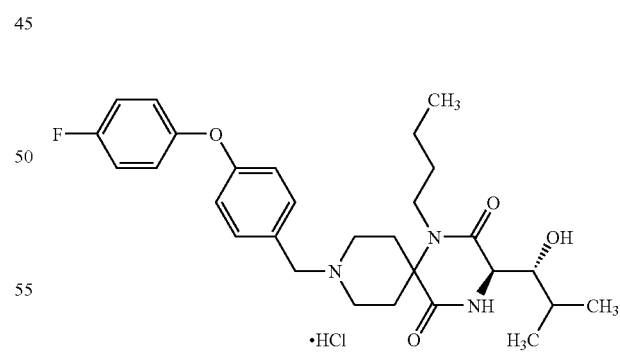

TLC: Rf 0.33 (ethyl acetate:methanol=10:1);

NMR (CD$_3$OD): δ 7.50 (d, J=8.7 Hz, 2H), 7.17–7.03 (m, 6H), 4.30 (s, 2H), 4.14 (d, J=2.1 Hz, 1H), 3.97–3.71 (m, 2H), 3.60–3.10 (m, 5H), 2.55–1.95 (m, 5H), 1.70 (m, 1H), 1.50–1.30 (m, 3H), 1.00–0.93 (m, 9H).

EXAMPLE 2(4)

(3R)-1-butyl-2,5-dioxo-3-((1R)-1-hydroxy-2-methylpropyl)-9-(4-(4-chlorophenyloxy)phenylmethyl)-1,4,9-triazaspiro[5.5]undecane.hydrochloride

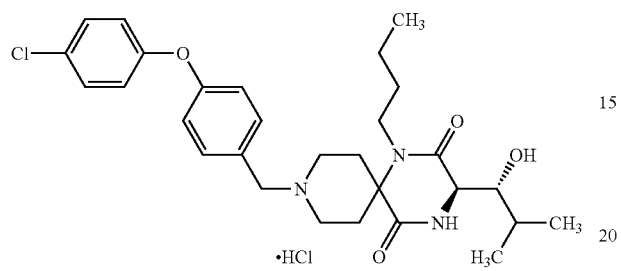

TLC: Rf 0.31 (ethyl acetate:methanol=10:1);
NMR (CD$_3$OD): δ 7.53 (d, J=8.7 Hz, 2H), 7.38 (d, J=9.3 Hz, 2H), 7.09 (d, J=8.7 Hz, 2H), 7.02 (d, J=9.3 Hz, 2H), 4.32 (s, 2H), 4.14 (d, J=1.8 Hz, 1H), 3.98–3.72 (m, 2H), 3.60–3.10 (m, 5H), 2.55–2.00 (m, 5H), 1.70 (m, 1H), 1.50–1.30 (m, 3H), 1.00–0.93 (m, 9H).

EXAMPLE 2(5)

(3R)-1-butyl-2,5-dioxo-3-((1R)-1-hydroxy-2-methylpropyl)-9-(4-(phenylcarbonyl)phenylmethyl)-1,4,9-triazaspiro[5.5]undecane.hydrochloride

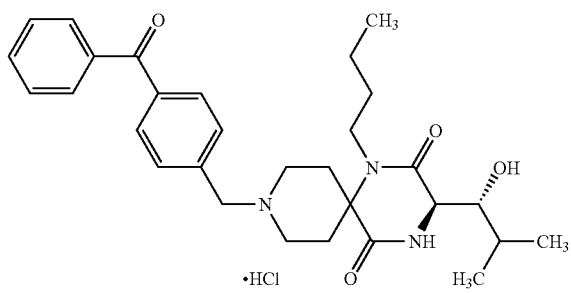

TLC: Rf 0.57 (chloroform:methanol=10:1);
NMR (CD$_3$OD): δ 7.87 (d, J=8.4 Hz, 2H), 7.83–7.72 (m, 4H), 7.67 (m, 1H), 7.59–7.48 (m, 2H), 4.48 (s, 2H), 4.14 (d, J=2.1 Hz, 1H), 4.05 (m, 1H), 3.80 (m, 1H), 3.59–3.37 (m, 3H), 3.20 (m, 1H), 3.19 (dd, J=9.6, 2.1 Hz, 1H), 2.60–2.28 (m, 3H), 2.14 (m, 1H), 2.00 (m, 1H), 1.70 (m, 1H), 1.52–1.23 (m, 3H), 0.99 (d, J=6.6 Hz, 3H), 0.97 (d, J=6.6 Hz, 3H), 0.95 (t, J=7.2 Hz, 3H).

EXAMPLE 2(6)

(3R)-1-butyl-2,5-dioxo-3-((1R)-1-hydroxy-2-methylpropyl)-9-(4-(1-phenyl-1-hydroxymethyl)phenylmethyl)-1,4,9-triazaspiro[5.5]undecane.hydrochloride

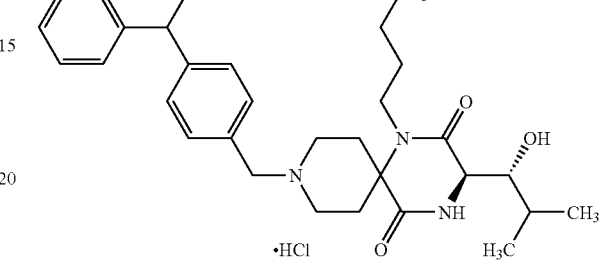

TLC: Rf 0.32 (chloroform:methanol=10:1);
NMR (CD$_3$OD): δ 7.62–7.40 (m, 4H), 7.40–7.18 (m, 5H), 5.81 (s, 1H), 4.32 (s, 2H), 4.13 (d, J=2.1 Hz, 1H), 3.99 (m, 1H), 3.73 (m, 1H), 3.55–3.38 (m, 3H), 3.13 (m, 1H), 3.19 (dd, J=9.6, 2.1 Hz, 1H), 2.52–2.33 (m, 2H), 2.24 (m, 1H), 2.09 (m, 1H), 1.98 (m, 1H), 1.67 (m, 1H), 1.50–1.25 (m, 3H), 0.98 (d, J=6.6 Hz, 3H), 0.96 (d, J=6.6 Hz, 3H), 0.93 (t, J=7.2 Hz, 3H).

EXAMPLE 2(7)

(3R)-1-butyl-2,5-dioxo-3-((1R)-1-hydroxy-2-methylpropyl)-9-(4-(4-(morpholin-4-ylcarbonyl)phenyloxy)phenylmethyl)-1,4,9-triazaspiro[5.5]undecane.hydrochloride

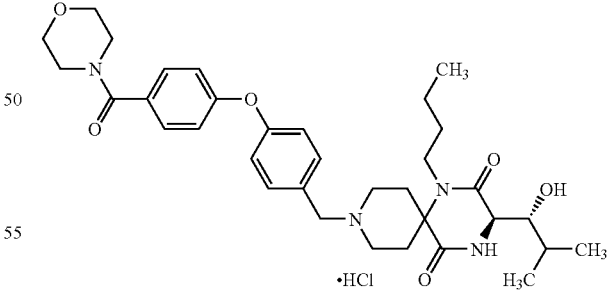

TLC: Rf 0.47 (chloroform:methanol=10:1);
NMR (CD$_3$OD): δ 7.59 (d, J=8.7 Hz, 2H), 7.48 (d, J=8.7 Hz, 2H), 7.14 (d, J=8.7 Hz, 2H), 7.10 (d, J=8.7 Hz, 2H), 4.35 (s, 2H), 4.14 (d, J=1.8 Hz, 1H), 3.99 (m, 1H), 3.85–3.35 (m, 12H), 3.23 (m, 1H), 3.19 (dd, J=9.3, 1.8 Hz, 1H), 2.55–2.41 (m, 2H), 2.32 (m, 1H), 2.12 (m, 1H), 2.01 (m, 1H), 1.68 (m, 1H), 1.50–1.25 (m, 3H), 0.99 (d, J=6.6 Hz, 3H), 0.97 (d, J=6.6 Hz, 3H), 0.95 (t, J=7.2 Hz, 3H).

EXAMPLE 2(8)

(3R)-1-butyl-2,5-dioxo-3-((1R)-1-hydroxy-2-methylpropyl)-9-(4-(6-methylpyridin-3-yloxy)phenylmethyl)-1,4,9-triazaspiro[5.5]undecane.2hydrochloride

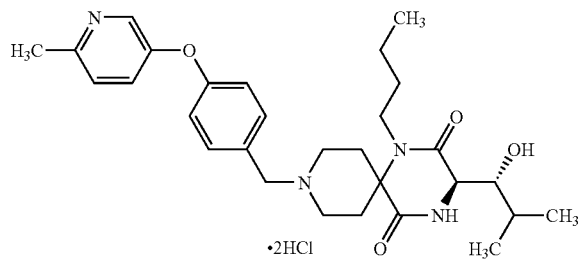

TLC: Rf 0.19 (ethyl acetate:methanol=10:1);

NMR (CD$_3$OD): δ 8.58 (d, J=2.7, 0.6 Hz, 1H), 8.17 (dd, J=9.0, 2.7 Hz, 1H), 7.89 (d, J=9.0 Hz, 1H), 7.74 (d, J=9.0 Hz, 2H), 7.31 (d, J=9.0 Hz, 2H), 4.40 (s, 2H), 4.15 (d, J=2.1 Hz, 1H), 4.02 (m, 1H), 3.78 (m, 1H), 3.60–3.42 (m, 3H), 3.30–3.16 (m, 2H), 2.76 (s, 3H), 2.64–2.32 (m, 3H), 2.18–1.94 (m, 2H), 1.70 (m, 1H), 1.48–1.26 (m, 3H), 1.00 (d, J=6.3 Hz, 3H), 0.98 (d, J=6.3 Hz, 3H), 0.96 (t, J=7.2 Hz, 3H).

EXAMPLE 2(9)

(3R)-1-butyl-2,5-dioxo-3-((1R)-1-hydroxy-2-methylpropyl)-9-(4-(pyridin-1-oxido-3-yloxy)phenylmethyl)-1,4,9-triazaspiro[5.5]undecane.hydrochloride

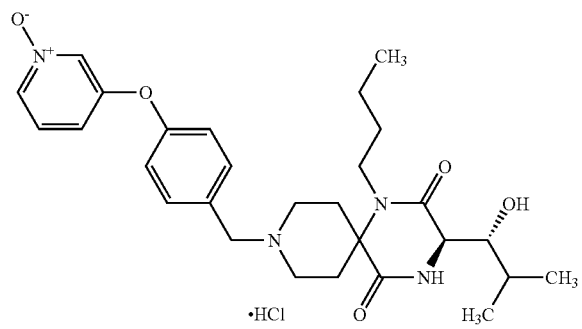

TLC: Rf 0.54 (chloroform:methanol=5:1);

NMR (CD$_3$OD): δ 8.56 (m, 1H), 8.45 (m, 1H), 7.81–7.68 (m, 2H), 7.75 (d, J=8.4 Hz, 2H), 7.33 (d, J=8.4 Hz, 2H), 4.41 (s, 2H), 4.15 (d, J=1.8 Hz, 1H), 4.00 (m, 1H), 3.78 (m, 1H), 3.58–3.42 (m, 3H), 3.28–3.16 (m, 2H), 2.64–2.26 (m, 3H), 2.20–1.92 (m, 2H), 1.68 (m, 1H), 1.52–1.28 (m, 3H), 1.00 (d, J=6.6 Hz, 3H), 0.98 (d, J=6.6 Hz, 3H), 0.96 (t, J=7.2 Hz, 3H).

EXAMPLE 2(10)

(3R)-1-butyl-2,5-dioxo-3-((1R)-1-hydroxy-2-methylpropyl)-9-(4-(4-hydroxypiperidin-1-ylmethyl)phenylmethyl)-1,4,9-triazaspiro[5.5]undecane.2hydrochloride

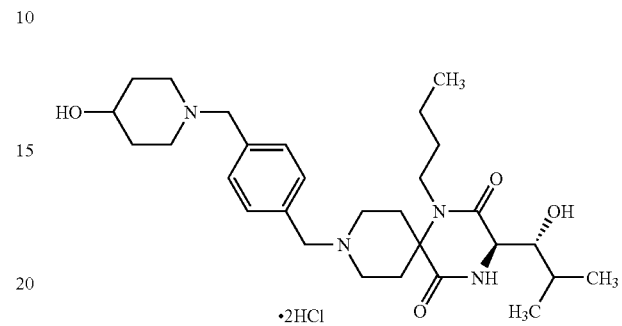

TLC: Rf 0.69 (chloroform:methanol:28% aqueous solution of ammonia=100:10:1);

NMR (CD$_3$OD): δ 7.75 (d, J=8.4 Hz, 2H), 7.67 (d, J=8.4 Hz, 2H), 4.41 (s, 2H), 4.38 (s, 2H), 4.14 (d, J=2.1 Hz, 1H), 4.14–3.94 (m, 2H), 3.78 (m, 1H), 3.58–3.40 (m, 4H), 3.30–3.00 (m, 4H), 2.68–2.36 (m, 3H), 2.20–1.58 (m, 8H), 1.50–1.26 (m, 3H), 0.99 (d, J=6.6 Hz, 3H), 0.98 (d, J=6.6 Hz, 3H), 0.95 (t, J=6.9 Hz, 3H).

EXAMPLE 2(11)

(3R)-1-butyl-2,5-dioxo-3-((1R)-1-hydroxy-2-methylpropyl)-9-(3,5-dimethyl-1-cyclohexylpyrazol-4-ylmethyl)-1,4,9-triazaspiro[5.5]undecane.2hydrochloride

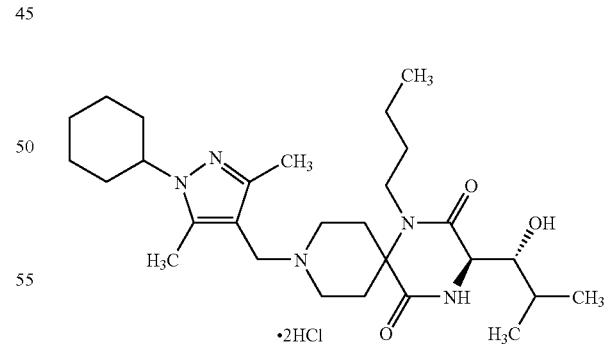

TLC: Rf 0.65 (chloroform:methanol=5:1);

NMR (CD$_3$OD): δ 4.32 (m, 1H), 4.27 (s, 2H), 4.15 (d, J=2.1 Hz, 1H), 4.00 (m, 1H), 3.76 (m, 1H), 3.60–3.42 (m, 3H), 3.36–3.16 (m, 2H), 2.64–2.42 (m, 3H), 2.49 (s, 3H), 2.44 (s, 3H), 2.18–1.22 (m, 16H), 1.00 (d, J=6.6 Hz, 3H), 0.99 (d, J=6.6 Hz, 3H), 0.95 (t, J=7.5 Hz, 3H).

EXAMPLE 2(12)

(3R)-1-butyl-2,5-dioxo-3-((1R)-1-hydroxy-2-methylpropyl)-9-(1,3,5-trimethylpyrazol-4-ylmethyl)-1,4,9-triazaspiro[5.5]undecane.2hydrochloride

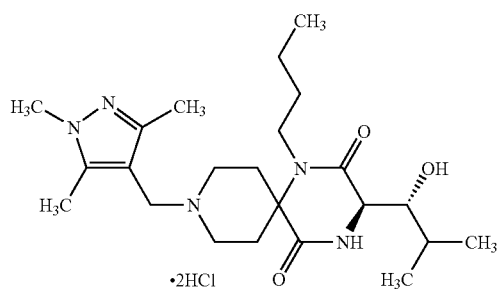

TLC: Rf 0.50 (chloroform:methanol=5:1);
NMR (CD$_3$OD): δ 4.27 (s, 2H), 4.15 (d, J=2.1 Hz, 1H), 4.00 (m, 1H), 3.85 (s, 3H), 3.76 (m, 1H), 3.60–3.44 (m, 3H), 3.28–3.16 (m, 2H), 2.64–2.32 (m, 3H), 2.44 (s, 3H), 2.40 (s, 3H), 2.18–1.92 (m, 2H), 1.70 (m, 1H), 1.48–1.26 (m, 3H), 1.00 (d, J=6.6 Hz, 3H) 0.99 (d, J=6.6 Hz, 3H), 0.95 (t, J=7.5 Hz, 3H).

EXAMPLE 2(13)

(3R)-1-butyl-2,5-dioxo-3-((1R)-1-hydroxy-2-methylpropyl)-9-(4-(4-aminosulfonylphenyloxy)phenylmethyl)-1,4,9-triazaspiro[5.5]undecane.hydrochloride

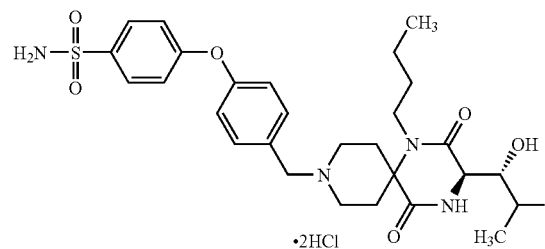

TLC: Rf 0.50 (chloroform:methanol=5:1);
NMR (CD$_3$OD): δ 7.91 (d, J=8.7 Hz, 2H), 7.60 (d, J=8.7 Hz, 2H), 7.19 (d, J=8.7 Hz, 2H), 7.14 (d, J=8.7 Hz, 2H), 4.35 (s, 2H), 4.15 (d, J=2.4 Hz, 1H), 3.98 (m, 1H), 3.72 (m, 1H), 3.58–3.38 (m, 3H), 3.28–3.18 (m, 2H), 2.56–1.92 (m, 5H), 1.70 (m, 1H), 1.54–1.28 (m, 3H), 1.00 (d, J=6.9 Hz, 3H), 0.98 (d, J=6.9 Hz, 3H), 0.96 (t, J=7.5 Hz, 3H).

EXAMPLE 2(14)

(3R)-1-butyl-2,5-dioxo-3-((1R)-1-hydroxy-2-methylpropyl)-9-(4-(4-methylthiophenyloxy)phenylmethyl)-1,4,9-triazaspiro[5.5]undecane.hydrochloride

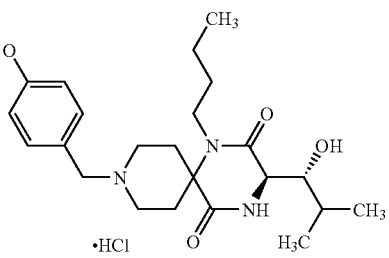

TLC: Rf 0.45 (chloroform:methanol=10:1);
NMR (CD$_3$OD): δ 7.53 (d, J=9.0 Hz, 2H), 7.32 (d, J=9.0 Hz, 2H), 7.05 (d, J=9.0 Hz, 2H), 6.99 (d, J=9.0 Hz, 2H), 4.33 (s, 2H), 4.14 (d, J=2.1 Hz, 1H), 3.98 (m, 1H), 3.72 (m, 1H), 3.58–3.40 (m, 3H), 3.28–3.10 (m, 2H), 2.52–1.92 (m, 5H), 2.47 (s, 3H), 1.70 (m, 1H), 1.50–1.28 (m, 3H), 1.02–0.86 (m, 9H).

EXAMPLE 2(15)

(3R)-1-butyl-2,5-dioxo-3-((1R)-1-hydroxy-2-methylpropyl)-9-(4-(4-methylsulfonylphenyloxy)phenylmethyl)-1,4,9-triazaspiro[5.5]undecane.hydrochloride

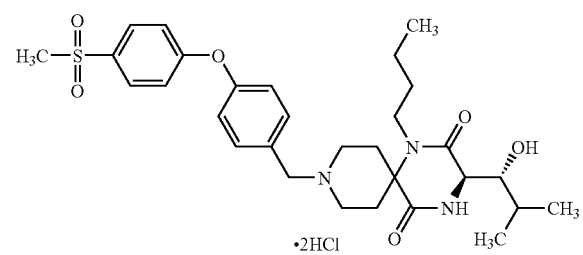

TLC: Rf 0.36 (chloroform:methanol=10:1);
NMR (CD$_3$OD): δ 7.95 (d, J=9.0 Hz, 2H), 7.63 (d, J=8.1 Hz, 2H), 7.24–7.18 (m, 4H), 4.39 (s, 2H), 4.14 (d, J=2.4 Hz, 1H), 4.02 (m, 1H), 3.78 (m, 1H), 3.60–3.46 (m, 3H), 3.28–3.10 (m, 2H), 3.12 (s, 3H), 2.54–1.94 (m, 5H), 1.70 (m, 1H), 1.50–1.30 (m, 3H), 1.02–0.86 (m, 9H).

EXAMPLE 2(16)

(3R)-1-butyl-2,5-dioxo-3-((1R)-1-hydroxy-2-methylpropyl)-9-(4-(4-cyanophenyloxy)phenylmethyl)-1,4,9-triazaspiro[5.5]undecane.hydrochloride

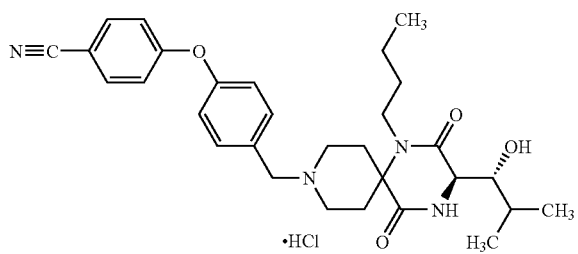

TLC: Rf 0.36 (chloroform:methanol=10:1);

NMR (CD$_3$OD): δ 7.73 (d, J=8.7 Hz, 2H), 7.64 (d, J=9.0 Hz, 2H), 7.21 (d, J=9.0 Hz, 2H), 7.14 (d, J=8.7 Hz, 2H), 4.38 (s, 2H), 4.14 (d, J=2.1 Hz, 1H), 4.02 (m, 1H), 3.76 (m, 1H), 3.60–3.40 (m, 3H), 3.28–3.14 (m, 2H), 2.54–2.26 (m, 3H), 2.20–1.90 (m, 2H), 1.66 (m, 1H), 1.50–1.28 (m, 3H), 1.02–0.84 (m, 9H).

EXAMPLE 2(17)

(3R)-1-butyl-2,5-dioxo-3-((1R)-1-hydroxy-2-methylpropyl)-9-(4-(phenylthio)phenylmethyl)-1,4,9-triazaspiro[5.5]undecane.hydrochloride

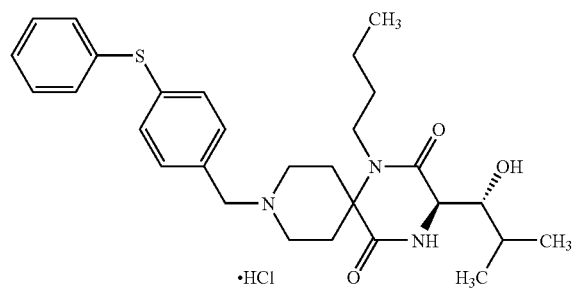

TLC: Rf 0.36 (chloroform:methanol=10:1);

NMR (CD$_3$OD): δ 7.50–7.34 (m, 7H), 7.30 (d, J=8.4 Hz, 2H), 4.31 (s, 2H), 4.13 (d, J=2.1 Hz, 1H), 3.98 (m, 1H), 3.72 (m, 1H), 3.56–3.36 (m, 3H), 3.24–3.08 (m, 2H), 2.50–2.18 (m, 3H), 2.18–1.94 (m, 2H), 1.68 (m, 1H), 1.50–1.28 (m, 3H), 1.10–0.88 (m, 9H).

EXAMPLE 2(18)

(3R)-1-butyl-2,5-dioxo-3-((1R)-1-hydroxy-2-methylpropyl)-9-(3,5-dimethyl-1-(4-hydroxyphenyl)pyrazol-4-ylmethyl)-1,4,9-triazaspiro[5.5]undecane.2hydrochloride

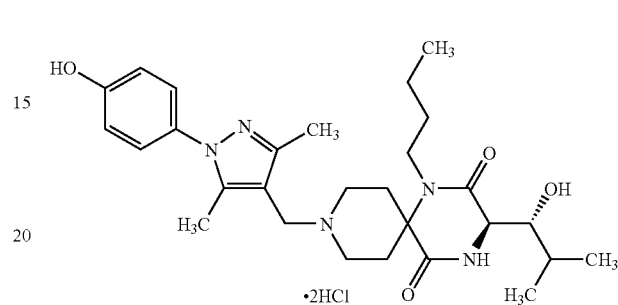

TLC: Rf 0.70 (chloroform:methanol=5:1);

NMR (CD$_3$OD): δ 7.31 (d, J=8.7 Hz, 2H), 6.94 (d, J=8.7 Hz, 2H), 4.32 (s, 2H), 4.15 (d, J=2.1 Hz, 1H), 4.04 (m, 1H), 3.80 (m, 1H), 3.64–3.48 (m, 3H), 3.38–3.18 (m, 2H), 2.70–2.30 (m, 3H), 2.44 (s, 3H), 2.36 (s, 3H), 2.20–1.94 (m, 2H), 1.68 (m, 1H), 1.50–1.26 (m, 3H), 1.02–0.84 (m, 9H).

EXAMPLE 2(19)

(3R)-1-butyl-2,5-dioxo-3-((1R)-1-hydroxy-2-methylpropyl)-9-(3,5-dimethyl-1-(4-methylsulfonylaminophenyl)pyrazol-4-ylmethyl)-1,4,9-triazaspiro[5.5]undecane.2hydrochloride

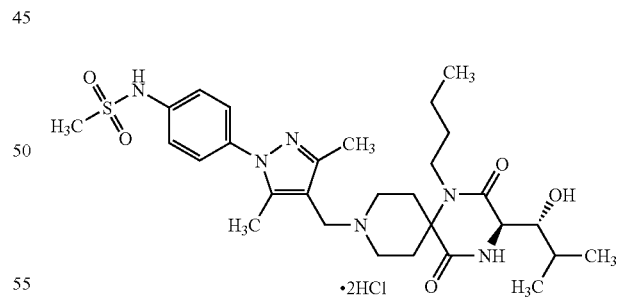

TLC: Rf 0.72 (chloroform:methanol=10:1);

NMR (CD$_3$OD): δ 7.47 (d, J=9.0 Hz, 2H), 7.41 (d, J=9.0 Hz, 2H), 4.31 (s, 2H), 4.15 (d, J=1.8 Hz, 1H), 4.02 (m, 1H), 3.78 (m, 1H), 3.62–3.48 (m, 3H), 3.38–3.18 (m, 2H), 3.04 (s, 3H), 2.68–2.36 (m, 3H), 2.41 (s, 3H), 2.39 (s, 3H), 2.20–1.96 (m, 2H), 1.68 (m, 1H), 1.50–1.30 (m, 3H), 1.02–0.88 (m, 9H).

EXAMPLE 2(20)

(3R)-1-butyl-2,5-dioxo-3-((1R)-1-hydroxy-2-methylpropyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane.3hydrochloride

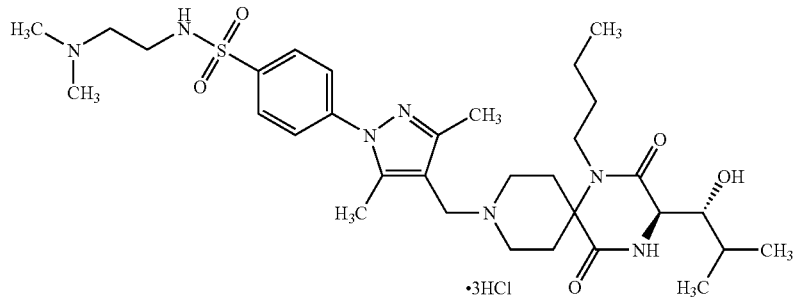

TLC: Rf 0.12 (chloroform:methanol=5:1);
NMR (CD₃OD): δ 8.07 (d, J=9.0 Hz, 2H), 7.78 (d, J=9.0 Hz, 2H), 4.30 (s, 2H), 4.15 (d, J=2.1 Hz, 1H), 4.02 (m, 1H), 3.76 (m, 1H), 3.62–3.48 (m, 3H), 3.40–3.18 (m, 6H), 2.95 (s, 6H), 2.64 (m, 1H), 2.49 (s, 3H), 2.42–2.36 (m, 2H), 2.41 (s, 3H), 2.18–1.96 (m, 2H), 1.68 (m, 1H), 1.50–1.32 (m, 3H), 1.08–0.90 (m, 9H).

EXAMPLE 2(21)

(3R)-1-butyl-2,5-dioxo-3-((1R)-1-hydroxy-2-methylpropyl)-9-(3,5-dimethyl-1-(4-(pyrrolidin-1-ylsulfonyl)phenyl)pyrazol-4-ylmethyl)-1,4,9-triazaspiro[5.5]undecane.2hydrochloride

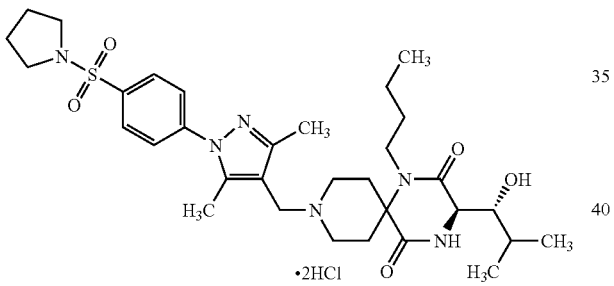

TLC: Rf 0.36 (chloroform:methanol=10:1);
NMR (CD₃OD): δ 8.01 (d, J=8.7 Hz, 2H), 7.77 (d, J=8.7 Hz, 2H), 4.31 (s, 2H), 4.15 (d, J=1.8 Hz, 1H), 4.04 (m, 1H), 3.78 (m, 1H), 3.62–3.48 (m, 3H), 3.40–3.18 (m, 6H), 2.66 (m, 1H), 2.54–2.38 (m, 2H), 2.49 (s, 3H), 2.42 (s, 3H), 2.20–1.94 (m, 2H), 1.82–1.62 (m, 5H), 1.50–1.30 (m, 3H), 1.02–0.88 (m, 9H).

EXAMPLE 2(22)

(3R)-1-butyl-2,5-dioxo-3-((1R)-1-hydroxy-2-methylpropyl)-9-(4-(6-methylpyridin-1-oxido-3-yloxy)phenylmethyl)-1,4,9-triazaspiro[5.5]undecane.hydrochloride

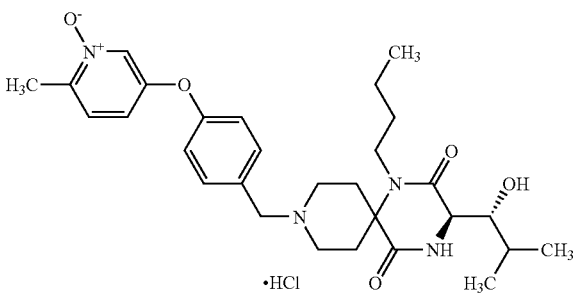

TLC: Rf 0.26 (chloroform:methanol=10:1);
NMR (CD₃OD): δ 8.58 (m, 1H), 7.81–7.71 (m, 2H), 7.73 (d, J=8.4 Hz, 2H), 7.30 (d, J=8.4 Hz, 2H), 4.40 (s, 2H), 4.15 (d, J=2.1 Hz, 1H), 4.00 (m, 1H), 3.78 (m, 1H), 3.62–3.40 (m, 3H), 3.30–3.16 (m, 2H), 2.66–2.38 (m, 3H), 2.66 (s, 3H), 2.18–1.94 (m, 2H), 1.70 (m, 1H), 1.50–1.28 (m, 3H), 1.00 (d, J=6.6 Hz, 3H), 0.98 (d, J=6.6 Hz, 3H), 0.96 (t, J=6.9 Hz, 3H).

EXAMPLE 2(23)

(3R)-1-butyl-2,5-dioxo-3-((1R)-1-hydroxy-2-methylpropyl)-9-(4-(4-hydroxyphenyloxy)phenylmethyl)-1,4,9-triazaspiro[5.5]undecane.hydrochloride

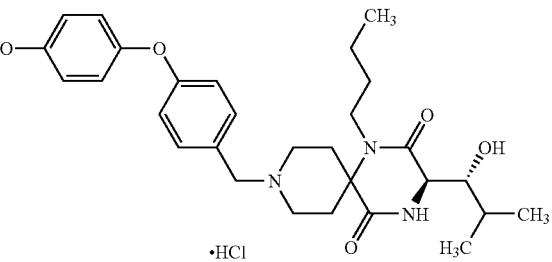

TLC: Rf 0.48 (ethyl acetate:methanol=10:1);
NMR (CD₃OD): δ 7.46 (d, J=8.7 Hz, 2H), 6.97 (d, J=8.7 Hz, 2H), 6.88 (d, J=9.0 Hz, 2H), 6.80 (d, J=9.0 Hz, 2H), 4.30 (s, 2H), 4.13 (d, J=2.0 Hz, 1H), 3.98 (m 1H), 3.72 (m, 1H), 3.53–3.42 (m, 3H), 3.23–3.11 (m, 2H), 2.50–1.97 (m, 6H), 1.70 (m, 1H), 1.39–1.30 (m, 3H), 0.98 (d, J=6.5 Hz, 3H), 0.96 (d, J=6.5 Hz, 3H), 0.95 (t, J=7.0 Hz, 3H).

EXAMPLE 2(24)

(3R)-1-butyl-2,5-dioxo-3-((1R)-1-hydroxy-2-methylpropyl)-9-(6-(4-methoxyphenyloxy)pyridin-3-ylmethyl)-1,4,9-triazaspiro[5.5]undecane.2hydrochloride

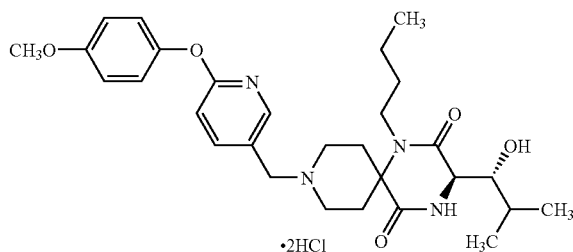

TLC: Rf 0.42 (chloroform:methanol=10:1);
NMR (CD$_3$OD): δ 8.41 (m, 1H), 8.18 (m, 1H), 7.13–6.99 (m, 5H), 4.40 (s, 2H), 4.13 (d, J=2.0 Hz, 1H), 4.00 (m, 1H), 3.82 (s, 3H), 3.75 (m, 1H), 3.53–3.45 (m, 3H), 3.24 (m, 1H), 3.19 (dd, J=9.5, 2.0 Hz, 1H), 2.59–2.39 (m, 3H), 2.15–1.95 (m, 2H), 1.70 (m, 1H), 1.40–1.31 (m, 3H), 0.98 (d, J=6.5 Hz, 3H), 0.97 (d, J=6.5 Hz, 3H), 0.94 (t, J=7.5 Hz, 3H).

EXAMPLE 2(25)

(3R)-1-butyl-2,5-dioxo-3-((1R)-1-hydroxy-2-methylpropyl)-9-(3,5-dimethyl-1-(4-(methylaminosulfonyl)phenyl)pyrazol-4-ylmethyl)-1,4,9-triazaspiro[5.5]undecane.2hydrochloride

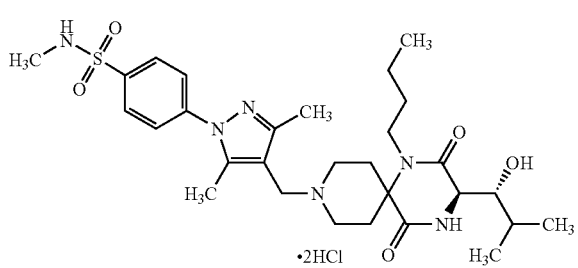

TLC: Rf 0.29 (ethyl acetate:methanol=4:1);
NMR (CD$_3$OD): δ 8.00 (d, J=9.0 Hz, 2H), 7.73 (d, J=9.0 Hz, 2H), 4.32 (s, 2H), 4.16 (d, J=2.0 Hz, 1H), 4.05 (m, 1H), 3.79 (m, 1H), 3.64–3.50 (m, 3H), 3.29–3.19 (m, 2H), 2.59–2.35 (m, 3H), 2.58 (s, 3H), 2.47 (s, 3H), 2.40 (s, 3H), 2.15 (m, 1H), 2.02 (m, 1H), 1.72 (m, 1H), 1.41–1.35 (m, 3H), 0.99 (d, J=6.5 Hz, 3H), 0.98 (d, J=6.5 Hz, 3H), 0.96 (t, J=7.5 Hz, 3H).

EXAMPLE 2(26)

(3R)-1-butyl-2,5-dioxo-3-((1R)-1-hydroxy-2-methylpropyl)-9-(3,5-dimethyl-1-(4-(N-methyl-N-(2-hydroxyethyl)aminosulfonyl)phenyl)pyrazol-4-ylmethyl)-1,4,9-triazaspiro[5.5]undecane.2hydrochloride

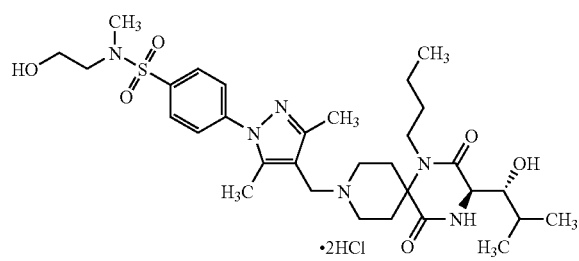

TLC: Rf 0.21 (ethyl acetate:methanol=4:1);
NMR (CD$_3$OD): δ 7.98 (d, J=8.5 Hz, 2H), 7.75 (d, J=8.5 Hz, 2H), 4.31 (s, 2H), 4.15 (d, J=2.0 Hz, 1H), 4.04 (m, 1H), 3.79 (m, 1H), 3.69 (t, J=6.0 Hz, 2H), 3.61–3.51 (m, 3H), 3.23–3.17 (m, 4H), 2.87 (s, 3H), 2.58–2.44 (m, 3H), 2.48 (s, 3H), 2.40 (s, 3H), 2.15 (m, 1H), 2.02 (m, 1H), 1.71 (m, 1H), 1.41–1.35 (m, 3H), 0.99 (d, J=6.5 Hz, 3H), 0.98 (d, J=6.5 Hz, 3H), 0.95 (t, J=7.0 Hz, 3H).

EXAMPLE 2(27)

(3R)-1-butyl-2,5-dioxo-3-((1R)-1-hydroxy-2-methylpropyl)-9-(3,5-dimethyl-1-(4-(2-hydroxyethylaminosulfonyl)phenyl)pyrazol-4-ylmethyl)-1,4,9-triazaspiro[5.5]undecane.2hydrochloride TLC: Rf 0.20 (ethyl acetate:methanol=4:1);
NMR (CD$_3$OD): δ 8.03 (d, J=8.7 Hz, 2H), 7.72 (d, J=8.7 Hz, 2H), 4.31 (s, 2H), 4.15 (d, J=2.0 Hz, 1H), 4.04 (m, 1H), 3.79 (m, 1H), 3.63–3.51 (m, 3H), 3.56 (t, J=6.0 Hz, 2H), 3.34–3.29 (m, 1H), 3.20 (dd, J=9.5, 2.0 Hz, 1H), 3.01 (t, J=6.0 Hz, 2H), 2.59–2.43 (m, 3H), 2.47 (s, 3H), 2.40 (s, 3H), 2.15 (m, 1H), 2.02 (m, 1H), 1.71 (m, 1H), 1.41–1.35 (m, 3H), 0.99 (d, J=6.5 Hz, 3H), 0.98 (d, J=6.5 Hz, 3H), 0.95 (t, J=7.2 Hz, 3H).

EXAMPLE 2(28)

(3R)-1-butyl-2,5-dioxo-3-((1R)-1-hydroxy-2-methylpropyl)-9-(3,5-dimethyl-1-(4-(N,N-dimethylaminocarbonyl)phenyl)pyrazol-4-ylmethyl)-1,4,9-triazaspiro[5.5]undecane.2hydrochloride

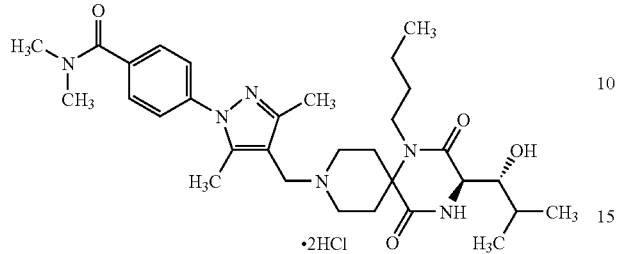

TLC: Rf 0.35 (ethyl acetate:methanol=2:1);

NMR (CD$_3$OD): δ 7.62 (d, J=9.0 Hz, 2H), 7.58 (d, J=9.0 Hz, 2H), 4.32 (s, 2H), 4.16 (d, J=2.0 Hz, 1H), 4.05 (m, 1H), 3.79 (m, 1H), 3.61–3.49 (m, 3H), 3.34–3.29 (m, 1H), 3.20 (dd, J=9.5, 2.0 Hz, 1H), 3.13 (s, 3H), 3.04 (s, 3H), 2.55–2.34 (m, 3H), 2.42 (s, 3H), 2.39 (s, 3H), 2.18 (m, 1H), 2.02 (m, 1H), 1.73 (m, 1H), 1.41–1.34 (m, 3H), 0.99 (d, J=6.5 Hz, 3H), 0.98 (d, J=6.5 Hz, 3H), 0.96 (t, J=7.0 Hz, 3H).

EXAMPLE 2(29)

(3R)-1-butyl-2,5-dioxo-3-((1R)-1-hydroxy-2-methylpropyl)-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride

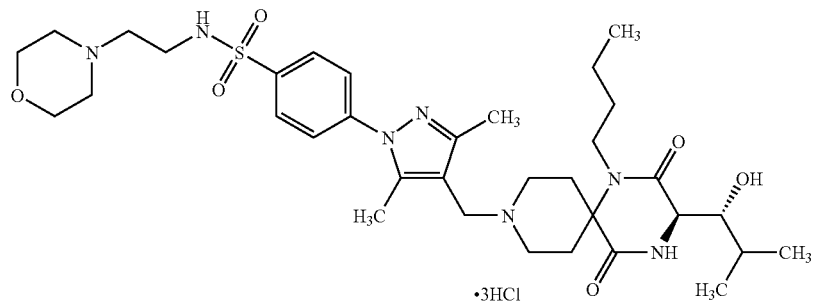

TLC: Rf 0.33 (ethyl acetate:methanol=2:1);

NMR (CD$_3$OD): δ 8.06 (d, J=8.7 Hz, 2H), 7.77 (d, J=8.7 Hz, 2H), 4.31 (s, 2H), 4.15 (d, J=2.0 Hz, 1H), 4.10–4.01 (m, 3H), 3.88–3.76 (m, 3H), 3.61–3.53 (m, 5H), 3.37–3.19 (m, 8H), 2.59–2.37 (m, 3H), 2.48 (s, 3H), 2.40 (s, 3H), 2.15 (m, 1H), 2.02 (m, 1H), 1.71 (m, 1H), 1.40–1.35 (m, 3H), 0.99 (d, J=6.5 Hz, 3H), 0.98 (d, J=6.5 Hz, 3H), 0.95 (t, J=7.0 Hz, 3H).

EXAMPLE 2(30)

(3R)-1-butyl-2,5-dioxo-3-((1R)-1-hydroxy-2-methylpropyl)-9-(3,5-dimethyl-1-(4-(pyrrolidin-1-ylcarbonyl)phenyl)pyrazol-4-ylmethyl)-1,4,9-triazaspiro[5.5]undecane.2hydrochloride

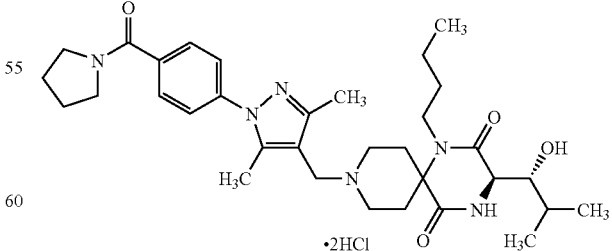

TLC: Rf 0.41 (chloroform:methanol=10:1);

NMR (CD$_3$OD): δ 7.72 (d, J=8.7 Hz, 2H), 7.59 (d, J=8.7 Hz, 2H), 4.31 (s, 2H), 4.15 (d, J=2.1 Hz, 1H), 4.05 (m, 1H), 3.79 (m, 1H), 3.66–3.46 (m, 7H), 3.25 (m, 1H), 3.21 (dd,

J=9.6, 2.1 Hz, 1H), 2.65–2.35 (m, 3H), 2.43 (s, 3H), 2.40 (s, 3H), 2.16 (m, 1H), 2.09–1.87 (m, 5H), 1.70 (m, 1H), 1.53–1.30 (m, 3H), 1.00 (d, J=6.6 Hz, 3H), 0.98 (d, J=6.6 Hz, 3H), 0.95 (t, J=7.2 Hz, 3H).

EXAMPLE 2(31)

(3R)-1-butyl-2,5-dioxo-3-((1R)-1-hydroxy-2-methylpropyl)-9-(4-(4-methylsulfinylphenyloxy)phenylmethyl)-1,4,9-triazaspiro[5.5]undecane.hydrochloride

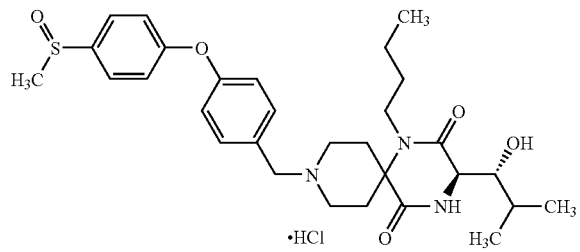

TLC: Rf 0.39 (chloroform:methanol=10:1);

NMR (CD$_3$OD): δ 7.74 (d, J=8.7 Hz, 2H), 7.60 (d, J=8.7 Hz, 2H), 7.22 (d, J=8.7 Hz, 2H), 7.17 (d, J=8.7 Hz, 2H), 4.37 (s, 2H), 4.14 (d, J=2.4 Hz, 1H), 4.02 (m, 1H), 3.76 (m, 1H), 3.58–3.42 (m, 3H), 3.25–3.14 (m, 2H), 2.80 (s, 3H), 2.55–2.38 (m, 2H), 2.29 (m, 1H), 2.15 (m, 1H), 2.01 (m, 1H), 1.70 (m, 1H), 1.50–1.27 (m, 3H), 1.04–0.90 (m, 9H).

EXAMPLE 2(32)

(3R)-1-butyl-2,5-dioxo-3-((1R)-1-hydroxy-2-methylpropyl)-9-(3,5-dimethyl-1-(4-(N,N-dimethylaminosulfonyl)phenyl)pyrazol-4-ylmethyl)-1,4,9-triazaspiro[5.5]undecane.2hydrochloride

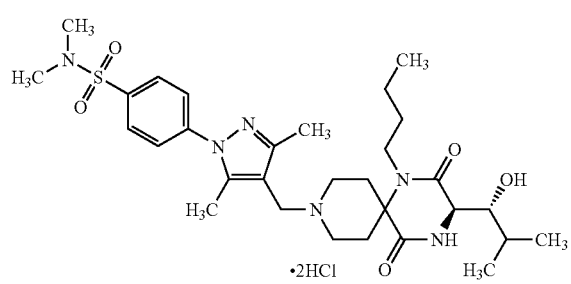

TLC: Rf 0.31 (chloroform:methanol=10:1);

NMR (CD$_3$OD): δ 7.96 (d, J=8.7 Hz, 2H), 7.77 (d, J=8.7 Hz, 2H), 4.32 (s, 2H), 4.15 (d, J=2.4 Hz, 1H), 4.06 (m, 1H), 3.79 (m, 1H), 3.64–3.46 (m, 3H), 3.29–3.14 (m, 2H), 2.73 (s, 6H), 2.59–2.44 (m, 2H), 2.47 (s, 3H), 2.39 (s, 3H), 2.35 (m, 1H), 2.17 (m, 1H), 2.02 (m, 1H), 1.71 (m, 1H), 1.51–1.26 (m, 3H), 1.05–0.89 (m, 9H).

EXAMPLE 2(33)

(3R)-1-butyl-2,5-dioxo-3-((1R)-1-hydroxy-2-methylpropyl)-9-(3,5-dimethyl-1-(4-(morpholin-4-ylsulfonyl)phenyl)pyrazol-4-ylmethyl)-1,4,9-triazaspiro[5.5]undecane.2hydrochloride

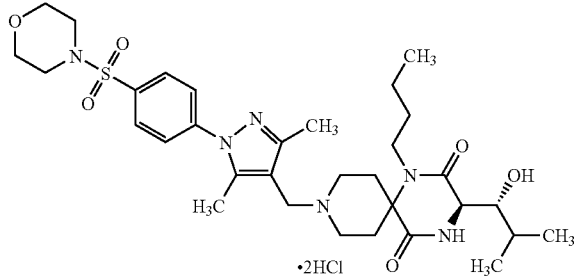

TLC: Rf 0.25 (chloroform:methanol=10:1);

NMR (CD$_3$OD): δ 7.95 (d, J=8.7 Hz, 2H), 7.78 (d, J=8.7 Hz, 2H), 4.32 (s, 2H), 4.15 (d, J=2.1 Hz, 1H), 4.06 (m, 1H), 3.80 (m, 1H), 3.74–3.68 (m, 4H), 3.64–3.48 (m, 3H), 3.28–3.14 (m, 2H), 3.05–2.98 (m, 4H), 2.59–2.44 (m, 2H), 2.47 (s, 3H), 2.39 (s, 3H), 2.35 (m, 1H), 2.17 (m, 1H), 2.02 (m, 1H), 1.71 (m, 1H), 1.52–1.30 (m, 3H), 1.05–0.90 (m, 9H).

EXAMPLE 2(34)

(3R)-1-butyl-2,5-dioxo-3-((1R)-1-hydroxy-2-methylpropyl)-9-(4-(4-aminocarbonylphenyloxy)phenylmethyl)-1,4,9-triazaspiro[5.5]undecane.hydrochloride TLC: Rf 0.22 (chloroform:methanol=10:1);

NMR (CD$_3$OD): δ 7.92 (d, J=8.7 Hz, 2H), 7.62 (d, J=8.7 Hz, 2H), 7.16 (d, J=8.7 Hz, 2H), 7.09 (d, J=8.7 Hz, 2H), 4.37 (s, 2H), 4.15 (d, J=2.1 Hz, 1H), 4.00 (m, 1H), 3.78 (m, 1H), 3.60–3.38 (m, 3H), 3.28–3.10 (m, 2H), 2.60–2.26 (m, 3H), 2.20–1.88 (m, 2H), 1.68 (m, 1H), 1.54–1.22 (m, 3H), 1.00 (d, J=6.6 Hz, 3H), 0.98 (d, J=6.6 Hz, 3H), 0.96 (t, J=7.5 Hz, 3H).

EXAMPLE 2(35)

(3R)-1-butyl-2,5-dioxo-3-((1R)-1-hydroxy-2-methylpropyl)-9-(4-(4-methylaminocarbonylphenyloxy)phenylmethyl)-1,4,9-triazaspiro[5.5]undecane.hydrochloride

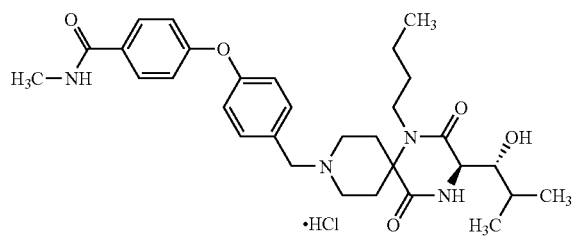

TLC: Rf 0.24 (chloroform:methanol=10:1);
NMR (CD$_3$OD): δ 7.85 (d, J=8.7 Hz, 2H), 7.62 (d, J=8.7 Hz, 2H), 7.15 (d, J=8.7 Hz, 2H), 7.08 (d, J=8.7 Hz, 2H), 4.37 (s, 2H), 4.15 (d, J=2.1 Hz, 1H), 4.00 (m, 1H), 3.76 (m, 1H), 3.56–3.42 (m, 3H), 3.26–3.18 (m, 2H), 2.92 (s, 3H), 2.60–2.28 (m, 3H), 2.18–1.94 (m, 2H), 1.70 (m, 1H), 1.50–1.30 (m, 3H), 1.00 (d, J=6.6 Hz, 3H), 0.98 (d, J=6.6 Hz, 3H), 0.96 (t, J=7.5 Hz, 3H).

EXAMPLE 2(36)

(3R)-1-butyl-2,5-dioxo-3-((1R)-1-hydroxy-2-methylpropyl)-9-(3,5-dimethyl-1-(4-methylphenyl)pyrazol-4-ylmethyl)-1,4,9-triazaspiro[5.5]undecane.2hydrochloride

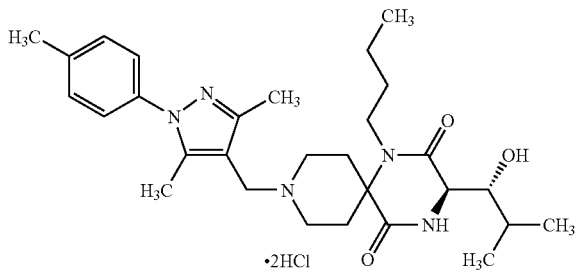

TLC: Rf 0.46 (chloroform:methanol=10:1);
NMR (CD$_3$OD): δ 7.41 (s, 4H), 4.34 (s, 2H), 4.15 (d, J=2.1 Hz, 1H), 4.04 (m, 1H), 3.79 (m, 1H), 3.65–3.50 (m, 3H), 3.34 (m, 1H), 3.21 (dd, J=9.6, 2.1 Hz, 1H), 2.66 (m, 1H), 2.55–2.42 (m, 2H), 2.47 (s, 3H), 2.45 (s, 3H), 2.40 (s, 3H), 2.14 (m, 1H), 2.01 (m, 1H), 1.69 (m, 1H), 1.52–1.30 (m, 3H), 1.00 (d, J=6.6 Hz, 3H), 0.98 (d, J=6.6 Hz, 3H), 0.95 (t, J=7.2 Hz, 3H).

EXAMPLE 2(37)

(3R)-1-butyl-2,5-dioxo-3-((1R)-1-hydroxy-2-methylpropyl)-9-(3,5-dimethyl-1-(4-(N,N-diethylaminosulfonyl)phenyl)pyrazol-4-ylmethyl)-1,4,9-triazaspiro[5.5]undecane.2hydrochloride

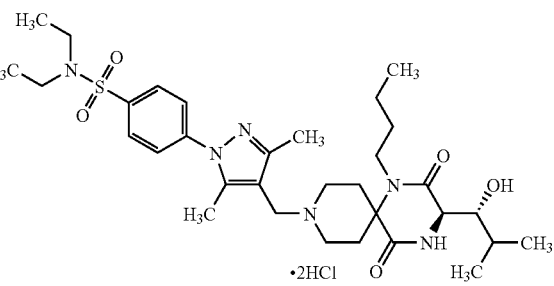

TLC: Rf 0.35 (chloroform:methanol=9:1);
NMR (CD$_3$OD): δ 7.99 (d, J=8.7 Hz, 2H), 7.72 (d, J=8.7 Hz, 2H), 4.32 (s, 2H), 4.16 (d, J=2.1 Hz, 1H), 4.06 (m, 1H), 3.80 (m, 1H), 3.63–3.48 (m, 3H), 3.32–3.17 (m, 2H), 3.29 (q, J=7.2 Hz, 4H), 2.54–2.13 (m, 4H), 2.45 (s, 3H), 2.39 (s, 3H), 2.02 (m, 1H), 1.72 (m, 1H), 1.52–1.33 (m, 3H), 1.15 (t, J=7.2 Hz, 6H), 1.00 (d, J=6.6 Hz, 3H), 0.98 (d, J=6.6 Hz, 3H), 0.96 (t, J=6.9 Hz, 3H).

EXAMPLE 2(38)

(3R)-1-butyl-2,5-dioxo-3-((1R)-1-hydroxy-2-methylpropyl)-9-(3,5-dimethyl-1-(4-(4-methylpiperazin-1-ylsulfonyl)phenyl)pyrazol-4-ylmethyl)-1,4,9-triazaspiro[5.5]undecane.3hydrochloride

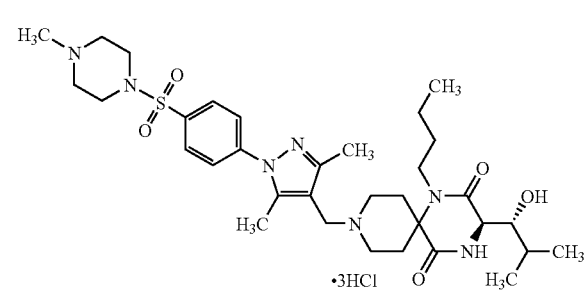

TLC: Rf 0.22 (chloroform:methanol=10:1);
NMR (CD$_3$OD): δ 8.01 (d, J=8.7 Hz, 2H), 7.82 (d, J=8.7 Hz, 2H), 4.31 (s, 2H), 4.15 (d, J=1.8 Hz, 1H), 4.11–3.94 (m, 3H), 3.80 (m, 1H), 3.65–3.48 (m, 5H), 3.34–3.18 (m, 4H), 2.91 (s, 3H), 2.86–2.70 (m, 2H), 2.68–2.36 (m, 3H), 2.49 (s, 3H), 2.40 (s, 3H), 2.15 (m, 1H), 2.02 (m, 1H), 1.70 (m, 1H), 1.50–1.27 (m, 3H), 1.05–0.90 (m, 9H).

EXAMPLE 2(39)

(3R)-1-butyl-2,5-dioxo-3-((1R)-1-hydroxy-2-methylpropyl)-9-(5-chloro-3-methyl-1-phenylpyrazol-4-ylmethyl)-1,4,9-triazaspiro[5.5]undecane.2hydrochloride

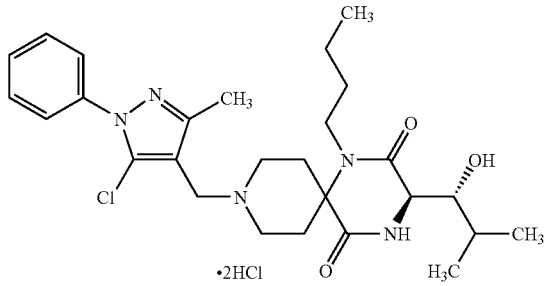

TLC: Rf 0.53(chloroform:methanol=10:1);
NMR (CD$_3$OD): δ 7.63–7.48 (m, 5H), 4.33 (s, 2H), 4.14 (d, J=1.8 Hz, 1H), 4.10 (m, 1H), 3.83 (m, 1H), 3.66–3.45 (m, 3H), 3.29–3.16 (m, 2H), 2.62–2.32 (m, 3H), 2.44 (s, 3H), 2.17 (m, 1H), 2.01 (m, 1H), 1.71 (m, 1H), 1.52–1.11 (m, 3H), 1.05–0.88 (m, 9H).

EXAMPLE 2(40)

(3R)-1-butyl-2,5-dioxo-3-((1R)-1-hydroxy-2-methylpropyl)-9-(3,5-dimethyl-1-(4-(morpholin-4-ylcarbonyl)phenyl)pyrazol-4-ylmethyl)-1,4,9-triazaspiro[5.5]undecane.2hydrochloride

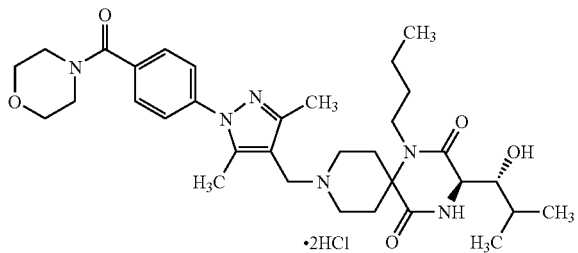

TLC: Rf 0.39 (chloroform:methanol=10:1);
NMR (CD$_3$OD): δ 7.66–7.57 (m, 4H), 4.31 (s, 2H), 4.15 (d, J=2.1 Hz, 1H), 4.05 (m, 1H), 3.88–3.39 (m, 12H), 3.25 (m, 1H), 3.20 (dd, J=9.6, 2.1 Hz, 1H), 2.65–2.27 (m, 3H), 2.43 (s, 3H), 2.40 (s, 3H), 2.17 (m, 1H), 2.02 (m, 1H), 1.71 (m, 1H), 1.54–1.27 (m, 3H), 1.00 (d, J=6.6 Hz, 3H), 0.98 (d, J=6.6 Hz, 3H), 0.96 (t, J=7.2 Hz, 3H).

EXAMPLE 2(41)

(3R)-1-butyl-2,5-dioxo-3-((1R)-1-hydroxy-2-methylpropyl)-9-(3,5-dimethyl-1-(4-(2-hydroxyethylaminocarbonyl)phenyl)pyrazol-4-ylmethyl)-1,4,9-triazaspiro[5.5]undecane.2hydrochloride

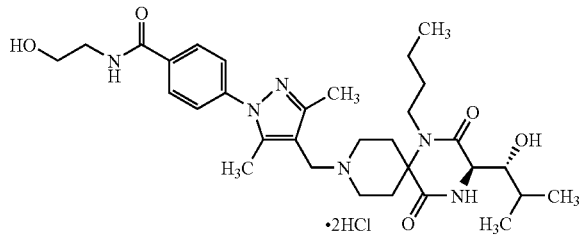

TLC: Rf 0.42 (chloroform:methanol=5:1);
NMR (CD$_3$OD): δ 8.03 (d, J=8.7 Hz, 2H), 7.61 (d, J=8.7 Hz, 2H), 4.32 (s, 2H), 4.16 (d, J=1.8 Hz, 1H), 4.04 (m, 1H), 3.80 (m, 1H), 3.74 (t, J=5.7 Hz, 2H), 3.64–3.48 (m, 3H), 3.54 (t, J=5.7 Hz, 2H), 3.30–3.16 (m, 2H), 2.64–2.34 (m, 3H), 2.45 (s, 3H), 2.41 (s, 3H), 2.22–1.92 (m, 2H), 1.72 (m, 1H), 1.52–1.26 (m, 3H), 1.01 (d, J=6.6 Hz, 3H), 0.99 (d, J=6.6 Hz, 3H), 0.96 (t, J=7.2 Hz, 3H).

EXAMPLE 2(42)

(3R)-1-butyl-2,5-dioxo-3-((1R)-1-hydroxy-2-methylpropyl)-9-(4-(4-(2-(N,N-dimethylamino)ethylaminocarbonyl)phenyloxy)phenylmethyl)-1,4,9-triazaspiro[5.5]undecane.2hydrochloride

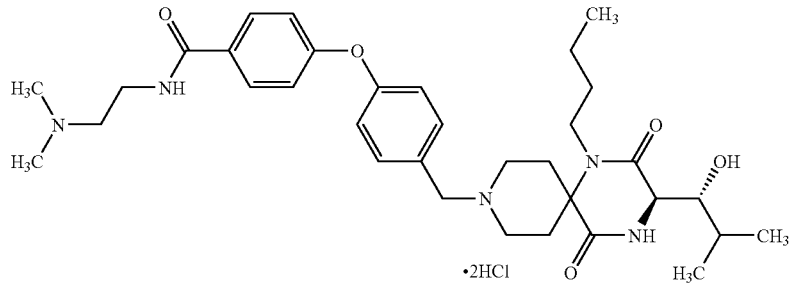

TLC: Rf 0.19 (chloroform:methanol=5:1);
NMR (CD₃OD): δ 7.93 (d, J=9.0 Hz, 2H), 7.61 (d, J=8.4 Hz, 2H), 7.18–7.08 (m, 4H), 4.36 (s, 2H), 4.14 (d, J=1.8 Hz, 1H), 4.00 (m, 1H), 3.80–3.70 (m, 3H), 3.54–3.42 (m, 3H), 3.38 (t, J=6.3 Hz, 2H), 3.26–3.18 (m, 2H), 2.98 (s, 6H), 2.60–2.30 (m, 3H), 2.18–1.96 (m, 2H), 1.68 (m, 1H), 1.50–1.30 (m, 3H), 1.00–0.90 (m, 9H).

EXAMPLE 2(43)

(3R)-1-butyl-2,5-dioxo-3-((1R)-1-hydroxy-2-methylpropyl)-9-(4-(pyridin-3-yloxy)phenylmethyl)-1,4,9-triazaspiro[5.5]undecane.2hydrochloride

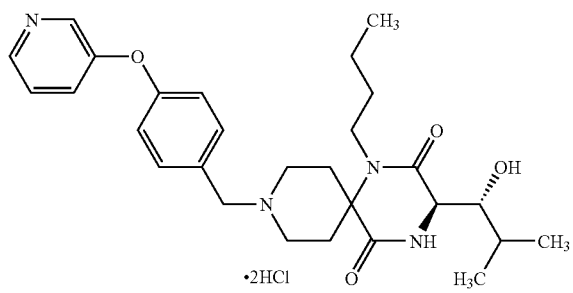

TLC: Rf 0.31 (chloroform:methanol=10:1);
NMR (CD₃OD): δ 8.74 (m, 1H), 8.62 (d, J=5.4 Hz, 1H), 8.24 (m, 1H), 8.14 (m, 1H), 7.76 (d, J=8.4 Hz, 2H), 7.34 (d, J=8.4 Hz, 2H), 4.40 (s, 2H), 4.14 (d, J=2.1 Hz, 1H), 4.00 (m, 1H), 3.76 (m, 1H), 3.60–3.44 (m, 3H), 3.30–3.16 (m, 2H), 2.60 (m, 1H), 2.50–2.40 (m, 2H), 2.26–1.86 (m, 2H), 1.66 (m, 1H), 1.50–1.30 (m, 3H), 1.02–0.88 (m, 9H).

EXAMPLE 2(44)

(3R)-1-butyl-2,5-dioxo-3-((1R)-1-hydroxy-2-methylpropyl)-9-(4-(4-carboxyphenyloxy)phenylmethyl)-1,4,9-triazaspiro[5.5]undecane.hydrochloride

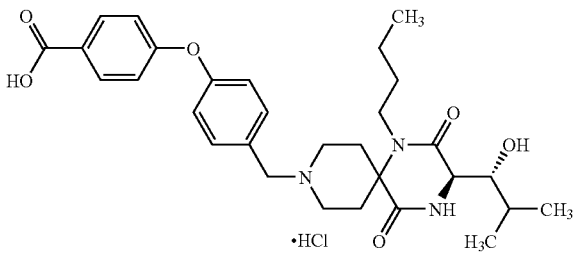

TLC: Rf 0.42 (chloroform:methanol=5:1);
NMR (CD₃OD): δ 8.04 (d, J=8.7 Hz, 2H), 7.59 (d, J=8.4 Hz, 2H), 7.18 (d, J=8.4 Hz, 2H), 7.07 (d, J=8.7 Hz, 2H), 4.37 (s, 2H), 4.15 (d, J=2.4 Hz, 1H), 4.02 (m, 1H), 3.76 (m, 1H), 3.60–3.44 (m, 3H), 3.24–3.08 (m, 2H), 2.56–1.92 (m, 5H), 1.70 (m, 1H), 1.50–1.26 (m, 3H), 1.08–0.90 (m, 9H).

EXAMPLE 2(45)

(3R)-1-butyl-2,5-dioxo-3-((1R)-1-hydroxy-2-methylpropyl)-9-(4-(4-methylphenyloxy)phenylmethyl)-1,4,9-triazaspiro[5.5]undecane.hydrochloride

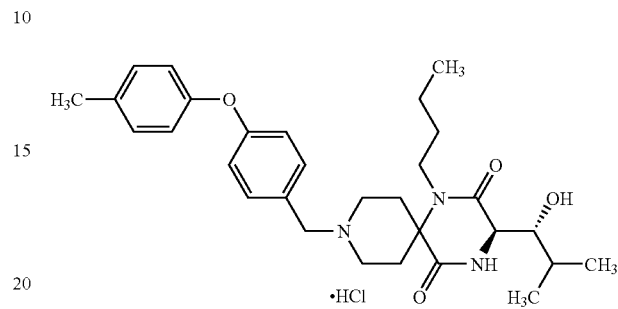

TLC: Rf 0.36 (chloroform:methanol=10:1);
NMR (CD₃OD): δ 7.49 (d, J=9.0 Hz, 2H), 7.20 (d, J=9.0 Hz, 2H), 7.02 (d, J=9.0 Hz, 2H), 6.92 (d, J=9.0 Hz, 2H), 4.32 (s, 2H), 4.14 (d, J=2.1 Hz, 1H), 3.98 (m, 1H), 3.72 (m, 1H), 3.58–3.36 (m, 3H), 3.26–3.08 (m, 2H), 2.52–1.82 (m, 5H), 2.33 (s, 3H), 1.68 (m, 1H), 1.50–1.28 (m, 3H), 1.02–0.86 (m, 9H).

EXAMPLE 2(46)

(3R)-1-butyl-2,5-dioxo-3-((1R)-1-hydroxy-2-methylpropyl)-9-(3,5-dimethyl-1-(2,4-difluorophenyl)pyrazol-4-ylmethyl)-1,4,9-triazaspiro[5.5]undecane.2hydrochloride

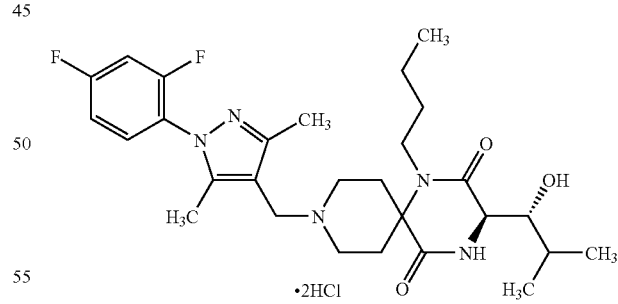

TLC: Rf 0.63 (chloroform:methanol=5:1);
NMR (CD₃OD): δ 7.56 (m, 1H), 7.33–7.16 (m, 2H), 4.32 (s, 2H), 4.16 (d, J=2.1 Hz, 1H), 4.06 (m, 1H), 3.80 (m, 1H), 3.62–3.44 (m, 3H), 3.28–3.16 (m, 2H), 2.62–1.84 (m, 5H), 2.39 (s, 3H), 2.28 (s, 3H), 1.72 (m, 1H), 1.54–1.28 (m, 3H), 1.01 (d, J=6.6 Hz, 3H), 0.99 (d, J=6.6 Hz, 3H), 0.97 (t, J=7.2 Hz, 3H).

EXAMPLE 2(47)

(3R)-1-butyl-2,5-dioxo-3-((1R)-1-hydroxy-2-methylpropyl)-9-(3,5-dimethyl-1-(pyridin-2-yl)pyrazol-4-ylmethyl)-1,4,9-triazaspiro[5.5]undecane.2hydrochloride

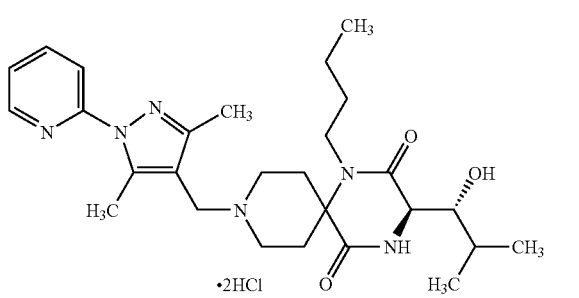

TLC: Rf 0.28 (chloroform:methanol=10:1);
NMR (CD$_3$OD): δ 8.52 (m, 1H), 8.01 (m, 1H), 7.81 (m, 1H), 7.41 (m, 1H), 4.33 (s, 2H), 4.16 (d, J=1.8 Hz, 1H), 4.06 (m, 1H), 3.80 (m, 1H), 3.64–3.46 (m, 3H), 3.26–3.12 (m, 2H), 2.68 (s, 3H), 2.58–2.24 (m, 3H), 2.41 (s, 3H), 2.18 (m, 1H), 2.04 (m, 1H), 1.70 (m, 1H), 1.54–1.26 (m, 3H), 1.00 (d, J=6.6 Hz, 3H), 0.99 (d, J=6.6 Hz, 3H), 0.96 (t, J=7.5 Hz, 3H).

EXAMPLE 2(48)

(3R)-1-butyl-2,5-dioxo-3-((1R)-1-hydroxy-2-methylpropyl)-9-(3,5-dimethyl-1-(4-methylaminocarbonylphenyl)pyrazol-4-ylmethyl)-1,4,9-triazaspiro[5.5]undecane.2hydrochloride

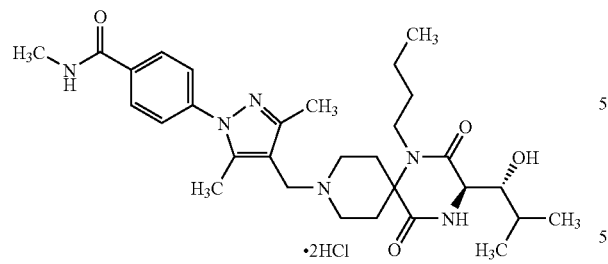

TLC: Rf 0.18 (chloroform:methanol=10:1);
NMR (CD$_3$OD): δ 7.99 (d, J=8.7 Hz, 2H), 7.61 (d, J=8.7 Hz, 2H), 4.31 (s, 2H), 4.15 (d, J=2.1 Hz, 1H), 4.04 (m, 1H), 3.79 (m, 1H), 3.64–3.49 (m, 3H), 3.30–3.17 (m, 2H), 2.94 (s, 3H), 2.59 (m, 1H), 2.51–2.36 (m, 2H), 2.44 (s, 3H), 2.41 (s, 3H), 2.15 (m, 1H), 2.02 (m, 1H), 1.70 (m, 1H), 1.52–1.27 (m, 3H), 1.05–0.91 (m, 9H).

EXAMPLE 2(49)

(3R)-1-butyl-2,5-dioxo-3-((1R)-1-hydroxy-2-methylpropyl)-9-(4-cyclohexyloxyphenylmethyl)-1,4,9-triazaspiro[5.5]undecane.hydrochloride

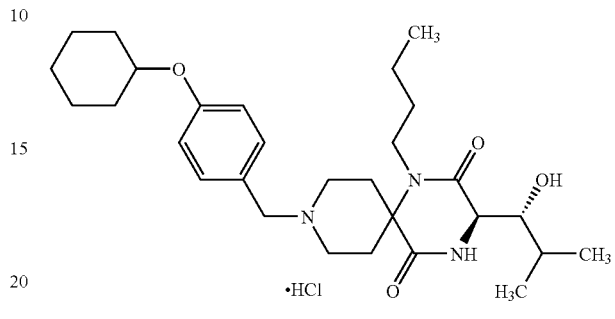

TLC: Rf 0.44 (chloroform:methanol=10:1);
NMR (CD$_3$OD): δ 7.44 (d, J=8.7 Hz, 2H), 7.01 (d, J=8.7 Hz, 2H), 4.38 (m, 1H), 4.27 (s, 2H), 4.14 (d, J=2.1 Hz, 1H), 3.96 (m, 1H), 3.70 (m, 1H), 3.58–3.36 (m, 3H), 3.26–3.08 (m, 2H), 2.54–1.26 (m, 19H), 0.99 (d, J=6.6 Hz, 3H), 0.98 (d, J=6.6 Hz, 3H), 0.96 (t, J=7.5 Hz, 3H).

EXAMPLE 2(50)

(3R)-1-butyl-2,5-dioxo-3-((1R)-1-hydroxy-2-methylpropyl)-9-(4-(3,4,5,6-tetrahydropyran-4-yloxy)phenylmethyl)-1,4,9-triazaspiro[5.5]undecane.hydrochloride

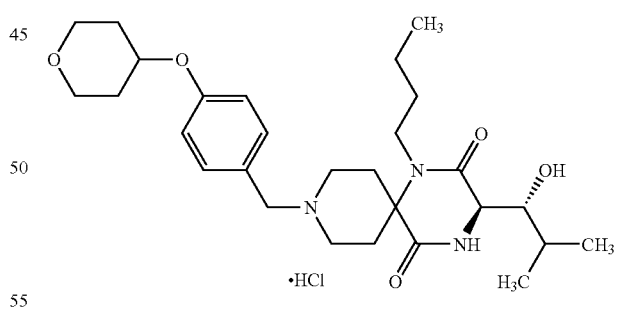

TLC: Rf 0.33(chloroform:methanol=10:1);
NMR (CD$_3$OD): δ 7.47 (d, J=8.7 Hz, 2H), 7.07 (d, J=8.7 Hz, 2H), 4.64 (m, 1H), 4.29 (s, 2H), 4.14 (d, J=2.4 Hz, 1H), 4.04–3.86 (m, 3H), 3.80–3.36 (m, 6H), 3.26–3.08 (m, 2H), 2.52–1.90 (m, 7H), 1.80–1.58 (m, 3H), 1.50–1.26 (m, 3H), 0.99 (d, J=6.6 Hz, 3H), 0.98 (d, J=6.6 Hz, 3H), 0.96 (t, J=7.5 Hz, 3H).

EXAMPLE 2(51)

(3R)-1-butyl-2,5-dioxo-3-((1R)-1-hydroxy-2-methylpropyl)-9-(4-(4-methoxyphenylmethylaminocarbonyl)phenylmethyl)-1,4,9-triazaspiro[5.5]undecane.hydrochloride

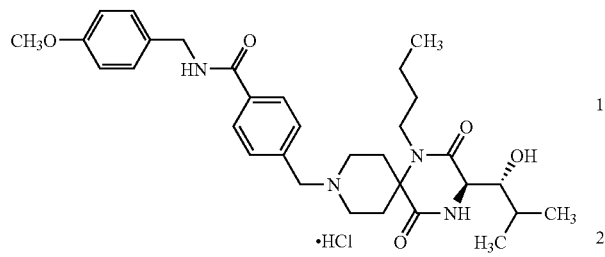

TLC: Rf 0.37 (chloroform:methanol=10:1);
NMR (CD$_3$OD): δ 7.96 (d, J=8.4 Hz, 2H), 7.67 (d, J=8.4 Hz, 2H), 7.28 (d, J=8.4 Hz, 2H), 6.88 (d, J=8.4 Hz, 2H), 4.52 (s, 2H), 4.43 (s, 2H), 4.14 (d, J=2.1 Hz, 1H), 4.04 (m, 1H), 3.77 (s, 3H), 3.77 (m, 1H), 3.58–3.40 (m, 3H), 3.26–3.10 (m, 2H), 2.54–2.22 (m, 3H), 2.20–1.90 (m, 2H), 1.66 (m, 1H), 1.50–1.26 (m, 3H), 0.99 (d, J=6.6 Hz, 3H), 0.98 (d, J=6.6 Hz, 3H), 0.95 (t, J=7.5 Hz, 3H).

EXAMPLE 2(52)

(3R)-1-butyl-2,5-dioxo-3-((1R)-1-hydroxy-2-methylpropyl)-9-(4-(cyclohexylaminocarbonyl)phenylmethyl)-1,4,9-triazaspiro[5.5]undecane.hydrochloride

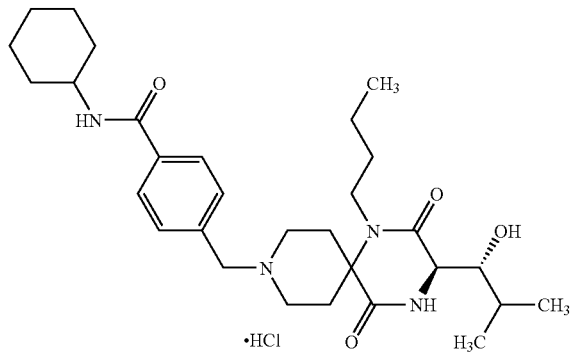

TLC: Rf 0.44 (ethyl acetate:methanol=4:1);
NMR (CD$_3$OD): δ 7.91 (d, J=8.3 Hz, 2H), 7.66 (d, J=8.3 Hz, 2H), 4.42 (s, 2H), 4.13 (d, J=2.0 Hz, 1H), 4.03 (m 1H), 3.90–3.72 (m, 2H), 3.56–3.43 (m, 3H), 3.25 (m, 1H), 3.18 (dd, J=9.6, 2.0 Hz, 1H), 2.53–2.40 (m, 2H), 2.30 (m, 1H), 2.14 (m, 1H), 2.06–1.67 (m, 8H), 1.50–1.33 (m, 7H), 0.98 (d, J=6.6 Hz, 3H), 0.96 (d, J=6.6 Hz, 3H), 0.94 (t, J=7.5 Hz, 3H).

EXAMPLE 2(53)

(3R)-1-butyl-2,5-dioxo-3-((1R)-1-hydroxy-2-methylpropyl)-9-(4-(4-(pyrrolidin-1-ylcarbonyl)phenyloxy)phenylmethyl)-1,4,9-triazaspiro[5.5]undecane.hydrochloride

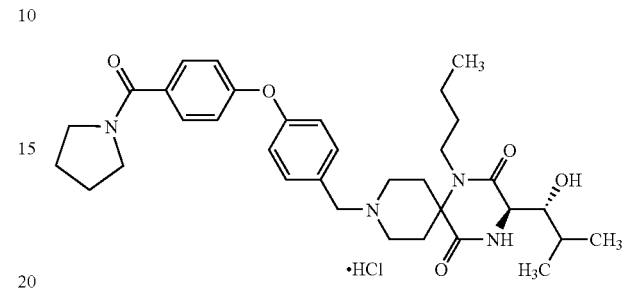

TLC: Rf 0.34 (ethyl acetate:methanol=4:1);
NMR (CD$_3$OD): δ 7.61–7.57 (m, 4H), 7.14 (d, J=8.7 Hz, 2H), 7.09 (d, J=8.7 Hz, 2H), 4.36 (s, 2H), 4.14 (d, J=2.0 Hz, 1H), 4.00 (m, 1H), 3.74 (m, 1H), 3.62–3.45 (m, 7H), 3.24 (m, 1H), 3.19 (dd, J=9.6, 2.0 Hz, 1H), 2.56–2.29 (m, 3H), 2.15–1.89 (m, 6H), 1.70 (m, 1H), 1.40–1.33 (m, 3H), 0.98 (d, J=6.6 Hz, 3H), 0.97 (d, J=6.6 Hz, 3H), 0.95 (t, J=7.2 Hz, 3H).

EXAMPLE 2(54)

(3R)-1-butyl-2,5-dioxo-3-((1R)-1-hydroxy-2-methylpropyl)-9-(3,5-dimethyl-1-(4-fluorophenyl)pyrazol-4-ylmethyl)-1,4,9-triazaspiro[5.5]undecane.2hydrochloride

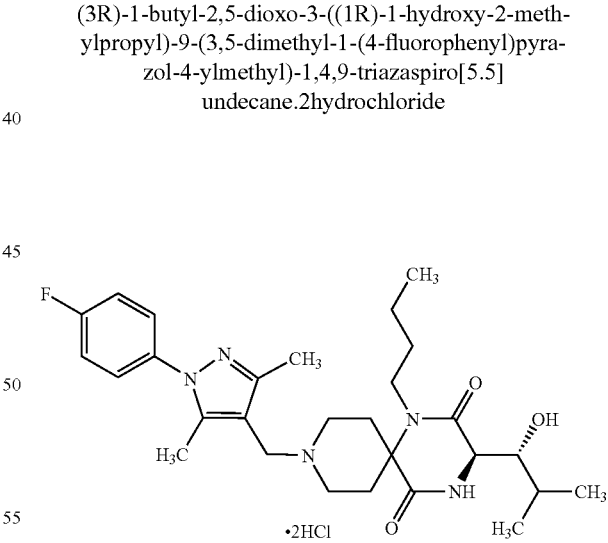

TLC: Rf 0.37 (ethyl acetate:methanol=4:1);
NMR (CD$_3$OD): δ 7.56–7.51 (m, 2H), 7.35–7.28 (m, 2H), 4.31 (s, 2H), 4.15 (d, J=2.0 Hz, 1H), 4.03 (m, 1H), 3.78 (m, 1H), 3.61–3.49 (m, 3H), 3.34 (m, 1H), 3.20 (dd, J=9.6, 2.0 Hz, 1H), 2.68–2.42 (m, 6H), 2.38 (s, 3H), 2.17 (m, 1H), 2.02 (m, 1H), 1.70 (m, 1H), 1.50–1.35 (m, 3H), 0.99 (d, J=6.6 Hz, 3H), 0.98 (d, J=6.6 Hz, 3H), 0.95 (t, J=7.2 Hz, 3H).

EXAMPLE 2(55)

(3R)-1-butyl-2,5-dioxo-3-((1R)-1-hydroxy-2-methylpropyl)-9-(3,5-dimethyl-1-(4-(2-phenylethyl)phenyl)pyrazol-4-ylmethyl)-1,4,9-triazaspiro[5.5]undecane.2hydrochloride

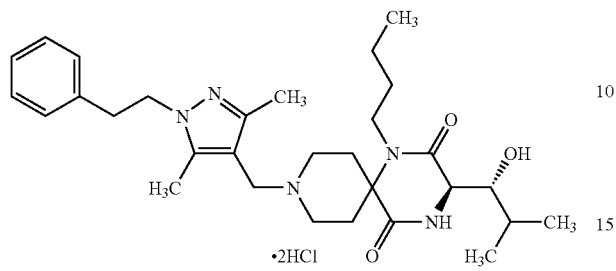

TLC: Rf 0.13(chloroform:methanol=10:1);

NMR (CD$_3$OD): δ 7.32–7.20 (m, 3H), 7.11–7.08 (m, 2H), 4.45 (t, J=6.6 Hz, 2H), 4.20 (s, 2H), 4.16 (d, J=1.8 Hz, 1H), 3.90 (m, 1H), 3.70–3.48 (m, 3H), 3.42–3.30 (m, 2H), 3.21 (m, 1H), 3.14 (t, J=6.6 Hz, 2H), 2.76–2.38 (m, 3H), 2.50 (s, 3H), 2.20–1.88 (m, 2H), 1.97 (s, 3H), 1.74 (m, 1H), 1.56–1.34 (m, 3H), 1.01 (d, J=6.6 Hz, 3H), 1.00 (d, J=6.6 Hz, 3H), 0.97 (t, J=6.9 Hz, 3H).

EXAMPLE 2(56)

(3R)-1-butyl-2,5-dioxo-3-((1R)-1-hydroxy-2-methylpropyl)-9-(3,5-dimethyl-1-(1-benzyloxycarbonylpiperidin-4-yl)pyrazol-4-ylmethyl)-1,4,9-triazaspiro[5.5]undecane.2hydrochloride

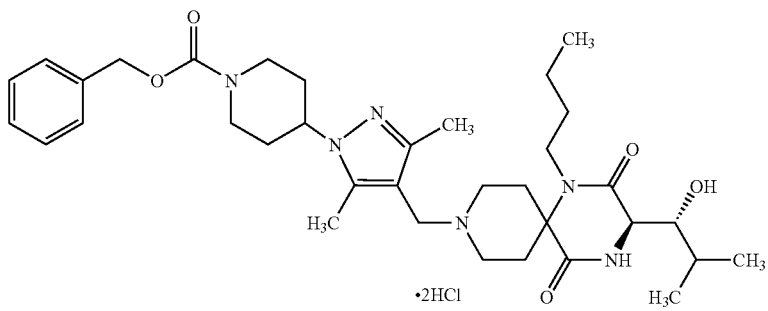

TLC: Rf 0.13 (chloroform:methanol=10:1);

NMR (CD$_3$OD): δ 7.44–7.24 (m, 5H), 5.16 (s, 2H), 4.54 (m, 1H), 4.40–4.20 (m, 2H), 4.25 (s, 2H), 4.15 (d, J=2.1 Hz, 1H), 4.00 (m, 1H), 3.82–3.42 (m, 5H), 3.30–2.88 (m, 3H), 2.64–2.30 (m, 3H), 2.47 (s, 3H), 2.37 (s, 3H), 2.20–1.84 (m, 6H), 1.70 (m, 1H), 1.52–1.26 (m, 3H), 1.00 (d, J=6.6 Hz, 3H), 0.98 (d, J=6.6 Hz, 3H), 0.95 (t, J=7.5 Hz, 3H).

EXAMPLE 2(57)

(3R)-1-butyl-2,5-dioxo-3-((1R)-1-hydroxy-2-methylpropyl)-9-(4-(4-(2-hydroxyethylaminocarbonyl)phenyloxy)phenylmethyl)-1,4,9triazaspiro[5.5]undecane.hydrochloride

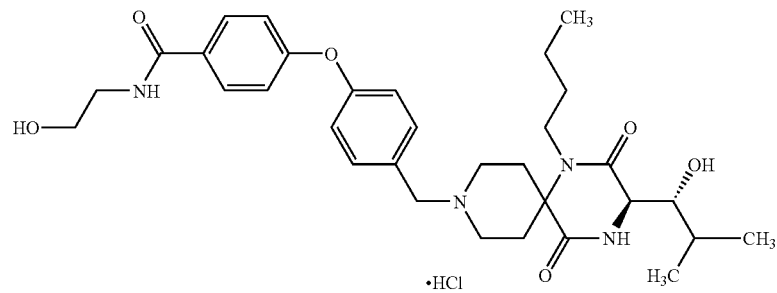

TLC: Rf 0.47 (chloroform:methanol=5:1);

NMR (CD$_3$OD): δ 7.89 (d, J=9.0 Hz, 2H), 7.61 (d, J=9.0 Hz, 2H), 7.16 (d, J=9.0 Hz, 2H), 7.09 (d, J=9.0 Hz, 2H), 4.37 (s, 2H), 4.16 (d, J=2.1 Hz, 1H), 4.00 (m, 1H), 3.78 (m, 1H), 3.71 (t, J=5.7 Hz, 2H), 3.60–3.40 (m, 3H), 3.51 (t, J=5.7 Hz, 2H), 3.30–3.12 (m, 2H), 2.60–2.24 (m, 3H), 2.22–1.92 (m, 2H), 1.70 (m, 1H), 1.56–1.24 (m, 3H), 1.00 (d, J=6.6 Hz, 3H), 0.98 (d, J=6.6 Hz, 3H), 0.96 (t, J=7.5 Hz, 3H).

EXAMPLE 2(58)

(3R)-1-butyl-2,5-dioxo-3-((1R)-1-hydroxy-2-methylpropyl)-9-(3,5-dimethyl-1-(1-methylsulfonylpiperidin-4-yl)pyrazol-4-ylmethyl)-1,4,9-triazaspiro[5.5]undecane.2hydrochloride

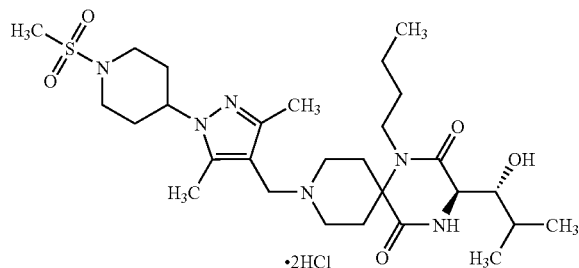

TLC: Rf 0.41 (chloroform:methanol=5:1);

NMR (CD$_3$OD): δ 4.44 (m, 1H), 4.25 (s, 2H), 4.15 (d, J=2.1 Hz, 1H), 4.06–3.64 (m, 4H), 3.60–3.44 (m, 3H), 3.28–3.16 (m, 2H), 3.06–2.92 (m, 2H), 2.90 (s, 3H), 2.64–1.90 (m, 9H), 2.47 (s, 3H), 2.37 (s, 3H), 1.68 (m, 1H), 1.50–1.24 (m, 3H), 1.00 (d, J=6.6 Hz, 3H), 0.99 (d, J=6.6 Hz, 3H), 0.95 (t, J=7.5 Hz, 3H).

EXAMPLE 2(59)

(3R)-1-butyl-2,5-dioxo-3-((1R)-1-hydroxy-2-methylpropyl)-9-(4-(4-hydroxymethylphenyloxy)phenylmethyl)-1,4,9-triazaspiro[5.5]undecane

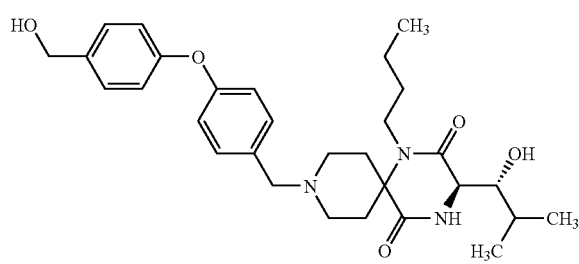

TLC: Rf 0.32 (chloroform:methanol=10:1);

NMR (CD$_3$OD): δ 7.36 (d, J=8.4 Hz, 2H), 7.35 (d, J=8.4 Hz, 2H), 6.97 (d, J=8.4 Hz, 4H), 4.58 (s, 2H), 4.12 (d, J=2.4 Hz, 1H), 3.73 (s, 2H), 3.47 (m, 1H), 3.30–2.90 (m, 6H), 2.31–1.83 (m, 5H), 1.64 (m, 1H), 1.55–1.23 (m, 3H), 0.97 (d, J=6.6 Hz, 6H), 0.95 (t, J=7.5 Hz, 3H).

EXAMPLE 3

(3S)-1-butyl-2,5-dioxo-3-((1S)-1-hydroxy-2-methylpropyl)-9-(6-phenyloxypyridin-3-ylmethyl)-1,4,9-triazaspiro[5.5]undecane.2hydrochloride

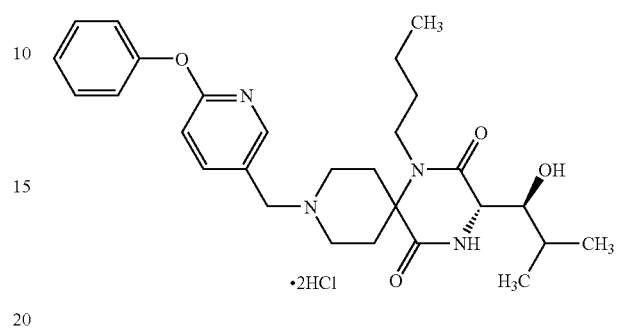

By the same procedure described in Example 2 using the compound prepared in Reference example 3(8) instead of the compound prepared in Reference example 3, the title compound (110 mg) having the following physical data was obtained.

TLC: Rf 0.48 (chloroform:methanol=10:1);

NMR (CD$_3$OD): δ 8.35 (d, J=2.1 Hz, 1H), 8.12 (dd, J=8.7, 2.1 Hz, 1H), 7.49–7.40 (m, 2H), 7.27 (t, J=7.8 Hz, 1H), 7.15 (d, J=7.8 Hz, 2H), 7.06 (d, J=8.7 Hz, 1H), 4.39 (s, 2H), 4.14 (d, J=2.1 Hz, 1H), 4.07–3.93 (m, 1H), 3.82–3.67 (m, 1H), 3.58–3.40 (m, 3H), 3.30–3.15 (m, 1H), 3.19 (dd, J=9.6, 2.1 Hz, 1H), 2.60–2.28 (m, 3H), 2.18–2.05 (m, 1H), 2.05–1.90 (m, 1H), 1.80–1.55 (m, 1H), 1.50–1.25 (m, 3H), 0.99 (d, J=6.6 Hz, 3H), 0.97 (d, J=6.6 Hz, 3H), 0.95 (t, J=7.2 Hz, 3H);

Optical rotation: [α]$_D$ –10.1 (c 1.04, methanol, 25° C.);

HPLC Conditions column: CHIRALCEL OJ-R, 0.46×15 cm, DAICEL, OJR0CD-JB026;

flow rate: 0.7 ml/min;

solvent

A solution: 0.1M aqueous solution of potassium dihydrogen phosphate, B solution: acetonitrile (A:B=76:24);

UV: 225 nm;

retention time: 8.65 min.

EXAMPLE 4

(3S)-1-butyl-2,5-dioxo-3-(2-methylpropyl)-9-(3,5-dimethyl-1-(4-(N,N-dimethylaminocarbonyl)phenyl)pyrazol-4-ylmethyl)-1,4,9-triazaspiro[5.5]undecane.2hydrochloride

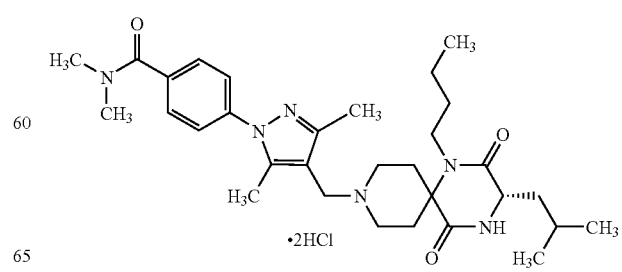

By the same procedure described in Example 2 using the compound prepared in Reference example 3(1) instead of the compound prepared in Reference example 3, and using [4-(4-formyl-3,5-dimethylpyrazolyl)phenyl]-N,N-dimethylcarboxamide instead of 3-formyl-6-phenyloxypyridine, the title compound having the following physical data was obtained.

TLC: Rf 0.62 (chloroform:methanol=5:1);

NMR (CD$_3$OD): δ 7.65–7.52 (m, 4H), 4.33 (s, 2H), 4.03 (dd, J=7.8, 4.5 Hz, 1H), 3.96–3.72 (m, 2H), 3.64–3.54 (m, 2H), 3.50–3.36 (m, 2H), 3.14 (s, 3H), 3.05 (s, 3H), 2.60–2.42 (m, 2H), 2.44 (s, 3H), 2.41 (s, 3H), 2.36–2.10 (m, 2H), 1.90–1.24 (m, 7H), 0.97 (t, J=7.2 Hz, 3H), 0.96 (d, J=6.6 Hz, 3H), 0.95 (d, J=6.6 Hz, 3H).

EXAMPLE 4(1)–4(43)

By the same procedure as described in Example 4 using the corresponding aldehyde derivatives respectively instead of [4-(4-formyl-3,5-dimethylpyrazolyl)phenyl]-N,N-dimethylcarboxamide, the following compounds having the following physical data were obtained.

EXAMPLE 4(1)

(3S)-1-butyl-2,5-dioxo-3-(2-methylpropyl)-9-(3,5-dimethyl-1-(4-(pyrrolidin-1-ylcarbonyl)phenyl)pyrazol-4-ylmethyl)-1,4,9-triazaspiro[5.5]undecane.2hydrochloride

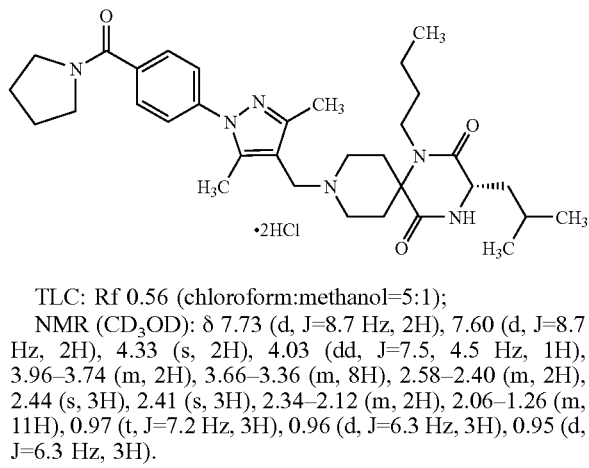

TLC: Rf 0.56 (chloroform:methanol=5:1);

NMR (CD$_3$OD): δ 7.73 (d, J=8.7 Hz, 2H), 7.60 (d, J=8.7 Hz, 2H), 4.33 (s, 2H), 4.03 (dd, J=7.5, 4.5 Hz, 1H), 3.96–3.74 (m, 2H), 3.66–3.36 (m, 8H), 2.58–2.40 (m, 2H), 2.44 (s, 3H), 2.41 (s, 3H), 2.34–2.12 (m, 2H), 2.06–1.26 (m, 11H), 0.97 (t, J=7.2 Hz, 3H), 0.96 (d, J=6.3 Hz, 3H), 0.95 (d, J=6.3 Hz, 3H).

EXAMPLE 4(2)

(3S)-1-butyl-2,5-dioxo-3-(2-methylpropyl)-9-(3,5-dimethyl-1-(4-(morpholin-4-ylcarbonyl)phenyl)pyrazol-4-ylmethyl)-1,4,9-triazaspiro[5.5]undecane.2hydrochloride

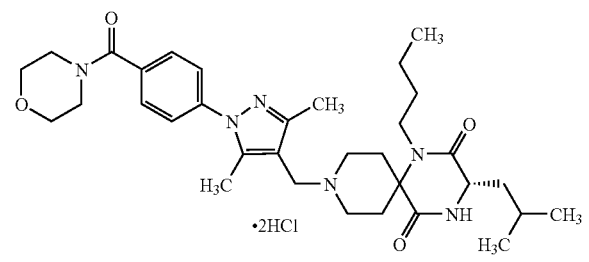

TLC: Rf 0.57 (chloroform:methanol=5:1);

NMR (CD$_3$OD): δ 7.64 (d, J=9.0 Hz, 2H), 7.60 (d, J=9.0 Hz, 2H), 4.33 (s, 2H), 4.03 (dd, J=7.5, 4.5 Hz, 1H), 3.98–3.36 (m, 14H), 2.58–2.36 (m, 2H), 2.44 (s, 3H), 2.40 (s, 3H), 2.32–2.14 (m, 2H), 1.90–1.24 (m, 7H), 0.97 (t, J=7.2 Hz, 3H), 0.96 (d, J=6.3 Hz, 3H), 0.95 (d, J=6.3 Hz, 3H).

EXAMPLE 4(3)

(3S)-1-butyl-2,5-dioxo-3-(2-methylpropyl)-9-(4-methylsulfonylphenylmethyl)-1,4,9-triazaspiro[5.5]undecane.hydrochloride

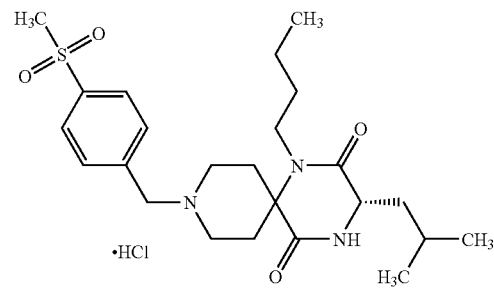

TLC: Rf 0.49 (chloroform:methanol=10:1);

NMR (CD$_3$OD): δ 8.09 (d, J=8.4 Hz, 2H), 7.85 (d, J=8.4 Hz, 2H), 4.48 (s, 2H), 4.02 (dd, J=7.8, 4.5 Hz, 1H), 3.92–3.70 (m, 2H), 3.56–3.36 (m, 4H), 3.16 (s, 3H), 2.48–2.30 (m, 2H), 2.28–2.06 (m, 2H), 1.90–1.24 (m, 7H), 0.96 (t, J=7.2 Hz, 3H), 0.95 (d, J=6.3 Hz, 3H), 0.94 (d, J=6.3 Hz, 3H).

EXAMPLE 4(4)

(3S)-1-butyl-2,5-dioxo-3-(2-methylpropyl)-9-(4-(4-methylsulfonylphenyloxy)phenylmethyl)-1,4,9-triazaspiro[5.5]undecane.hydrochloride

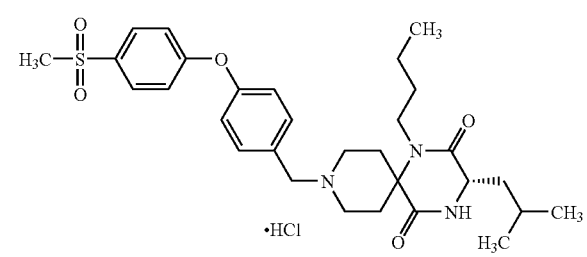

TLC: Rf 0.45 (chloroform:methanol=10:1);

NMR (CD$_3$OD): δ 7.96 (d, J=8.7 Hz, 2H), 7.66 (d, J=8.7 Hz, 2H), 7.23 (d, J=8.7 Hz, 2H), 7.21 (d, J=8.7 Hz, 2H), 4.40 (s, 2H), 4.02 (dd, J=7.5, 4.5 Hz, 1H), 3.94–3.72 (m, 2H), 3.58–3.36 (m, 4H), 3.12 (s, 3H), 2.54–2.36 (m, 2H), 2.18–2.08 (m, 2H), 1.88–1.26 (m, 7H), 0.96 (t, J=6.9 Hz, 3H), 0.95 (d, J=6.3 Hz, 3H), 0.94 (d, J=6.3 Hz, 3H).

EXAMPLE 4(5)

(3S)-1-butyl-2,5-dioxo-3-(2-methylpropyl)-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride

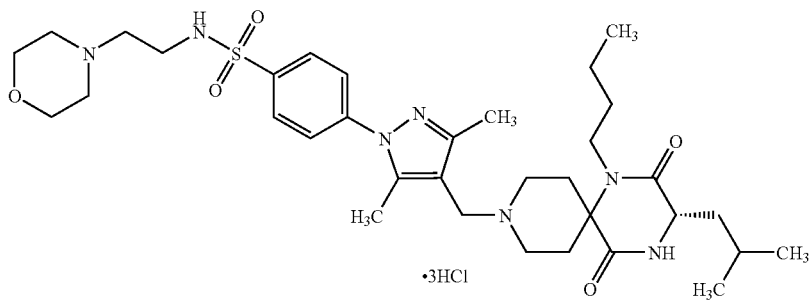

TLC: Rf 0.60 (chloroform:methanol=5:1);

NMR (CD$_3$OD): δ 8.07 (d, J=8.4 Hz, 2H), 7.78 (d, J=8.4 Hz, 2H), 4.32 (s, 2H), 4.16–3.98 (m, 3H), 3.94–3.76 (m, 4H), 3.64–3.40 (m, 6H), 3.38–3.18 (m, 6H), 2.62–2.44 (m, 2H), 2.49 (s, 3H), 2.41 (s, 3H), 2.36–2.12 (m, 2H), 1.90–1.24 (m, 7H), 0.97 (t, J=6.6 Hz, 3H), 0.96 (d, J=6.3 Hz, 3H), 0.95 (d, J=6.3 Hz, 3H).

EXAMPLE 4(6)

(3S)-1-butyl-2,5-dioxo-3-(2-methylpropyl)-9-(3,5-dimethyl-1-(4-(4-methylpiperazin-1-ylsulfonyl)phenyl)pyrazol-4-ylmethyl)-1,4,9-triazaspiro[5.5]undecane.3hydrochloride

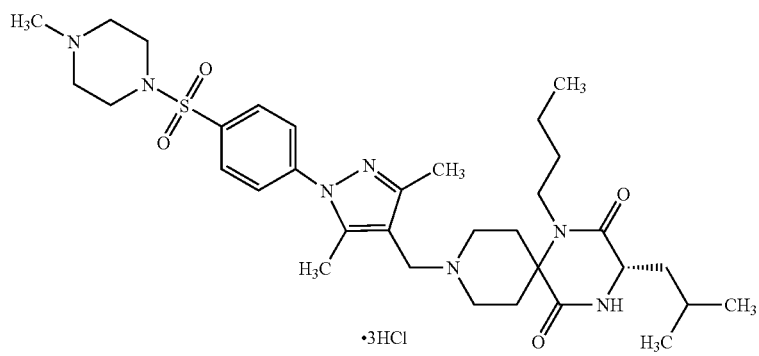

TLC: Rf 0.50 (chloroform:methanol=5:1);

NMR (CD$_3$OD): δ 8.02 (d, J=9.0 Hz, 2H), 7.83 (d, J=9.0 Hz, 2H), 4.32 (s, 2H), 4.03 (dd, J=7.8, 4.5 Hz, 1H), 4.03–3.76 (m, 4H), 3.68–3.56 (m, 4H), 3.54–3.42 (m, 2H), 3.30–3.20 (m, 2H), 2.92 (s, 3H), 2.86–2.72 (m, 2H), 2.64–2.48 (m, 2H), 2.51 (s, 3H), 2.42 (s, 3H), 2.32–2.12 (m, 2H), 1.90–1.26 (m, 7H), 0.97 (t, J=6.6 Hz, 3H), 0.96 (d, J=6.3 Hz, 3H), 0.95 (d, J=6.3 Hz, 3H).

EXAMPLE 4(7)

(3S)-1-butyl-2,5-dioxo-3-(2-methylpropyl)-9-(4-(4-methylsulfinylphenyloxy)phenylmethyl)-1,4,9-triazaspiro[5.5]undecane.hydrochloride

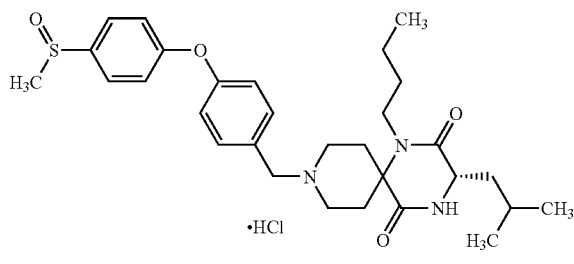

TLC: Rf 0.28 (chloroform:methanol=10:1);

NMR (CD$_3$OD): δ 7.75 (d, J=9.0 Hz, 2H), 7.62 (d, J=9.0 Hz, 2H), 7.23 (d, J=9.0 Hz, 2H), 7.18 (d, J=9.0 Hz, 2H), 4.38 (s, 2H), 4.02 (dd, J=7.5, 4.5 Hz, 1H), 3.92–3.72 (m, 2H), 3.58–3.36 (m, 4H), 2.81 (s, 3H), 2.52–2.36 (m, 2H), 2.30–2.10 (m, 2H), 1.90–1.26 (m, 7H), 0.96 (t, J=7.2 Hz, 3H), 0.95 (d, J=6.3 Hz, 3H), 0.94 (d, J=6.3 Hz, 3H).

EXAMPLE 4(8)

(3S)-1-butyl-2,5-dioxo-3-(2-methylpropyl)-9-(4-(pyridin-1-oxido-3-yloxy)phenylmethyl)-1,4,9-triazaspiro[5.5]undecane.hydrochloride

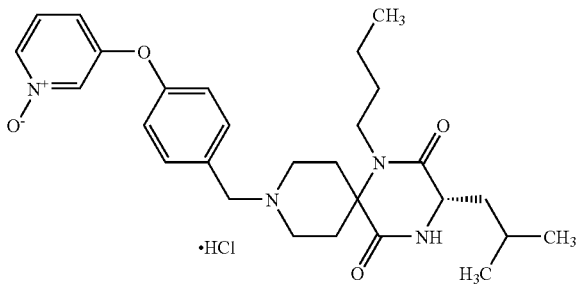

TLC: Rf 0.48 (chloroform:methanol=5:1);

NMR (CD$_3$OD): δ 8.66 (s, 1H), 8.53–8.52 (m, 1H), 7.88–7.78 (m, 2H), 7.77 (d, J=8.7 Hz, 2H), 7.34 (d, J=8.7 Hz, 2H), 4.41 (s, 2H), 4.03 (dd, J=7.5, 4.5 Hz, 1H), 3.92–3.70 (m, 2H), 3.66–3.40 (m, 4H), 2.66–2.48 (m, 2H), 2.26–2.08 (m, 2H), 1.90–1.26 (m, H), 0.96 (t, J=7.5 Hz, 3H), 0.95 (d, J=6.6 Hz, 3H), 0.94 (d, J=6.6 Hz, 3H).

EXAMPLE 4(9)

(3S)-1-butyl-2,5-dioxo-3-(2-methylpropyl)-9-(3,5-dimethyl-1-(4-(2-hydroxyethylaminocarbonyl)phenyl)pyrazol-4-ylmethyl)-1,4,9triazaspiro[5.5]undecane.2hydrochloride

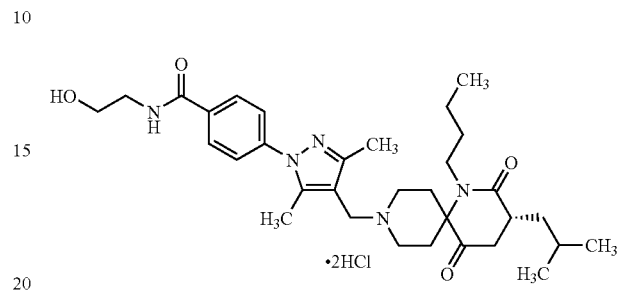

TLC: Rf 0.53 (chloroform:methanol=5:1);

NMR (CD$_3$OD): δ 8.03 (d, J=8.4 Hz, 2H), 7.62 (d, J=8.4 Hz, 2H), 4.33 (s, 2H), 4.03 (dd, J=7.8, 4.5 Hz, 1H), 3.98–3.76 (m, 2H), 3.74 (t, J=5.7 Hz, 2H), 3.68–3.58 (m, 2H), 3.54 (t, J=5.7 Hz, 2H), 3.54–3.40 (m, 2H), 2.64–2.48 (m, 2H), 2.46 (s, 3H), 2.43 (s, 3H), 2.32–2.10 (m, 2H), 1.90–1.30 (m, 7H), 0.97 (t, J=6.6 Hz, 3H), 0.96 (d, J=6.3 Hz, 3H), 0.95 (d, J=6.3 Hz, 3H).

EXAMPLE 4(10)

(3S)-1-butyl-2,5-dioxo-3-(2-methylpropyl)-9-(4-(4-(morpholin-4-ylcarbonyl)phenyloxy)phenylmethyl)-1,4,9-triazaspiro[5.5]undecane.hydrochloride

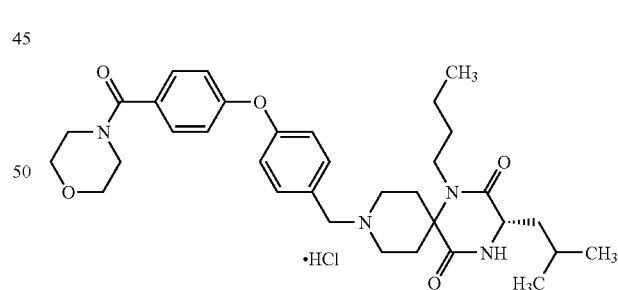

TLC: Rf 0.55 (chloroform:methanol=5:1);

NMR (CD$_3$OD): δ 7.61 (d, J=8.7 Hz, 2H), 7.49 (d, J=8.7 Hz, 2H), 7.15 (d, J=8.7 Hz, 2H), 7.11 (d, J=8.7 Hz, 2H), 4.37 (s, 2H), 4.02 (dd, J=7.8, 4.8 Hz, 1H), 3.90–3.36 (m, 14H), 2.58–2.38 (m, 2H), 2.28–2.08 (m, 2H), 1.88–1.28 (m, 7H), 0.96 (t, J=7.2 Hz 3H), 0.95 (d, J=6.3 Hz, 3H), 0.94 (d, J=6.3 Hz, 3H).

EXAMPLE 4(11)

(3S)-1-butyl-2,5-dioxo-3-(2-methylpropyl)-9-(3,5-dimethyl-1-(4-(N,N-diethylaminosulfonyl)phenyl)pyrazol-4-ylmethyl)-1,4,9-triazaspiro[5.5]undecane·2hydrochloride

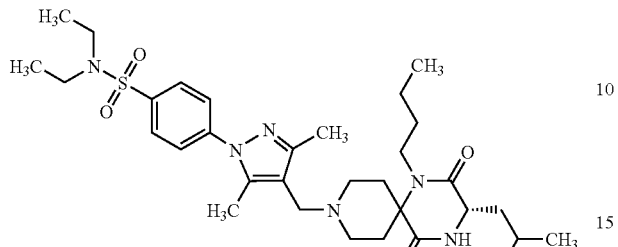

TLC: Rf 0.66 (chloroform:methanol=5:1);

NMR (CD₃OD): δ 8.00 (d, J=8.4 Hz, 2H), 7.73 (d, J=8.4 Hz, 2H), 4.34 (s, 2H), 4.04 (dd, J=7.8, 4.5 Hz, 1H), 3.96–3.76 (m, 2H), 3.68–3.56 (m, 2H), 3.48–3.38 (m, 2H), 3.36–3.22 (m, 4H), 2.52–2.38 (m, 2H), 2.46 (s, 3H), 2.40 (s, 3H), 2.36–2.14 (m, 2H), 1.90–1.28 (m, 7H), 1.20–1.08 (m, 6H), 0.97 (t, J=7.5 Hz, 3H), 0.96 (d, J=6.3 Hz, 3H), 0.95 (d, J=6.3 Hz, 3H).

EXAMPLE 4(12)

(3S)-1-butyl-2,5-dioxo-3-(2-methylpropyl)-9-(4-(4-(2-hydroxyethylaminocarbonyl)phenyloxy)phenylmethyl)-1,4,9-triazaspiro[5.5]undecane·hydrochloride

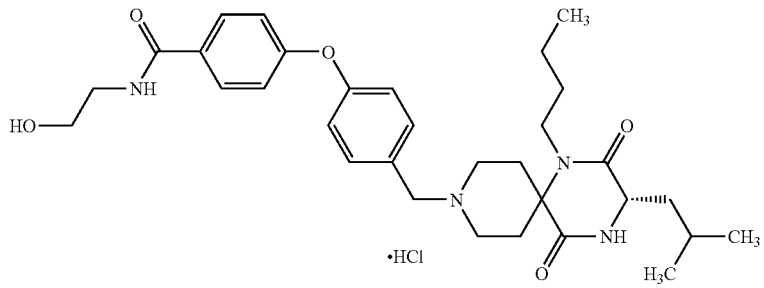

TLC: Rf 0.36 (chloroform:methanol=10:1);

NMR (CD₃OD): δ 7.88 (d, J=8.7 Hz, 2H), 7.60 (d, J=8.4 Hz, 2H), 7.15 (d, J=8.4 Hz, 2H), 7.07 (d, J=8.7 Hz, 2H), 4.36 (s, 2H), 4.01 (dd, J=7.8, 4.5 Hz, 1H), 3.90–3.76 (m, 2H), 3.70 (t, J=6.0 Hz, 2H), 3.56–3.36 (m, 4H), 3.50 (t, J=6.0 Hz, 2H), 2.52–2.38 (m, 2H), 2.24–2.08 (m, 2H), 1.88–1.16 (m, 7H), 1.02–0.88 (m, 9H).

EXAMPLE 4(13)

(3S)-1-butyl-2,5-dioxo-3-(2-methylpropyl)-9-(4-(4-(pyrrolidin-1-ylcarbonyl)phenyloxy)phenylmethyl)-1,4,9-triazaspiro[5.5]undecane·hydrochloride

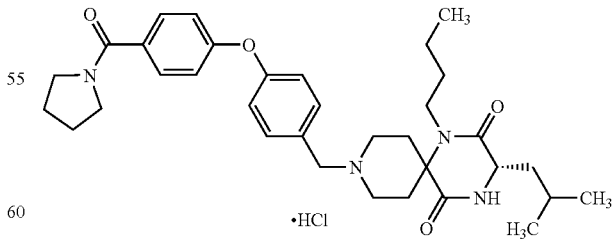

TLC: Rf 0.22 (ethyl acetate:methanol=10:1);

NMR (CD₃OD): δ 7.59 (d, J=8.4 Hz, 2H), 7.58 (d, J=8.4 Hz, 2H), 7.16 (d, J=8.4 Hz, 2H), 7.09 (d, J=8.4 Hz, 2H), 4.38 (s, 2H), 4.02 (dd, J=7.5, 4.5 Hz, 1H), 3.92–3.72 (m, 2H), 3.64–3.36 (m, 8H), 2.48–2.10 (m, 4H), 2.04–1.26 (m, 11H), 0.96 (t, J=6.9 Hz, 3H), 0.95 (d, J=6.3 Hz, 3H), 0.94 (d, J=6.3 Hz, 3H).

EXAMPLE 4(14)

(3S)-1-butyl-2,5-dioxo-3-(2-methylpropyl)-9-(3,5-dimethyl-1-(4-(cyclohexylaminosulfonyl)phenyl)pyrazol-4-ylmethyl)-1,4,9-triazaspiro[5.5]undecane.2hydrochloride

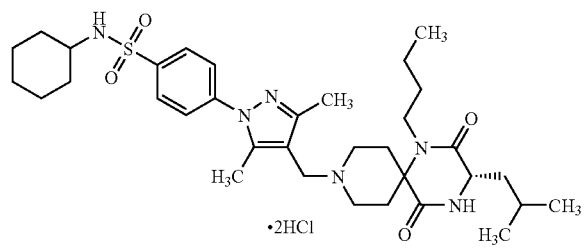

TLC: Rf 0.42 (chloroform:methanol=10:1);

NMR (CD₃OD): δ 8.02 (d, J=8.4 Hz, 2H), 7.70 (d, J=8.4 Hz, 2H), 4.31 (s, 2H), 4.05 (dd, J=7.8, 4.8 Hz, 1H), 3.92–3.72 (m, 2H), 3.68–3.58 (m, 2H), 3.56–3.44 (m, 2H), 3.06 (m, 1H), 2.68–2.50 (m, 2H), 2.47 (s, 3H), 2.41 (s, 3H), 2.38–2.08 (m, 2H), 1.82–1.06 (m, 25H), 1.02–0.86 (m, 5H).

EXAMPLE 4(15)

(3S)-1-butyl-2,5-dioxo-3-(2-methylpropyl)-9-(3,5-dimethyl-1-(4-(3-methoxypropylaminosulfonyl)phenyl)pyrazol-4-ylmethyl)-1,4,9-triazaspiro[5.5]undecane.2hydrochloride

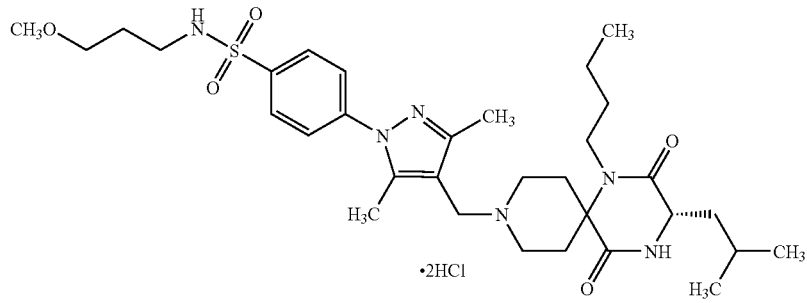

TLC: Rf 0.42 (chloroform:methanol=10:1);

NMR (CD₃OD): δ 8.01 (d, J=8.7 Hz, 2H), 7.73 (d, J=8.7 Hz, 2H), 4.31 (s, 2H), 4.02 (dd, J=7.8, 4.8 Hz, 1H), 3.94–3.72 (m, 2H), 3.68–3.58 (m, 2H), 3.56–3.46 (m, 2H), 3.39 (t, J=6.0 Hz, 2H), 3.26 (s, 3H), 2.98 (t, J=6.9 Hz, 2H), 2.72–2.58 (m, 2H), 2.48 (s, 3H), 2.42 (s, 3H), 2.26–2.10 (m, 2H), 1.90–1.28 (m, 9H), 0.98–0.90 (m, 9H).

EXAMPLE 4(16)

(3S)-1-butyl-2,5-dioxo-3-(2-methylpropyl)-9-(4-methylsulfinylphenylmethyl)-1,4,9-triazaspiro[5.5]undecane.hydrochloride

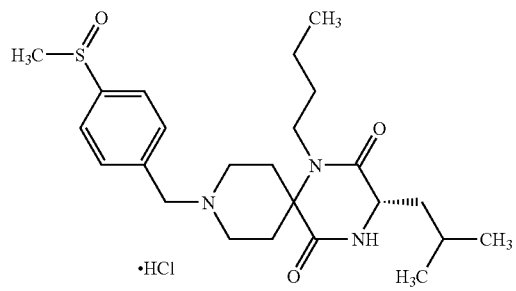

TLC: Rf 0.13 (ethyl acetate:methanol=10:1);

NMR (CD₃OD): δ 7.88 (d, J=8.7 Hz, 2H), 7.81 (d, J=8.7 Hz, 2H), 4.47 (s, 2H), 4.02 (dd, J=7.8, 4.8 Hz, 1H), 3.96–3.74 (m, 2H), 3.56–3.36 (m, 4H), 2.83 (s, 3H), 2.52–2.34 (m, 2H), 2.28–2.08 (m, 2H), 1.90–1.26 (m, 7H), 0.95 (t, J=7.2 Hz, 3H), 0.95 (d, J=6.3 Hz, 3H), 0.94 (d, J=6.3 Hz, 3H).

EXAMPLE 4(17)

(3S)-1-butyl-2,5-dioxo-3-(2-methylpropyl)-9-(3,5-dimethyl-1-propylpyrazol-4-ylmethyl)-1,4,9-triazaspiro[5.5]undecane.2hydrochloride

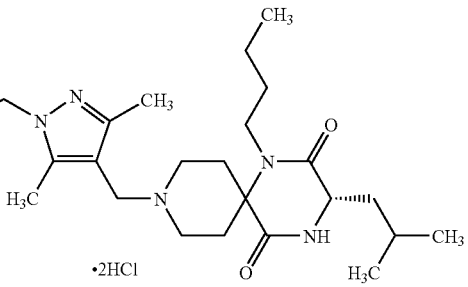

TLC: Rf 0.58 (chloroform:methanol=5:1);

NMR (CD₃OD): δ 4.26 (s, 2H), 4.10 (t, J=7.2 Hz, 2H), 4.02 (dd, J=7.5, 4.5 Hz, 1H), 3.90–3.68 (m, 2H), 3.58–3.36 (m, 4H), 2.58–2.38 (m, 2H), 2.44 (s, 3H), 2.38 (s, 3H), 2.30–2.10 (m, 2H), 1.92–1.24 (m, 9H), 0.96 (t, J=7.2 Hz, 6H), 0.96 (d, J=6.6 Hz, 3H), 0.95 (d, J=6.6 Hz, 3H).

EXAMPLE 4(18)

(3S)-1-butyl-2,5-dioxo-3-(2-methylpropyl)-9-(3,5-dimethyl-1-ethylpyrazol-4-ylmethyl)-1,4,9-triazaspiro[5.5]undecane.2hydrochloride

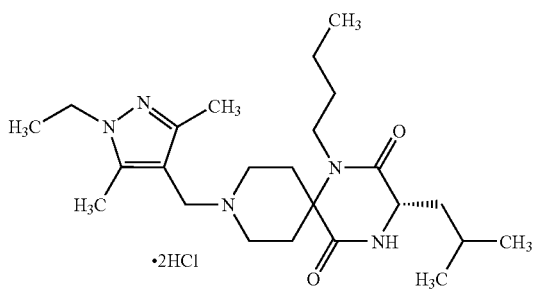

TLC: Rf 0.58 (chloroform:methanol=10:1);

NMR (CD$_3$OD): δ 4.34–4.24 (m, 4H), 4.01 (dd, J=7.8, 4.5 Hz, 1H), 3.92–3.68 (m, 2H), 3.62–3.46 (m, 4H), 2.74–2.60 (m, 2H), 2.53 (s, 3H), 2.50 (s, 3H), 2.24–2.06 (m, 2H), 1.88–1.26 (m, 10H), 1.02–0.86 (m, 9H).

EXAMPLE 4(19)

(3S)-1-butyl-2,5-dioxo-3-(2-methylpropyl)-9-(3,5-dimethyl-1-cyclopentylpyrazol-4-ylmethyl)-1,4,9-triazaspiro[5.5]undecane.2hydrochloride

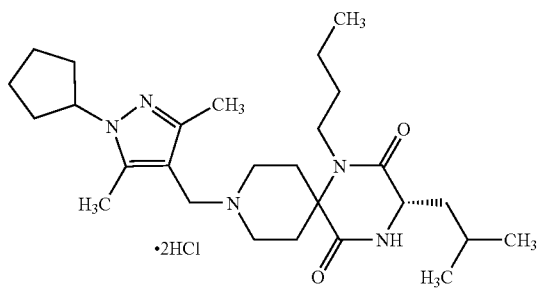

TLC: Rf 0.53 (chloroform:methanol=10:1);

NMR (CD$_3$OD): δ 5.00–4.82 (m, 1H), 4.31 (s, 2H), 4.01 (dd, J=7.5, 4.5 Hz, 1H), 3.92–3.70 (m, 2H), 3.62–3.46 (m, 4H), 2.78–2.58 (m, 2H), 2.55 (s, 3H), 2.53 (s, 3H), 2.32–2.04 (m, 4H), 2.04–1.26 (m, 13H), 0.98–0.84 (m, 9H).

EXAMPLE 4(20)

(3S)-1-butyl-2,5-dioxo-3-(2-methylpropyl)-9-(3,5-dimethyl-1-(1,1-dimethylethyl)pyrazol-4-ylmethyl)-1,4,9-triazaspiro[5.5]undecane.2hydrochloride

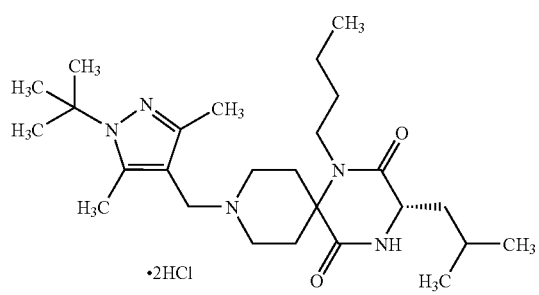

TLC: Rf 0.15 (ethyl acetate:methanol=10:1);

NMR (CD$_3$OD): δ 4.23 (s, 2H), 4.02 (dd, J=7.5, 4.5 Hz, 1H), 3.90–3.68 (m, 2H), 3.58–3.36 (m, 4H), 2.56 (s, 3H), 2.56–2.38 (m, 2H), 2.32 (s, 3H), 2.32–2.10 (m, 2H), 1.88–1.26 (m, 7H), 1.67 (s, 9H), 0.96 (t, J=7.2 Hz, 3H), 0.96 (d, J=6.3 Hz, 3H), 0.95 (d, J=6.3 Hz, 3H).

EXAMPLE 4(21)

(3S)-1-butyl-2,5-dioxo-3-(2-methylpropyl)-9-(3,5-dimethyl-1-(1-benzyloxycarbonylpiperidin-4-yl)pyrazol-4-ylmethyl)-1,4,9-triazaspiro[5.5]undecane.2hydrochloride

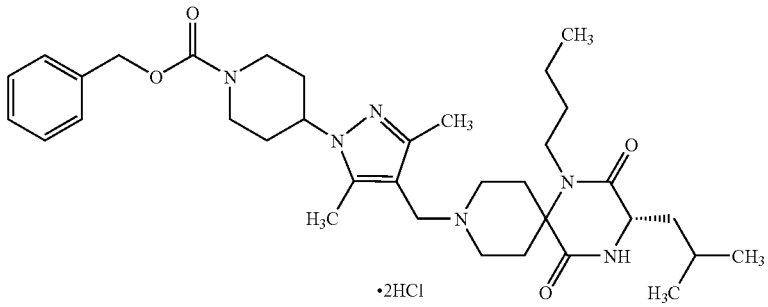

TLC: Rf 0.17 (ethyl acetate:methanol=10:1);

NMR (CD$_3$OD): δ 7.42–7.26 (m, 5H), 5.15 (s, 2H), 4.48–4.22 (m, 3H), 4.23 (s, 2H), 4.02 (dd, J=7.8, 4.5 Hz, 1H), 3.88–3.68 (m, 2H), 3.58–3.36 (m, 4H), 3.12–2.90 (m, 2H), 2.50–1.28 (m, 15H), 2.42 (s, 3H), 2.30 (s, 3H), 0.96 (t, J=6.9 Hz, 3H), 0.95 (d, J=6.3 Hz, 3H), 0.94 (d, J=6.3 Hz, 3H).

EXAMPLE 4(22)

(3S)-1-butyl-2,5-dioxo-3-(2-methylpropyl)-9-(4-((4-methoxyphenyl)methylaminocarbonyl)phenylmethyl)-1,4,9-triazaspiro[5.5]undecane.hydrochloride

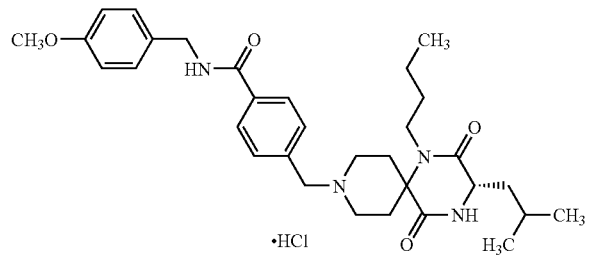

TLC: Rf 0.50 (chloroform:methanol=9:1);

NMR (CD₃OD): δ 7.95 (d, J=8.7 Hz, 2H), 7.67 (d, J=8.7 Hz, 2H), 7.27 (d, J=8.7 Hz, 2H), 6.87 (d, J=8.7 Hz, 2H), 4.51 (s, 2H), 4.42 (s, 2H), 4.00 (dd, J=7.5, 4.8 Hz, 1H), 3.91–3.72 (m, 2H), 3.76 (s, 3H), 3.53–3.35 (m, 4H), 2.50–2.35 (m, 2H), 2.26–2.08 (m, 2H), 1.87–1.28 (m, 7H), 0.94 (t, J=7.5 Hz, 3H), 0.94 (d, J=6.6 Hz, 3H), 0.93 (d, J=6.6 Hz, 3H).

EXAMPLE 4(23)

(3S)-1-butyl-2,5-dioxo-3-(2-methylpropyl)-9-(4-(3-methoxypropylaminocarbonyl)phenylmethyl)-1,4,9-triazaspiro[5.5]undecane.hydrochloride

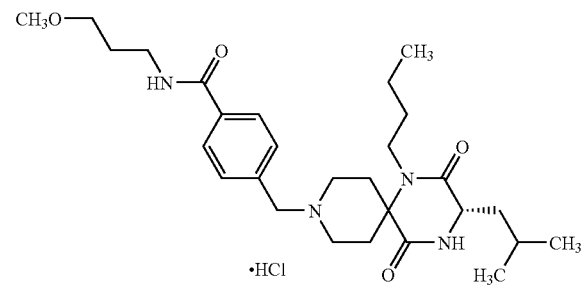

TLC: Rf 0.48 (chloroform:methanol=9:1);

NMR (CD₃OD): δ 7.92 (d, J=8.4 Hz, 2H), 7.67 (d, J=8.4 Hz, 2H), 4.43 (s, 2H), 4.00 (dd, J=7.8, 4.5 Hz, 1H), 3.92–3.75 (m, 2H), 3.53–3.35 (m, 8H), 3.34 (s, 3H), 2.50–2.35 (m, 2H), 2.27–2.10 (m, 2H), 1.92–1.28 (m, 9H), 0.94 (t, J=7.2 Hz, 3H), 0.94 (d, J=6.6 Hz, 3H), 0.93 (d, J=6.6 Hz, 3H).

EXAMPLE 4(24)

(3S)-1-butyl-2,5-dioxo-3-(2-methylpropyl)-9-(3,5-dimethyl-1-(4-methoxycarbonylphenyl)pyrazol-4-ylmethyl)-1,4,9-triazaspiro[5.5]undecane.2hydrochloride

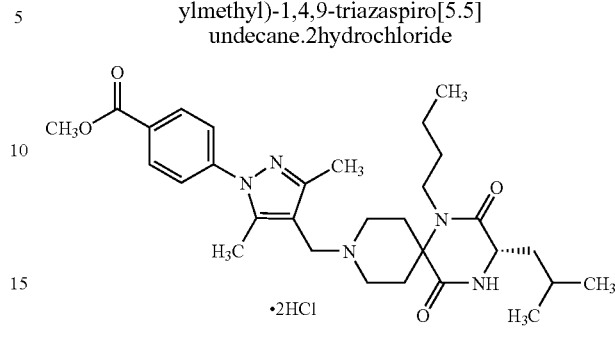

TLC: Rf 0.29 (ethyl acetate:methanol=10:1);

NMR (CD₃OD): δ 8.19 (d, J=9.0 Hz, 2H), 7.63 (d, J=9.0 Hz, 2H), 4.28 (s, 2H), 4.03 (m, 1H), 3.94 (s, 3H), 3.95–3.30 (m, 6H), 2.50–2.15 (m, 4H), 2.44 (s, 3H), 2.39 (s, 3H), 1.90–1.30 (m, 7H), 0.96 (t, J=7.2 Hz, 3H), 0.95 (d, J=6.6 Hz, 3H) 0.94 (d, J=6.6 Hz, 3H).

EXAMPLE 4(25)

(3S)-1-butyl-2,5-dioxo-3-(2-methylpropyl)-9-(3,5-dimethyl-1-(4-methoxyphenyl)pyrazol-4-ylmethyl)-1,4,9-triazaspiro[5.5]undecane.2hydrochloride

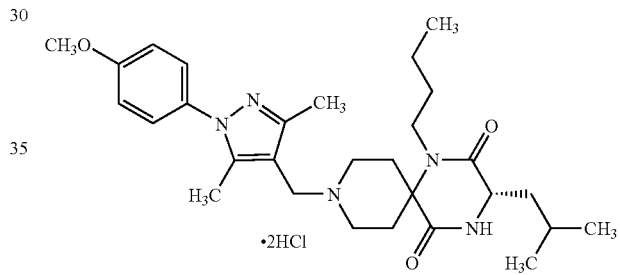

TLC: Rf 0.31 (ethyl acetate:methanol=10:1);

NMR (CD₃OD): δ 7.37 (d, J=9.0 Hz, 2H), 7.09 (d, J=9.0 Hz, 2H), 4.31 (s, 2H), 4.02 (m, 1H), 4.00–3.30 (m, 6H), 3.86 (s, 3H), 2.65–2.15 (m, 4H), 2.39 (s, 3H), 2.34 (s, 3H), 1.90–1.30 (m, 7H), 0.96 (t, J=7.2 Hz, 3H), 0.95 (d, J=6.6 Hz, 3H) 0.94 (d, J=6.6 Hz, 3H).

EXAMPLE 4(26)

(3S)-1-butyl-2,5-dioxo-3-(2-methylpropyl)-9-(3,5-dimethyl-1-(4-(3-(morpholin-4-yl)propylaminosulfonyl)phenyl)pyrazol-4-ylmethyl)-1,4,9-triazaspiro[5.5]undecane.3hydrochloride

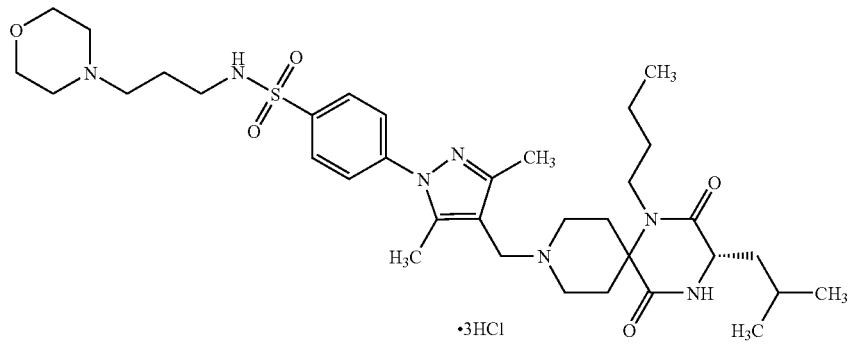

TLC: Rf 0.18 (ethyl acetate:methanol=3:1);

NMR (CD$_3$OD): δ 8.02 (d, J=8.7 Hz, 2H), 7.74 (d, J=8.7 Hz, 2H), 4.31 (s, 2H), 4.10–4.00 (m, 3H), 4.00–3.00 (m, 16H), 2.70–2.10 (m, 4H), 2.48 (s, 3H), 2.40 (s, 3H), 2.10–1.90 (m, 2H), 1.90–1.30 (m, 7H), 0.96 (t, J=7.2 Hz, 3H), 0.95 (d, J=6.6 Hz, 3H), 0.94 (d, J=6.6 Hz, 3H).

EXAMPLE 4(27)

(3S)-1-butyl-2,5-dioxo-3-(2-methylpropyl)-9-(4-(pyrrolidin-1-ylcarbonyl)phenylmethyl)-1,4,9-triaza-spiro[5.5]undecane.hydrochloride

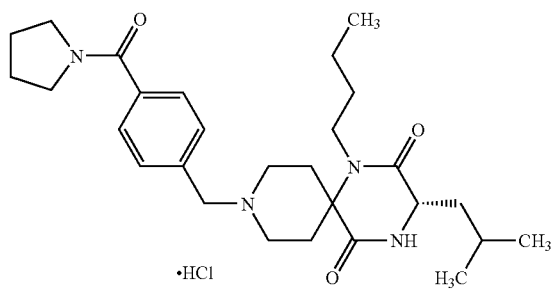

TLC: Rf 0.55 (chloroform:methanol=10:1);

NMR (CD$_3$OD): δ 7.71–7.59 (m, 4H), 4.41 (s, 2H), 4.01 (dd, J=7.8, 4.5 Hz, 1H), 3.83–3.72 (m, 2H), 3.60 (t, J=6.9 Hz, 2H), 3.55–3.32 (m, 4H), 3.45 (t, J=6.9 Hz, 2H), 2.57–2.37 (m, 2H), 2.27–2.08 (m, 2H), 2.05–1.44 (m, 9H), 1.44–1.27 (m, 2H), 0.99–0.90 (m, 9H).

EXAMPLE 4(28)

(3S)-1-butyl-2,5-dioxo-3-(2-methylpropyl)-9-(4-(piperidin-1-ylcarbonyl)phenylmethyl)-1,4,9-triaza-spiro[5.5]undecane.hydrochloride

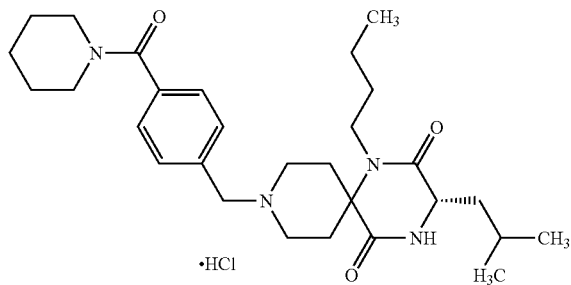

TLC: Rf 0.60 (chloroform:methanol=10:1);

NMR (CD$_3$OD): δ 7.69 (d, J=8.4 Hz, 2H), 7.50 (d, J=8.4 Hz, 2H), 4.41 (s, 2H), 4.01 (dd, J=7.5, 4.5 Hz, 1H), 3.93–3.72 (m, 4H), 3.55–3.30 (m, 6H), 2.57–2.39 (m, 2H), 2.26–2.07 (m, 2H), 1.90–1.44 (m, 11H), 1.44–1.26 (m, 2H), 0.98–0.90 (m, 9H).

EXAMPLE 4(29)

(3S)-1-butyl-2,5-dioxo-3-(2-methylpropyl)-9-(4-(morpholin-4-ylcarbonyl)phenylmethyl)-1,4,9-triaza-spiro[5.5]undecane.hydrochloride

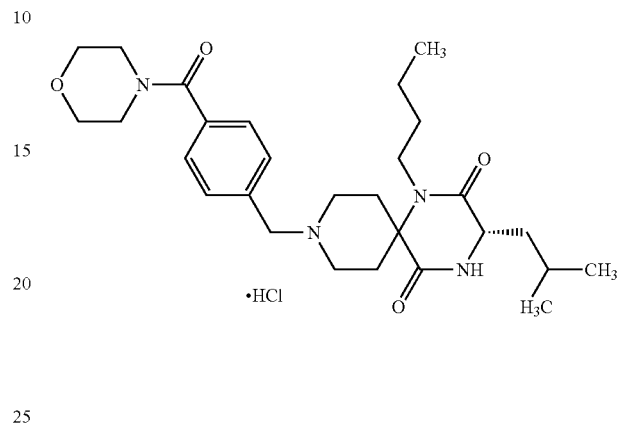

TLC: Rf 0.59 (chloroform:methanol=10:1);

NMR (CD$_3$OD): δ 7.69 (d, J=8.1 Hz, 2H), 7.55 (d, J=8.1 Hz, 2H), 4.41 (s, 2H), 4.01 (dd, J=7.8, 4.5 Hz, 1H), 3.93–3.55 (m, 8H), 3.55–3.34 (m, 6H), 2.55–2.36 (m, 2H), 2.27–2.08 (m, 2H), 1.88–1.44 (m, 5H), 1.44–1.28 (m, 2H), 0.98–0.90 (m, 9H).

EXAMPLE 4(30)

(3S)-1-butyl-2,5-dioxo-3-(2-methylpropyl)-9-(4-(N-methylN-(2-(pyridin-2-yl)ethyl)aminocarbonyl)phenylmethyl)-1,4,9-triazaspiro[5.5]undecane.2hydrochloride

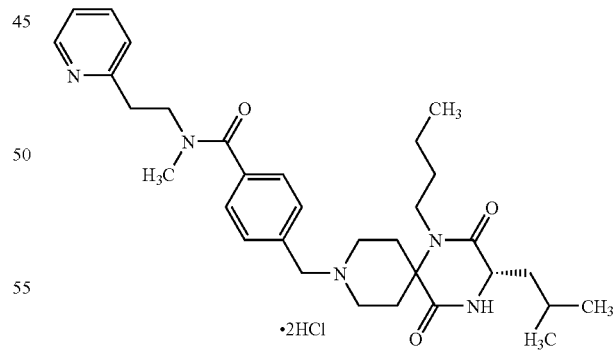

TLC: Rf 0.49 (chloroform:methanol=10:1);

NMR (CD$_3$OD): δ 8.80 (d, J=6.0 Hz, 1H), 8.58 (m, 1H), 8.10 (d, J=8.4 Hz, 1H), 7.98 (m, 1H), 7.70 (d, J=7.8 Hz, 2H), 7.41 (d, J=7.8 Hz, 2H), 4.39 (s, 2H), 4.05–3.95 (m, 3H), 3.94–3.69 (m, 2H), 3.60–3.37 (m, 6H), 3.08 (s, 3H), 2.70–2.43 (m, 2H), 2.26–2.05 (m, 2H), 1.90–1.44 (m, 5H), 1.44–1.26 (m, 2H), 0.99–0.90 (m, 9H).

EXAMPLE 4(31)

(3S)-1-butyl-2,5-dioxo-3-(2-methylpropyl)-9-(4-(cyclohexylaminocarbonyl)phenylmethyl)-1,4,9-triazaspiro[5.5]undecane.hydrochloride

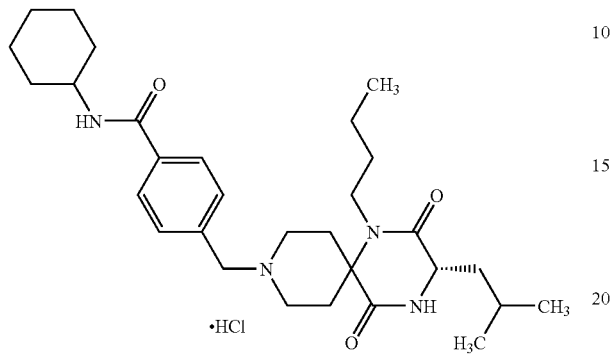

TLC: Rf 0.33 (ethyl acetate:methanol=10:1);

NMR (CD$_3$OD): δ 7.92 (d, J=8.1 Hz, 2H), 7.69 (d, J=8.1 Hz, 2H), 4.43 (s, 2H), 4.01 (dd, J=7.5, 4.5 Hz, 1H), 3.96–3.70 (m, 2H), 3.58–3.36 (m, 4H), 2.58–2.38 (m, 2H), 2.28–2.06 (m, 2H), 2.04–1.12 (m, 18H), 0.95 (t, J=6.9 Hz, 3H), 0.94 (d, J=6.3 Hz, 3H), 0.93 (d, J=6.3 Hz, 3H).

EXAMPLE 4(32)

(3S)-1-butyl-2,5-dioxo-3-(2-methylpropyl)-9-(4-(N,N-dimethylaminosulfonyl)phenylmethyl)-1,4,9-triazaspiro[5.5]undecane.hydrochloride

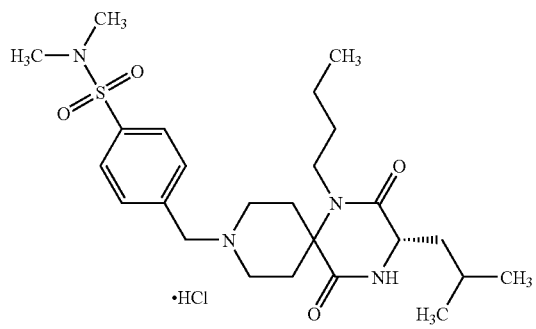

TLC: Rf 0.44 (ethyl acetate:methanol=10:1);

NMR (CD$_3$OD): δ 7.91 (d, J=8.7 Hz, 2H), 7.86 (d, J=8.7 Hz, 2H), 4.49 (s, 2H), 4.02 (dd, J=7.5, 4.8 Hz, 1H), 3.96–3.76 (m, 2H), 3.56–3.38 (m, 4H), 2.72 (s, 6H), 2.60–2.40 (m, 2H), 2.28–2.06 (m, 2H), 1.90–1.28 (m, 7H), 0.95 (t, J=7.2 Hz, 3H), 0.95 (d, J=6.3 Hz, 3H), 0.94 (d, J=6.3 Hz, 3H).

EXAMPLE 4(33)

(3S)-1-butyl-2,5-dioxo-3-(2-methylpropyl)-9-(4-(4-methoxycarbonylphenyloxy)phenylmethyl)-1,4,9-triazaspiro[5.5]undecane.hydrochloride

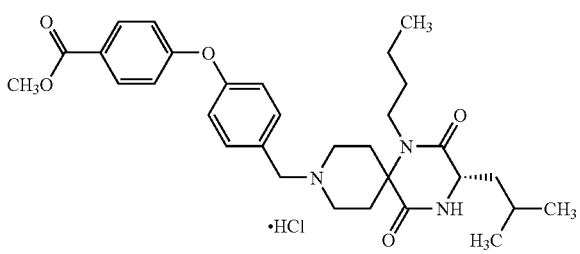

TLC: Rf 0.50 (ethyl acetate:methanol=10:1);

NMR (CD$_3$OD): δ 8.04 (d, J=9.0 Hz, 2H), 7.63 (d, J=9.0 Hz, 2H), 7.19 (d, J=9.0 Hz, 2H), 7.08 (d, J=9.0 Hz, 2H), 4.38 (s, 2H), 4.02 (dd, J=7.5, 4.5 Hz, 1H), 3.90 (s, 3H), 3.88–3.72 (m, 2H), 3.58–3.36 (m, 4H), 2.58–2.38 (m, 2H), 2.30–2.08 (m, 2H), 1.90–1.28 (m, 7H), 0.96 (t, J=6.9 Hz, 3H), 0.95 (d, J=6.3 Hz, 3H), 0.94 (d, J=6.3 Hz, 3H).

EXAMPLE 4(34)

(3S)-1-butyl-2,5-dioxo-3-(2-methylpropyl)-9-(3,5-dimethyl-1-(1-methylpiperidin-4-yl)pyrazol-4-ylmethyl)-1,4,9-triazaspiro[5.5]undecane.3hydrochloride

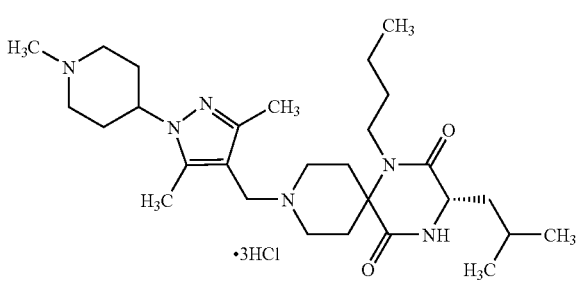

TLC: Rf 0.15 (chloroform:methanol=5:1);

NMR (CD$_3$OD): δ 4.56 (m, 1H), 4.20 (s, 2H), 4.01 (dd, J=7.8, 4.8 Hz, 1H), 3.86–3.42 (m, 8H), 3.30–3.20 (m, 2H), 2.93 (s, 3H), 2.64–2.48 (m, 2H), 2.44–2.28 (m, 2H), 2.44 (s, 3H), 2.31 (s, 3H), 2.22–2.06 (m, 4H), 1.86–1.28 (m, 7H), 0.98–0.88 (m, 9H).

EXAMPLE 4(35)

(3S)-1-butyl-2,5-dioxo-3-(2-methylpropyl)-9-(3,5-dimethyl-1-(1-methylsulfonylpiperidin-4-yl)pyrazol-4-ylmethyl)-1,4,9-triazaspiro[5.5]undecane.2hydrochloride

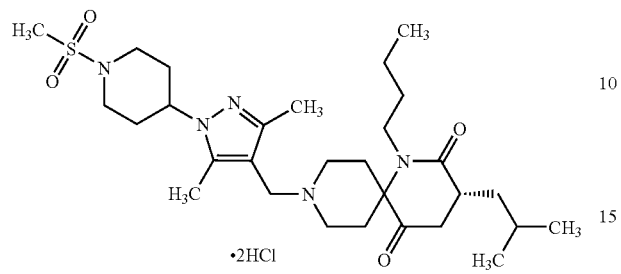

TLC: Rf 0.36 (chloroform:methanol=10:1);

NMR (CD$_3$OD): δ 4.46 (m, 1H), 4.25 (s, 2H), 4.01 (dd, J=7.8, 4.8 Hz, 1H), 3.92–3.68 (m, 4H), 3.60–3.42 (m, 4H), 3.04–2.90 (m, 2H), 2.89 (s, 3H), 2.62–2.46 (m, 2H), 2.48 (s, 3H), 2.38 (s, 3H), 2.24–1.98 (m, 6H), 1.90–1.28 (m, 7H), 0.98–0.90 (m, 9H).

EXAMPLE 4(36)

(3S)-1-butyl-2,5-dioxo-3-(2-methylpropyl)-9-(3,5-dimethyl-1-(4-(3-(N,N-dimethylamino)propylaminosulfonyl)phenyl)pyrazol-4-ylmethyl)-1,4,9-triazaspiro[5.5]undecane.3hydrochloride

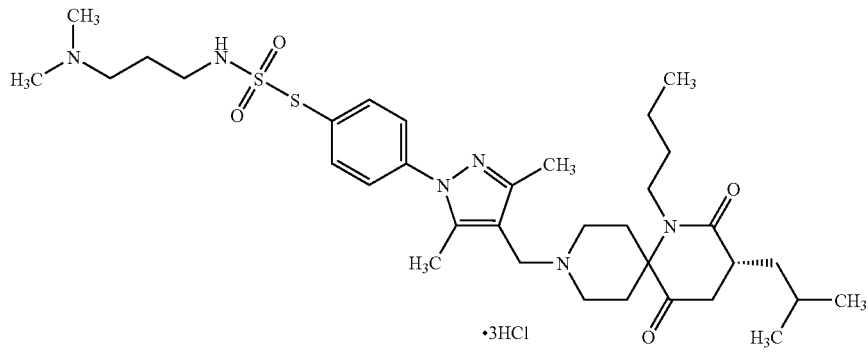

TLC: Rf 0.22 (chloroform:methanol:28% aqueous solution of ammonia=100:10:1);

NMR (CD$_3$OD): δ 8.02 (d, J=8.7 Hz, 2H), 7.74 (d, J=8.7 Hz, 2H), 4.30 (s, 2H), 4.02 (dd, J=7.8, 4.5 Hz, 1H), 3.84–3.73 (m, 2H), 3.66–3.56 (m, 2H), 3.55–3.44 (m, 2H), 3.27–3.18 (m, 2H), 3.02 (t, J=6.3 Hz, 2H), 2.89 (s, 6H), 2.70–2.52 (m, 2H), 2.48 (s, 3H), 2.40 (s, 3H), 2.28–2.11 (m, 2H), 2.00–1.28 (m, 9H), 1.00–0.90 (m, 9H).

EXAMPLE 4(37)

(3S)-1-butyl-2,5-dioxo-3-(2-methylpropyl)-9-(4-(4-(N,N-dimethylamino)phenyloxy)phenylmethyl)-1,4,9-triazaspiro[5.5]undecane.2hydrochloride

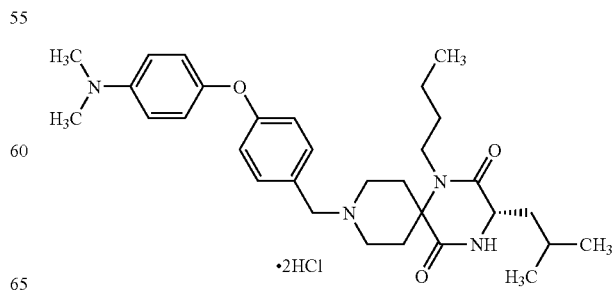

TLC: Rf 0.61 (chloroform:methanol=10:1);

NMR (CD$_3$OD): δ 7.68–7.60 (m, 4H), 7.21 (d, J=8.7 Hz, 2H), 7.14 (d, J=8.7 Hz, 2H), 4.35 (s, 2H), 4.00 (dd, J=7.8, 4.8 Hz, 1H), 3.89–3.77 (m, 2H), 3.54–3.40 (m, 4H), 3.28 (s, 6H), 2.62–2.44 (m, 2H), 2.26–2.07 (m, 2H), 1.90–1.26 (m, 7H), 1.00–0.90 (m, 9H).

EXAMPLE 4(38)

(3S)-1-butyl-2,5-dioxo-3-(2-methylpropyl)-9-(3,5-dimethyl-1-(4-(N-methyl-N-(2-(N',N'-dimethylamino)ethyl)aminosulfonylphenyl)pyrazol-4-ylmethyl)-1,4,9-triazaspiro[5.5]undecane.3hydrochloride

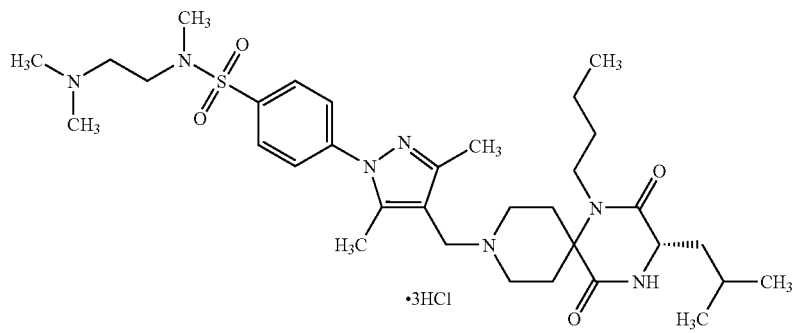

TLC: Rf 0.34 (chloroform:methanol:28% aqueous solution of ammonia=100:10:1);

NMR (CD$_3$OD): δ 8.04 (d, J=8.7 Hz, 2H), 7.81 (d, J=8.7 Hz, 2H), 4.31 (s, 2H), 4.02 (dd, J=7.8, 4.5 Hz, 1H), 3.95–3.73 (m, 2H), 3.66–3.54 (m, 2H), 3.54–3.43 (m, 2H), 3.42 (s, 4H), 3.01 (s, 6H), 2.85 (s, 3H), 2.68–2.52 (m, 2H), 2.50 (s, 3H), 2.41 (s, 3H), 2.29–2.10 (m, 2H), 1.90–1.28 (m, 7H), 1.00–0.90 (m, 9H).

EXAMPLE 4(39)

(3S)-1-butyl-2,5-dioxo-3-(2-methylpropyl)-9-(4-(4-((N,N-dimethylamino)methyl)phenyloxy)phenylmethyl)-1,4,9-triazaspiro[5.5]undecane.2hydrochloride

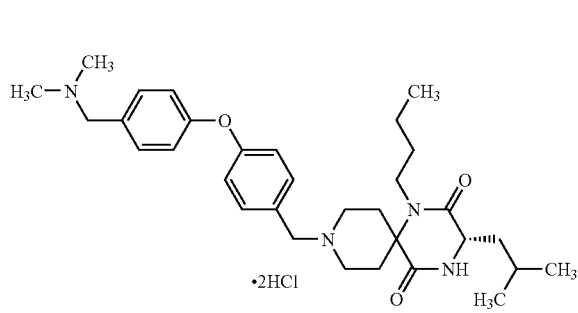

TLC: Rf 0.29 (chloroform:methanol:28% aqueous solution of ammonia=100:10:1);

NMR (CD$_3$OD): δ 7.62 (d, J=8.7 Hz, 2H), 7.53 (d, J=8.7 Hz, 2H), 7.18–7.10 (m, 4H), 4.35 (s, 2H), 4.30 (s, 2H), 4.00 (dd, J=7.8, 4.5 Hz, 1H), 3.88–3.68 (m, 2H), 3.54–3.38 (m, 4H), 2.86 (s, 6H), 2.59–2.42 (m, 2H), 2.26–2.07 (m, 2H), 1.88–1.25 (m, 7H), 1.02–0.89 (m, 9H).

EXAMPLE 4(40)

(3S)-1-butyl-2,5-dioxo-3-(2-methylpropyl)-9-(4-(4-carboxyphenyloxy)phenylmethyl)-1,4,9-triazaspiro[5.5]undecane.hydrochloride

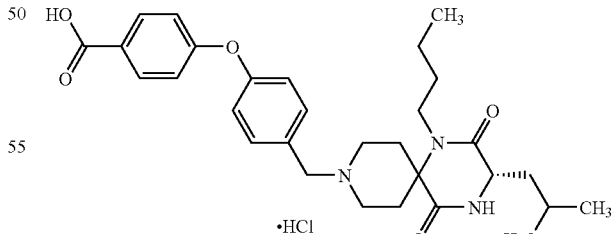

TLC: Rf 0.25 (chloroform:methanol=10:1);

NMR (CD$_3$OD): δ 8.03 (d, J=8.7 Hz, 2H), 7.58 (d, J=8.7 Hz, 2H), 7.16 (d, J=8.7 Hz, 2H), 7.05 (d, J=8.7 Hz, 2H), 4.32 (s, 2H), 4.01 (dd, J=7.8, 4.5 Hz, 1H), 3.84–3.64 (m, 2H), 3.52–3.35 (m, 4H), 2.48–2.32 (m, 2H), 2.27–2.10 (m, 2H), 1.90–1.44 (m, 5H), 1.44–1.26 (m, 2H), 0.99–0.90 (m, 9H).

EXAMPLE 4(41)

(3S)-1-butyl-2,5-dioxo-3-(2-methylpropyl)-9-(3,5-dimethyl-1-(4-methylaminocarbonylphenyl)pyrazol-4-ylmethyl)-1,4,9-triazaspiro[5.5]undecane.2hydrochloride

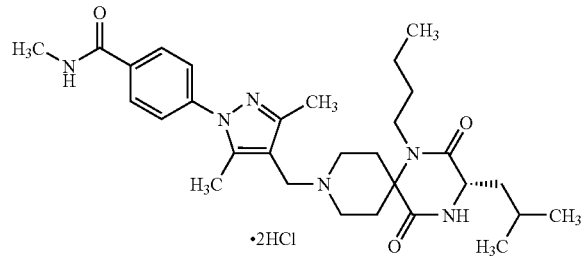

TLC: Rf 0.35 (chloroform:methanol=10:1);

NMR (CD$_3$OD): δ 8.01 (d, J=8.7 Hz, 2H), 7.64 (d, J=8.7 Hz, 2H), 4.34 (s, 2H), 4.03 (dd, J=7.8, 4.8 Hz, 1H), 3.96–3.74 (m, 2H), 3.70–3.42 (m, 4H), 2.96 (s, 3H), 2.74–2.54 (m, 2H), 2.47 (s, 3H), 2.46 (s, 3H), 2.30–2.10 (m, 2H), 1.92–1.28 (m, 7H), 0.96 (t, J=6.9 Hz, 3H), 0.96 (d, J=6.6 Hz, 3H), 0.95 (d, J=6.6 Hz, 3H).

EXAMPLE 4(42)

(3S)-1-butyl-2,5-dioxo-3-(2-methylpropyl)-9-(4-((methoxycarbonyl)methylaminocarbonyl)phenylmethyl)-1,4,9-triazaspiro[5.5]undecane

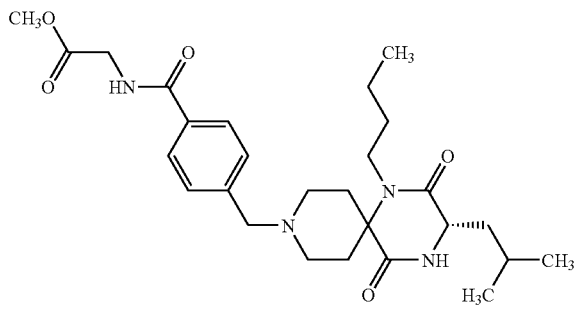

NMR (CDCl$_3$): δ 7.78 (d, J=8.1 Hz, 2H), 7.42 (d, J=8.1 Hz, 2H), 6.70 (t, J=4.8 Hz, 1H), 6.40 (brs, 1H), 4.26 (d, J=4.8 Hz, 2H), 3.96 (m, 1H), 3.81 (s, 3H), 3.62 (s, 2H), 3.50–3.28 (m, 2H), 3.00–2.48 (m, 8H), 2.26–1.20 (m, 7H), 0.99–0.94 (m, 9H).

EXAMPLE 4(43)

(3S)-1-butyl-2,5-dioxo-3-(2-methylpropyl)-9-(3-(3,5-dimethyl-1-phenylpyrazol-4-yl)-2E-propenyl)-1,4,9-triazaspiro[5.5]undecane.2hydrochloride

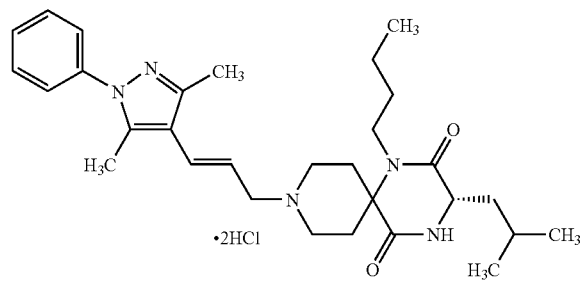

NMR (CDCl$_3$): δ 7.56–7.32 (m, 5H), 6.54 (m, 1H), 6.38 (brs, 1H), 5.96 (m, 1H), 4.00 (m, 1H), 3.76–2.90 (m, 8H), 2.38 (s, 3H), 2.34 (s, 3H), 2.14–1.22 (m, 11H), 1.00–0.86 (m, 9H).

EXAMPLE 5

(3S)-1-butyl-2,5-dioxo-3-(2-methylpropyl)-9-(4-(carboxymethylaminocarbonyl)phenylmethyl)-1,4,9-triazaspiro[5.5]undecane.hydrochloride

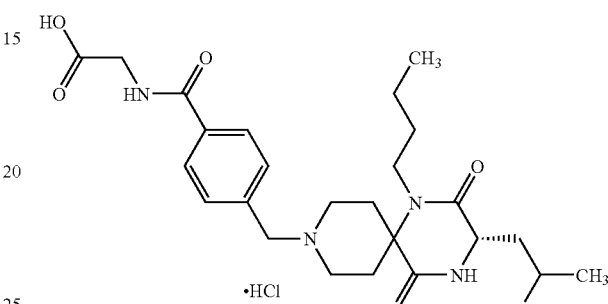

To a solution of the compound prepared in Example 4(42) (106 mg) in methanol (3 ml) was added 5N aqueous solution of sodium hydroxide (0.1 ml). The reaction mixture was stirred for 3 hours at room temperature. The reaction mixture was concentrated and the residue was dissolved in dioxane. 4N hydrogen chloride/ethyl acetate solution was added to the solution. The reaction mixture was concentrated and the obtained residue was added dioxane and filtrated. The filtrate was concentrated and the obtained residue was washed with diethyl ether and dried to give the title compound (62 mg) having the following physical data.

TLC: Rf 0.28 (butanol:acetic acid:water=4:2:1);

NMR (CD$_3$OD): δ 7.99 (d, J=8.7 Hz, 2H), 7.70 (d, J=8.7 Hz, 2H), 4.44 (s, 2H), 4.11 (s, 2H), 4.02 (dd, J=7.5, 4.8 Hz, 1H), 3.94–3.74 (m, 2H), 3.56–3.36 (m, 4H), 2.48–2.32 (m, 2H), 2.28–2.08 (m, 2H), 1.88–1.30 (m, 7H), 0.96 (t, J=7.2 Hz, 3H), 0.95 (d, J=6.3 Hz, 3H), 0.94 (d, J=6.3 Hz, 3H).

EXAMPLE 6

(3S)-1-butyl-2,5-dioxo-3-(2-methylpropyl)-9-(3-(3,5-dimethyl-1-phenylpyrazol-4-yl)propyl)-1,4,9-triazaspiro[5.5]undecane.2hydrochloride

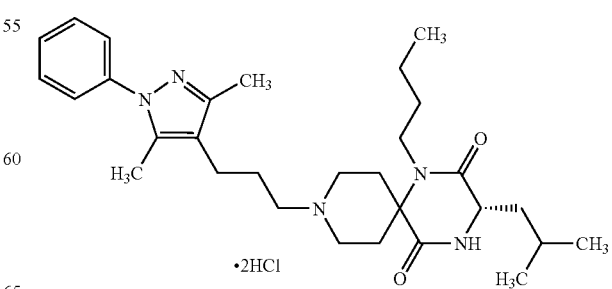

To a solution of the compound prepared in Example 4(43) (85 mg) in methanol (10 ml) solution was added 5% palladium on carbon (10 mg). Under an atmosphere of hydrogen, the reaction mixture was stirred for 22 hours at room temperature. The reaction mixture was filtrated through Celite (brand name) and the filtrate was concentrated. The obtained residue was purified by column chromatography on silica gel (ethyl acetate:methanol=15:1). To the solution of the obtained compound in methanol was added 4N hydrogen chloride/ethyl acetate solution. The reaction mixture was concentrated and the obtained residue was washed with diethyl ether and dried to give the title compound (23 mg) having the following physical data.

TLC: Rf 0.18 (chloroform:methanol=10:1);

NMR (CD$_3$OD): δ 7.70–7.50 (m, 5H), 4.03 (dd J=7.2, 4.2 Hz, 1H), 3.86–3.68 (m, 2H), 3.66–3.40 (m, 4H), 3.30–3.16 (m, 2H), 2.74–2.48 (m, 4H), 2.46 (s, 3H), 2.35 (s, 3H), 2.28–1.98 (m, 4H), 1.90–1.24 (m, 7H), 0.97 (t, J=7.2 Hz, 3H), 0.96 (d, J=6.6 Hz, 3H), 0.95 (d, J=6.6 Hz, 3H).

EXAMPLE 7

(3S)-1-butyl-2,5-dioxo-3-cyclohexylmethyl-9-(3,5-dimethyl-1-(4-(N,N-dimethylaminocarbonyl)phenyl)pyrazol-4-ylmethyl)-1,4,9-triazaspiro[5.5]undecane.2hydrochloride

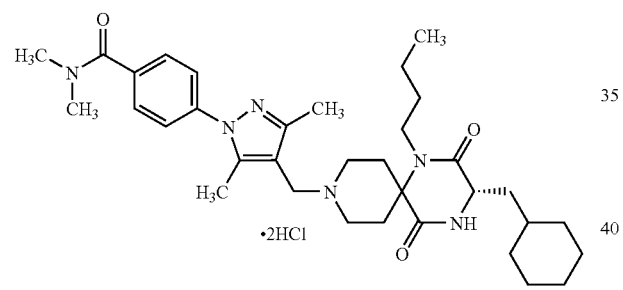

By the same procedure as described in Example 2 using the compound prepared in Reference example 3(2) instead of the compound prepared in Reference example 3, and using [4-(4-formyl-3,5-dimethylpyrazolyl)phenyl]-N,N-dimethylcarboxamide instead of 3-formyl-6-phenyloxypyridine, the title compound having the following physical data was obtained.

TLC: Rf 0.59 (chloroform:methanol=10:1);

NMR (CD$_3$OD): δ 7.62 (d, J=9.0 Hz, 2H), 7.58 (d, J=9.0 Hz, 2H), 4.32 (s, 2H), 4.05 (dd, J=7.8, 4.5 Hz, 1H), 3.96–3.78 (m, 2H), 3.66–3.58 (m, 2H), 3.46–3.34 (m, 2H), 3.13 (s, 3H), 3.04 (s, 3H), 2.52–2.38 (m, 2H), 2.42 (s, 3H), 2.39 (s, 3H), 2.32–2.14 (m, 2H), 1.82–1.16 (m, 15H), 1.02–0.88 (m, 5H).

EXAMPLE 7(1)–7(41)

By the same procedure as described in Example 7 using the corresponding aldehyde derivatives respectively instead of [4-(4-formyl-3,5-dimethylpyrazolyl)phenyl]-N,N-dimethylcarboxamide, the following compounds were obtained.

EXAMPLE 7(1)

(3S)-1-butyl-2,5-dioxo-3-cyclohexylmethyl-9-(3,5-dimethyl-1-(4-(pyrrolidin-1-ylcarbonyl)phenyl)pyrazol-4-ylmethyl)-1,4,9-triazaspiro[5.5]undecane.2hydrochloride

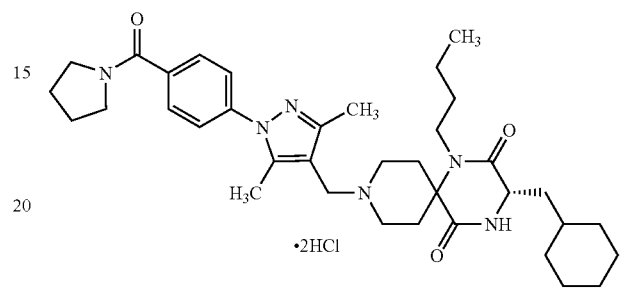

TLC: Rf 0.53(chloroform:methanol=10:1);

NMR (CD$_3$OD): δ 7.72 (d, J=8.7 Hz, 2H), 7.58 (d, J=8.7 Hz, 2H), 4.33 (s, 2H), 4.05 (dd, J=7.5, 4.5 Hz, 1H), 3.98–3.78 (m, 2H), 3.64–3.56 (m, 4H), 3.56–3.44 (m, 2H), 3.44–3.32 (m, 2H), 2.50–2.10 (m, 4H), 2.42 (s, 3H), 2.39 (s, 3H), 2.10–1.88 (m, 4H), 1.88–1.10 (m, 15H), 1.10–0.90 (m, 5H).

EXAMPLE 7(2)

(3S)-1-butyl-2,5-dioxo-3-cyclohexylmethyl-9-(3,5-dimethyl-1-(4-(morpholin-4-ylcarbonyl)phenyl)pyrazol-4-ylmethyl)-1,4,9-triazaspiro[5.5]undecane.2hydrochloride

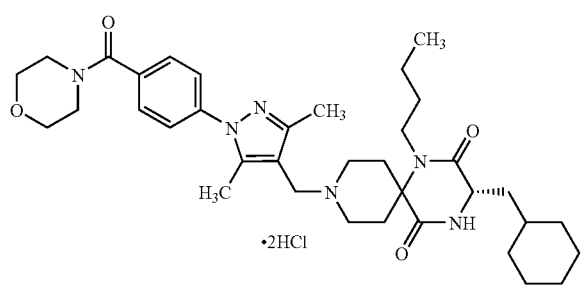

TLC: Rf 0.53(chloroform:methanol=10:1);

NMR (CD$_3$OD): δ 7.65–7.56 (m, 4H), 4.32 (s, 2H), 4.05 (dd, J=7.5, 4.5 Hz, 1H), 3.96–3.30 (m, 14H), 2.54–2.32 (m, 2H), 2.43 (s, 3H), 2.39 (s, 3H), 2.32–2.12 (m, 2H), 1.84–1.10 (m, 15H), 1.02–0.86 (m, 5H).

EXAMPLE 7(3)

(3S)-1-butyl-2,5-dioxo-3-cyclohexylmethyl-9-(3,5-dimethyl-1-(4-(2-(N,N-dimethylamino)ethylaminocarbonyl)phenyl)pyrazol-4-ylmethyl)-1,4,9-triazaspiro[5.5]undecane.3hydrochloride

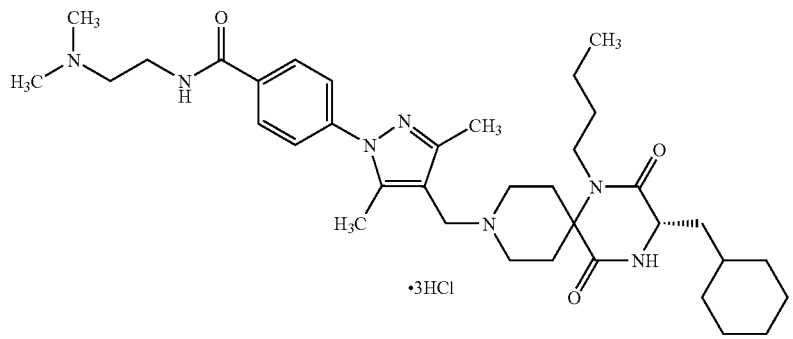

TLC: Rf 0.15 (chloroform:methanol=10:1);

NMR (CD$_3$OD): δ 8.07 (d, J=8.1 Hz, 2H), 7.64 (d, J=8.1 Hz, 2H), 4.31 (s, 2H), 4.05 (dd, J=7.2, 5.1 Hz, 1H), 3.94–3.76 (m, 2H), 3.79 (t, J=6.0 Hz, 2H), 3.66–3.54 (m, 2H), 3.54–3.36 (m, 2H), 3.41 (t, J=6.0 Hz, 2H), 3.00 (s, 6H), 2.66–2.48 (m, 2H), 2.46 (s, 3H), 2.41 (s, 3H), 2.28–2.10 (m, 2H), 1.82–1.10 (m, 15H), 1.02–0.86 (m, 5H).

EXAMPLE 7(4)

(3S)-1-butyl-2,5-dioxo-3-cyclohexylmethyl-9-(4-(4-(morpholin-4-ylcarbonyl)phenyloxy)phenylmethyl)-1,4,9-triazaspiro[5.5]undecane.hydrochloride

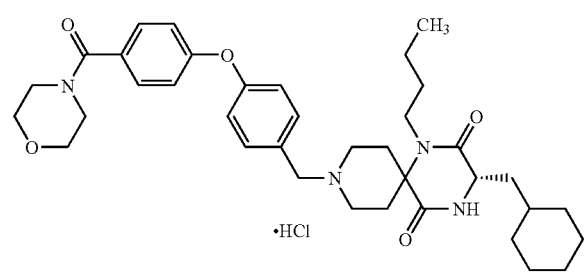

TLC: Rf 0.60 (chloroform:methanol=10:1);

NMR (CD$_3$OD): δ 7.59 (d, J=8.4 Hz, 2H), 7.48 (d, J=8.7 Hz, 2H), 7.22–7.09 (m, 4H), 4.36 (s, 2H), 4.04 (dd, J=7.5, 4.8 Hz, 1H), 3.88–3.34 (m, 14H), 2.52–2.34 (m, 2H), 2.28–2.08 (m, 2H), 1.81–1.10 (m, 15H), 1.04–0.84 (m, 5H).

EXAMPLE 7(5)

(3S)-1-butyl-2,5-dioxo-3-cyclohexylmethyl-9-(4-methylsulfonylphenylmethyl)-1,4,9-triazaspiro[5.5]undecane.hydrochloride TLC: Rf 0.57 (chloroform:methanol=10:1);

NMR (CD$_3$OD): δ 8.08 (d, J=8.4 Hz, 2H), 7.87 (d, J=8.4 Hz, 2H), 4.50 (s, 2H), 4.03 (dd, J=7.5, 4.5 Hz, 1H), 3.94–3.76 (m, 2H), 3.52–3.36 (m, 4H), 3.15 (s, 3H), 2.56–2.38 (m, 2H), 2.26–2.08 (m, 2H), 1.80–1.10 (m, 15H), 1.02–0.86 (m, 5H).

EXAMPLE 7(6)

(3S)-1-butyl-2,5-dioxo-3-cyclohexylmethyl-9-(4-(4-methylsulfonylphenyloxy)phenylmethyl)-1,4,9-triazaspiro[5.5]undecane.hydrochloride

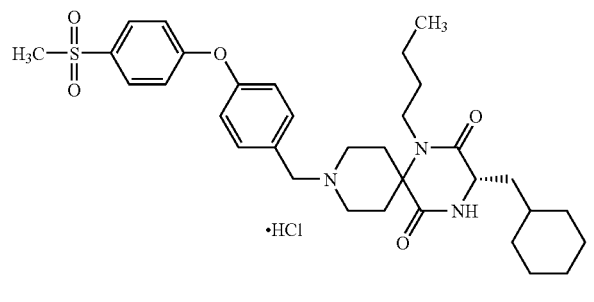

TLC: Rf 0.57 (chloroform:methanol=10:1);

NMR (CD$_3$OD): δ 7.95 (d, J=9.0 Hz, 2H), 7.64 (d, J=8.7 Hz, 2H), 7.25–7.18 (m, 4H), 4.39 (s, 2H), 4.04 (dd, J=7.8, 4.8 Hz, 1H), 3.90–3.76 (m, 2H), 3.58–3.34 (m, 4H), 3.12 (s, 3H), 2.50–2.36 (m, 2H), 2.30–2.10 (m, 2H), 1.82–1.10 (m, 15H), 1.02–0.88 (m, 5H).

EXAMPLE 7(7)

(3S)-1-butyl-2,5-dioxo-3-cyclohexylmethyl-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride

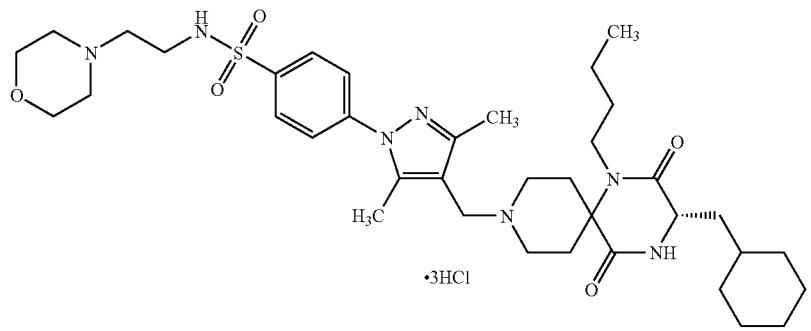

TLC: Rf 0.43 (chloroform:methanol=10:1);

NMR (CD$_3$OD): δ 8.06 (d, J=8.7 Hz, 2H), 7.57 (d, J=8.7 Hz, 2H), 4.31 (s, 2H), 4.12–4.01 (m, 3H), 3.92–3.76 (m, 4H), 3.65–3.40 (m, 6H), 3.40–3.16 (m, 6H), 2.64–2.44 (m, 2H), 2.48 (s, 3H), 2.41 (s, 3H), 2.28–2.12 (m, 2H), 1.84–1.10 (m, 15H), 1.02–0.86 (m, 5H).

EXAMPLE 7(8)

(3S)-1-butyl-2,5-dioxo-3-cyclohexylmethyl-9-(3,5-dimethyl-1-(4-(4-methylpiperazin-1-ylsulfonyl)phenyl)pyrazol-4-ylmethyl)-1,4,9-triazaspiro[5.5]undecane.3hydrochloride

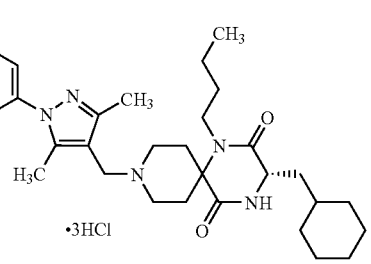

TLC: Rf 0.43(chloroform:methanol=10:1);

NMR (CD$_3$OD): δ 8.01 (d, J=8.7 Hz, 2H), 7.83 (d, J=8.7 Hz, 2H), 4.31 (s, 2H), 4.08–3.95 (m, 3H), 3.95–3.74 (m, 2H), 3.68–3.46 (m, 6H), 3.28–3.20 (m, 2H), 2.91 (s, 3H), 2.88–2.72 (m, 2H), 2.70–2.52 (m, 2H), 2.51 (s, 3H), 2.42 (s, 3H), 2.26–2.08 (m, 2H), 1.82–1.10 (m, 15H), 1.02–0.86 (m, 5H).

EXAMPLE 7(9)

(3S)-1-butyl-2,5-dioxo-3-cyclohexylmethyl-9-(4-(4-methylsulfinylphenyloxy)phenylmethyl)-1,4,9-triazaspiro[5.5]undecane.hydrochloride

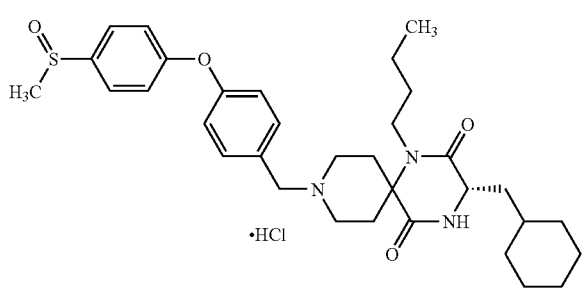

TLC: Rf 0.53(chloroform:methanol=10:1);

NMR (CD₃OD): δ7.74 (d, J=9.0 Hz, 2H), 7.62 (d, J=8.7 Hz, 2H), 7.25–7.14 (m, 4H), 4.37 (s, 2H), 4.04 (dd, J=7.5, 4.5 Hz, 1H), 3.88–3.72 (m, 2H), 3.54–3.36 (m, 4H), 2.80 (s, 3H), 2.52–2.36 (m, 2H), 2.26–2.10 (m, 2H), 1.80–1.10 (m, 15H), 1.02–0.86 (m, 5H).

EXAMPLE 7(10)

(3S)-1-butyl-2,5-dioxo-3-cyclohexylmethyl-9-(3,5-dimethyl-1-(4-(2-hydroxyethylaminocarbonyl)phenyl)pyrazol-4-ylmethyl)-1,4,9-triazaspiro[5.5]undecane.2hydrochloride

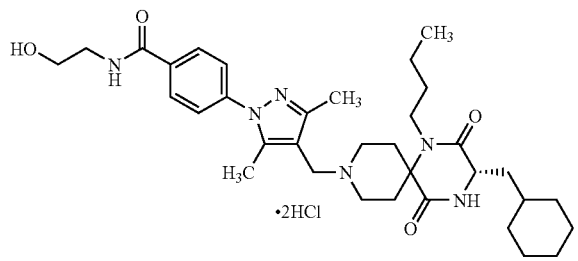

TLC: Rf 0.41 (chloroform:methanol=10:1);

NMR (CD₃OD): δ 8.01 (d, J=8.7 Hz, 2H), 7.60 (d, J=8.7 Hz, 2H), 4.30 (s, 2H), 4.05 (dd, J=7.5, 4.2 Hz, 1H), 3.92–3.68 (m, 4H), 3.66–3.42 (m, 6H), 2.70–2.50 (m, 2H), 2.45 (s, 3H), 2.40 (s, 3H), 2.28–2.08 (m, 2H), 1.82–1.10 (m, 15H), 1.02–0.84 (m, 5H).

EXAMPLE 7(11)

(3S)-1-butyl-2,5-dioxo-3-cyclohexylmethyl-9-(4-(4-(2-hydroxyethylaminocarbonyl)phenyloxy)phenylmethyl)-1,4,9-triazaspiro[5.5]undecane.hydrochloride

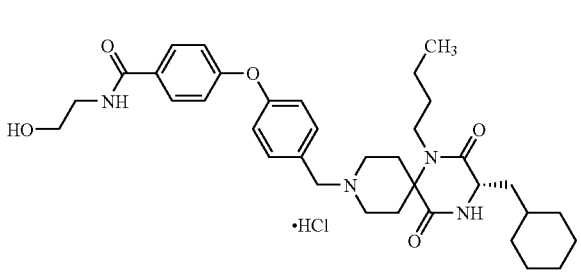

TLC: Rf 0.36 (chloroform:methanol=10:1);

NMR (CD₃OD): δ 7.89 (d, J=9.0 Hz, 2H), 7.58 (d, J=8.7 Hz, 2H), 7.16 (d, J=8.7 Hz, 2H), 7.08 (d, J=9.0 Hz, 2H), 4.37 (s, 2H), 4.04 (dd, J=7.5, 4.5 Hz, 1H), 3.90–3.70 (m, 2H), 3.70 (t, J=6.0 Hz, 2H), 3.58–3.46 (m, 2H), 3.50 (t, J=6.0 Hz, 2H), 3.42–3.34 (m, 2H), 2.44–2.30 (m, 2H), 2.30–2.08 (m, 2H), 1.82–1.12 (m, 15H), 1.02–0.84 (m, 5H).

EXAMPLE 7(12)

(3S)-1-butyl-2,5-dioxo-3-cyclohexylmethyl-9-(4-(4-(pyrrolidin-1-ylcarbonyl)phenyloxy)phenylmethyl)-1,4,9-triazaspiro[5.5]undecane.hydrochloride

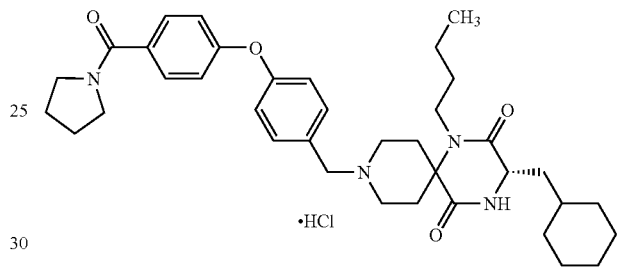

TLC: Rf 0.25 (ethyl acetate:methanol=10:1);

NMR (CD₃OD): δ 7.59 (d, J=8.7 Hz, 2H), 7.59 (d, J=8.7 Hz, 2H), 7.16 (d, J=8.7 Hz, 2H), 7.10 (d, J=8.7 Hz, 2H), 4.37 (s, 2H), 4.05 (dd, J=7.5, 4.8 Hz, 1H), 3.90–3.74 (m, 2H), 3.62–3.36 (m, 8H), 2.48–2.08 (m, 4H), 2.04–1.08 (m, 19H), 0.96 (t, J=7.2 Hz, 3H), 1.04–0.84 (m, 2H).

EXAMPLE 7(13)

(3S)-1-butyl-2,5-dioxo-3-cyclohexylmethyl-9-(3,5-dimethyl-1-(4-(cyclohexylaminosulfonyl)phenyl)pyrazol-4-ylmethyl)-1,4,9-triazaspiro[5.5]undecane.2hydrochloride

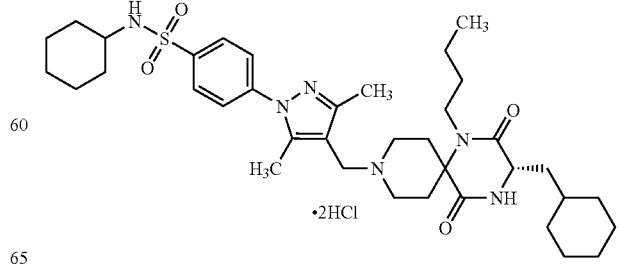

TLC: Rf 0.42 (chloroform:methanol=10:1);

NMR (CD₃OD): δ 8.03 (d, J=8.7 Hz, 2H), 7.70 (d, J=8.7 Hz, 2H), 4.31 (s, 2H), 4.05 (dd, J=7.8, 4.8 Hz, 1H), 3.92–3.72 (m, 2H), 3.68–3.58 (m, 2H), 3.56–3.44 (m, 2H), 3.06 (m, 1H), 2.68–2.50 (m, 2H), 2.47 (s, 3H), 2.41 (s, 3H), 2.38–2.08 (m, 2H), 1.82–1.06 (m, 25H), 1.02–0.86 (m, 5H).

EXAMPLE 7(14)

(3S)-1-butyl-2,5-dioxo-3-cyclohexylmethyl-9-(3,5-dimethyl-1-(4-(3-methoxypropylaminosulfonyl)phenyl)pyrazol-4-ylmethyl)-1,4,9-triazaspiro[5.5]undecane.2hydrochloride

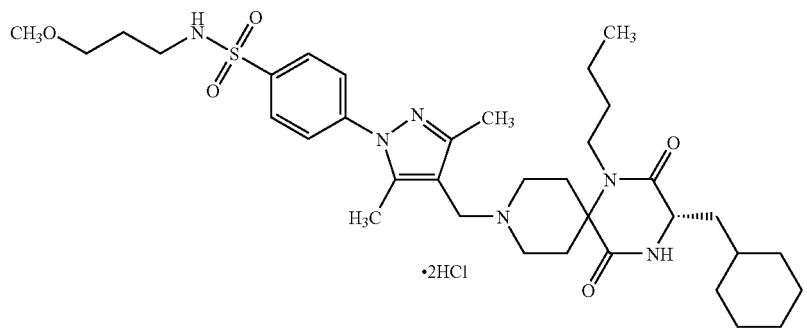

TLC: Rf 0.48 (chloroform:methanol=10:1);

NMR (CD₃OD): δ 8.01 (d, J=8.4 Hz, 2H), 7.74 (d, J=8.4 Hz, 2H), 4.31 (s, 2H), 4.05 (dd, J=7.8, 4.8 Hz, 1H), 3.92–3.72 (m, 2H), 3.68–3.58 (m, 2H), 3.56–3.46 (m, 4H), 3.39 (t, J=6.0 Hz, 2H), 3.26 (s, 3H), 2.98 (t, J=6.9 Hz, 2H), 2.72–2.56 (m, 2H), 2.48 (s, 3H), 2.43 (s, 3H), 2.26–2.08 (m, 2H), 1.82–1.10 (m, 15H), 1.02–0.86 (m, 5H).

EXAMPLE 7(15)

(3S)-1-butyl-2,5-dioxo-3-cyclohexylmethyl-9-(4-methylsulfinylphenylmethyl)-1,4,9-triazaspiro[5.5]undecane.hydrochloride

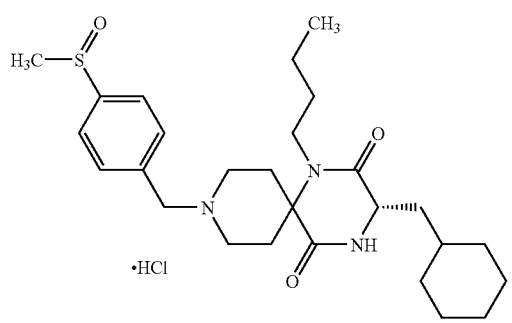

TLC: Rf 0.15 (ethyl acetate:methanol=10:1);

NMR (CD₃OD): δ 7.85 (d, J=8.7 Hz, 2H), 7.81 (d, J=8.7 Hz, 2H), 4.47 (s, 2H), 4.05 (dd, J=7.2, 4.8 Hz, 1H), 3.94–3.76 (m, 2H), 3.58–3.36 (m, 4H), 2.83 (s, 3H), 2.54–2.34 (m, 2H), 2.18–2.06 (m, 2H), 1.82–1.10 (m, 15H), 0.96 (t, J=7.5 Hz, 3H), 1.06–0.86 (m, 2H).

EXAMPLE 7(16)

((3S)-1-butyl-2,5-dioxo-3-cyclohexylmethyl-9-(3,5-dimethyl-1-propylpyrazol-4-ylmethyl)-1,4,9-triazaspiro[5.5]undecane.2hydrochloride

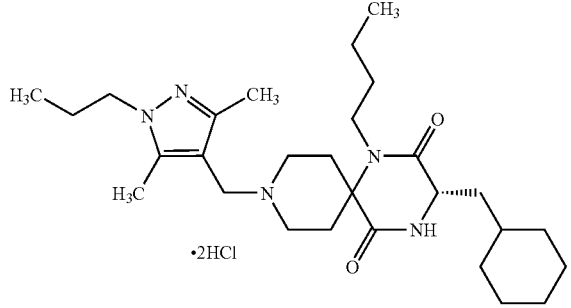

TLC: Rf 0.61 (chloroform:methanol=10:1);

NMR (CD₃OD): δ 4.28 (s, 2H), 4.13 (t, J=7.2 Hz, 2H), 4.05 (dd, J=7.5, 4.5 Hz, 1H), 3.88–3.72 (m, 2H), 3.60–3.38 (m, 4H), 2.62–2.32 (m, 2H), 2.46 (s, 3H), 2.42 (s, 3H), 2.28–2.08 (m, 2H), 1.94–1.08 (m, 17H), 0.96 (t, J=7.2 Hz, 6H), 1.06–0.86 (m, 2H).

EXAMPLE 7(17)

(3S)-1-butyl-2,5-dioxo-3-cyclohexylmethyl-9-(3,5-dimethyl-1-ethylpyrazol-4-ylmethyl)-1,4,9-triazaspiro[5.5]undecane.2hydrochloride

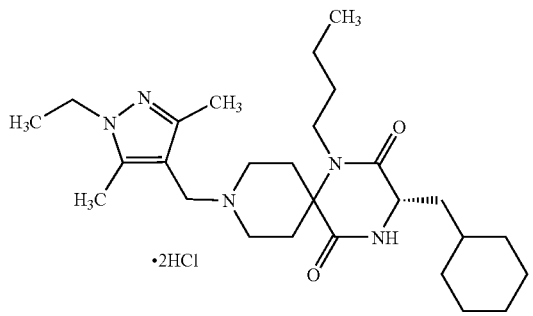

TLC: Rf 0.51 (chloroform:methanol=10:1);

NMR (CD$_3$OD): δ 4.34–4.20 (m, 4H), 4.04 (dd, J=7.8, 4.8 Hz, 1H), 3.88–3.70 (m, 2H), 3.62–3.46 (m, 4H), 2.72–2.54 (m, 2H), 2.52 (s, 3H), 2.48 (s, 3H), 2.24–2.06 (m, 2H), 1.82–1.08 (m, 18H), 1.02–0.86 (m, 5H).

EXAMPLE 7(18)

(3S)-1-butyl-2,5-dioxo-3-cyclohexylmethyl-9-(3,5-dimethyl-1-cyclopentylpyrazol-4-ylmethyl)-1,4,9-triazaspiro[5.5]undecane.2hydrochloride

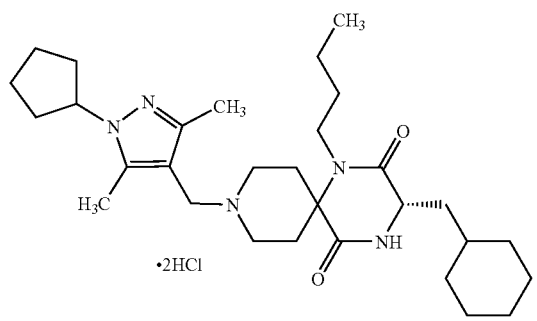

TLC: Rf 0.49 (chloroform:methanol=10:1);

NMR (CD$_3$OD): δ 5.02–4.82 (m, 1H), 4.33 (s, 2H), 4.04 (dd, J=7.5, 4.8 Hz, 1H), 3.90–3.70 (m, 2H), 3.64–3.48 (m, 4H), 2.80–2.60 (m, 2H), 2.58 (s, 3H), 2.57 (s, 3H), 2.36–1.08 (m, 25H), 1.04–0.84 (m, 5H).

EXAMPLE 7(19)

(3S)-1-butyl-2,5-dioxo-3-cyclohexylmethyl-9-(3,5-dimethyl-1-(4-(3-(morpholin-4-yl)propylaminosulfonyl)phenyl)pyrazol-4-ylmethyl)-1,4,9-triazaspiro[5.5]undecane.3hydrochloride

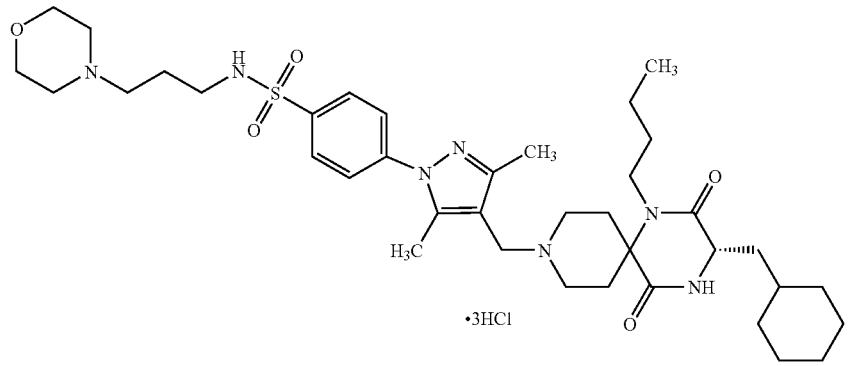

TLC: Rf 0.20 (ethyl acetate:methanol=3:1);

NMR (CD$_3$OD): δ 8.02 (d, J=8.7 Hz, 2H), 7.74 (d, J=8.7 Hz, 2H), 4.31 (s, 2H), 4.10–4.00 (m, 3H), 4.00–3.00 (m, 16H), 2.65–2.10 (m, 4H), 2.47 (s, 3H), 2.40 (s, 3H), 2.05–1.95 (m, 2H), 1.85–1.15 (m, 15H), 1.10–0.90 (m, 2H), 0.95 (t, J=7.2 Hz, 3H).

EXAMPLE 7(20)

(3S)-1-butyl-2,5-dioxo-3-cyclohexylmethyl-9-(4-(N,N-dimethylaminosulfonyl)phenylmethyl)-1,4,9-triazaspiro[5.5]undecane.hydrochloride

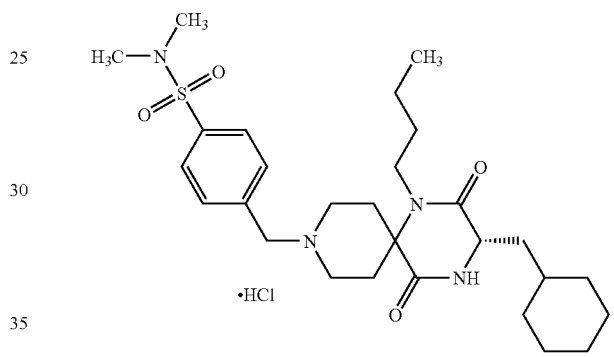

TLC: Rf 0.60 (chloroform:methanol=10:1);

NMR (CD$_3$OD): δ 7.90 (d, J=8.4 Hz, 2H), 7.84 (d, J=8.4 Hz, 2H), 4.48 (s, 2H), 4.04 (dd, J=7.5, 4.5 Hz, 1H), 3.94–3.76 (m, 2H), 3.56–3.36 (m, 4H), 2.71 (s, 6H), 2.56–2.36 (m, 2H), 2.28–2.06 (m, 2H), 1.83–1.10 (m, 15H), 1.08–0.85 (m, 2H), 0.95 (t, J=7.2 Hz, 3H).

EXAMPLE 7(21)

(3S)-1-butyl-2,5-dioxo-3-cyclohexylmethyl-9-(4-(pyrrolidin-1-ylcarbonyl)phenylmethyl)-1,4,9-triazaspiro[5.5]undecane.hydrochloride

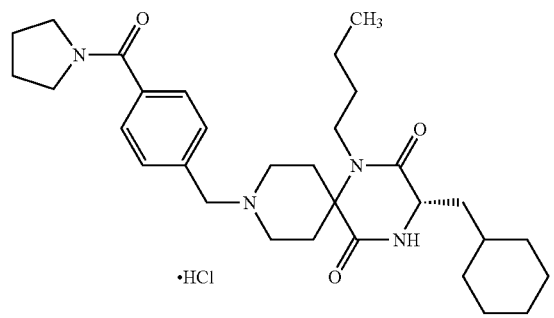

TLC: Rf 0.59 (chloroform:methanol=10:1);

NMR (CD$_3$OD): δ 7.68 (d, J=8.7 Hz, 2H), 7.63 (d, J=8.7 Hz, 2H), 4.41 (s, 2H), 4.04 (dd, J=7.5, 4.5 Hz, 1H), 3.92–3.73 (m, 2H), 3.60 (t, J=6.9 Hz, 2H), 3.55–3.34 (m, 4H), 3.45 (t, J=6.9 Hz, 2H), 2.56–2.36 (m, 2H), 2.27–2.07 (m, 2H), 2.06–1.84 (m, 4H), 1.83–1.10 (m, 15H), 1.06–0.83 (m, 2H), 0.95 (t, J=7.2 Hz, 3H).

EXAMPLE 7(22)

(3S)-1-butyl-2,5-dioxo-3-cyclohexylmethyl-9-(4-(4-(N,N-dimethylamino)phenyloxy)phenylmethyl)-1,4,9-triazaspiro[5.5]undecane.2hydrochloride

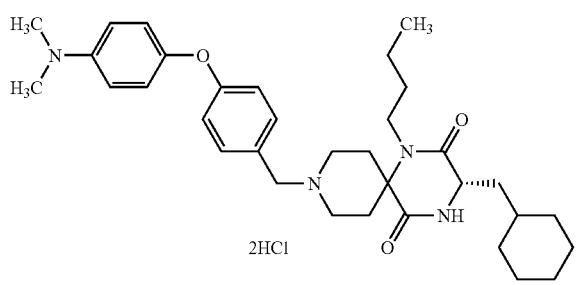

TLC: Rf 0.51 (chloroform:methanol=10:1);

NMR (CD$_3$OD): δ 7.70–7.62 (m, 4H), 7.22 (d, J=9.0 Hz, 2H), 7.14 (d, J=8.4 Hz, 2H), 4.36 (s, 2H), 4.03 (dd, J=7.5, 4.5 Hz, 1H), 3.86–3.70 (m, 2H), 3.52–3.40 (m, 4H), 3.30 (s, 6H), 2.62–2.44 (m, 2H), 2.24–2.06 (m, 2H), 1.80–1.14 (m, 15H), 1.02–0.86 (m, 5H).

EXAMPLE 7(23)

(3S)-1-butyl-2,5-dioxo-3-cyclohexylmethyl-9-(4-(cyclohexylaminocarbonyl)phenylmethyl)-1,4,9-triazaspiro[5.5]undecane.hydrochloride

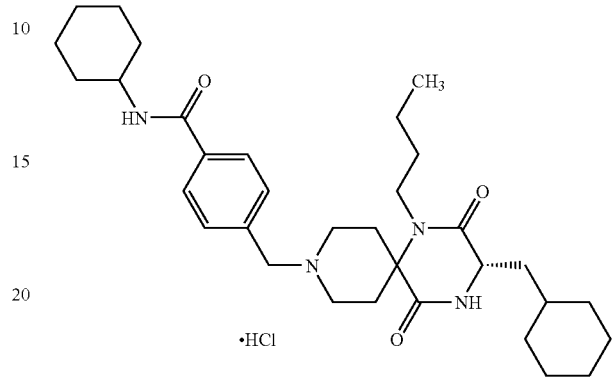

TLC: Rf 0.38 (chloroform:methanol=10:1);

NMR (CD$_3$OD): δ 7.91 (d, J=8.1 Hz, 2H), 7.68 (d, J=8.1 Hz, 2H), 4.42 (s, 2H), 4.03 (dd, J=7.5, 4.5 Hz, 1H), 3.90–3.72 (m, 3H), 3.52–3.36 (m, 4H), 2.56–2.38 (m, 2H), 2.24–2.06 (m, 2H), 2.00–1.10 (m, 25H), 1.04–0.86 (m, 5H).

EXAMPLE 7(24)

(3S)-1-butyl-2,5-dioxo-3-cyclohexylmethyl-9-(3,5-dimethyl-1-(4-methoxycarbonylphenyl)pyrazol-4-ylmethyl)-1,4,9-triazaspiro[5.5]undecane.2hydrochlorideundecane.2hydrochloride

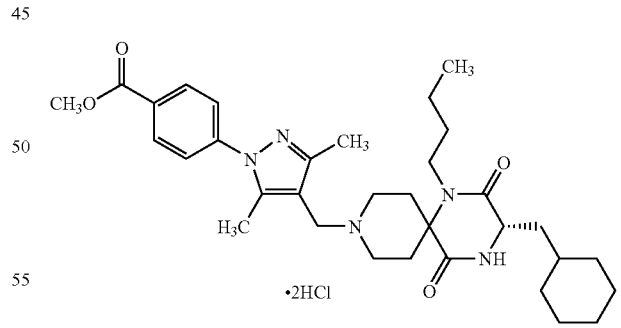

TLC: Rf 0.33 (ethyl acetate:methanol=10:1);

NMR (CD$_3$OD): δ 8.18 (d, J=8.7 Hz, 2H), 7.64 (d, J=8.7 Hz, 2H), 4.31 (s, 2H), 4.05 (m, 1H), 3.94 (s, 3H), 3.94–3.45 (m, 6H), 2.70–2.50 (m, 2H), 2.46 (s, 3H), 2.41 (s, 3H), 2.30–2.10 (m, 2H), 1.85–1.10 (m, 15H), 1.10–0.90 (m, 2H), 0.95 (t, J=6.9 Hz, 3H).

EXAMPLE 7(25)

(3S)-1-butyl-2,5-dioxo-3-cyclohexylmethyl-9-(4-(3-methoxypropylaminocarbonyl)phenylmethyl)-1,4,9-triazaspiro[5.5]undecane.hydrochlorideundecane.hydrochloride

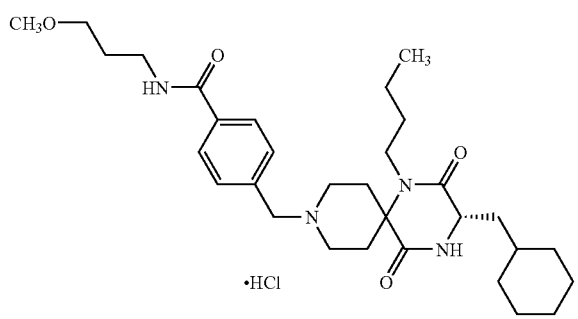

TLC: Rf 0.18 (ethyl acetate:methanol=10:1);
NMR (CD$_3$OD): δ 7.93 (d, J=8.4 Hz, 2H), 7.69 (d, J=8.4 Hz, 2H), 4.44 (s, 2H), 4.04 (dd, J=7.5, 4.8 Hz, 1H), 3.92–3.74 (m, 2H), 3.58–3.36 (m, 10H), 3.35 (s, 3H), 2.54–2.36 (m, 2H), 2.28–2.06 (m, 2H), 1.94–1.08 (m, 15H), 1.04–0.84 (m, 2H), 0.95 (t, J=6.9 Hz, 3H).

EXAMPLE 7(26)

(3S)-1-butyl-2,5-dioxo-3-cyclohexylmethyl-9-(4-(N-methyl-N-(2-(pyridin-2-yl)ethyl)aminocarbonyl)phenylmethyl)-1,4,9-triazaspiro[5.5]undecane.2hydrochlorideundecane.2hydrochloride

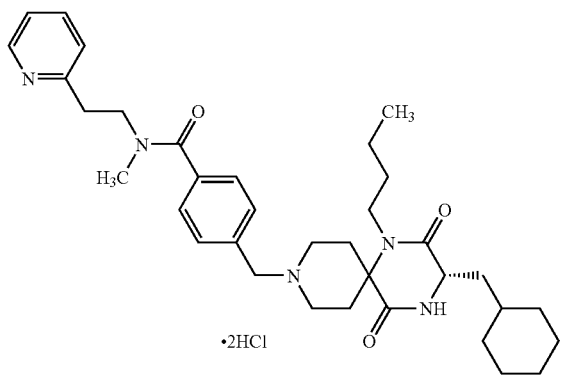

TLC: Rf 0.27 (ethyl acetate:methanol=10:1);
NMR (CD$_3$OD): δ 8.81 (m, 1H), 8.59 (m, 1H), 8.16–7.94 (m, 2H), 7.71 (d, J=7.8 Hz, 2H), 7.42 (d, J=7.8 Hz, 2H), 4.40 (s, 2H), 4.06–3.70 (m, 5H), 3.60–3.36 (m, 6H), 3.09 (s, 3H), 2.72–2.42 (m, 2H), 2.26–2.02 (m, 2H), 1.84–1.14 (m, 15H), 1.06–0.84 (m, 2H), 0.95 (t, J=6.9 Hz, 3H).

EXAMPLE 7(27)

(3S)-1-butyl-2,5-dioxo-3-cyclohexylmethyl-9-(4-((4-methoxyphenyl)methylaminocarbonyl)phenylmethyl)-1,4,9-triazaspiro[5.5]undecane.hydrochlorideundecane.hydrochloride

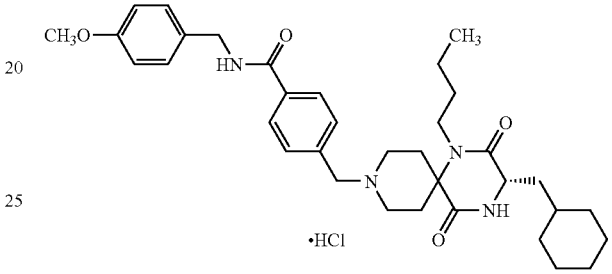

TLC: Rf 0.38 (chloroform:methanol=10:1);
NMR (CD$_3$OD): δ 7.96 (d, J=9.0 Hz, 2H), 7.69 (d, J=9.0 Hz, 2H), 7.28 (d, J=9.0 Hz, 2H), 6.88 (d, J=9.0 Hz, 2H), 4.52 (s, 2H), 4.43 (s, 2H), 4.04 (dd, J=7.5, 4.5 Hz, 1H), 3.92–3.78 (m, 2H), 3.77 (s, 3H), 3.56–3.36 (m, 4H), 2.52–2.34 (m, 2H), 2.26–2.06 (m, 2H), 1.82–1.10 (m, 15H), 1.06–0.84 (m, 2H), 0.95 (t, J=7.2 Hz, 3H).

EXAMPLE 7(28)

(3S)-1-butyl-2,5-dioxo-3-cyclohexylmethyl-9-(4-(4-methoxycarbonylphenyloxy)phenylmethyl)-1,4,9-triazaspiro[5.5]undecane.hydrochloride

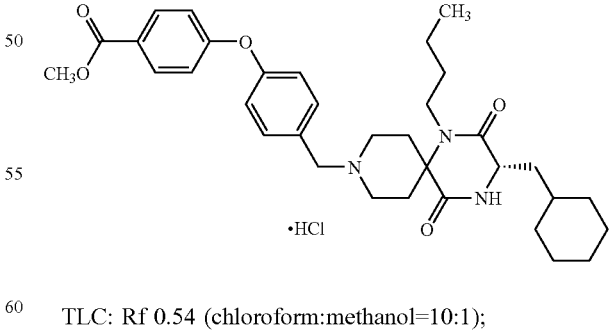

TLC: Rf 0.54 (chloroform:methanol=10:1);
NMR (CD$_3$OD): δ 8.04 (d, J=9.0 Hz, 2H), 7.63 (d, J=9.0 Hz, 2H), 7.19 (d, J=9.0 Hz, 2H), 7.08 (d, J=9.0 Hz, 2H), 4.38 (s, 2H), 4.05 (dd, J=7.5, 4.5 Hz, 1H), 3.90 (s, 3H), 3.88–3.72 (m, 2H), 3.58–3.38 (m, 4H), 2.58–2.38 (m, 2H), 2.28–2.08 (m, 2H), 1.84–1.08 (m, 15H), 1.06–0.86 (m, 2H), 0.96 (t, J=7.2 Hz, 3H).

EXAMPLE 7(29)

(3S)-1-butyl-2,5-dioxo-3-cyclohexylmethyl-9-(3,5-dimethyl-1-(4-methoxyphenyl)pyrazol-4-ylmethyl)-1,4,9-triazaspiro[5.5]undecane.2hydrochloride

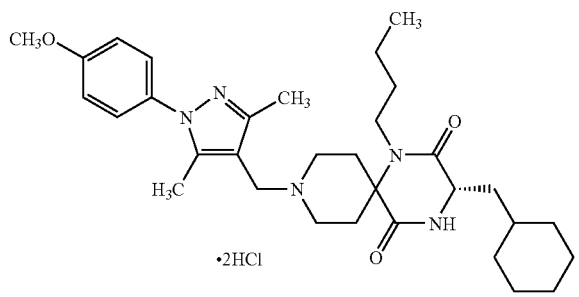

TLC: Rf 0.40 (chloroform:methanol=10:1);
NMR (CD$_3$OD): δ 7.42 (d, J=9.0 Hz, 2H), 7.12 (d, J=9.0 Hz, 2H), 4.33 (s, 2H), 4.06 (dd, J=7.5, 4.5 Hz, 1H), 3.96–3.76 (m, 2H), 3.88 (s, 3H), 3.68–3.40 (m, 4H), 2.68–2.48 (m, 2H), 2.45 (s, 3H), 2.38 (s, 3H), 2.32–2.08 (m, 2H), 1.84–1.12 (m, 15H), 1.06–0.84 (m, 2H), 0.97 (t, J=7.2 Hz, 3H).

EXAMPLE 7(30)

(3S)-1-butyl-2,5-dioxo-3-cyclohexylmethyl-9-(3,5-dimethyl-1-(1-methylpiperidin-4-yl)pyrazol-4-ylmethyl)-1,4,9-triazaspiro[5.5]undecane.3hydrochloride

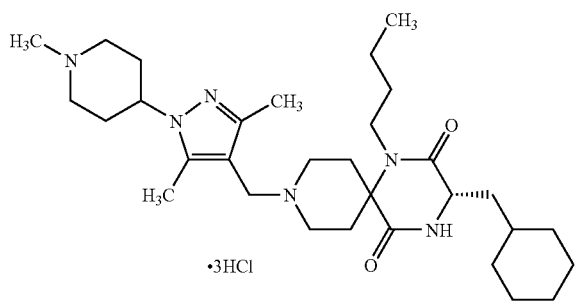

TLC: Rf 0.18 (chloroform:methanol=5:1);
NMR (CD$_3$OD): δ 4.58 (m, 1H), 4.21 (s, 2H), 4.03 (dd, J=7.5, 4.5 Hz, 1H), 3.86–3.42 (m, 8H), 3.32–3.20 (m, 2H), 2.93 (s, 3H), 2.70–2.50 (m, 2H), 2.50–2.26 (m, 2H), 2.45 (s, 3H), 2.33 (s, 3H), 2.24–2.04 (m, 4H), 1.82–1.06 (m, 15H), 1.02–0.86 (m, 5H).

EXAMPLE 7(31)

(3S)-1-butyl-2,5-dioxo-3-cyclohexylmethyl-9-(3,5-dimethyl-1-(1-methylsulfonylpiperidin-4-yl)pyrazol-4-ylmethyl)-1,4,9-triazaspiro[5.5]undecane.2hydrochloride

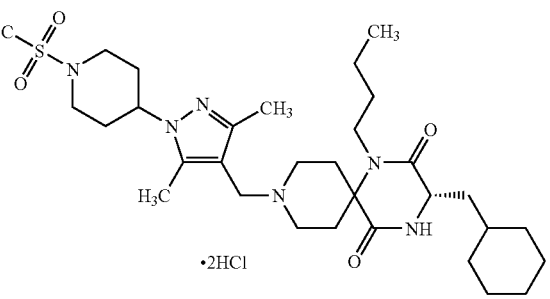

TLC: Rf 0.41 (chloroform:methanol=10:1);
NMR (CD$_3$OD): δ 4.44 (m, 1H), 4.24 (s, 2H), 4.04 (dd, J=7.8, 4.8 Hz, 1H), 3.92–3.68 (m, 4H), 3.60–3.40 (m, 4H), 3.02–2.90 (m, 2H), 2.89 (s, 3H), 2.60–2.40 (m, 2H), 2.46 (s, 3H), 2.36 (s, 3H), 2.26–1.96 (m, 6H), 1.82–1.10 (m, 15H), 1.02–0.86 (m, 5H).

EXAMPLE 7(32)

(3S)-1-butyl-2,5-dioxo-3-cyclohexylmethyl-9-(3,5-dimethyl-1-(4-(3-(N,N-dimethylamino)propylaminosulfonyl)phenyl)pyrazol-4-ylmethyl)-1,4,9-triazaspiro[5.5]undecane.3hydrochloride

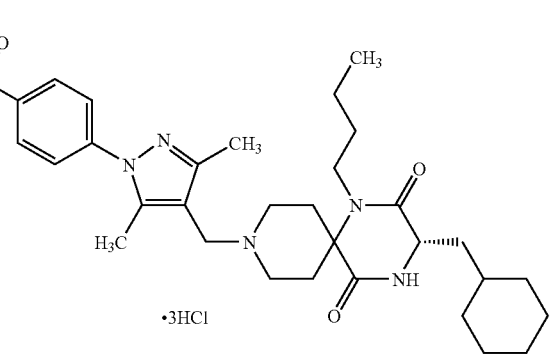

TLC: Rf 0.22 (chloroform:methanol:28% aqueous solution of ammonia=100:10:1);

NMR (CD$_3$OD): δ 8.02 (d, J=8.7 Hz, 2H), 7.74 (d, J=8.7 Hz, 2H), 4.30 (s, 2H), 4.04 (dd, J=7.5, 4.5 Hz, 1H), 3.94–3.73 (m, 2H), 3.66–3.56 (m, 2H), 3.54–3.43 (m, 2H), 3.27–3.18 (m, 2H), 3.05–2.97 (m, 2H), 2.89 (s, 6H), 2.68–2.51 (m, 2H), 2.48 (s, 3H), 2.40 (s, 3H), 2.28–2.08 (m, 2H), 2.00–1.88 (m, 2H), 1.84–1.10 (m, 15H), 1.04–0.88 (m, 5H).

EXAMPLE 7(33)

(3S)-1-butyl-2,5-dioxo-3-cyclohexylmethyl-9-(3,5-dimethyl-1-(4-(N-methyl-N-(2-(N',N'-dimethylamino)ethyl)aminosulfonylphenyl)pyrazol-4-ylmethyl)-1,4,9-triazaspiro[5.5]undecane.3hydrochloride

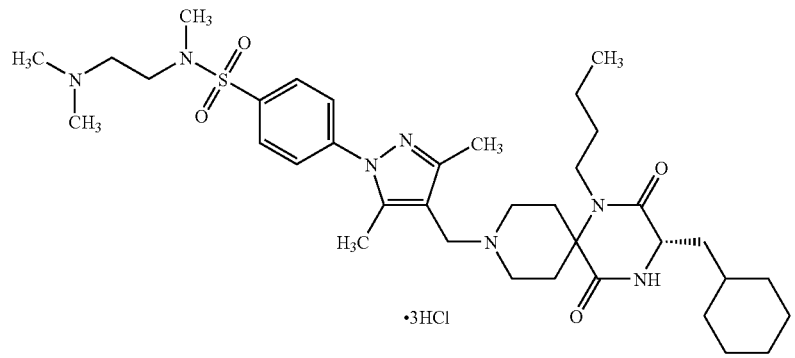

TLC: Rf 0.32 (chloroform:methanol:28% aqueous solution of ammonia=100:10:1);

NMR (CD$_3$OD): δ 8.04 (d, J=8.7 Hz, 2H), 7.82 (d, J=8.7 Hz, 2H), 4.30 (s, 2H), 4.04 (dd, J=7.5, 4.5 Hz, 1H), 3.94–3.74 (m, 2H), 3.67–3.56 (m, 2H), 3.55–3.45 (m, 2H), 3.42 (s, 4H), 3.01 (s, 6H), 2.85 (s, 3H), 2.72–2.53 (m, 2H), 2.50 (s, 3H), 2.41 (s, 3H), 2.27–2.08 (m, 2H), 1.84–1.11 (m, 15H), 1.06–0.84 (m, 5H).

EXAMPLE 7(34)

(3S)-1-butyl-2,5-dioxo-3-cyclohexylmethyl-9-(4-(piperidin-1-ylcarbonyl)phenylmethyl)-1,4,9-triazaspiro[5.5]undecane.hydrochloride

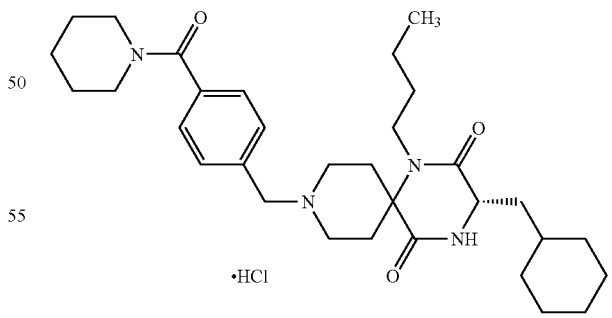

TLC: Rf 0.56 (chloroform:methanol=10:1);

NMR (CD$_3$OD): δ 7.68 (d, J=8.1 Hz, 2H), 7.50 (d, J=8.1 Hz, 2H), 4.41 (s, 2H), 4.04 (dd, J=7.5, 4.8 Hz, 1H), 3.92–3.65 (m, 4H), 3.56–3.30 (m, 6H), 2.57–2.36 (m, 2H), 2.26–2.07 (m, 2H), 1.83–1.10 (m, 21H), 1.06–0.83 (m, 2H), 0.95 (t, J=7.2 Hz, 3H).

EXAMPLE 7(35)

(3S)-1-butyl-2,5-dioxo-3-cyclohexylmethyl-9-(4-(morpholin-4-ylcarbonyl)phenylmethyl)-1,4,9-triaza-spiro[5.5]undecane.hydrochloride

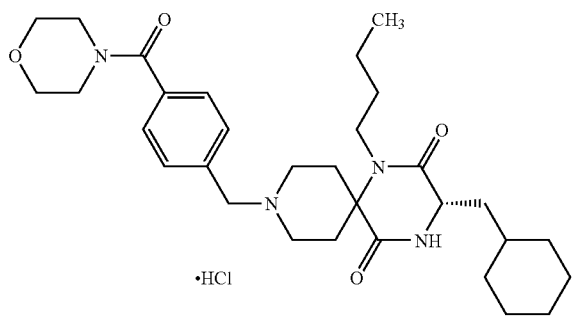

TLC: Rf 0.54 (chloroform:methanol=10:1);

NMR (CD$_3$OD): δ 7.69 (d, J=8.1 Hz, 2H), 7.55 (d, J=8.1 Hz, 2H), 4.41 (s, 2H), 4.04 (dd, J=7.5, 4.5 Hz, 1H), 3.91–3.55 (m, 8H), 3.55–3.30 (m, 6H), 2.57–2.37 (m, 2H), 2.27–2.05 (m, 2H), 1.83–1.08 (m, 15H), 1.06–0.83 (m, 2H), 0.94 (t, J=7.2 Hz, 3H).

EXAMPLE 7(36)

(3S)-1-butyl-2,5-dioxo-3-cyclohexylmethyl-9-(4-(4-((N,N-dimethylamino)methyl)phenyloxy)phenylmethyl)-1,4,9-triazaspiro[5.5]undecane.2hydrochloride

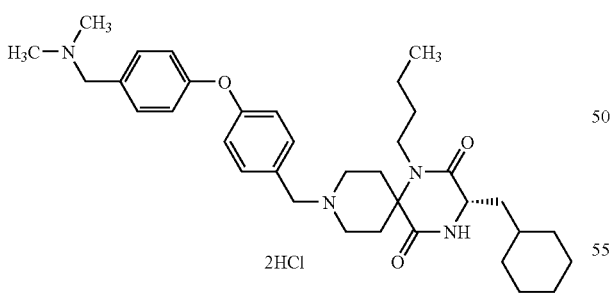

TLC: Rf 0.37 (chloroform:methanol=10:1);

NMR (CD$_3$OD): δ 7.62 (d, J=8.7 Hz, 2H), 7.53 (d, J=8.7 Hz, 2H), 7.16–7.10 (m, 4H), 4.35 (s, 2H), 4.31 (s, 2H), 4.04 (dd, J=7.5, 4.5 Hz, 1H), 3.86–3.70 (m, 2H), 3.52–3.38 (m, 4H), 2.86 (s, 6H), 2.62–2.46 (m, 2H), 2.26–2.06 (m, 2H), 1.82–1.12 (m, 15H), 1.06–0.88 (m, 5H).

EXAMPLE 7(37)

(3S)-1-butyl-2,5-dioxo-3-cyclohexylmethyl-9-(3,5-dimethyl-1-(4-methylaminocarbonylphenyl)pyrazol-4-ylmethyl)-1,4,9-triazaspiro[5.5]undecane.2hydrochloride

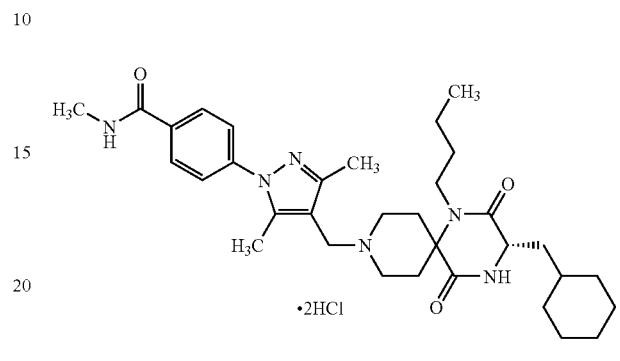

TLC: Rf 0.13 (ethyl acetate:methanol=10:1);

NMR (CD$_3$OD): δ 8.00 (d, J=8.7 Hz, 2H), 7.61 (d, J=8.7 Hz, 2H), 4.33 (s, 2H), 4.06 (dd, J=7.8, 4.8 Hz, 1H), 3.94–3.76 (m, 2H), 3.66–3.56 (m, 2H), 3.52–3.40 (m, 2H), 2.95 (s, 3H), 2.62–2.38 (m, 2H), 2.50 (s, 3H), 2.42 (s, 3H), 2.32–2.10 (m, 2H), 1.84–1.18 (m, 15H), 1.06–0.84 (m, 2H), 0.97 (t, J=6.9 Hz, 3H).

EXAMPLE 7(38)

(3S)-1-butyl-2,5-dioxo-3-cyclohexylmethyl-9-(3,5-dimethyl-1-(1,1-dimethylethyl)pyrazol-4-ylmethyl)-1,4,9-triazaspiro[5.5]undecane.2hydrochloride

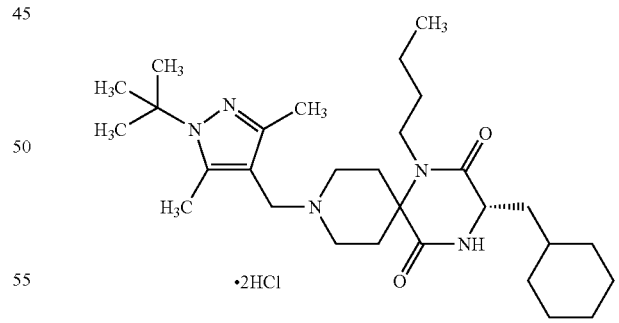

TLC: Rf 0.38 (ethyl acetate:methanol=4:1);

NMR (CD$_3$OD): δ 4.25 (s, 2H), 4.04 (dd, J=7.8, 4.8 Hz, 1H), 3.88–3.73 (m, 2H), 3.59–3.50 (m, 2H), 3.47–3.42 (m, 2H), 2.60 (s, 3H), 2.57–2.45 (m, 2H), 2.38 (s, 3H), 2.23–2.10 (m, 2H), 1.80–1.15 (m, 24H), 1.02–0.92 (m, 5H).

EXAMPLE 7(39)

(3S)-1-butyl-2,5-dioxo-3-cyclohexylmethyl-9-(3,5-dimethyl-1-(1-benzyloxycarbonylpiperidin-4-yl)pyrazol-4-ylmethyl)-1,4,9-triazaspiro[5.5]undecane.2hydrochloride

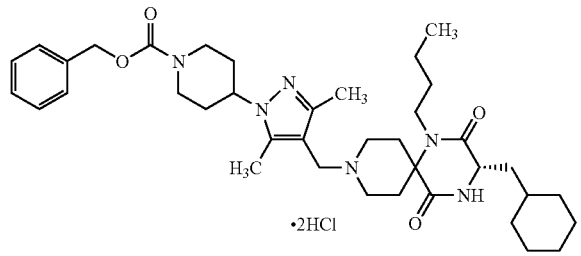

TLC: Rf 0.33(ethyl acetate:methanol=4:1);

NMR (CD$_3$OD): δ 7.39–7.29 (m, 5H), 5.14 (s, 2H), 4.52 (m, 1H), 4.33–4.29 (m, 2H), 4.25 (s, 2H), 4.04 (dd, J=7.8, 4.8 Hz, 1H), 3.87–3.72 (m, 2H), 3.55–3.42 (m, 4H), 3.10–2.98 (m, 2H), 2.60–2.43 (m, 5H), 2.36 (s, 3H), 2.23–1.95 (m, 6H), 1.80–1.15 (m, 15H), 1.02–0.92 (m, 5H).

EXAMPLE 7(40)

(3S)-1-butyl-2,5-dioxo-3-cyclohexylmethyl-9-(4-(4-hydroxymethylphenyloxy)phenylmethyl)-1,4,9-triazaspiro[5.5]undecane

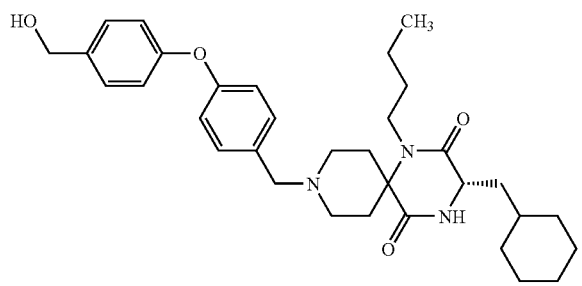

TLC: Rf 0.24 (chloroform:methanol=20:1);

NMR (CD$_3$OD): δ 7.34 (d, J=8.7 Hz, 2H), 7.31 (d, J=8.7 Hz, 2H), 6.95 (d, J=8.7 Hz, 2H), 6.94 (d, J=8.7 Hz, 2H), 4.57 (s, 2H), 4.00 (dd, J=7.5, 4.5 Hz, 1H), 3.55 (s, 2H), 3.47–3.38 (m, 2H), 2.93–2.74 (m, 4H), 2.24–2.04 (m, 2H), 2.00–1.83 (m, 2H), 1.83–1.08 (m, 15H), 1.05–0.84 (m, 2H), 0.95 (t, J=7.5 Hz, 3H).

EXAMPLE 7(41)

(3S)-1-butyl-2,5-dioxo-3-cyclohexylmethyl-9-(4-((methoxycarbonyl)methylaminocarbonyl)phenylmethyl)-1,4,9-triazaspiro[5.5]undecane

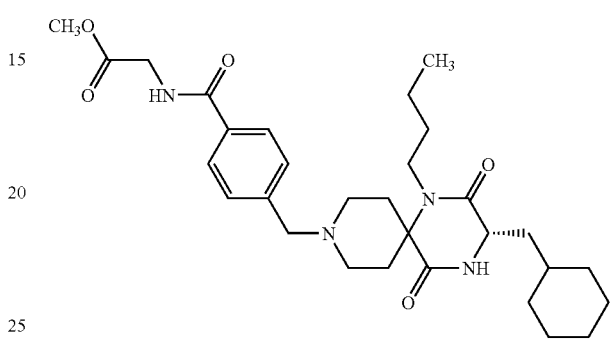

NMR (CDCl$_3$): δ 7.78 (d, J=8.1 Hz, 2H), 7.43 (d, J=8.1 Hz, 2H), 6.71 (t, J=4.8 Hz, 1H), 6.32 (brs, 1H), 4.26 (d, J=4.8 Hz, 2H), 4.00 (m, 1H), 3.81 (s, 3H), 3.64 (s, 2H), 3.54–3.28 (m, 2H), 3.06–2.72 (m, 8H), 2.26–1.10 (m, 15H), 1.06–0.82 (m, 2H), 0.94 (t, J=6.9 Hz, 3H).

EXAMPLE 8

(3S)-1-butyl-2,5-dioxo-3-cyclohexylmethyl-9-(4-(carboxymethylaminocarbonyl)phenylmethyl))-1,4,9-triazaspiro[5.5]undecane.hydrochloride

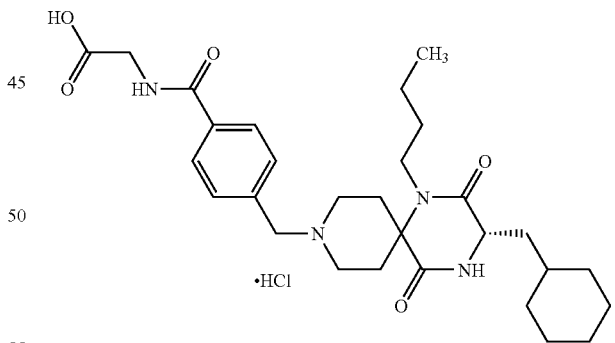

By the same procedure as described in Example 5 using the compound prepared in Example 7(41) instead of the compound prepared in Example 4(42), the title compound having the following physical data was obtained.

TLC: Rf 0.36 (butanol:acetic acid:water=4:2:1);

NMR (CD$_3$OD): δ 7.99 (d, J=8.1 Hz, 2H), 7.70 (d, J=8.1 Hz, 2H), 4.45 (s, 2H), 4.11 (s, 2H), 4.04 (dd, J=7.2, 4.5 Hz, 1H), 3.94–3.74 (m, 2H), 3.58–3.36 (m, 4H), 2.56–2.34 (m, 2H), 2.30–2.06 (m, 2H), 1.84–1.16 (m, 15H), 1.06–0.86 (m, 2H), 0.96 (t, J=7.2 Hz, 3H).

EXAMPLE 9

(3R)-1-butyl-2,5-dioxo-3-((1R)-1-hydroxy-1-cyclo-hexylmethyl)-9-(4-phenyloxyphenylmethyl)-1,4,9-triazaspiro[5.5]undecane.hydrochloride

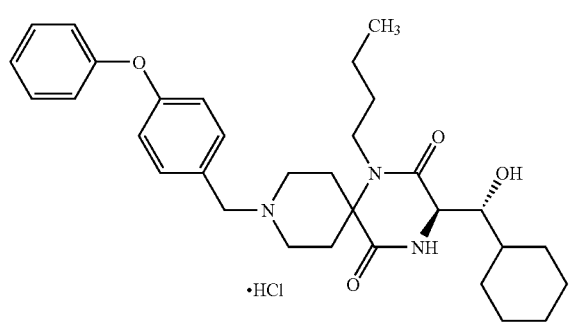

By the same procedure as described in Example 2 using the compound prepared in Reference example 3(3) instead of the compound prepared in Reference example 3, using 4-phenyloxybenzaldehyde instead of 3-formyl-6-phenyloxypyridine, the title compound having the following physical data was obtained.

TLC: Rf 0.46 (ethyl acetate:methanol=10:1);
NMR (CD$_3$OD): δ 7.50 (d, J=8.7 Hz, 2H), 7.42–7.37 (m, 2H), 7.18 (m, 1H), 7.07–7.01 (m, 4H), 4.31 (s, 2H), 4.15 (d, J=2.1 Hz, 1H), 3.97 (m, 1H), 3.71 (m, 1H), 3.60–3.05 (m, 5H), 2.55–1.90 (m, 6H), 1.90–1.60 (m, 5H), 1.60–1.10 (m, 6H), 1.10–0.90 (m, 2H), 0.95 (t, J=7.2 Hz, 3H).

EXAMPLE 9(1)–9(71)

By the same procedure as described in Example 9 using the corresponding aldehyde derivatives respectively instead of 4-phenyloxybenzaldehyde, the following compounds having the following physical data were obtained.

EXAMPLE 9(1)

(3R)-1-butyl-2,5-dioxo-3-((1R)-1-hydroxy-1-cyclo-hexylmethyl)-9-(6-phenyloxypyridin-3-ylmethyl)-1,4,9-triazaspiro[5.5]undecane.2hydrochloride

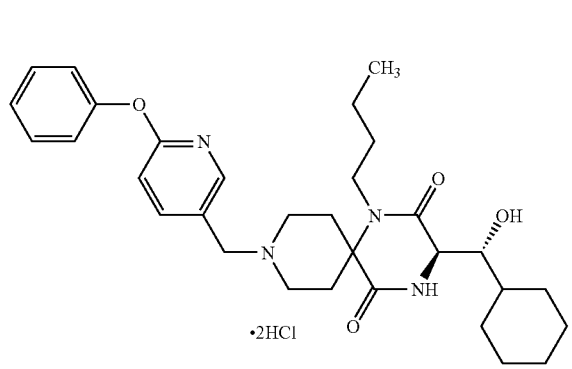

TLC: Rf 0.36 (ethyl acetate:methanol=10:1);
NMR (CD$_3$OD): δ 8.28 (d, J=2.7 Hz, 1H), 8.01 (dd, J=8.4, 2.7 Hz, 1H), 7.43 (t, J=8.4 Hz, 2H), 7.25 (t, J=8.4 Hz, 1H), 7.13 (d, J=8.4 Hz, 2H), 7.06 (d, J=8.4 Hz, 1H), 4.38 (s, 2H), 4.15 (d, J=1.8 Hz, 1H), 4.02 (m, 1H), 3.77 (m, 1H), 3.60–3.05 (m, 5H), 2.55–1.90 (m, 6H), 1.90–1.60 (m, 5H), 1.60–1.10 (m, 6H), 1.10–0.90 (m, 2H), 0.95 (t, J=7.2 Hz, 3H).

EXAMPLE 9(2)

(3R)-1-butyl-2,5-dioxo-3-((1R)-1-hydroxy-1-cyclo-hexylmethyl)-9-(4-(4-fluorophenyloxy)phenylmethyl)-1,4,9-triazaspiro[5.5]undecane.hydrochloride

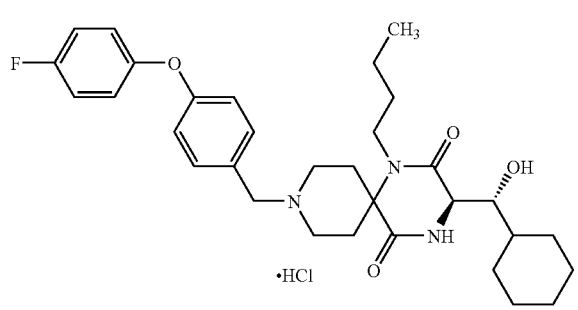

TLC: Rf 0.48 (chloroform:methanol=9:1);
NMR (CD$_3$OD): δ 7.54–7.48 (m, 2H), 7.14 (dd, J=9.6, 8.1 Hz, 2H), 7.09–7.02 (m, 4H), 4.33 (s, 2H), 4.15 (d, J=2.1 Hz, 1H), 4.00 (m, 1H), 3.73 (m, 1H), 3.57–3.40 (m, 3H), 3.33–3.08 (m, 2H), 2.54–1.88 (m, 6H), 1.82–1.63 (m, 5H), 1.48–1.12 (m, 6H), 1.03–0.85 (m, 2H), 0.95 (t, J=7.2 Hz, 3H).

EXAMPLE 9(3)

(3R)-1-butyl-2,5-dioxo-3-((1R)-1-hydroxy-1-cyclo-hexylmethyl)-9-(4-(4-chlorophenyloxy)phenylmethyl)-1,4,9-triazaspiro[5.5]undecane.hydrochloride

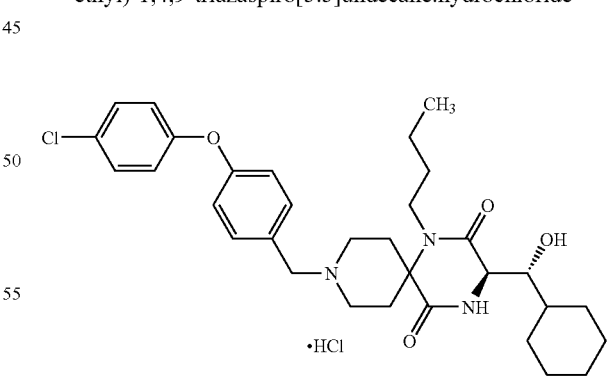

TLC: Rf 0.50 (chloroform:methanol=9:1);
NMR (CD$_3$OD): δ 7.58–7.51 (m, 2H), 7.38 (d, J=9.3 Hz, 2H), 7.09 (brd, J=8.4 Hz, 2H), 7.02 (d, J=9.3 Hz, 2H), 4.34 (s, 2H), 4.15 (d, J=2.1 Hz, 1H), 3.99 (m, 1H), 3.73 (m, 1H), 3.58–3.40 (m, 3H), 3.32–3.09 (m, 2H), 2.53–1.89 (m, 6H), 1.81–1.62 (m, 5H), 1.48–1.13 (m, 6H), 1.03–0.82 (m, 2H), 0.95 (t, J=7.2 Hz, 3H).

EXAMPLE 9(4)

(3R)-1-butyl-2,5-dioxo-3-((1R)-1-hydroxy-1-cyclohexylmethyl)-9-(4-(4-cyanophenyloxy)phenylmethyl)-1,4,9-triazaspiro[5.5]undecane.hydrochloride

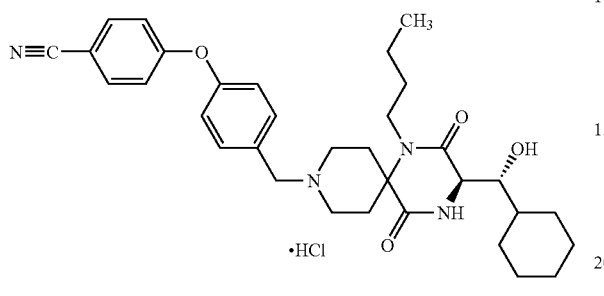

TLC: Rf 0.52 (chloroform:methanol=9:1);

NMR (CD$_3$OD): δ 7.74 (d, J=9.0 Hz, 2H), 7.64–7.58 (m, 2H), 7.21 (d, J=8.4 Hz, 2H), 7.13 (d, J=9.0 Hz, 2H), 4.38 (s, 2H), 4.16 (d, J=2.1 Hz, 1H), 4.02 (m, 1H), 3.77 (m, 1H), 3.57–3.43 (m, 3H), 3.33–3.08 (m, 2H), 2.54–1.90 (m, 6H), 1.80–1.63 (m, 5H), 1.48–1.13 (m, 6H), 1.03–0.82 (m, 2H), 0.96 (t, J=7.2 Hz, 3H).

EXAMPLE 9(5)

(3R)-1-butyl-2,5-dioxo-3-((1R)-1-hydroxy-1-cyclohexylmethyl)-9-(4-(4-methylsulfonylaminophenyloxy)phenylmethyl)-1,4,9-triazaspiro[5.5]undecane.hydrochloride

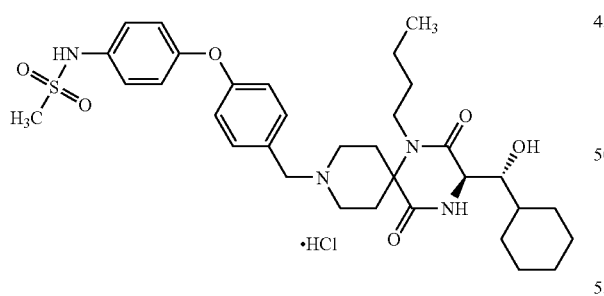

TLC: Rf 0.41 (chloroform:methanol=9:1);

NMR (CD$_3$OD): δ 7.53 (d, J=8.7 Hz, 2H), 7.29 (d, J=8.7 Hz, 2H), 7.06 (d, J=8.7 Hz, 2H), 7.03 (d, J=8.7 Hz, 2H), 4.33 (s, 2H), 4.15 (d, J=1.8 Hz, 1H), 3.98 (m, 1H), 3.73 (m, 1H), 3.58–3.40 (m, 3H), 3.32–3.03 (m, 2H), 2.95 (s, 3H), 2.52–2.24 (m, 3H), 2.17–1.88 (m, 3H), 1.80–1.62 (m, 5H), 1.48–1.08 (m, 6H), 1.03–0.82 (m, 2H), 0.95 (t, J=7.2 Hz, 3H).

EXAMPLE 9(6)

(3R)-1-butyl-2,5-dioxo-3-((1R)-1-hydroxy-1-cyclohexylmethyl)-9-(4-(6-methylpyridin-3-yloxy)phenylmethyl)-1,4,9-triazaspiro[5.5]undecane.2hydrochloride

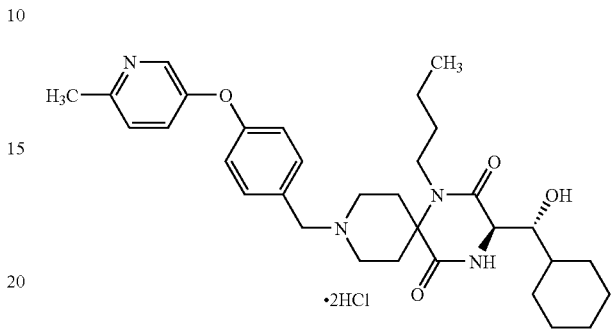

TLC: Rf 0.21 (ethyl acetate:methanol=10:1);

NMR (CD$_3$OD): δ 8.54 (d, J=3.0 Hz, 1H), 8.08 (m, 1H), 7.82 (d, J=9.0 Hz, 1H), 7.70 (d, J=9.0 Hz, 2H), 7.28 (d, J=9.0 Hz, 2H), 4.39 (s, 2H), 4.10 (d, J=2.1 Hz, 1H), 4.01 (m, 1H), 3.75 (m, 1H), 3.60–3.20 (m, 5H), 2.73 (s, 3H), 2.70–2.35 (m, 3H), 2.20–1.90 (m, 3H), 1.90–1.60 (m, 5H), 1.50–1.15 (m, 6H), 1.10–0.90 (m, 2H), 0.95 (t, J=7.2 Hz, 3H).

EXAMPLE 9(7)

(3R)-1-butyl-2,5-dioxo-3-((1R)-1-hydroxy-1-cyclohexylmethyl)-9-(4-(1-methylethyl)phenylmethyl)-1,4,9-triazaspiro[5.5]undecane.hydrochloride

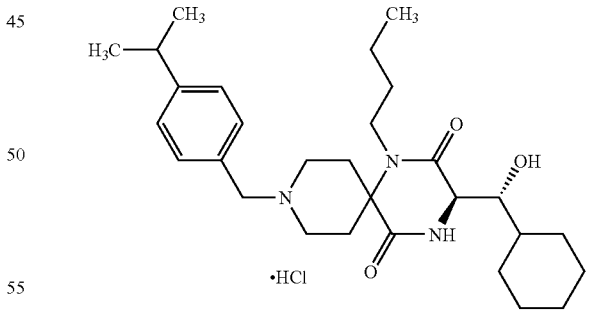

TLC: Rf 0.41 (ethyl acetate:methanol=10:1);

NMR (CD$_3$OD): δ 7.45 (d, J=8.1 Hz, 2H), 7.37 (d, J=8.1 Hz, 2H), 4.30 (s, 2H), 4.15 (d, J=2.1 Hz, 1H), 3.98 (m, 1H), 3.72 (m, 1H), 3.60–3.05 (m, 5H), 2.95 (quint, J=6.9 Hz, 1H), 2.50–1.90 (m, 6H), 1.85–1.60 (m, 5H), 1.50–1.10 (m, 6H), 1.25 (d, J=6.9 Hz, 6H), 1.10–0.90 (m, 2H), 0.95 (t, J=6.9 Hz, 3H).

EXAMPLE 9(8)

(3R)-1-butyl-2,5-dioxo-3-((1R)-1-hydroxy-1-cyclohexylmethyl)-9-(4-(4-methylsulfinylphenyloxy)phenylmethyl)-1,4,9-triazaspiro[5.5]undecane.hydrochloride

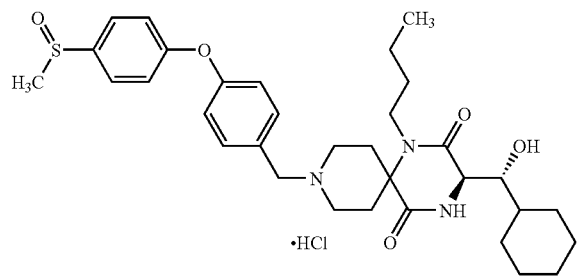

TLC: Rf 0.32 (chloroform:methanol=9:1);

NMR (CD₃OD): δ 7.74 (d, J=9.0 Hz, 2H), 7.61 (d, J=9.0 Hz, 2H), 7.22 (d, J=9.0 Hz, 2H), 7.17 (d, J=9.0 Hz, 2H), 4.36 (s, 2H), 4.16 (d, J=2.1 Hz, 1H), 4.00 (dt, J=3.6, 12.6 Hz, 1H), 3.75 (dt, J=3.6, 12.6 Hz, 1H), 3.58–3.42 (m, 3H), 3.32–3.13 (m, 2H), 2.80 (s, 3H), 2.54–2.25 (m, 3H), 2.17–1.88 (m, 3H), 1.80–1.63 (m, 5H), 1.49–1.13 (m, 6H), 1.02–0.82 (m, 2H), 0.96 (t, J=7.2 Hz, 3H).

EXAMPLE 9(9)

(3R)-1-butyl-2,5-dioxo-3-((1R)-1-hydroxy-1-cyclohexylmethyl)-9-(4-(3,4,5,6-tetrahydropyran-4-yloxy)phenylmethyl)-1,4,9-triazaspiro[5.5]undecane.hydrochloride

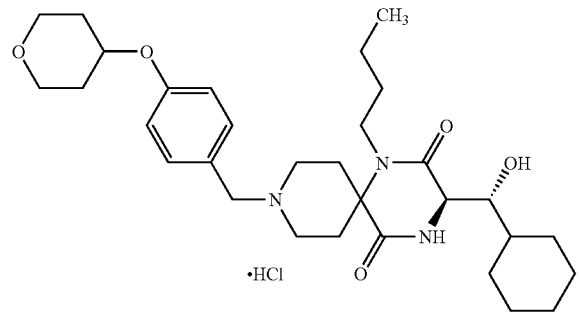

TLC: Rf 0.43(ethyl acetate:methanol=4:1);

NMR (CD₃OD): δ 7.45 (d, J=9.0 Hz, 2H), 7.06 (d, J=9.0 Hz, 2H), 4.63 (m, 1H), 4.28 (s, 2H), 4.15 (d, J=2.0 Hz, 1H), 4.01–3.90 (m, 3H), 3.72 (m, 1H), 3.63–3.53 (m, 2H), 3.50–3.41 (m, 3H), 3.27 (m, 1H), 3.15 (m, 1H), 2.50–1.91 (m, 8H), 1.68–1.65 (m, 7H), 1.39–1.15 (m, 6H), 1.01–0.87 (m, 5H).

EXAMPLE 9(10)

(3R)-1-butyl-2,5-dioxo-3-((1R)-1-hydroxy-1-cyclohexylmethyl)-9-(4-phenylcarbonylphenylmethyl)-1,4,9-triazaspiro[5.5]undecane.hydrochloride

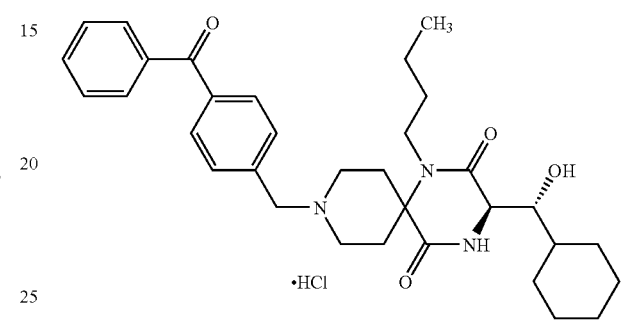

TLC: Rf 0.75 (ethyl acetate:methanol=4:1);

NMR (CD₃OD): δ 7.87 (d, J=7.5 Hz, 2H), 7.81–7.72 (m, 4H), 7.67 (t, J=7.5 Hz, 1H), 7.54 (t, J=7.5 Hz, 2H), 4.48 (s, 2H), 4.16 (d, J=2.0 Hz, 1H), 4.07 (m, 1H), 3.81 (m, 1H), 3.53–3.47 (m, 3H), 3.33–3.17 (m, 2H), 2.51–2.31 (m, 3H), 2.17–1.92 (m, 3H), 1.76–1.70 (m, 5H), 1.40–1.15 (m, 6H), 1.01–0.87 (m, 5H).

EXAMPLE 9(11)

(3R)-1-butyl-2,5-dioxo-3-((1R)-1-hydroxy-1-cyclohexylmethyl)-9-(4-(1-phenyl-1-hydroxymethyl)phenylmethyl)-1,4,9-triazaspiro[5.5]undecane.hydrochloride

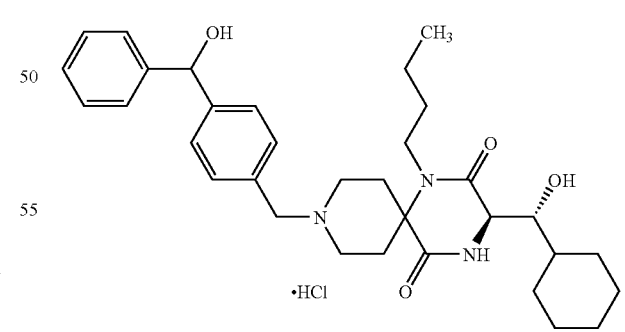

TLC: Rf 0.57 (ethyl acetate:methanol=4:1);

NMR (CD₃OD): δ 7.53 (d, J=8.0 Hz, 2H), 7.48 (d, J=8.0 Hz, 2H), 7.39–7.20 (m, 5H), 5.81 (s, 1H), 4.33 (s, 2H), 4.14 (d, J=2.0 Hz, 1H), 4.00 (m, 1H), 3.74 (m, 1H), 3.45–3.41 (m, 3H), 3.26 (m, 1H), 3.10 (m, 1H), 2.48–1.91 (m, 6H), 1.80–1.60 (m, 5H), 1.44–1.14 (m, 6H), 1.00–0.86 (m, 5H).

EXAMPLE 9(12)

(3R)-1-butyl-2,5-dioxo-3-((1R)-1-hydroxy-1-cyclo-hexylmethyl)-9-(3,5-dimethyl-1-(4-(morpholin-4-ylsulfonyl)phenyl)pyrazol-4-ylmethyl)-1,4,9-triaza-spiro[5.5]undecane.2hydrochloride

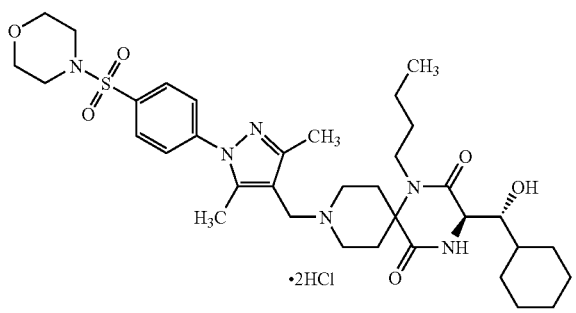

TLC: Rf 0.49(chloroform:methanol=10:1);
NMR (CD$_3$OD): δ 7.95 (d, J=8.7 Hz, 2H), 7.79 (d, J=8.7 Hz, 2H), 4.31 (s, 2H), 4.17 (d, J=2.1 Hz, 1H), 4.04 (m, 1H), 3.79 (m, 1H), 3.75–3.67 (m, 4H), 3.64–3.49 (m, 3H), 3.35–3.18 (m, 2H), 3.05–2.97 (m, 4H), 2.66–2.34 (m, 3H), 2.49 (s, 3H), 2.40 (s, 3H), 2.20–1.87 (m, 3H), 1.84–1.60 (m, 5H), 1.52–1.10 (m, 6H), 1.05–0.80 (m, 2H), 0.96 (t, J=7.2 Hz, 3H).

EXAMPLE 9(13)

(3R)-1-butyl-2,5-dioxo-3-((1R)-1-hydroxy-1-cyclo-hexylmethyl)-9-(3,5-dimethyl-1-(4-methylaminosul-fonylphenyl)pyrazol-4-ylmethyl)-1,4,9-triazaspiro[5.5]undecane.2hydrochloride

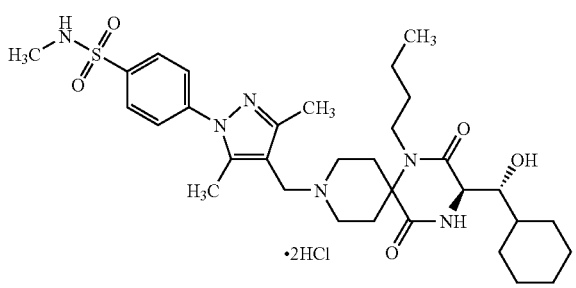

TLC: Rf 0.36 (ethyl acetate:methanol=4:1);
NMR (CD$_3$OD): δ 8.01 (d, J=8.7 Hz, 2H), 7.73 (d, J=8.7 Hz, 2H), 4.31 (s, 2H), 4.16 (d, J=2.0 Hz, 1H), 4.05 (m, 1H), 3.80 (m, 1H), 3.63–3.53 (m, 3H), 3.34–3.23 (m, 2H), 2.59–2.34 (m, 3H), 2.57 (s, 3H), 2.46 (s, 3H), 2.39 (s, 3H), 2.16 (m, 1H), 2.05–1.93 (m, 2H), 1.77–1.66 (m, 5H), 1.45–1.17 (m, 6H), 1.01–0.88 (m, 5H).

EXAMPLE 9(14)

(3R)-1-butyl-2,5-dioxo-3-((1R)-1-hydroxy-1-cyclo-hexylmethyl)-9-(3,5-dimethyl-1-(4-(N-methyl-N-(2-hydroxyethyl)aminosulfonyl)phenyl)pyrazol-4-ylm-ethyl)-1,4,9-triazaspiro[5.5]undecane.2hydrochloride

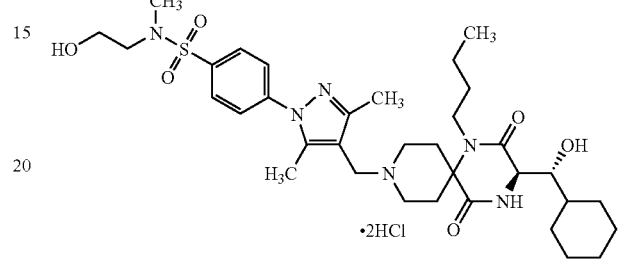

TLC: Rf 0.44 (chloroform:methanol=10:1);
NMR (CD$_3$OD): δ 7.98 (d, J=8.7 Hz, 2H), 7.75 (d, J=8.7 Hz, 2H), 4.31 (s, 2H), 4.17 (d, J=2.0 Hz, 1H), 4.04 (m, 1H), 3.78 (m, 1H), 3.69 (t, J=5.7 Hz, 2H), 3.64–3.50 (m, 3H), 3.38–3.24 (m, 2H), 3.19 (t, J=5.7 Hz, 2H), 2.87 (s, 3H), 2.60–2.34 (m, 3H), 2.47 (s, 3H), 2.40 (s, 3H), 2.20–1.88 (m, 3H), 1.82–1.60 (m, 5H), 1.50–1.12 (m, 6H), 1.04–0.82 (m, 5H).

EXAMPLE 9(15)

(3R)-1-butyl-2,5-dioxo-3-((1R)-1-hydroxy-1-cyclo-hexylmethyl)-9-(3,5-dimethyl-1-(pyridin-2-yl)pyra-zol-4-ylmethyl)-1,4,9-triazaspiro[5.5]undecane.2hydrochloride

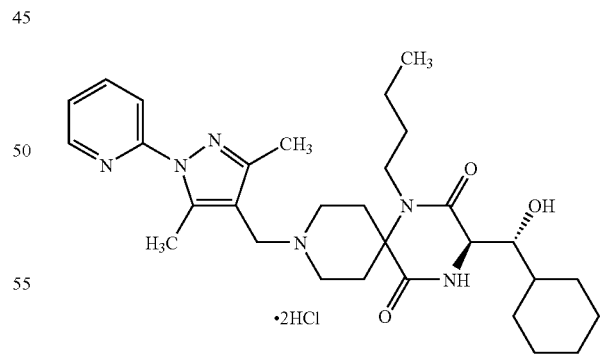

TLC: Rf 0.40 (ethyl acetate:methanol=4:1);
NMR (CD$_3$OD): δ 8.51 (d, J=4.5 Hz, 1H), 8.01 (m, 1H), 7.80 (d, J=8.0 Hz, 1H), 7.41 (m, 1H), 4.32 (s, 2H), 4.16 (d, J=2.0 Hz, 1H), 4.05 (m, 1H), 3.80 (m, 1H), 3.60–3.49 (m, 3H), 3.33–3.10 (m, 2H), 2.67 (s, 3H), 2.53–2.35 (m, 3H), 2.41 (s, 3H), 2.16 (m, 1H), 2.05–1.93 (m, 2H), 1.80–1.65 (m, 5H), 1.50–1.15 (m, 6H), 1.01–0.88 (m, 5H).

EXAMPLE 9(16)

(3R)-1-butyl-2,5-dioxo-3-((1R)-1-hydroxy-1-cyclohexylmethyl)-9-(3,5-dimethyl-1-cyclohexylpyrazol-4-ylmethyl)-1,4,9-triazaspiro[5.5]undecane.2hydrochloride

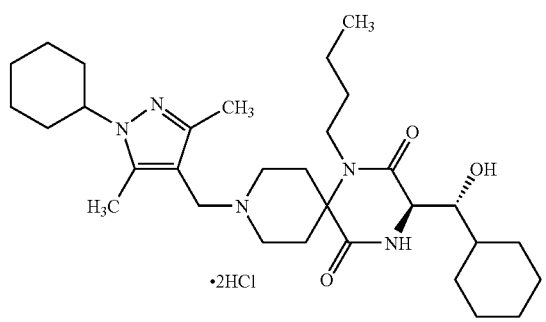

TLC: Rf 0.34 (ethyl acetate:methanol=4:1);

NMR (CD$_3$OD): δ 4.32 (m, 1H), 4.27 (s, 2H), 4.15 (d, J=2.0 Hz, 1H), 4.00 (m, 1H), 3.73 (m, 1H), 3.60–3.50 (m, 3H), 3.37–3.20 (m, 2H), 2.58–2.40 (m, 9H), 2.13–1.70 (m, 15H), 1.58–1.15 (m, 9H), 1.01–0.88 (m, 5H).

EXAMPLE 9(17)

(3R)-1-butyl-2,5-dioxo-3-((1R)-1-hydroxy-1-cyclohexylmethyl)-9-(1,3,5-trimethylpyrazol-4-ylmethyl)-1,4,9-triazaspiro[5.5]undecane.2hydrochloride

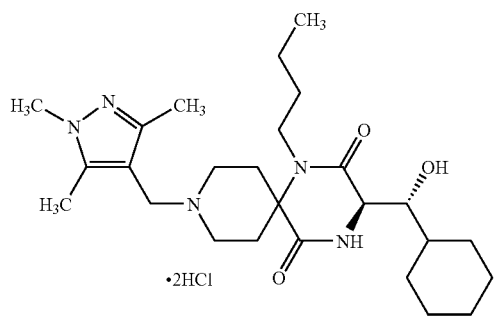

TLC: Rf 0.28 (chloroform:methanol=10:1);

NMR (CD$_3$OD): δ 4.27 (s, 2H), 4.15 (d, J=2.1 Hz, 1H), 3.98 (m, 1H), 3.85 (s, 3H), 3.73 (m, 1H), 3.62–3.56 (m, 3H), 3.40–3.20 (m, 2H), 2.60 (m, 1H), 2.50–2.36 (m, 2H), 2.45 (s, 3H), 2.41 (s, 3H), 2.16–1.88 (m, 3H), 1.84–1.60 (m, 5H), 1.50–1.10 (m, 6H), 1.04–0.80 (m, 2H), 0.95 (t, J=7.2 Hz, 3H).

EXAMPLE 9(18)

(3R)-1-butyl-2,5-dioxo-3-((1R)-1-hydroxy-1-cyclohexylmethyl)-9-(3,5-dimethyl-1-(4-(N,N-dimethylaminocarbonyl)phenyl)pyrazol-4-ylmethyl)-1,4,9-triazaspiro[5.5]undecane.2hydrochloride

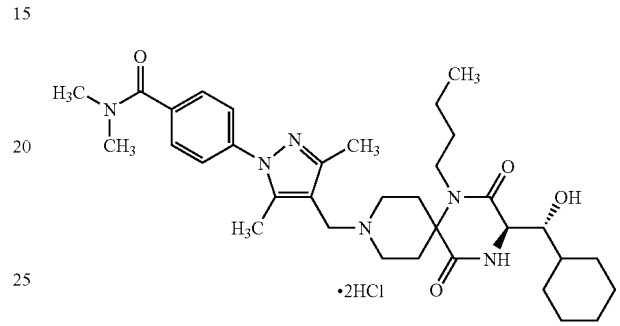

TLC: Rf 0.19(ethyl acetate:methanol=4:1);

NMR (CD$_3$OD): δ 7.62 (d, J=9.0 Hz, 2H), 7.58 (d, J=9.0 Hz, 2H), 4.32 (s, 2H), 4.17 (d, J=2.0 Hz, 1H), 4.05 (m, 1H), 3.80 (m, 1H), 3.60–3.53 (m, 3H), 3.33–3.27 (m, 2H), 3.13 (s, 3H), 3.04 (s, 3H), 2.53–2.35 (m, 3H), 2.42 (s, 3H), 2.39 (s, 3H), 2.17 (m, 1H), 2.05–1.92 (m, 2H), 1.77–1.65 (m, 5H), 1.39–1.15 (m, 6H), 1.01–0.88 (m, 5H).

EXAMPLE 9(19)

(3R)-1-butyl-2,5-dioxo-3-((1R)-1-hydroxy-1-cyclohexylmethyl)-9-(4-(N,N-bismethylsulfonyl)phenylmethyl)-1,4,9-triazaspiro[5.5]undecane.hydrochloride

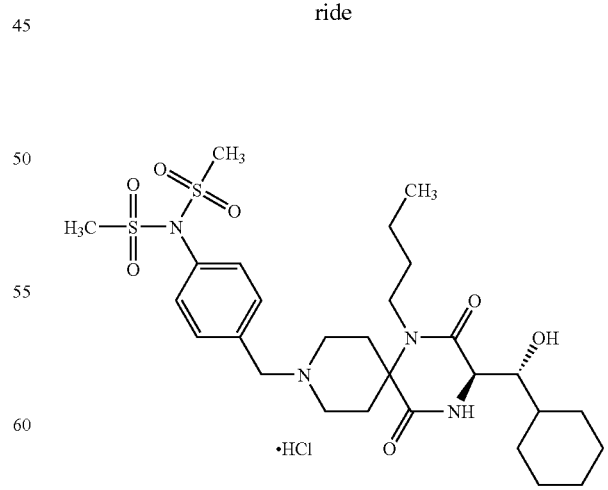

TLC: Rf 0.47 (ethyl acetate:methanol=10:1);

NMR (CD$_3$OD): δ 7.69 (d, J=8.4 Hz, 2H), 7.60 (d, J=8.4 Hz, 2H), 4.42 (s, 2H), 4.16 (d, J=2.1 Hz, 1H), 4.06 (m, 1H), 3.80 (m, 1H), 3.60–3.10 (m, 5H), 3.46 (s, 6H), 2.55–1.90 (m, 6H), 1.90–1.60 (m, 5H), 1.50–1.10 (m, 6H), 1.10–0.90 (m, 2H), 0.95 (t, J=6.9 Hz, 3H).

EXAMPLE 9(20)

(3R)-1-butyl-2,5-dioxo-3-((1R)-1-hydroxy-1-cyclohexylmethyl)-9-(3,5-dimethyl-1-(4-methylsulfonylaminophenyl)pyrazol-4-ylmethyl)-1,4,9-triazaspiro[5.5]undecane.2hydrochloride

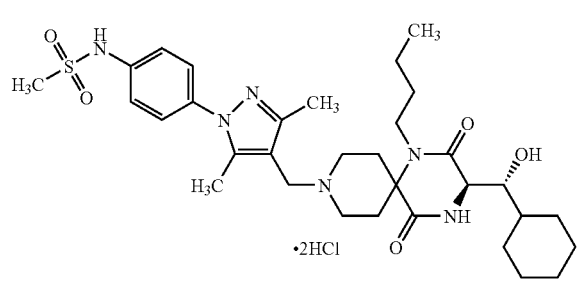

TLC: Rf 0.30 (chloroform:methanol=9:1);

NMR (CD$_3$OD): δ 7.48–7.38 (m, 4H), 4.30 (s, 2H), 4.17 (d, J=2.1 Hz, 1H), 4.03 (m, 1H), 3.78 (m, 1H), 3.62–3.49 (m, 3H), 3.37–3.21 (m, 2H), 3.04 (s, 3H), 2.62–2.35 (m, 3H), 2.40 (s, 3H), 2.38 (s, 3H), 2.18–1.90 (m, 3H), 1.83–1.63 (m, 5H), 1.48–1.13 (m, 6H), 1.03–0.82 (m, 2H), 0.96 (t, J=7.2 Hz, 3H).

EXAMPLE 9(21)

(3R)-1-butyl-2,5-dioxo-3-((1R)-1-hydroxy-1-cyclohexylmethyl)-9-(3,5-dimethyl-1-(4-(N,N-dimethylsulfonyl)phenyl)pyrazol-4-ylmethyl)-1,4,9-triazaspiro[5.5]undecane.2hydrochloride

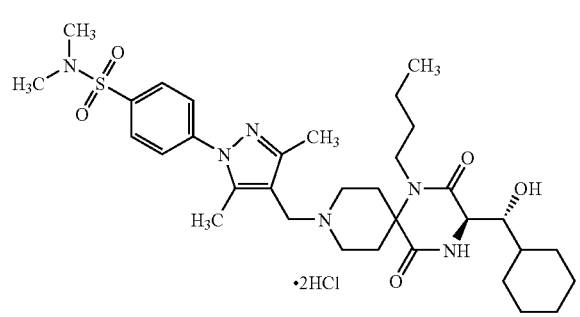

TLC: Rf 0.36 (chloroform:methanol=9:1);

NMR (CD$_3$OD): δ 7.96 (d, J=8.7 Hz, 2H), 7.77 (d, J=8.7 Hz, 2H), 4.32 (s, 2H), 4.17 (d, J=2.1 Hz, 1H), 4.05 (m, 1H), 3.79 (m, 1H), 3.63–3.48 (m, 3H), 3.34–3.15 (m, 2H), 2.74 (s, 6H), 2.58–2.32 (m, 3H), 2.47 (s, 3H), 2.40 (s, 3H), 2.21–1.90 (m, 3H), 1.82–1.62 (m, 5H), 1.48–1.13 (m, 6H), 1.03–0.82 (m, 2H), 0.96 (t, J=7.2 Hz, 3H).

EXAMPLE 9(22)

(3R)-1-butyl-2,5-dioxo-3-((1R)-1-hydroxy-1-cyclohexylmethyl)-9-(3,5-dimethyl-1-(4-(pyrrolidin-1-ylcarbonyl)phenyl)pyrazol-4-ylmethyl)-1,4,9-triazaspiro[5.5]undecane.2hydrochloride

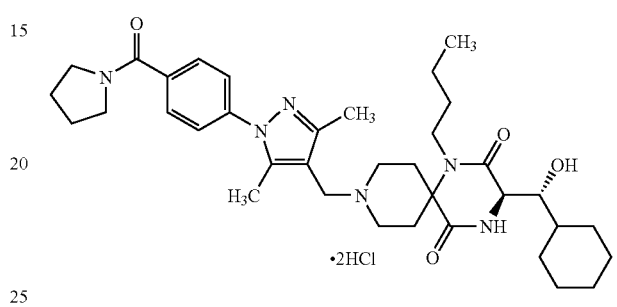

TLC: Rf 0.38 (chloroform:methanol=9:1);

NMR (CD$_3$OD): δ 7.72 (d, J=8.7 Hz, 2H), 7.59 (d, J=8.7 Hz, 2H), 4.31 (s, 2H), 4.17 (d, J=2.4 Hz, 1H), 4.04 (m, 1H), 3.78 (m, 1H), 3.65–3.47 (m, 3H), 3.62 (t, J=6.6 Hz, 2H), 3.50 (t, J=6.6 Hz, 2H), 3.33–3.18 (m, 2H), 2.60–2.32 (m, 3H), 2.43 (s, 3H), 2.39 (s, 3H), 2.20–1.87 (m, 7H), 1.82–1.62 (m, 5H), 1.48–1.13 (m, 6H), 1.03–0.82 (m, 2H), 0.96 (t, J=7.2 Hz, 3H).

EXAMPLE 9(23)

(3R)-1-butyl-2,5-dioxo-3-((1R)-1-hydroxy-1-cyclohexylmethyl)-9-(3,5-dimethyl-1-(4-(morpholin-4-ylcarbonyl)phenyl)pyrazol-4-ylmethyl)-1,4,9-triazaspiro[5.5]undecane.2hydrochloride

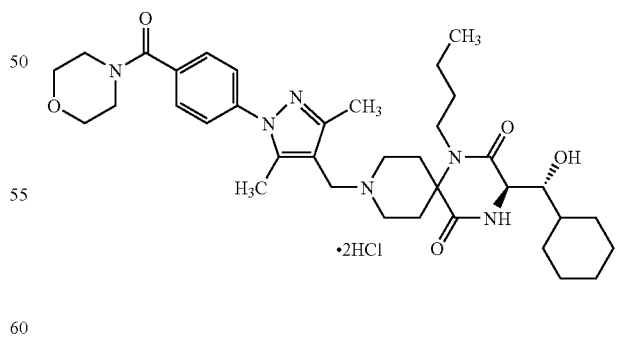

TLC: Rf 0.38 (chloroform:methanol=9:1);

NMR (CD$_3$OD): δ 7.65–7.57 (m, 4H), 4.31 (s, 2H), 4.17 (d, J=2.4 Hz, 1H), 4.04 (m, 1H), 3.85–3.46 (m, 12H), 3.34–3.17 (m, 2H), 2.60–2.32 (m, 3H), 2.43 (s, 3H), 2.39 (s, 3H), 2.20–1.90 (m, 3H), 1.82–1.62 (m, 5H), 1.48–1.13 (m, 6H), 1.03–0.82 (m, 2H), 0.96 (t, J=7.2 Hz, 3H).

EXAMPLE 9(24)

(3R)-1-butyl-2,5-dioxo-3-((1R)-1-hydroxy-1-cyclohexylmethyl)-9-(4-aminocarbonylphenylmethyl)-1,4,9-triazaspiro[5.5]undecane.hydrochloride

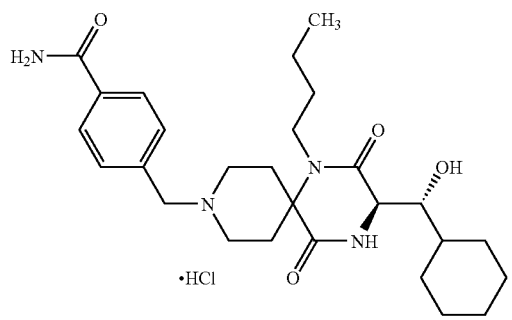

TLC: Rf 0.40 (ethyl acetate:methanol=3:1);

NMR (CD$_3$OD): δ 7.99 (d, J=8.4 Hz, 2H), 7.70 (d, J=8.4 Hz, 2H), 4.44 (s, 2H), 4.16 (d, J=2.1 Hz, 1H), 4.04 (m, 1H), 3.78 (m, 1H), 3.60–3.38 (m, 3H), 3.30–3.08 (m, 2H), 2.60–2.24 (m, 3H), 2.20–1.86 (m, 3H), 1.82–1.58 (m, 5H), 1.50–1.06 (m, 6H), 1.04–0.80 (m, 2H), 0.96 (t, J=7.2 Hz, 3H).

EXAMPLE 9(25)

(3R)-1-butyl-2,5-dioxo-3-((1R)-1-hydroxy-1-cyclohexylmethyl)-9-(4-(4-aminocarbonylphenyloxy)phenylmethyl)-1,4,9-triazaspiro[5.5]undecane.hydrochloride

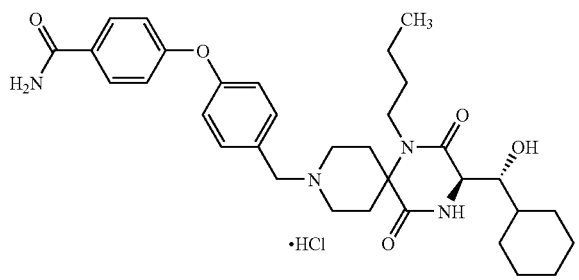

TLC: Rf 0.25 (chloroform:methanol=10:1);

NMR (CD$_3$OD): δ 7.90 (d, J=8.7 Hz, 2H), 7.57 (d, J=8.7 Hz, 2H), 7.16 (d, J=8.7 Hz, 2H), 7.07 (d, J=8.7 Hz, 2H), 4.36 (s, 2H), 4.15 (d, J=2.1 Hz, 1H), 4.02 (m, 1H), 3.76 (m, 1H), 3.56–3.42 (m, 3H), 3.33–2.99 (m, 2H), 2.54–1.88 (m, 6H), 1.81–1.60 (m, 5H), 1.48–1.12 (m, 6H), 1.04–0.81 (m, 5H).

EXAMPLE 9(26)

(3R)-1-butyl-2,5-dioxo-3-((1R)-1-hydroxy-1-cyclohexylmethyl)-9-(4-(4-aminosulfonylphenyloxy)phenylmethyl)-1,4,9-triazaspiro[5.5]undecane.hydrochloride

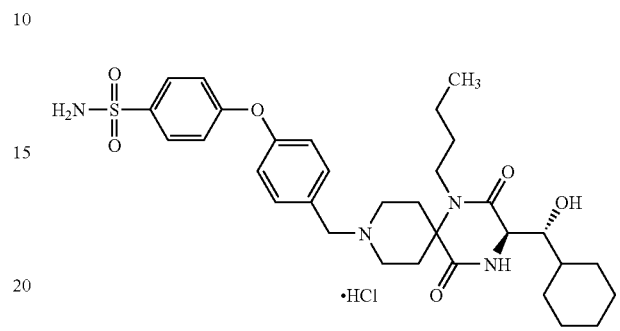

TLC: Rf 0.28 (chloroform:methanol=10:1);

NMR (CD$_3$OD): δ 7.89 (d, J=8.7 Hz, 2H), 7.61 (d, J=8.7 Hz, 2H), 7.17 (d, J=8.7 Hz, 2H), 7.13 (d, J=8.7 Hz, 2H), 4.36 (s, 2H), 4.15 (d, J=2.1 Hz, 1H), 4.01 (m, 1H), 3.75 (m, 1H), 3.58–3.42 (m, 3H), 3.32–3.14 (m, 2H), 2.55–2.40 (m, 2H), 2.32 (m, 1H), 2.13 (m, 1H), 2.07–1.89 (m, 2H), 1.82–1.60 (m, 5H), 1.50–1.12 (m, 6H), 1.06–0.80 (m, 5H).

EXAMPLE 9(27)

(3R)-1-butyl-2,5-dioxo-3-((1R)-1-hydroxy-1-cyclohexylmethyl)-9-(4-(6-methylpyridin-1-oxido-3-yloxy)phenylmethyl)-1,4,9-triazaspiro[5.5]undecane.hydrochloride

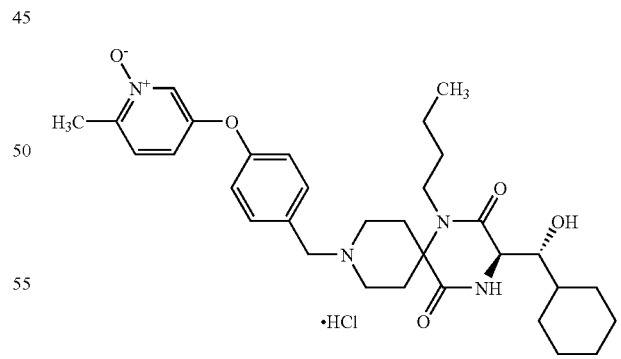

TLC: Rf 0.62 (chloroform:methanol=5:1);

NMR (CD$_3$OD): δ 8.51 (s, 1H), 7.80–7.56 (m, 2H), 7.72 (d, J=8.7 Hz, 2H), 7.29 (d, J=8.7 Hz, 2H), 4.39 (s, 2H), 4.16 (d, J=2.1 Hz, 1H), 4.00 (m, 1H), 3.78 (m, 1H), 3.62–3.40 (m, 3H), 3.36–3.18 (m, 2H), 2.64–2.30 (m, 3H), 2.63 (s, 3H), 2.20–1.86 (m, 3H), 1.84–1.58 (m, 5H), 1.52–1.08 (m, 6H), 1.04–0.82 (m, 2H), 0.96 (t, J=7.2 Hz, 3H).

EXAMPLE 9(28)

(3R)-1-butyl-2,5-dioxo-3-((1R)-1-hydroxy-1-cyclohexylmethyl)-9-(4-(4-hydroxyphenyloxy)phenylmethyl)-1,4,9-triazaspiro[5.5]undecane.hydrochloride

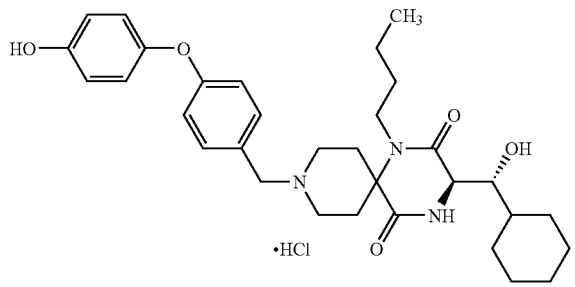

TLC: Rf 0.35 (chloroform:methanol=10:1);

NMR (CD$_3$OD): δ 7.46 (d, J=9.0 Hz, 2H), 6.97 (d, J=9.0 Hz, 2H), 6.88 (d, J=9.0 Hz, 2H), 6.80 (d, J=9.0 Hz, 2H), 4.30 (s, 2H), 4.15 (d, J=2.1 Hz, 1H), 3.98 (m, 1H), 3.72 (m, 1H), 3.67–3.39 (m, 3H), 3.27 (m, 1H), 3.15 (m, 1H), 2.53–2.35 (m, 2H), 2.26 (m, 1H), 2.18–1.87 (m, 3H), 1.84–1.60 (m, 5H), 1.51–1.05 (m, 6H), 1.04–0.80 (m, 2H), 0.95 (t, J=7.2 Hz, 3H).

EXAMPLE 9(29)

(3R)-1-butyl-2,5-dioxo-3-((1R)-1-hydroxy-1-cyclohexylmethyl)-9-(3,5-dimethyl-1-(4-hydroxyphenyl)pyrazol-4-ylmethyl)-1,4,9-triazaspiro[5.5]undecane.2hydrochloride

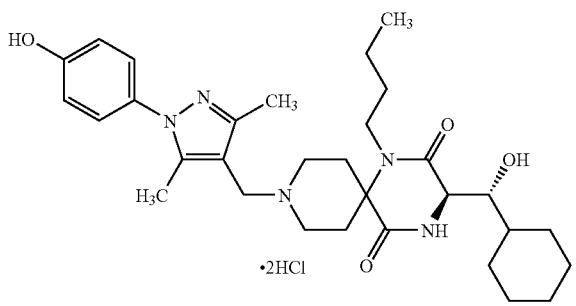

TLC: Rf 0.25 (chloroform:methanol=10:1);

NMR (CD$_3$OD): δ 7.34 (d, J=8.7 Hz, 2H), 6.96 (d, J=8.7 Hz, 2H), 4.34 (s, 2H), 4.16 (d, J=2.1 Hz, 1H), 4.04 (m, 1H), 3.79 (m, 1H), 3.65–3.50 (m, 3H), 3.32 (m, 1H), 3.29 (m, 1H), 2.64 (m, 1H), 2.55–2.42 (m, 2H), 2.48 (s, 3H), 2.38 (s, 3H), 2.20–1.88 (m, 3H), 1.83–1.60 (m, 5H), 1.52–1.05 (m, 6H), 1.04–0.81 (m, 2H), 0.96 (t, J=6.9 Hz, 3H).

EXAMPLE 9(30)

(3R)-1-butyl-2,5-dioxo-3-((1R)-1-hydroxy-1-cyclohexylmethyl)-9-(3,5-dimethyl-1-(4-(2-hydroxyethylaminosulfonyl)phenyl)pyrazol-4-ylmethyl)-1,4,9-triazaspiro[5.5]undecane.2hydrochloride

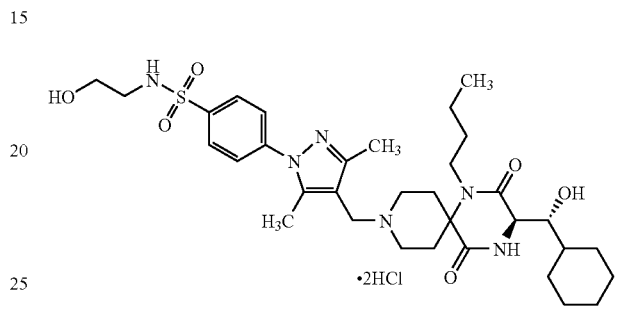

TLC: Rf 0.32 (chloroform:methanol=10:1);

NMR (CD$_3$OD): δ 8.03 (d, J=8.7 Hz, 2H), 7.71 (d, J=8.7 Hz, 2H), 4.32 (s, 2H), 4.17 (d, J=2.1 Hz, 1H), 4.06 (m, 1H), 3.80 (m, 1H), 3.62–3.48 (m, 5H), 3.38–3.18 (m, 2H), 3.01 (t, J=5.7 Hz, 2H), 2.58–2.30 (m, 3H), 2.46 (s, 3H), 2.39 (s, 3H), 2.20–1.88 (m, 3H), 1.82–1.62 (m, 5H), 1.50–1.10 (m, 6H), 1.02–0.82 (m, 5H).

EXAMPLE 9(31)

(3R)-1-butyl-2,5-dioxo-3-((1R)-1-hydroxy-1-cyclohexylmethyl)-9-(3,5-dimethyl-1-(4-(pyrrolidin-1-ylsulfonyl)phenyl)pyrazol-4-ylmethyl)-1,4,9-triazaspiro[5.5]undecane.2hydrochloride

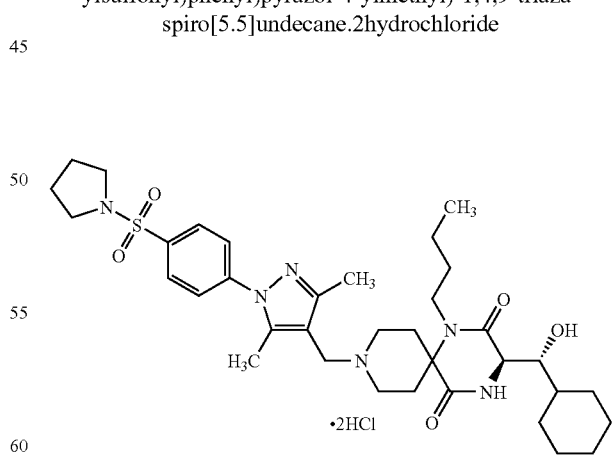

TLC: Rf 0.59(chloroform:methanol=10:1);

NMR (CD$_3$OD): δ 8.01 (d, J=8.7 Hz, 2H), 7.75 (d, J=8.7 Hz, 2H), 4.32 (s, 2H), 4.17 (d, J=2.4 Hz, 1H), 4.06 (m, 1H), 3.80 (m, 1H), 3.62–3.48 (m, 3H), 3.38–3.18 (m, 6H), 2.60–2.30 (m, 3H), 2.47 (s, 3H), 2.39 (s, 3H), 2.20–1.88 (m, 3H), 1.82–1.60 (m, 9H), 1.50–1.10 (m, 6H), 1.02–0.82 (m, 5H).

EXAMPLE 9(32)

(3R)-1-butyl-2,5-dioxo-3-((1R)-1-hydroxy-1-cyclohexylmethyl)-9-(5-chloro-3-methyl-1-phenylpyrazol-4-ylmethyl)-1,4,9-triazaspiro[5.5]undecane.2hydrochloride

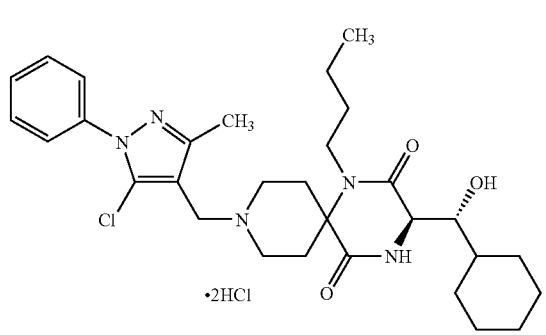

TLC: Rf 0.52 (chloroform:methanol=10:1);

NMR (CD$_3$OD): δ 7.62–7.46 (m, 5H), 4.34 (s, 2H), 4.17 (d, J=1.8 Hz, 1H), 4.10 (m, 1H), 3.83 (m, 1H), 3.66–3.47 (m, 3H), 3.39–3.13 (m, 2H), 2.60–2.28 (m, 3H), 2.44 (s, 3H), 2.18 (m, 1H), 2.09–1.88 (m, 2H), 1.85–1.62 (m, 5H), 1.54–1.13 (m, 6H), 1.03–0.81 (m, 2H), 0.97 (t, J=7.2 Hz, 3H).

EXAMPLE 9(33)

(3R)-1-butyl-2,5-dioxo-3-((1R)-1-hydroxy-1-cyclohexylmethyl)-9-(4-(4-methoxyphenyloxy)phenylmethyl)-1,4,9-triazaspiro[5.5]undecane.hydrochloride

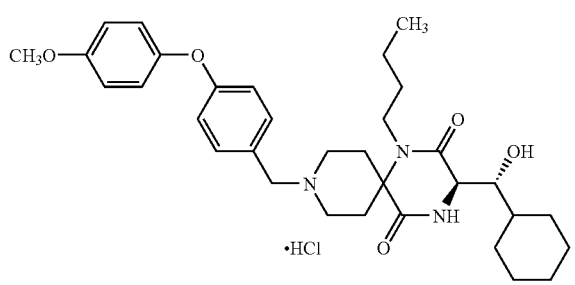

TLC: Rf 0.50 (chloroform:methanol=10:1);

NMR (CD$_3$OD): δ 7.49 (d, J=8.7 Hz, 2H), 6.98 (d, J=8.7 Hz, 2H), 7.02–6.92 (m, 4H), 4.30 (s, 2H), 4.15 (d, J=2.1 Hz, 1H), 3.97 (m, 1H), 3.79 (s, 3H), 3.72 (m, 1H), 3.58–3.38 (m, 3H), 3.30–3.13 (m, 2H), 2.55–2.40 (m, 2H), 2.32 (m, 1H), 2.16–1.86 (m, 3H), 1.81–1.60 (m, 5H), 1.50–1.10 (m, 6H), 1.03–0.80 (m, 2H), 0.95 (t, J=7.2 Hz, 3H).

EXAMPLE 9(34)

(3R)-1-butyl-2,5-dioxo-3-((1R)-1-hydroxy-1-cyclohexylmethyl)-9-(4-(3-methoxyphenyloxy)phenylmethyl)-1,4,9-triazaspiro[5.5]undecane.hydrochloride

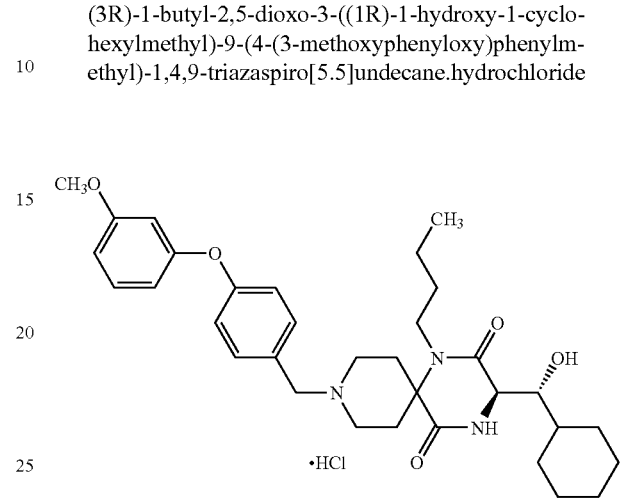

TLC: Rf 0.50 (chloroform:methanol=10:1);

NMR (CD$_3$OD): δ 7.54 (d, J=8.7 Hz, 2H), 7.28 (m, 1H), 7.70 (d, J=8.7 Hz, 2H), 6.75 (ddd, J=8.7, 2.1, 1.2 Hz, 1H), 6.63–6.56 (m, 2H), 4.33 (s, 2H), 4.15 (d, J=2.1 Hz, 1H), 3.98 (m, 1H), 3.77 (s, 3H), 3.75 (m, 1H), 3.58–3.40 (m, 3H), 3.30–3.11 (m, 2H), 2.55–2.23 (m, 3H), 2.17–1.88 (m, 3H), 1.81–1.59 (m, 5H), 1.50–1.06 (m, 6H), 1.03–0.80 (m, 2H), 0.95 (t, J=7.2 Hz, 3H).

EXAMPLE 9(35)

(3R)-1-butyl-2,5-dioxo-3-((1R)-1-hydroxy-1-cyclohexylmethyl)-9-(4-(N,N-dimethylaminocarbonyl)phenylmethyl)-1,4,9-triazaspiro[5.5]undecane.hydrochloride

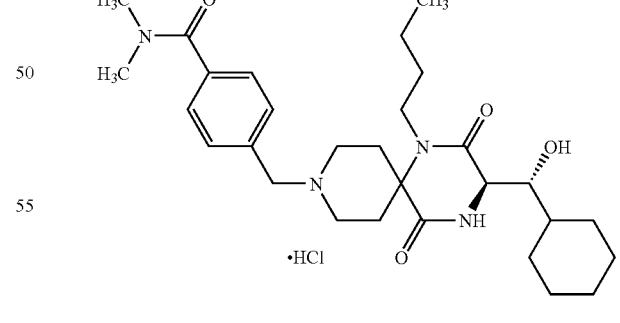

TLC: Rf 0.43(chloroform:methanol=10:1);

NMR (CD$_3$OD): δ 7.66 (d, J=8.4 Hz, 2H), 7.55 (d, J=8.4 Hz, 2H), 4.41 (s, 2H), 4.15 (d, J=1.8 Hz, 1H), 4.04 (m, 1H), 3.78 (m, 1H), 3.59–3.42 (m, 3H), 3.30–3.10 (m, 2H), 3.11 (s, 3H), 2.99 (s, 3H), 2.53–2.20 (m, 3H), 2.14 (m, 1H), 2.08–1.88 (m, 2H), 1.83–1.60 (m, 5H), 1.52–1.10 (m, 6H), 1.06–0.80 (m, 2H), 0.95 (t, J=7.2 Hz, 3H).

EXAMPLE 9(36)

(3R)-1-butyl-2,5-dioxo-3-((1R)-1-hydroxy-1-cyclo-hexylmethyl)-9-(3,5-dimethyl-1-phenylpyrazol-4-ylmethyl)-1,4,9-triazaspiro[5.5]undecane.2hydrochloride

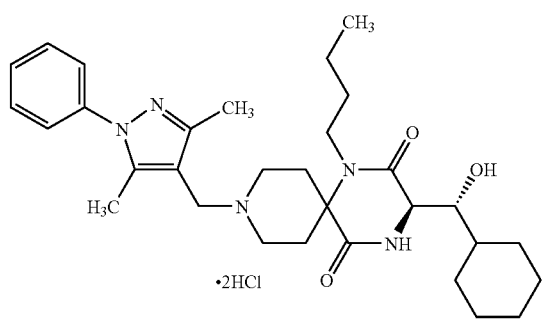

TLC: Rf 0.48 (chloroform:methanol=10:1);

NMR (CD$_3$OD): δ 7.63–7.43 (m, 5H), 4.32 (s, 2H), 4.17 (d, J=2.1 Hz, 1H), 4.04 (m, 1H), 3.79 (m, 1H), 3.64–3.49 (m, 3H), 3.30–3.20 (m, 2H), 2.70–2.30 (m, 9H), 2.20–1.88 (m, 3H), 1.83–1.58 (m, 5H), 1.52–1.06 (m, 6H), 1.06–0.80 (m, 2H), 0.96 (t, J=7.2 Hz, 3H).

EXAMPLE 9(37)

(3R)-1-butyl-2,5-dioxo-3-((1R)-1-hydroxy-1-cyclo-hexylmethyl)-9-(3,5-dimethyl-1-(4-methylphenyl)pyrazol-4-ylmethyl)-1,4,9-triazaspiro[5.5]undecane.2hydrochloride

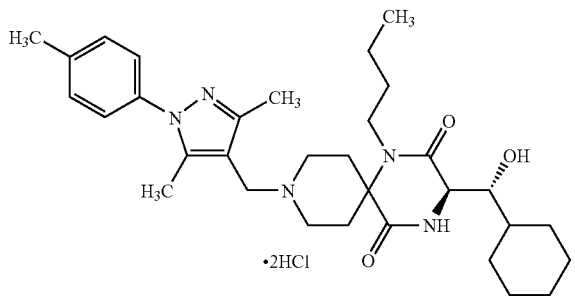

TLC: Rf 0.48 (chloroform:methanol=10:1);

NMR (CD$_3$OD): δ 7.37 (d, J=8.7 Hz, 2H), 7.34 (d, J=8.7 Hz, 2H), 4.30 (s, 2H), 4.17 (d, J=2.1 Hz, 1H), 4.04 (m, 1H), 3.79 (m, 1H), 3.63–3.47 (m, 3H), 3.35–3.06 (m, 2H), 2.63–2.26 (m, 3H), 2.43 (s, 3H), 2.38 (s, 3H), 2.35 (s, 3H), 2.16 (m, 1H), 2.09–1.88 (m, 2H), 1.83–1.60 (m, 5H), 1.55–1.10 (m, 6H), 1.08–0.80 (m, 2H), 0.96 (t, J=7.2 Hz, 3H).

EXAMPLE 9(38)

(3R)-1-butyl-2,5-dioxo-3-((1R)-1-hydroxy-1-cyclo-hexylmethyl)-9-(3,5-dimethyl-1-(4-fluorophenyl)pyrazol-4-ylmethyl)-1,4,9-triazaspiro[5.5]undecane.2hydrochloride

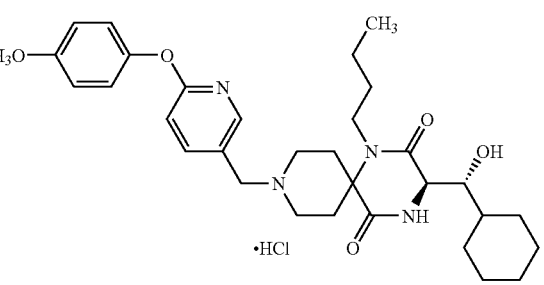

TLC: Rf 0.49(chloroform:methanol=10:1);

NMR (CD$_3$OD): δ 7.50 (dd, J=8.4, 4.8 Hz, 2H), 7.30 (dd, J=8.4, 8.4 Hz, 2H), 4.30 (s, 2H), 4.17 (d, J=2.1 Hz, 1H), 4.04 (m, 1H), 3.78 (m, 1H), 3.63–3.45 (m, 3H), 3.30–3.12 (m, 2H), 2.61–2.30 (m, 3H), 2.37 (s, 3H), 2.36 (s, 3H), 2.16 (m, 1H), 2.08–1.88 (m, 2H), 1.82–1.60 (m, 5H), 1.52–1.07 (m, 6H), 1.04–0.80 (m, 2H), 0.96 (t, J=7.2 Hz, 3H).

EXAMPLE 9(39)

(3R)-1-butyl-2,5-dioxo-3-((1R)-1-hydroxy-1-cyclo-hexylmethyl)-9-(6-(4-methoxyphenyloxy)pyridin-3-ylmethyl)-1,4,9-triazaspiro[5.5]undecane.hydrochloride TLC: Rf 0.38 (chloroform:methanol=10:1);

NMR (CD$_3$OD): δ 8.36 (m, 1H), 8.12 (m, 1H), 7.12–6.98 (m, 5H), 4.39 (s, 2H), 4.15 (d, J=2.1 Hz, 1H), 4.00 (m, 1H), 3.81 (s, 3H), 3.74 (m, 1H), 3.60–3.42 (m, 3H), 3.30–3.16 (m, 2H), 2.58–2.30 (m, 3H), 2.16–1.86 (m, 3H), 1.80–1.62 (m, 5H), 1.50–1.10 (m, 6H), 1.02–0.80 (m, 5H).

EXAMPLE 9(40)

(3R)-1-butyl-2,5-dioxo-3-((1R)-1-hydroxy-1-cyclohexylmethyl)-9-(4-(4-methylsulfonylphenyloxy)phenylmethyl)-1,4,9-triazaspiro[5.5]undecane.hydrochloride

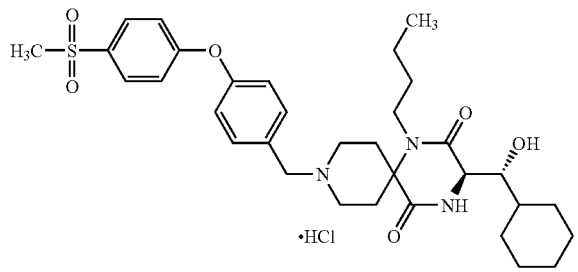

TLC: Rf 0.46 (chloroform:methanol=10:1);

NMR (CD₃OD): δ 7.95 (d, J=9.0 Hz, 2H), 7.65 (d, J=8.4 Hz, 2H), 7.25–7.16 (m, 4H), 4.38 (s, 2H), 4.15 (d, J=2.4 Hz, 1H), 4.02 (m, 1H), 3.76 (m, 1H), 3.60–3.44 (m, 3H), 3.30–3.10 (m, 2H), 3.11 (s, 3H), 2.54–2.26 (m, 3H), 2.18–1.88 (m, 3H), 1.82–1.62 (m, 5H), 1.50–1.10 (m, 6H), 1.02–0.82 (m, 5H).

EXAMPLE 9(41)

(3R)-1-butyl-2,5-dioxo-3-((1R)-1-hydroxy-1-cyclohexylmethyl)-9-(4-(4-(2-(N,N-dimethylamino)ethylaminocarbonyl)phenyloxy)phenylmethyl)-1,4,9-triazaspiro[5.5]undecane.hydrochloride

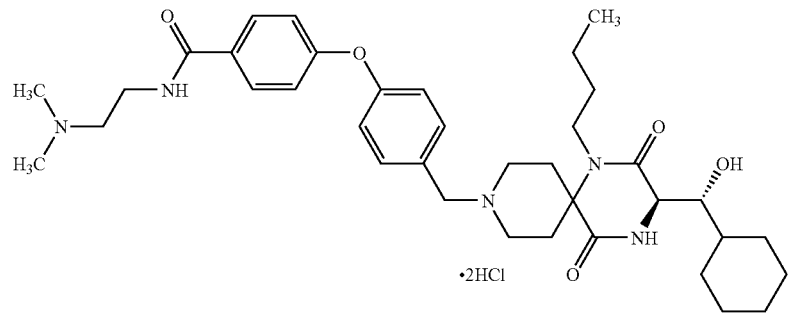

TLC: Rf 0.15 (chloroform:methanol=5:1);
NMR (CD₃OD): δ 7.93 (d, J=9.0 Hz, 2H), 7.62 (d, J=8.4 Hz, 2H), 7.20–7.08 (m, 4H), 3.98 (s, 2H), 4.16 (d, J=2.1 Hz, 1H), 3.98 (m, 1H), 3.75 (m, 1H), 3.75 (t, J=5.4 Hz, 2H), 3.58–3.42 (m, 3H), 3.38 (t, J=5.4 Hz, 2H), 3.30–3.18 (m, 2H), 2.98 (s, 6H), 2.56–2.28 (m, 3H), 2.18–1.88 (m, 3H), 1.82–1.62 (m, 5H), 1.46–1.14 (m, 6H), 1.02–0.84 (m, 5H).

EXAMPLE 9(42)

(3R)-1-butyl-2,5-dioxo-3-((1R)-1-hydroxy-1-cyclohexylmethyl)-9-(3,5-dimethyl-1-(4-(2-hydroxyethylaminocarbonyl)phenyl)pyrazol-4-ylmethyl)-1,4,9-triazaspiro[5.5]undecane.2hydrochloride

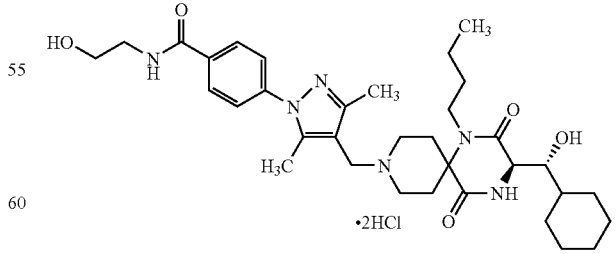

TLC: Rf 0.46 (chloroform:methanol=10:1);
NMR (CD₃OD): δ 8.01 (d, J=8.7 Hz, 2H), 7.60 (d, J=8.7 Hz, 2H), 4.31 (s, 2H), 4.17 (d, J=2.4 Hz, 1H), 4.04 (m, 1H), 3.80 (m, 1H), 3.73 (t, J=6.0 Hz, 2H), 3.72–3.48 (m, 5H), 3.30–3.16 (m, 2H), 2.60–2.30 (m, 3H), 2.43 (s, 3H), 2.39 (s, 3H), 2.22–1.88 (m, 3H), 1.80–1.62 (m, 5H), 1.50–1.12 (m, 6H), 1.06–0.82 (m, 5H).

EXAMPLE 9(43)

(3R)-1-butyl-2,5-dioxo-3-((1R)-1-hydroxy-1-cyclohexylmethyl)-9-(3,5-dimethyl-1-(4-(2-(N,N-dimethylamino)ethylaminocarbonyl)phenyl)pyrazol-4-ylmethyl)-1,4,9-triazaspiro[5.5]undecane.3hydrochloride

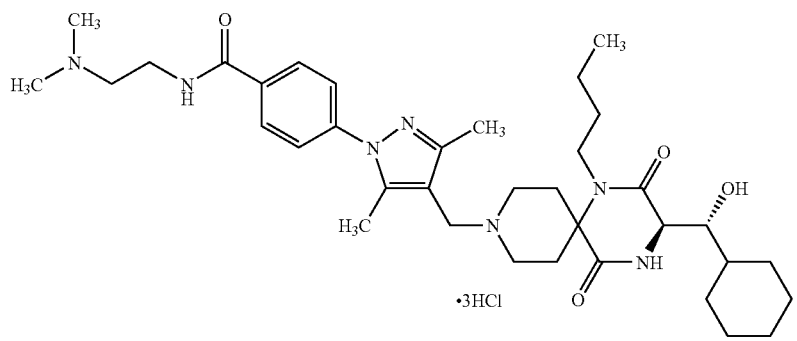

TLC: Rf 0.14 (chloroform:methanol:28% aqueous solution of ammonia=200:20:1);

NMR (CD$_3$OD): δ 8.07 (d, J=8.7 Hz, 2H), 7.64 (d, J=8.7 Hz, 2H), 4.31 (s, 2H), 4.17 (d, J=2.1 Hz, 1H), 4.04 (m, 1H), 3.79 (t, J=5.7 Hz, 2H), 3.78 (m, 1H), 3.63–3.49 (m, 3H), 3.41 (t, J=5.7 Hz, 2H), 3.32–3.20 (m, 2H), 3.00 (s, 6H), 2.63–2.35 (m, 3H), 2.45 (s, 3H), 2.39 (s, 3H), 2.20–1.90 (m, 3H), 1.82–1.63 (m, 5H), 1.48–1.13 (m, 6H), 1.03–0.82 (m, 2H), 0.96 (t, J=7.2 Hz, 3H).

EXAMPLE 9(44)

(3R)-1-butyl-2,5-dioxo-3-((1R)-1-hydroxy-1-cyclohexylmethyl)-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride

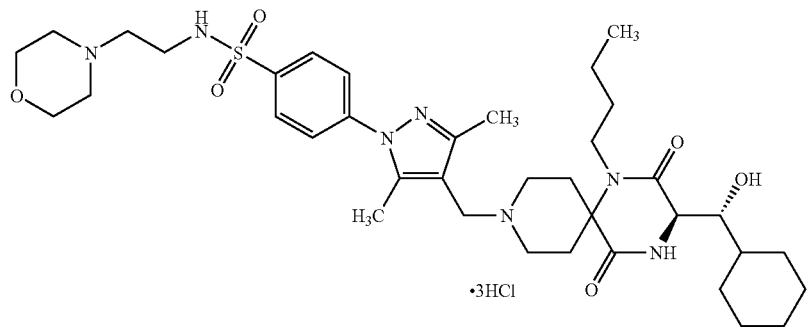

TLC: Rf 0.42 (chloroform:methanol=10:1);
NMR (CD$_3$OD): δ 8.07 (d, J=9.0 Hz, 2H), 7.77 (d, J=9.0 Hz, 2H), 4.30 (s, 2H), 4.17 (d, J=2.4 Hz, 1H), 4.12–3.96 (m, 3H), 3.90–3.70 (m, 4H), 3.62–3.48 (m, 6H), 3.20–3.16 (m, 6H), 2.70–2.30 (m, 3H), 2.49 (s, 3H), 2.41 (s, 3H), 2.20–1.88 (m, 3H), 1.82–1.62 (m, 5H), 1.50–1.10 (m, 6H), 1.04–0.84 (m, 5H).

EXAMPLE 9(45)

(3R)-1-butyl-2,5-dioxo-3-((1R)-1-hydroxy-1-cyclohexylmethyl)-9-(4-(4-(morpholin-4-ylcarbonyl)phenyloxy)phenylmethyl)-1,4,9-triazaspiro[5.5]undecane.hydrochloride

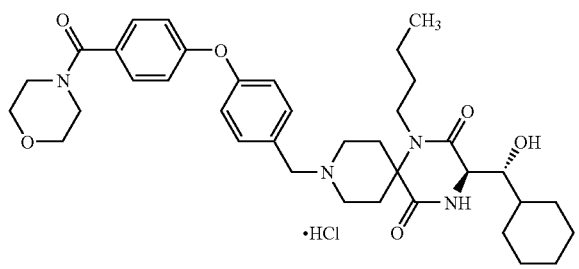

TLC: Rf 0.31 (chloroform:methanol=10:1);
NMR (CD$_3$OD): δ 7.58 (d, J=8.4 Hz, 2H), 7.48 (d, J=8.7 Hz, 2H), 7.18–7.06 (m, 4H), 4.36 (s, 2H), 4.16 (d, J=2.4 Hz, 1H), 4.00 (m, 1H), 3.82–3.40 (m, 12H), 3.38–3.12 (m, 2H), 2.52–2.24 (m, 3H), 2.18–1.86 (m, 3H), 1.82–1.62 (m, 5H), 1.50–1.10 (m, 6H), 1.02–0.82 (m, 5H).

EXAMPLE 9(46)

(3R)-1-butyl-2,5-dioxo-3-((1R)-1-hydroxy-1-cyclohexyl methyl)-9-(1,4-benzodioxan-6-ylmethyl)-1,4,9-triazaspiro[5.5]undecane.hydrochloride

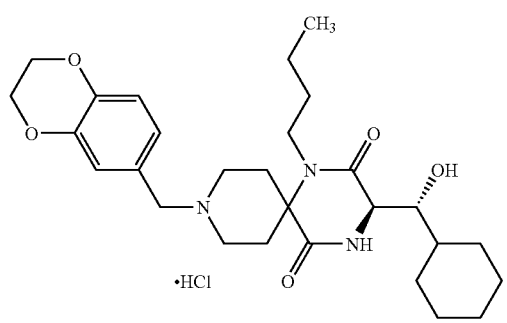

TLC: Rf 0.38 (chloroform:methanol=10:1);

NMR (CD$_3$OD): δ 7.05 (d, J=2.1 Hz, 1H), 7.00–6.90 (m, 2H), 4.26 (s, 4H), 4.23 (s, 2H), 4.15 (d, J=1.8 Hz, 1H), 3.94 (m, 1H), 3.68 (m, 1H), 3.58–3.34 (m, 3H), 3.30–3.08 (m, 2H), 2.50–1.86 (m, 6H), 1.80–1.62 (m, 5H), 1.50–1.04 (m, 6H), 1.02–0.82 (m, 5H).

EXAMPLE 9(47)

(3R)-1-butyl-2,5-dioxo-3-((1R)-1-hydroxy-1-cyclohexylmethyl)-9-(3,5-dimethyl-1-(4-(N,N-diethylaminosulfonyl)phenyl)pyrazol-4-ylmethyl)-1,4,9-triazaspiro[5.5]undecane.2hydrochloride

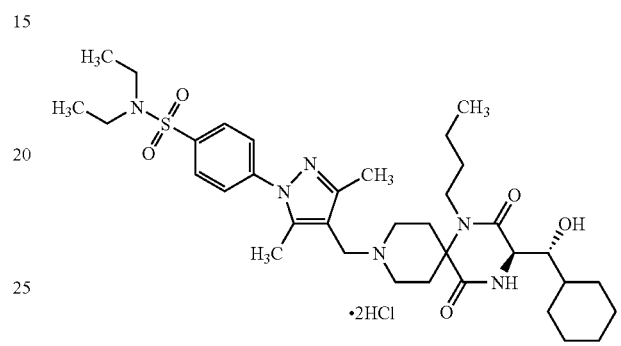

TLC: Rf 0.36 (chloroform:methanol=10:1);
NMR (CD$_3$OD): δ 7.99 (d, J=9.0 Hz, 2H), 7.73 (d, J=9.0 Hz, 2H), 4.31 (s, 2H), 4.17 (d, J=2.1 Hz, 1H), 4.06 (m, 1H), 3.78 (m, 1H), 3.62–3.48 (m, 3H), 3.34–3.14 (m, 6H), 2.60–2.30 (m, 3H), 2.45 (s, 3H), 2.39 (s, 3H), 2.20–1.88 (m, 3H), 1.82–1.62 (m, 5H), 1.50–1.08 (m, 6H), 1.15 (t, J=7.5 Hz, 6H), 1.02–0.82 (m, 5H).

EXAMPLE 9(48)

(3R)-1-butyl-2,5-dioxo-3-((1R)-1-hydroxy-1-cyclohexylmethyl)-9-(4-(pyridin-1-oxido-3-yloxy)phenylmethyl)-1,4,9-triazaspiro[5.5]undecane.hydrochloride

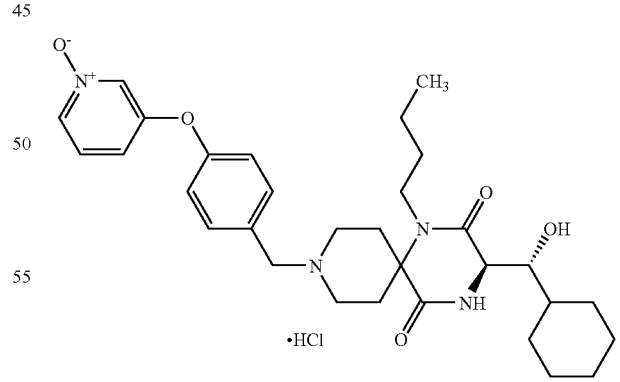

TLC: Rf 0.10 (ethyl acetate:methanol=3:1);
NMR (CD$_3$OD): δ δ 8.48–8.37 (m, 2H), 7.73 (d, J=9.0 Hz, 2H), 7.73–7.60 (m, 2H), 7.31 (d, J=9.0 Hz, 2H), 4.39 (s, 2H), 4.15 (d, J=2.1 Hz, 1H), 4.01 (m, 1H), 3.76 (m, 1H), 3.60–3.20 (m, 5H), 2.70–2.40 (m, 3H), 2.20–1.90 (m, 3H), 1.90–1.60 (m, 5H), 1.60–1.10 (m, 6H), 1.10–0.80 (m, 2H), 0.95 (t, J=7.2 Hz, 3H).

EXAMPLE 9(49)

(3R)-1-butyl-2,5-dioxo-3-((1R)-1-hydroxy-1-cyclo-hexylmethyl)-9-(3,5-dimethyl-1-(4-(4-methylpiperazin-1-ylsulfonyl)phenyl)pyrazol-4-ylmethyl)-1,4,9-triazaspiro[5.5]undecane.hydrochloride

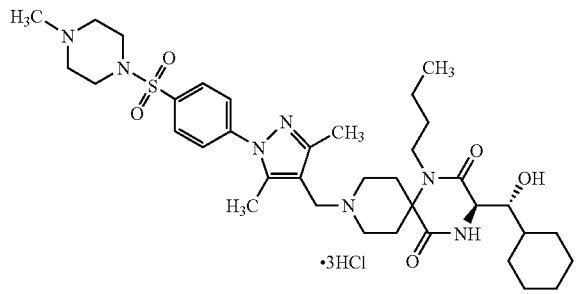

TLC: Rf 0.34 (chloroform:methanol=10:1);

NMR (CD$_3$OD): δ 8.01 (d, J=8.7 Hz, 2H), 7.85 (d, J=8.7 Hz, 2H), 4.31 (s, 2H), 4.17 (d, J=2.4 Hz, 1H), 4.10–3.94 (m, 3H), 3.78 (m, 1H), 3.66–3.56 (m, 5H), 3.40–3.20 (m, 4H), 2.91 (s, 3H), 2.88–2.72 (m, 2H), 2.70–2.40 (m, 3H), 2.50 (s, 3H), 2.40 (s, 3H), 2.20–1.88 (m, 3H), 1.84–1.60 (m, 5H), 1.56–1.10 (m, 6H), 1.04–0.82 (m, 5H).

EXAMPLE 9(50)

(3R)-1-butyl-2,5-dioxo-3-((1R)-1-hydroxy-1-cyclo-hexylmethyl)-9-(4-(4-methylaminocarbonylphenyloxy)phenylmethyl)-1,4,9-triazaspiro[5.5]undecane-.hydrochloride

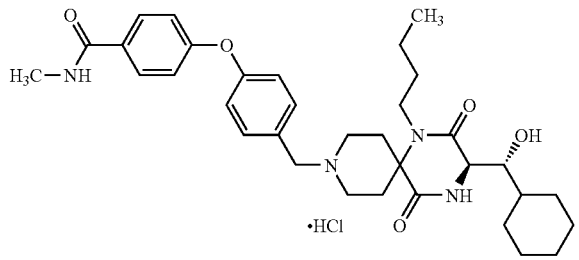

TLC: Rf 0.44 (chloroform:methanol=10:1);

NMR (CD$_3$OD): δ 7.84 (d, J=9.0 Hz, 2H), 7.59 (d, J=8.7 Hz, 2H), 7.15 (d, J=8.7 Hz, 2H), 7.07 (d, J=9.0 Hz, 2H), 4.36 (s, 2H), 4.16 (d, J=2.1 Hz, 1H), 4.00 (m, 1H), 3.74 (m, 1H), 3.60–3.44 (m, 3H), 3.28–3.16 (m, 2H), 2.91 (s, 3H), 2.52–2.26 (m, 3H), 2.18–1.88 (m, 3H), 1.82–1.62 (m, 5H), 1.50–1.10 (m, 6H), 1.02–0.82 (m, 5H).

EXAMPLE 9(51)

(3R)-1-butyl-2,5-dioxo-3-((1R)-1-hydroxy-1-cyclo-hexylmethyl)-9-(3,5-dimethyl-1-(2,4-difluorophenyl)pyrazol-4-ylmethyl)-1,4,9-triazaspiro[5.5]undecane.3hydrochloride

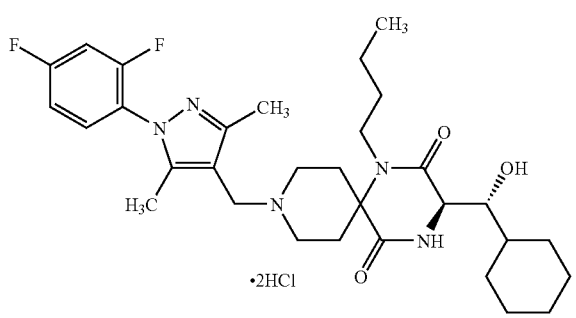

TLC: Rf 0.63 (chloroform:methanol=5:1);

NMR (CD$_3$OD): δ 7.56 (m, 1H), 7.33–7.16 (m, 2H), 4.32 (s, 2H), 4.18 (d, J=2.4 Hz, 1H), 4.04 (m, 1H), 3.80 (m, 1H), 3.64–3.46 (m, 3H), 3.30–3.16 (m, 2H), 2.62–1.88 (m, 6H), 2.39 (s, 3H), 2.28 (s, 3H), 1.84–1.60 (m, 5H), 1.52–1.10 (m, 6H), 1.06–0.82 (m, 2H), 0.97 (t, J=6.9 Hz, 3H).

EXAMPLE 9(52)

(3R)-1-butyl-2,5-dioxo-3-((1R)-1-hydroxy-1-cyclo-hexylmethyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane.hydrochloride-1,4,9-triazaspiro[5.5]undecane.3hydrochloride

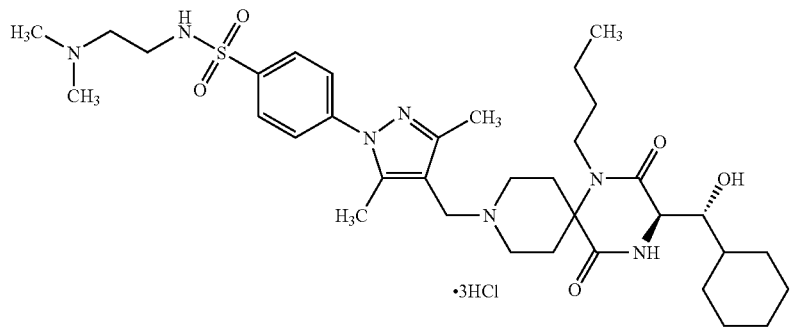

TLC: Rf 0.21 (chloroform:methanol:28% aqueous solution of ammonia=100:10:1);

NMR (CD₃OD): δ 8.07 (d, J=8.7 Hz, 2H), 7.78 (d, J=8.7 Hz, 2H), 4.31 (s, 2H), 4.17 (d, J=2.1 Hz, 1H), 4.04 (m, 1H), 3.80 (m, 1H), 3.64–3.50 (m, 3H), 3.40–3.22 (m, 6H), 2.96 (s, 6H), 2.74–2.38 (m, 3H), 2.49 (s, 3H), 2.41 (s, 3H), 2.22–1.88 (m, 3H), 1.84–1.60 (m, 5H), 1.52–1.10 (m, 6H), 1.06–0.82 (m, 2H), 0.96 (t, J=7.2 Hz, 3H).

EXAMPLE 9(53)

(3R)-1-butyl-2,5-dioxo-3-((1R)-1-hydroxy-1-cyclohexylmethyl)-9-(3,5-dimethyl-1-(4-methylaminocarbonylphenyl)pyrazol-4-ylmethyl)-1,4,9-triazaspiro[5.5]undecane.2hydrochloride

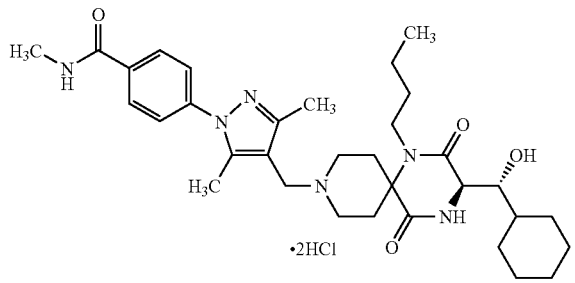

TLC: Rf 0.21 (chloroform:methanol=10:1);

NMR (CD₃OD): δ 7.98 (d, J=8.7 Hz, 2H), 7.60 (d, J=8.7 Hz, 2H), 4.31 (s, 2H), 4.16 (d, J=2.1 Hz, 1H), 4.04 (m, 1H), 3.79 (m, 1H), 3.64–3.49 (m, 3H), 3.37–3.20 (m, 2H), 2.94 (s, 3H), 2.63–2.33 (m, 3H), 2.43 (s, 3H), 2.40 (s, 3H), 2.16 (m, 1H), 2.09–1.90 (m, 2H), 1.83–1.62 (m, 5H), 1.50–1.12 (m, 6H), 1.04–0.82 (m, 5H).

EXAMPLE 9(54)

(3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane.hydrochloride

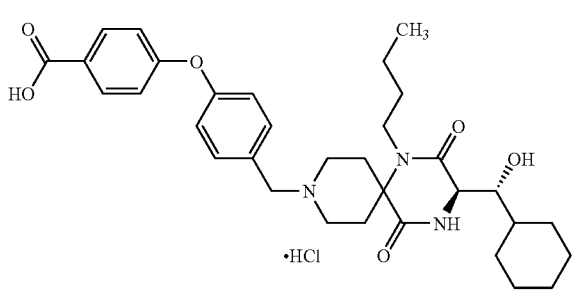

TLC: Rf 0.43 (chloroform:methanol=5:1);

NMR (CD₃OD): δ 8.05 (d, J=9.0 Hz, 2H), 7.61 (d, J=9.0 Hz, 2H), 7.19 (d, J=9.0 Hz, 2H), 7.08 (d, J=9.0 Hz, 2H), 4.38 (s, 2H), 4.17 (d, J=2.1 Hz, 1H), 4.02 (m, 1H), 3.78 (m, 1H), 3.60–3.40 (m, 3H), 3.30–3.10 (m, 2H), 2.56–1.86 (m, 6H), 1.82–1.60 (m, 5H), 1.52–1.16 (m, 6H), 1.06–0.82 (m, 2H), 0.97 (t, J=7.2 Hz, 3H).

EXAMPLE 9(55)

(3R)-1-butyl-2,5-dioxo-3-((1R)-1-hydroxy-1-cyclohexylmethyl)-9-(4-((4-methoxyphenyl)methylaminocarbonyl)phenylmethyl)-1,4,9-triazaspiro[5.5]undecane.hydrochloride

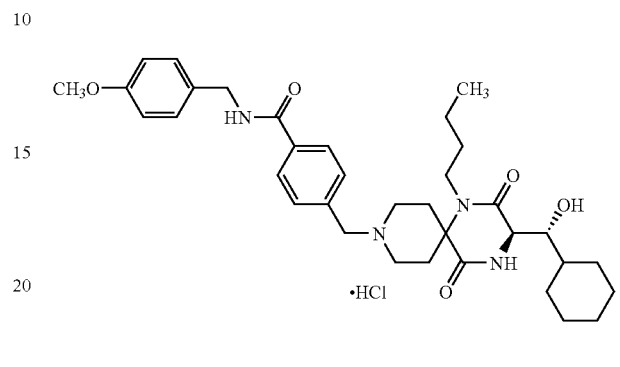

TLC: Rf 0.33 (chloroform:methanol=10:1);

NMR (CD₃OD): δ 7.96 (d, J=8.4 Hz, 2H), 7.66 (d, J=8.4 Hz, 2H), 7.28 (d, J=8.4 Hz, 2H), 6.88 (d, J=8.4 Hz, 2H), 4.52 (s, 2H), 4.43 (s, 2H), 4.15 (d, J=2.1 Hz, 1H), 4.02 (m, 1H), 3.77 (s, 3H), 3.77 (m, 1H), 3.58–3.38 (m, 3H), 3.30–3.10 (m, 2H), 2.54–2.22 (m, 3H), 2.18–1.86 (m, 3H), 1.82–1.60 (m, 5H), 1.50–1.08 (m, 6H), 1.04–0.80 (m, 2H), 0.95 (t, J=6.9 Hz, 3H).

EXAMPLE 9(56)

(3R)-1-butyl-2,5-dioxo-3-((1R)-1-hydroxy-1-cyclohexylmethyl)-9-(4-(3-methoxypropylaminocarbonyl)phenylmethyl)-1,4,9-triazaspiro[5.5]undecane.hydrochloride

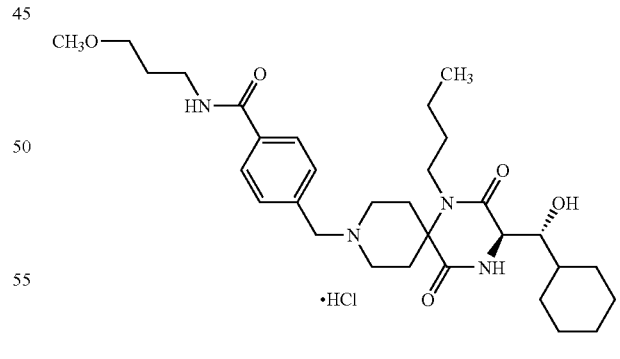

TLC: Rf 0.27 (chloroform:methanol=10:1);

NMR (CD₃OD): δ 7.93 (d, J=8.1 Hz, 2H), 7.68 (d, J=8.1 Hz, 2H), 4.43 (s, 2H), 4.16 (d, J=1.8 Hz, 1H), 4.04 (m, 1H), 3.78 (m, 1H), 3.60–3.40 (m, 7H), 3.35 (s, 3H), 3.30–3.10 (m, 2H), 2.58–1.60 (m, 13H), 1.52–1.08 (m, 6H), 1.06–0.80 (m, 2H), 0.96 (t, J=7.2 Hz, 3H).

EXAMPLE 9(57)

(3R)-1-butyl-2,5-dioxo-3-((1R)-1-hydroxy-1-cyclohexylmethyl)-9-(4-(N-methyl-N-(2-(pyridin-2-yl)ethyl)aminocarbonyl)phenylmethyl)-1,4,9-triazaspiro[5.5]undecane.2hydrochloride

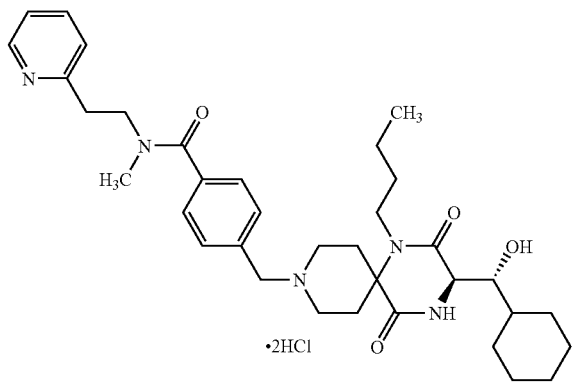

TLC: Rf 0.22 (chloroform:methanol=10:1);

NMR (CD$_3$OD): δ 8.80 (m, 1H), 8.57 (m, 1H), 8.08 (m, 1H), 7.96 (m, 1H), 7.69 (d, J=8.4 Hz, 2H), 7.43 (d, J=8.4 Hz, 2H), 4.40 (s, 2H), 4.16 (d, J=2.1 Hz, 1H), 4.06–3.90 (m, 3H), 3.80 (m, 1H), 3.62–3.38 (m, 5H), 3.30–3.10 (m, 2H), 3.08 (s, 3H), 2.64–2.30 (m, 3H), 2.18–1.84 (m, 3H), 1.82–1.60 (m, 5H), 1.50–1.06 (m, 6H), 1.04–0.80 (m, 2H), 0.96 (t, J=7.2 Hz, 3H).

EXAMPLE 9(58)

(3R)-1-butyl-2,5-dioxo-3-((1R)-1-hydroxy-1-cyclohexylmethyl)-9-(4-(4-(pyrrolidin-1-ylcarbonyl)phenyloxy)phenylmethyl)-1,4,9-triazaspiro[5.5]undecane.hydrochloride

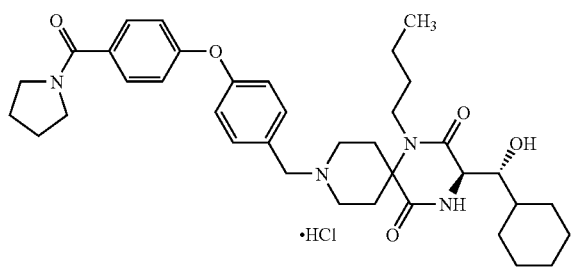

TLC: Rf 0.41 (ethyl acetate: methanol=4:1);

NMR (CD$_3$OD): δ 7.59–7.56 (m, 4H), 7.15 (d, J=8.7 Hz, 2H), 7.09 (d, J=8.7 Hz, 2H), 4.36 (s, 2H), 4.15 (d, J=2.0 Hz, 1H), 4.01 (m, 1H), 3.75 (m, 1H), 3.60–3.46 (m, 7H), 3.30–3.13 (m, 2H), 2.51–2.11 (m, 4H), 2.04–1.89 (m, 6H), 1.80–1.65 (m, 5H), 1.50–1.15 (m, 6H), 1.00–0.87 (m, 5H).

EXAMPLE 9(59)

(3R)-1-butyl-2,5-dioxo-3-((1R)-1-hydroxy-1-cyclohexylmethyl)-9-(3,5-dimethyl-1-(4-chlorophenyl)pyrazol-4-ylmethyl)-1,4,9-triazaspiro[5.5]undecane.2hydrochloride

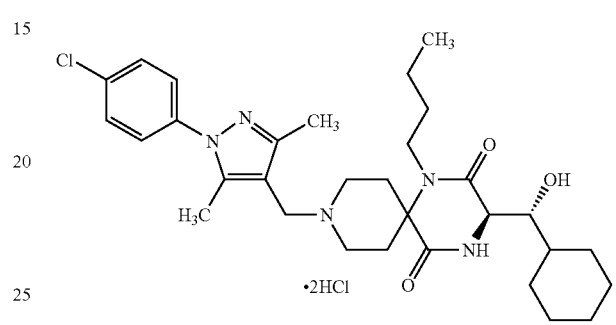

TLC: Rf 0.51 (chloroform:methanol=10:1);

NMR (CD$_3$OD): δ 7.58 (d, J=9.0 Hz, 2H), 7.49 (d, J=9.0 Hz, 2H), 4.31 (s, 2H), 4.17 (d, J=2.1 Hz, 1H), 4.04 (m, 1H), 3.78 (m, 1H), 3.62–3.48 (m, 3H), 3.30–3.16 (m, 2H), 2.62–2.32 (m, 3H), 2.40 (s, 3H), 2.39 (s, 3H), 2.22–1.86 (m, 3H), 1.84–1.60 (m, 5H), 1.54–1.10 (m, 6H), 1.06–0.82 (m, 2H), 0.97 (t, J=7.2 Hz, 3H).

EXAMPLE 9(60)

(3R)-1-butyl-2,5-dioxo-3-((1R)-1-hydroxy-1-cyclohexylmethyl)-9-(3,5-dimethyl-1-(4-trifluoromethylphenyl)pyrazol-4-ylmethyl)-1,4,9-triazaspiro[5.5]undecane.2hydrochloride

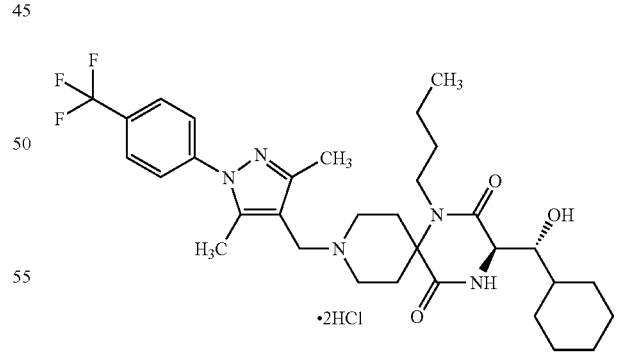

TLC: Rf 0.53 (chloroform:methanol=10:1);

NMR (CD$_3$OD): δ 7.88 (d, J=8.7 Hz, 2H), 7.73 (d, J=8.7 Hz, 2H), 4.33 (s, 2H), 4.18 (d, J=2.1 Hz, 1H), 4.04 (m, 1H), 3.80 (m, 1H), 3.64–3.46 (m, 3H), 3.30–3.16 (m, 2H), 2.62–2.28 (m, 3H), 2.46 (s, 3H), 2.40 (s, 3H), 2.24–1.88 (m, 3H), 1.84–1.60 (m, 5H), 1.56–1.06 (m, 6H), 1.06–0.82 (m, 2H), 0.97 (t, J=7.2 Hz, 3H).

EXAMPLE 9(61)

(3R)-1-butyl-2,5-dioxo-3-((1R)-1-hydroxy-1-cyclohexylmethyl)-9-(3,5-dimethyl-1-(4-methoxyphenyl)pyrazol-4-ylmethyl)-1,4,9-triazaspiro[5.5]undecane.2hydrochloride

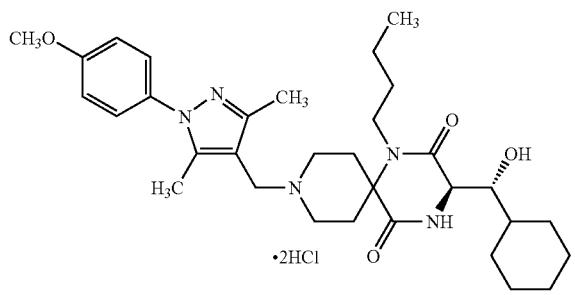

TLC: Rf 0.44 (chloroform:methanol=10:1);
NMR (CD$_3$OD): δ 7.40 (d, J=8.7 Hz, 2H), 7.11 (d, J=8.7 Hz, 2H), 4.32 (s, 2H), 4.18 (d, J=2.4 Hz, 1H), 4.04 (m, 1H), 3.88 (s, 3H), 3.80 (m, 1H), 3.66–3.48 (m, 3H), 3.30–3.18 (m, 2H), 2.64–2.30 (m, 3H), 2.42 (s, 3H), 2.36 (s, 3H), 2.22–1.88 (m, 3H), 1.84–1.60 (m, 5H), 1.54–1.10 (m, 6H), 1.06–0.82 (m, 2H), 0.97 (t, J=7.2 Hz, 3H).

EXAMPLE 9(62)

(3R)-1-butyl-2,5-dioxo-3-((1R)-1-hydroxy-1-cyclohexylmethyl)-9-(3,5-dimethyl-1-ethylpyrazol-4-ylmethyl)-1,4,9-triazaspiro[5.5]undecane.2hydrochloride

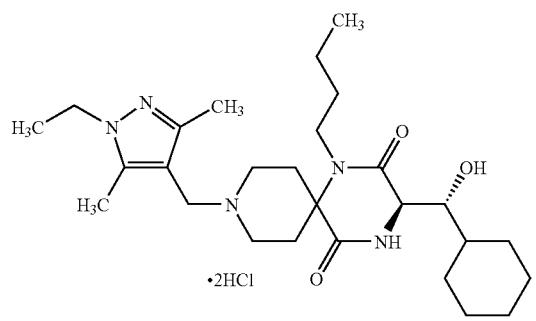

TLC: Rf 0.27 (chloroform:methanol=10:1);
NMR (CD$_3$OD): δ 4.28 (s, 2H), 4.23 (q, J=7.2 Hz, 2H), 4.17 (d, J=2.4 Hz, 1H), 4.00 (m, 1H), 3.78 (m, 1H), 3.64–3.44 (m, 3H), 3.30–3.18 (m, 2H), 2.70–2.34 (m, 3H), 2.48 (s, 3H), 2.43 (s, 3H), 2.22–1.86 (m, 3H), 1.84–1.60 (m, 5H), 1.52–1.08 (m, 6H), 1.43 (t, J=7.2 Hz, 3H), 1.06–0.80 (m, 2H), 0.96 (t, J=7.2 Hz, 3H).

EXAMPLE 9(63)

(3R)-1-butyl-2,5-dioxo-3-((1R)-1-hydroxy-1-cyclohexylmethyl)-9-(3,5-dimethyl-1-propylpyrazol-4-ylmethyl)-1,4,9-triazaspiro[5.5]undecane.2hydrochloride

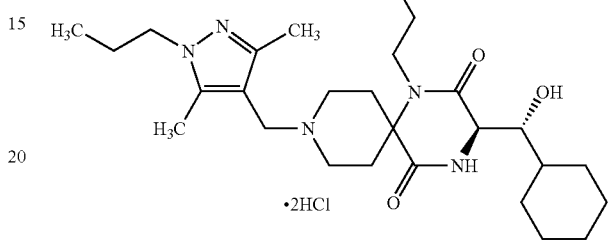

TLC: Rf 0.31 (chloroform:methanol=10:1);
NMR (CD$_3$OD): δ 4.28 (s, 2H), 4.16 (d, J=2.4 Hz, 1H), 4.15 (t, J=7.2 Hz, 2H), 4.00 (m, 1H), 3.76 (m, 1H), 3.62–3.46 (m, 3H), 3.30–3.18 (m, 2H), 2.66–2.36 (m, 3H), 2.47 (s, 3H), 2.43 (s, 3H), 2.20–1.60 (m, 10H), 1.52–1.10 (m, 6H), 1.18 (t, J=7.2 Hz, 3H), 1.06–0.80 (m, 2H), 0.96 (t, J=7.2 Hz, 3H).

EXAMPLE 9(64)

(3R)-1-butyl-2,5-dioxo-3-((1R)-1-hydroxy-1-cyclohexylmethyl)-9-(3,5-dimethyl-1-(1,1-dimethylethyl)pyrazol-4-ylmethyl)-1,4,9-triazaspiro[5.5]undecane.2hydrochloride

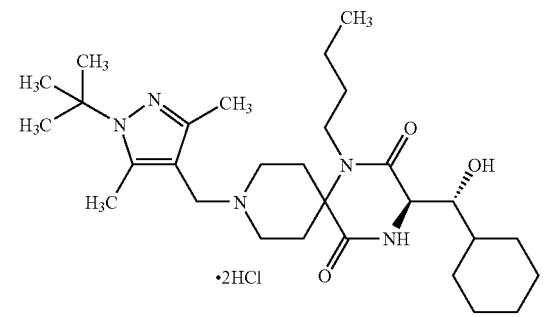

TLC: Rf 0.33 (chloroform:methanol=10:1);
NMR (CD$_3$OD): δ 4.26 (s, 2H), 4.17 (d, J=2.4 Hz, 1H), 4.02 (m, 1H), 3.78 (m, 1H), 3.62–3.46 (m, 3H), 3.30–3.22 (m, 2H), 2.64–2.40 (m, 3H), 2.63 (s, 3H), 2.42 (s, 3H), 2.20–1.86 (m, 3H), 1.84–1.62 (m, 5H), 1.72 (s, 9H), 1.54–1.16 (m, 6H), 1.04–0.82 (m, 2H), 0.96 (t, J=6.9 Hz, 3H).

EXAMPLE 9(65)

(3R)-1-butyl-2,5-dioxo-3-((1R)-1-hydroxy-1-cyclohexylmethyl)-9-(3,5-dimethyl-1-cyclopentylpyrazol-4-ylmethyl)-1,4,9-triazaspiro[5.5]undecane.2hydrochloride

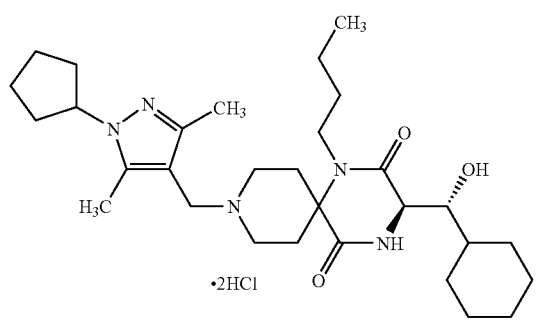

TLC: Rf 0.33 (chloroform:methanol=10:1);

NMR (CD$_3$OD): δ 4.27 (s, 2H), 4.16 (d, J=2.1 Hz, 1H), 4.00 (m, 1H), 3.78 (m, 1H), 3.64–3.44 (m, 4H), 3.30–3.20 (m, 2H), 2.66–2.36 (m, 3H), 2.47 (s, 3H), 2.42 (s, 3H), 2.28–1.60 (m, 16H), 1.58–1.10 (m, 6H), 1.08–0.82 (m, 2H), 0.96 (t, J=6.9 Hz, 3H).

EXAMPLE 9(66)

(3R)-1-butyl-2,5-dioxo-3-((1R)-1-hydroxy-1-cyclohexylmethyl)-9-(3,5-dimethyl-1-(2-phenylethyl)pyrazol-4-ylmethyl)-1,4,9-triazaspiro[5.5]undecane.2hydrochloride

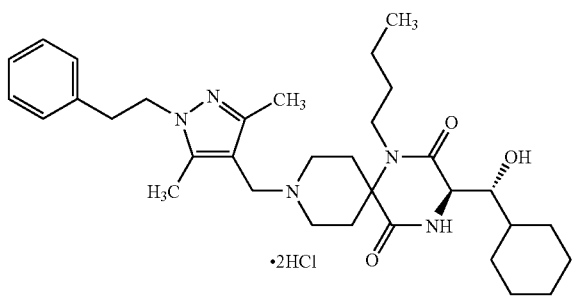

TLC: Rf 0.25 (chloroform:methanol=10:1);

NMR (CD$_3$OD): δ 7.36–7.18 (m, 3H), 7.16–7.00 (m, 2H), 4.39 (t, J=6.3 Hz, 2H), 4.18 (s, 2H), 4.17 (d, J=2.4 Hz, 1H), 3.88 (m, 1H), 3.72–3.46 (m, 2H), 3.42–3.22 (m, 4H), 3.12 (t, J=6.3 Hz, 2H), 2.66–2.34 (m, 3H), 2.44 (s, 3H), 2.18–1.86 (m, 3H), 1.92 (s, 3H), 1.84–1.62 (m, 5H), 1.54–1.10 (m, 6H), 1.06–0.82 (m, 2H), 0.97 (t, J=6.9 Hz, 3H).

EXAMPLE 9(67)

(3R)-1-butyl-2,5-dioxo-3-((1R)-1-hydroxy-1-cyclohexylmethyl)-9-(3,5-dimethyl-1-(1-benzyl-oxycarbonylpiperidin-4-yl)pyrazol-4-ylmethyl)-1,4,9-triazaspiro[5.5]undecane.2hydrochloride

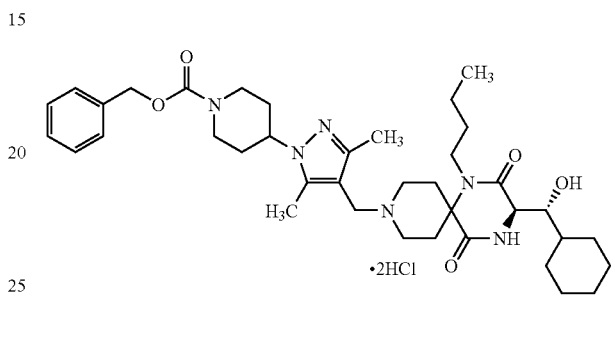

TLC: Rf 0.40 (chloroform:methanol=10:1);

NMR (CD$_3$OD): δ 7.42–7.25 (m, 5H), 5.14 (s, 2H), 4.56 (m, 1H), 4.36–4.25 (m, 2H), 4.25 (s, 2H), 4.15 (d, J=2.1 Hz, 1H), 3.98 (m, 1H), 3.73 (m, 1H), 3.62–3.45 (m, 3H), 3.40–3.20 (m, 2H), 3.18–2.94 (m, 2H), 2.67–2.30 (m, 9H), 2.20–1.85 (m, 7H), 1.83–1.58 (m, 5H), 1.50–1.08 (m, 6H), 1.05–0.80 (m, 2H), 0.95 (t, J=7.2 Hz, 3H).

EXAMPLE 9(68)

(3R)-1-butyl-2,5-dioxo-3-((1R)-1-hydroxy-1-cyclohexylmethyl)-9-(4-(cyclohexylaminocarbonyl)phenylmethyl)-1,4,9-triazaspiro[5.5]undecane.hydrochloride

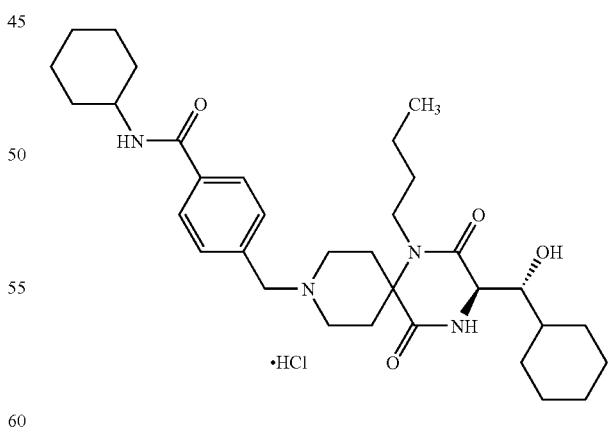

TLC: Rf 0.45 (chloroform:methanol=10:1);

NMR (CD$_3$OD): 7.92 (d, J=8.7 Hz, 2H), 7.67 (d, J=8.7 Hz, 2H), 4.42 (s, 2H), 4.15 (d, J=2.1 Hz, 1H), 4.02 (m, 1H), 3.92–3.69 (m, 2H), 3.60–3.39 (m, 3H), 3.30–3.12 (m, 2H), 2.56–2.26 (m, 3H), 2.17–1.58 (m, 14H), 1.51–1.08 (m, 10H), 1.06–0.80 (m, 2H), 0.95 (t, J=6.9 Hz, 3H).

EXAMPLE 9(69)

(3R)-1-butyl-2,5-dioxo-3-((1R)-1-hydroxy-1-cyclohexylmethyl)-9-(3,5-dimethyl-1-(1-methylsulfonylpiperidin-4-yl)pyrazol-4-ylmethyl)-1,4,9-triazaspiro[5.5]undecane.2hydrochloride

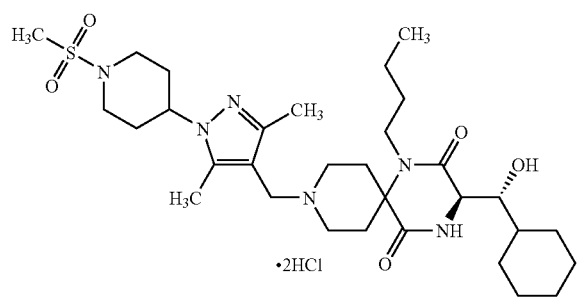

TLC: Rf 0.26 (chloroform:methanol=10:1);

NMR (CD₃OD): δ 4.48 (m, 1H), 4.25 (s, 2H), 4.15 (d, J=2.1 Hz, 1H), 4.05–3.83 (m, 3H), 3.74 (m, 1H), 3.60–3.46 (m, 3H), 3.40–3.20 (m, 2H), 3.05–2.92 (m, 2H), 2.90 (s, 3H), 2.60 (m, 1H), 2.52–2.40 (m, 2H), 2.49 (s, 3H), 2.39 (s, 3H), 2.26–1.88 (m, 7H), 1.84–1.60 (m, 5H), 1.50–1.10 (m, 6H), 1.05–0.80 (m, 2H), 0.95 (t, J=6.9 Hz, 3H).

EXAMPLE 9(70)

(3R)-1-butyl-2,5-dioxo-3-((1R)-1-hydroxy-1-cyclohexylmethyl)-9-(4-(4-(2-hydroxyethylaminocarbonyl)phenyloxy)phenylmethyl)-1,4,9-triazaspiro[5.5]undecane.hydrochloride

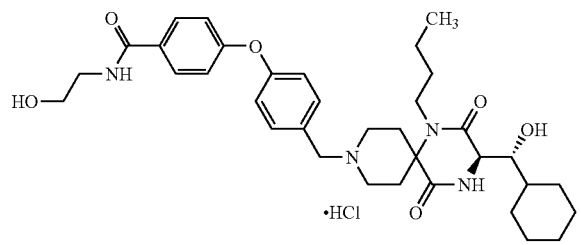

TLC: Rf 0.50 (chloroform:methanol=5:1);

NMR (CD₃OD): δ 7.89 (d, J=9.0 Hz, 2H), 7.60 (d, J=9.0 Hz, 2H), 7.16 (d, J=9.0 Hz, 2H), 7.09 (d, J=9.0 Hz, 2H), 4.37 (s, 2H), 4.17 (d, J=2.1 Hz, 1H), 4.02 (m, 1H), 3.78 (m, 1H), 3.71 (t, J=5.7 Hz, 2H), 3.60–3.40 (m, 3H), 3.51 (t, J=5.7 Hz, 2H), 3.30–3.10 (m, 2H), 2.58–1.84 (m, 6H), 1.82–1.56 (m, 5H), 1.54–1.06 (m, 6H), 1.04–0.80 (m, 2H), 0.96 (t, J=6.9 Hz, 3H).

EXAMPLE 9(71)

(3R)-1-butyl-2,5-dioxo-3-((1R)-1-hydroxy-1-cyclohexylmethyl)-9-(4-(4-hydroxymethylphenyloxy)phenylmethyl)-1,4,9-triazaspiro[5.5]undecane

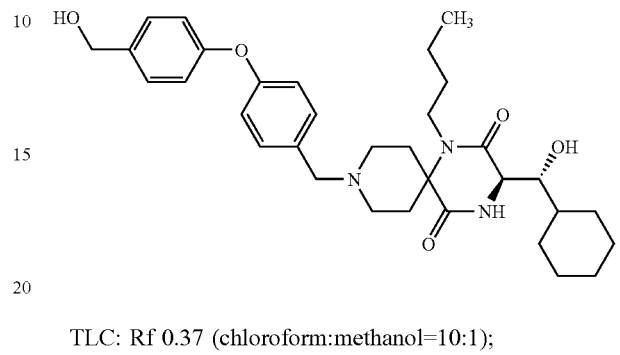

TLC: Rf 0.37 (chloroform:methanol=10:1);

NMR (CD₃OD): δ 7.34 (d, J=8.7 Hz, 4H), 6.97 (d, J=8.7 Hz, 2H), 6.96 (d, J=8.7 Hz, 2H), 4.57 (s, 2H), 4.13 (d, J=2.1 Hz, 1H), 3.71 (s, 2H), 3.47 (m, 1H), 3.35 (dd, J=9.0, 2.1 Hz, 1H), 3.30–2.88 (m, 5H), 2.31–1.81 (m, 6H), 1.81–1.58 (m, 5H), 1.55–1.05 (m, 6H), 1.05–0.83 (m, 2H), 0.95 (t, J=7.2 Hz, 3H).

EXAMPLE 10

(3S)-1-butyl-2,5-dioxo-3-((1S)-1-hydroxy-1-cyclohexylmethyl)-9-(4-(4-methylsulfonylaminophenyloxy)phenylmethyl)-1,4,9-triazaspiro[5.5]undecane-.hydrochloride

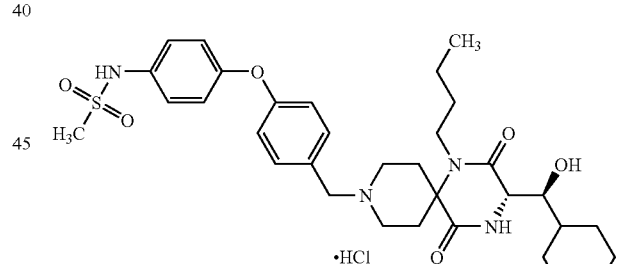

By the same procedure as described in Example 2 using the compound prepared in Reference example 3(9) instead of the compound prepared in Reference example 3, and using 4-(4-methylsulfonylaminophenyloxy)benzaldehyde instead of 3-formyl-6-phenyloxypyridine, the title compound having the following physical data was obtained.

TLC: Rf 0.54 (ethyl acetate:methanol=4:1);

NMR (CD₃OD): δ 7.54 (d, J=8.4 Hz, 2H), 7.29 (d, J=8.7 Hz, 2H), 7.06 (d, j=8.4 Hz, 2H), 7.03 (d, J=8.7 Hz, 2H), 4.32 (s, 2H), 4.15 (d, J=2.0 Hz, 1H), 3.98 (m, 1H), 3.73 (m, 1H), 3.55–3.43 (m, 3H), 3.30–3.16 (m, 2H), 2.95 (s, 3H), 2.52–2.28 (m, 3H), 2.14–1.91 (m, 3H), 1.76–1.65 (m, 5H), 1.50–1.15 (m, 6H), 1.00–0.86 (m, 5H).

EXAMPLE 11

(3R)-1-butyl-2,5-dioxo-3-((1R)-1-hydroxy-1-(3,4,5,6-tetrahydropyran-4-yl)methyl)-9-(3,5-dimethyl-1-phenylpyrazol-4-ylmethyl)-1,4,9-triazaspiro[5.5]undecane.2hydrochloride

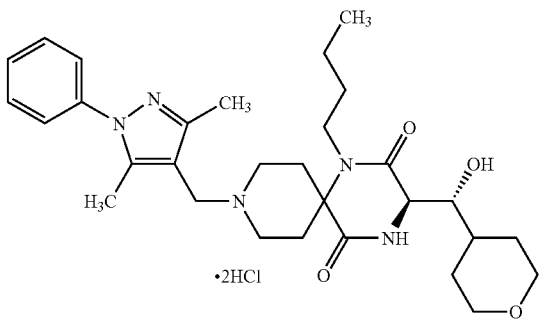

By the same procedure as described in Example 2 using the compound prepared in Reference example 3(4) instead of the compound prepared in Reference example 3, and using 4-formyl-3,5-dimethyl-1-phenylpyrazole instead of 3-formyl-6-phenyloxypyridine, the title compound having the following physical data was obtained.

TLC: Rf 0.31 (ethyl acetate:methanol=4:1);

NMR (CD$_3$OD): δ 7.67–7.56 (m, 5H), 4.37 (s, 2H), 4.13 (d, J=2.0 Hz, 1H), 4.06 (m, 1H), 3.98–3.91 (m, 2H), 3.80 (m, 1H), 3.64–3.53 (m, 4H), 3.46–3.37 (m, 3H), 2.80–2.52 (m, 5H), 2.45 (s, 3H), 2.16–2.01 (m, 2H), 1.91–1.82 (m, 2H), 1.71 (m, 1H), 1.50–1.17 (m, 6H), 0.95 (t, J=7.5 Hz, 3H).

EXAMPLE 11(1)–11(5)

By the same procedure as described in Example 11 using the corresponding aldehyde derivatives respectively instead of 4-formyl-3,5-dimethyl-1-phenylpyrazole, the following compounds having the following physical data were obtained.

EXAMPLE 11(1)

(3R)-1-butyl-2,5-dioxo-3-((1R)-1-hydroxy-1-(3,4,5,6-tetrahydropyran-4-yl)methyl)-9-(4-(4-methylaminocarbonylphenyloxy)phenylmethyl)-1,4,9-triazaspiro[5.5]undecane.hydrochloride

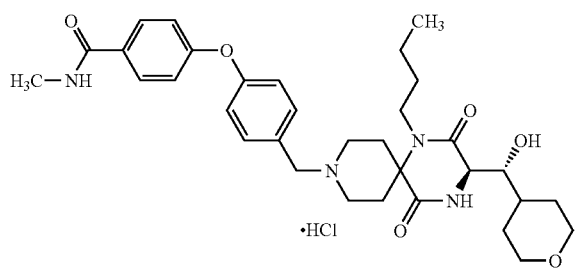

TLC: Rf 0.28 (ethyl acetate:methanol=4:1);
NMR (CD$_3$OD): δ 7.84 (d, J=8.7 Hz, 2H), 7.59 (d, J=8.7 Hz, 2H), 7.15 (d, J=8.7 Hz, 2H), 7.07 (d, J=8.7 Hz, 2H), 4.36 (s, 2H), 4.12 (d, J=2.0 Hz, 1H), 4.06–3.90 (m, 3H), 3.75 (m, 1H), 3.56–3.34 (m, 5H), 3.30–3.20 (m, 2H), 2.91 (s, 3H), 2.51–2.28 (m, 3H), 2.16–1.69 (m, 5H), 1.50–1.15 (m, 5H), 0.95 (t, J=7.0 Hz, 3H).

EXAMPLE 11(2)

(3R)-1-butyl-2,5-dioxo-3-((1R)-1-hydroxy-1-(3,4,5,6-tetrahydropyran-4-yl)methyl)-9-(4-(4-(4-methoxyphenylmethylaminocarbonyl)phenylmethyl)-1,4,9-triazaspiro[5.5]undecane.hydrochloride

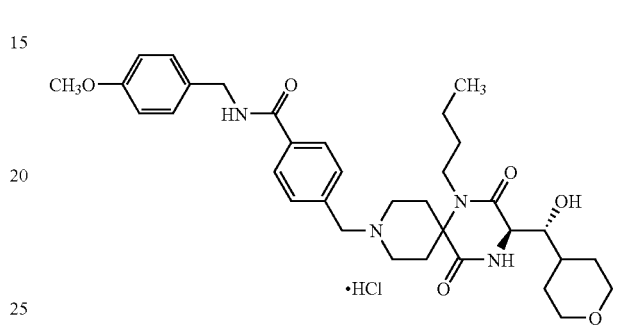

TLC: Rf 0.36 (ethyl acetate:methanol=4:1);
NMR (CD$_3$OD): δ 7.95 (d, J=8.3 Hz, 2H), 7.66 (d, J=8.3 Hz, 2H), 7.27 (d, J=8.8 Hz, 2H), 6.87 (d, J=8.8 Hz, 2H), 4.51 (s, 2H), 4.42 (s, 2H), 4.11 (d, J=2.0 Hz, 1H), 4.04–3.91 (m, 3H), 3.76 (m, 1H), 3.76 (s, 3H), 3.56–3.37 (m, 5H), 3.30–3.13 (m, 2H), 2.50–1.70 (m, 8H), 1.39–1.15 (m, 5H), 0.95 (t, J=7.0 Hz, 3H).

EXAMPLE 11(3)

(3R)-1-butyl-2,5-dioxo-3-((1R)-1-hydroxy-1-(3,4,5,6-tetrahydropyran-4-yl)methyl)-9-(3,5-dimethyl-1-(4-(N,N-dimethylaminocarbonyl)phenylpyrazol-4-ylmethyl)-1,4,9-triazaspiro[5.5]undecane.2hydrochloride

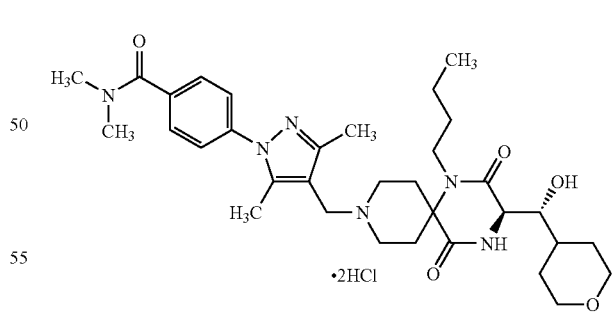

TLC: Rf 0.55 (chloroform:methanol=4:1);
NMR (CD$_3$OD): δ 7.63 (d, J=9.0 Hz, 2H), 7.60 (d, J=9.0 Hz, 2H), 4.32 (s, 2H), 4.13 (d, J=2.0 Hz, 1H), 4.06 (m, 1H), 4.00–3.91 (m, 2H), 3.79 (m, 1H), 3.63–3.52 (m, 4H), 3.46–3.34 (m, 3H), 3.13 (s, 3H), 3.04 (s, 3H), 2.62–2.37 (m, 2H), 2.44 (s, 3H), 2.41 (s, 3H), 2.15 (m, 1H), 2.03 (m, 1H), 1.90–1.70 (m, 3H), 1.50–1.15 (m, 6H), 0.96 (t, J=7.0 Hz, 3H).

EXAMPLE 11(4)

(3R)-1-butyl-2,5-dioxo-3-((1R)-1-hydroxy-1-(3,4,5,6-tetrahydropyran-4-yl)methyl)-9-(4-(4-carboxyphenyloxy)phenylmethyl)-1,4,9-triazaspiro[5.5]undecane.2hydrochloride

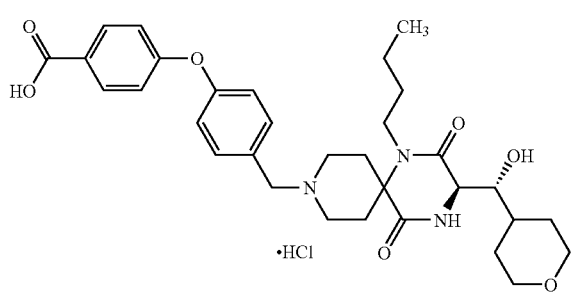

TLC: Rf 0.30 (chloroform:methanol=4:1);

NMR (CD$_3$OD): δ 8.04 (d, J=9.0 Hz, 2H), 7.60 (d, J=8.5 Hz, 2H), 7.18 (d, J=8.5 Hz, 2H), 7.07 (d, J=9.0 Hz, 2H), 4.37 (s, 2H), 4.12 (d, J=2.0 Hz, 1H), 4.08–3.93 (m, 3H), 3.75 (m, 1H), 3.57–3.34 (m, 5H), 3.30–3.15 (m, 2H), 2.52–1.69 (m, 8H), 1.50–1.18 (m, 5H), 0.96 (t, J=7.2 Hz, 3H).

EXAMPLE 11(5)

(3R)-1-butyl-2,5-dioxo-3-((1R)-1-hydroxy-1-(3,4,5,6-tetrahydropyran-4-yl)methyl)-9-(4-(4-methylsulfonylaminophenyloxy)phenylmethyl)-1,4,9-triazaspiro[5.5]undecane.hydrochloride

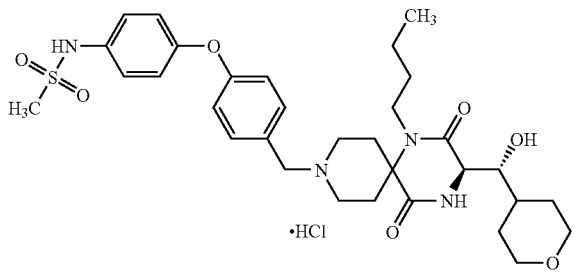

TLC: Rf 0.35 (ethyl acetate:methanol=4:1);

NMR (CD$_3$OD): δ 7.53 (d, J=8.7 Hz, 2H), 7.29 (d, J=8.7 Hz, 2H), 7.06 (d, J=8.7 Hz, 2H), 7.03 (d, J=8.7 Hz, 2H), 4.33 (s, 2H), 4.12 (d, J=2.0 Hz, 1H), 4.04–3.92 (m, 3H), 3.72 (m, 1H), 3.54–3.38 (m, 5H), 3.30–3.13 (m, 2H), 2.95 (s, 3H), 2.51–2.26 (m, 3H), 2.16–2.00 (m, 2H), 1.89–1.70 (m, 3H), 1.50–1.15 (m, 5H), 0.95 (t, J=7.0 Hz, 3H).

EXAMPLE 12

(3R)-1-butyl-2,5-dioxo-3-((1R)-1-hydroxy-1-cyclopentylmethyl)-9-(3,5-dimethyl-1-phenylpyrazol-4-ylmethyl)-1,4,9-triazaspiro[5.5]undecane.2hydrochloride

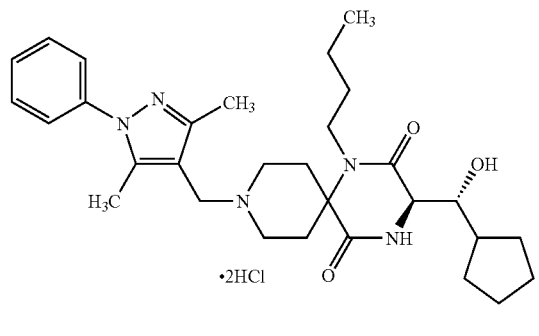

By the same procedure as described in Example 2 using the compound prepared in Reference example 3(5) instead of the compound prepared in Reference example 3, and using 4-formyl-3,5-dimethyl-1-phenylpyrazole instead of 3-formyl-6-phenyloxypyridine, title compound having the following physical data was obtained.

TLC: Rf 0.45 (ethyl acetate:methanol=4:1);

NMR (CD$_3$OD): δ 7.64–7.51 (m, 5H), 4.34 (s, 2H), 4.05 (m, 1H), 4.01 (d, J=2.0 Hz, 1H), 3.79 (m, 1H), 3.63–3.52 (m, 3H), 3.39 (dd, J=9.9, 2.0 Hz, 1H), 3.30 (m, 1H), 2.64 (m, 1H), 2.48 (m, 1H), 2.47 (s, 3H), 2.42 (s, 3H), 2.37–2.12 (m, 2H), 1.90–1.82 (m, 2H), 1.74–1.15 (m, 11H), 0.96 (t, J=7.5 Hz, 3H).

EXAMPLE 12(1)–12(3)

By the same procedure as described in Example 12 using the corresponding aldehyde derivatives respectively instead of 4-formyl-3,5-dimethyl-1-phenylpyrazole, the following compounds were obtained.

EXAMPLE 12(1)

(3R)-1-butyl-2,5-dioxo-3-((1R)-1-hydroxy-1-cyclopentylmethyl)-9-(4-(4-(4-methoxyphenylmethylaminocarbonyl)phenylmethyl)-1,4,9-triazaspiro[5.5]undecane.hydrochloride

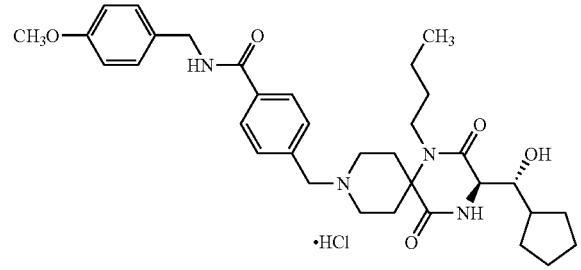

TLC: Rf 0.35 (chloroform:methanol=10:1);

NMR (CD$_3$OD): δ 7.96 (d, J=8.7 Hz, 2H), 7.66 (d, J=8.7 Hz, 2H), 7.28 (d, J=8.7 Hz, 2H), 6.88 (d, J=8.7 Hz, 2H), 4.52

(s, 2H), 4.42 (s, 2H), 4.02 (m, 1H), 4.00 (d, J=1.8 Hz, 1H), 3.77 (s, 3H), 3.77 (m, 1H), 3.60–3.02 (m, 5H), 2.58–2.04 (m, 5H), 2.00–1.06 (m, 12H), 0.96 (t, J=7.5 Hz, 3H).

EXAMPLE 12(2)

(3R)-1-butyl-2,5-dioxo-3-((1R)-1-hydroxy-1-cyclopentylmethyl)-9-(4-(4-methylaminocarbonylphenyloxy)phenylmethyl)-1,4,9-triazaspiro[5.5]undecane.hydrochloride

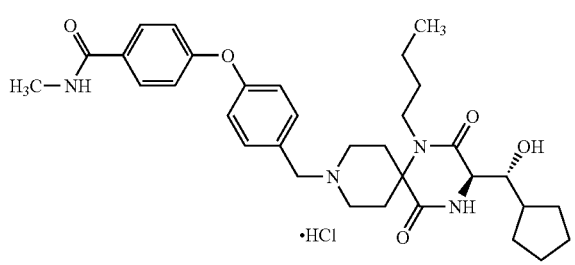

TLC: Rf 0.25 (chloroform:methanol=10:1);

NMR (CD₃OD): δ 7.85 (d, J=8.7 Hz, 2H), 7.60 (d, J=8.7 Hz, 2H), 7.16 (d, J=8.7 Hz, 2H), 7.08 (d, J=8.7 Hz, 2H), 4.37 (s, 2H), 4.02 (m, 1H), 4.01 (d, J=2.1 Hz, 1H), 3.78 (m, 1H), 3.40–3.12 (m, 5H), 2.92 (s, 3H), 2.60–2.06 (m, 5H), 2.00–1.08 (m, 12H), 0.96 (t, J=7.2 Hz, 3H).

EXAMPLE 12(3)

(3R)-1-butyl-2,5-dioxo-3-((1R)-1-hydroxy-1-cyclopentylmethyl)-9-(4-(4-carboxyphenyloxy)phenylmethyl)-1,4,9-triazaspiro[5.5]undecane.hydrochloride

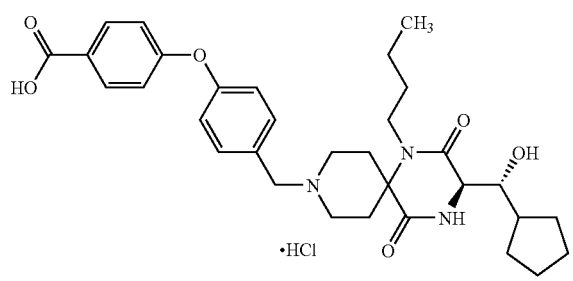

TLC: Rf 0.36 (chloroform:methanol=5:1);

NMR (CD₃OD): δ 8.05 (d, J=8.7 Hz, 2H), 7.61 (d, J=8.7 Hz, 2H), 7.19 (d, J=8.7 Hz, 2H), 7.08 (d, J=8.7 Hz, 2H), 4.38 (s, 2H), 4.02 (m, 1H), 4.01 (d, J=1.8 Hz, 1H), 3.78 (m, 1H), 3.62–3.08 (m, 5H), 2.60–2.06 (m, 5H), 2.00–1.08 (m, 12H), 0.96 (t, J=6.9 Hz, 3H).

EXAMPLE 13

(3R)-1-propyl-2,5-dioxo-3-((1R)-1-hydroxy-2-methylpropyl)-9-(4-(4-methylaminocarbonylphenyloxy)phenylmethyl)-1,4,9-triazaspiro[5.5]undecane.hydrochloride

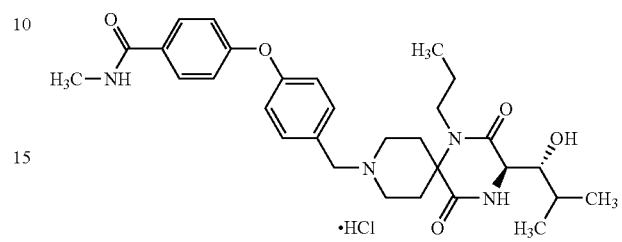

By the same procedure as described in Example 2 using the compound prepared in Reference example 3(6) instead of the compound prepared in Reference example 3, using 4-(4-methylaminocarobonylphenyloxy)benzaldehyde instead of 3-formyl-6-phenyloxypyridine, the title compound having the following physical data was obtained.

TLC: Rf 0.35 (chloroform:methanol=10:1);

NMR (CD₃OD): δ 7.84 (d, J=9.0 Hz, 2H), 7.61 (d, J=8.7 Hz, 2H), 7.14 (d, J=8.7 Hz, 2H), 7.07 (d, J=9.0 Hz, 2H), 4.36 (s, 2H), 4.14 (d, J=1.8 Hz, 1H), 3.99 (m, 1H), 3.74 (m, 1H), 3.55–3.40 (m, 3H), 3.20 (m, 1H), 3.19 (dd, J=9.6, 1.8 Hz, 1H), 2.91 (s, 3H), 2.59–2.29 (m, 3H), 2.12 (m, 1H), 2.00 (m, 1H), 1.74 (m, 1H), 1.46 (m, 1H), 0.99 (d, J=6.6 Hz, 3H), 0.97 (d, J=6.6 Hz, 3H), 0.93 (t, J=7.5 Hz, 3H).

EXAMPLE 13(1) AND 13(2)

By the same procedure as described in Example 13 using the corresponding aldehyde derivatives respectively instead of 4-(4-methylaminocarobonylphenyloxy)benzaldehyde, the following compounds were obtained.

EXAMPLE 13(1)

(3R)-1-propyl-2,5-dioxo-3-((1R)-1-hydroxy-2-methylpropyl)-9-(3,5-dimethyl-1-cyclohexylpyrazol-4-ylmethyl)-1,4,9-triazaspiro[5.5]undecane.2hydrochloride

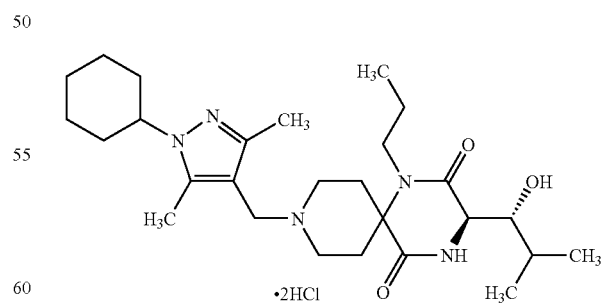

TLC: Rf 0.39 (chloroform:methanol=10:1);

NMR (CD₃OD): δ 4.40 (m, 1H), 4.30 (s, 2H), 4.14 (d, J=2.1 Hz, 1H), 4.00 (m, 1H), 3.76 (m, 1H), 3.59–3.43 (m, 3H), 3.22 (m, 1H), 3.20 (dd, J=9.6, 2.1 Hz, 1H), 2.66 (m, 1H), 2.53 (s, 3H), 2.49 (s, 3H), 2.50–2.38 (m, 2H), 2.15–1.10 (m, 14H), 0.99 (d, J=6.6 Hz, 3H), 0.98 (d, J=6.6 Hz, 3H), 0.93 (t, J=7.5 Hz, 3H).

EXAMPLE 13(2)

(3R)-1-propyl-2,5-dioxo-3-((1R)-1-hydroxy-2-methylpropyl)-9-(4-(4-methoxyphenylmethylaminocarbonyl)phenylmethyl)-1,4,9-triazaspiro[5.5]undecane.hydrochloride

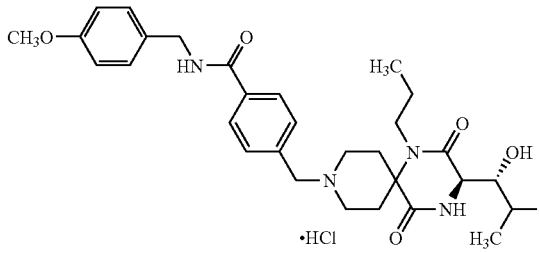

TLC: Rf 0.41 (chloroform:methanol=10:1);

NMR (CD₃OD): δ 7.95 (d, J=8.7 Hz, 2H), 7.69 (d, J=8.7 Hz, 2H), 7.27 (d, J=8.7 Hz, 2H), 6.87 (d, J=8.7 Hz, 2H), 4.51 (s, 2H), 4.42 (s, 2H), 4.13 (d, J=2.1 Hz, 1H), 4.01 (m, 1H), 3.76 (m, 1H), 3.76 (s, 3H), 3.54–3.39 (m, 3H), 3.19 (m, 1H), 3.18 (dd, J=9.6, 2.1 Hz, 1H), 2.58–2.26 (m, 3H), 2.10 (m, 1H), 1.99 (m, 1H), 1.72 (m, 1H), 1.46 (m, 1H), 0.98 (d, J=6.6 Hz, 3H), 0.96 (d, J=6.6 Hz, 3H), 0.92 (t, J=7.5 Hz, 3H).

EXAMPLE 14

(3R)-1-propyl-2,5-dioxo-3-((1R)-1-hydroxy-1-cyclohexylmethyl)-9-(4-(4-methylaminocarbonylphenyloxy)phenylmethyl-1,4,9-triazaspiro[5.5]undecane-.hydrochloride

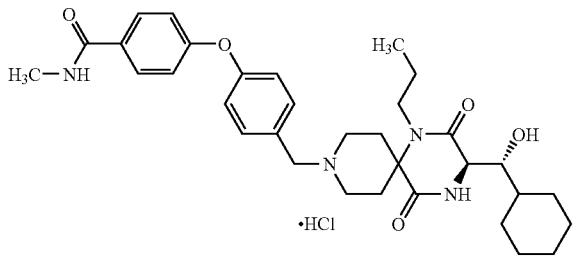

By the same procedure as described in Example 2 using the compound prepared in Reference example 3(7) instead of the compound prepared in Reference example 3, and using 4-(4-methylaminocarobonylphenyloxy)benzaldehyde instead of 3-formyl-6-phenyloxypyridine, the title compound having the following physical data was obtained.

TLC: Rf 0.38 (chloroform:methanol=10:1);

NMR (CD₃OD): δ 7.84 (d, J=9.0 Hz, 2H), 7.60 (d, J=9.0 Hz, 2H), 7.15 (d, J=9.0 Hz, 2H), 7.07 (d, J=9.0 Hz, 2H), 4.36 (s, 2H), 4.15 (d, J=2.1 Hz, 1H), 3.99 (m, 1H), 3.75 (m, 1H), 3.54–3.39 (m, 3H), 3.30–3.10 (m, 3H), 2.91 (s, 3H), 2.56–2.27 (m, 3H), 2.18–1.88 (m, 3H), 1.83–1.60 (m, 5H), 1.46 (m, 1H), 1.37–1.11 (m, 3H), 1.04–0.80 (m, 2H), 0.93 (t, J=7.5 Hz, 3H).

EXAMPLE 14(1)–14(5)

By the same procedure as described in Example 14 using the corresponding aldehyde derivatives respectively instead of 4-(4-methylaminocarobonylphenyloxy)benzaldehyde, the following compounds were obtained.

EXAMPLE 14(1)

(3R)-1-propyl-2,5-dioxo-3-((1R)-1-hydroxy-1-cyclohexylmethyl)-9-(3,5-dimethyl-1-cyclohexylpyrazol-4-ylmethyl)-1,4,9-triazaspiro[5.5]undecane.2hydrochloride

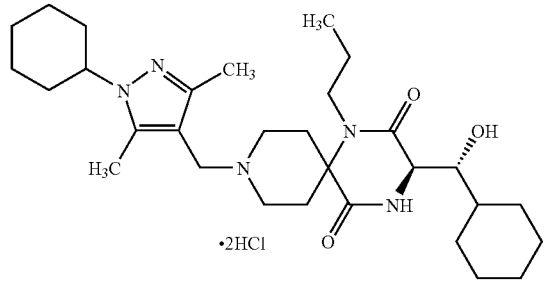

TLC: Rf 0.41 (chloroform:methanol=10:1);

NMR (CD₃OD): δ 4.39 (m, 1H), 4.29 (s, 2H), 4.15 (d, J=2.1 Hz, 1H), 4.00 (m, 1H), 3.76 (m, 1H), 3.60–3.42 (m, 3H), 3.40–3.20 (m, 2H), 2.65 (m, 1H), 2.53 (s, 3H), 2.49 (s, 3H), 2.53–2.35 (m, 2H), 2.15–1.05 (m, 22H), 1.05–0.80 (m, 2H), 0.93 (t, J=7.2 Hz, 3H).

EXAMPLE 14(2)

(3R)-1-propyl-2,5-dioxo-3-((1R)-1-hydroxy-1-cyclohexylmethyl)-9-(4-(4-methoxyphenylmethylaminocarbonyl)phenylmethyl)-1,4,9-triazaspiro[5.5]undecane.hydrochloride

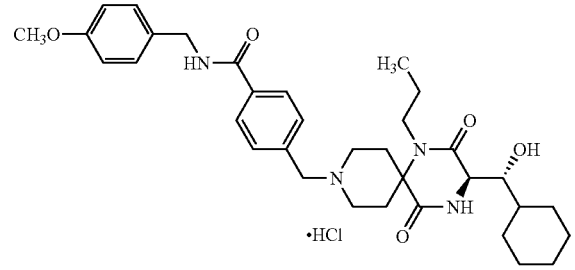

TLC: Rf 0.42 (chloroform:methanol=10:1);

NMR (CD₃OD): δ 7.94 (d, J=8.7 Hz, 2H), 7.68 (d, J=8.7 Hz, 2H), 7.27 (d, J=8.7 Hz, 2H), 6.87 (d, J=8.7 Hz, 2H), 4.51 (s, 2H), 4.41 (s, 2H), 4.14 (d, J=1.8 Hz, 1H), 4.01 (m, 1H), 3.76 (m, 1H), 3.76 (s, 3H), 3.54–3.38 (m, 3H), 3.27 (dd, J=9.6, 1.8 Hz, 1H), 3.18 (m, 1H), 2.57–2.26 (m, 3H), 2.16–1.86 (m, 3H), 1.82–1.60 (m, 5H), 1.54–1.05 (m, 4H), 1.03–0.80 (m, 2H), 0.92 (t, J=7.5 Hz, 3H).

EXAMPLE 14(3)

(3R)-1-propyl-2,5-dioxo-3-((1R)-1-hydroxy-1-cyclohexylmethyl)-9-(3,5-dimethyl-1-(4-(N,N-dimethylaminocarbonyl)phenyl)pyrazol-4-ylmethyl)-1,4,9-triazaspiro[5.5]undecane.2hydrochloride

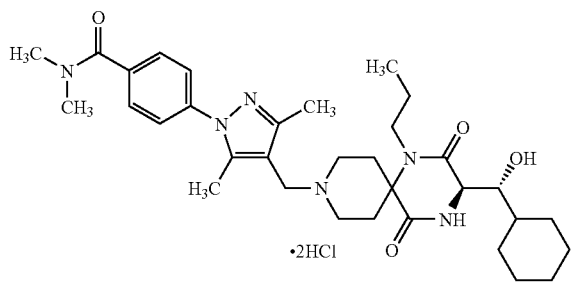

TLC: Rf 0.36 (chloroform:methanol=10:1);
NMR (CD$_3$OD): δ 7.63 (s, 4H), 4.32 (s, 2H), 4.16 (d, J=2.1 Hz, 1H), 4.04 (m, 1H), 3.79 (m, 1H), 3.64–3.43 (m, 3H), 3.34–3.20 (m, 2H), 3.13 (s, 3H), 3.04 (s, 3H), 2.62 (m, 1H), 2.53–2.39 (m, 2H), 2.45 (s, 3H), 2.44 (s, 3H), 2.19–1.88 (m, 3H), 1.83–1.60 (m, 5H), 1.46 (m, 1H), 1.38–1.10 (m, 3H), 1.05–0.80 (m, 2H), 0.95 (t, J=7.5 Hz, 3H).

EXAMPLE 14(4)

(3R)-1-propyl-2,5-dioxo-3-((1R)-1-hydroxy-1-cyclohexylmethyl)-9-(4-(4-carboxyphenyloxy)phenylmethyl)-1,4,9-triazaspiro[5.5]undecane.hydrochloride

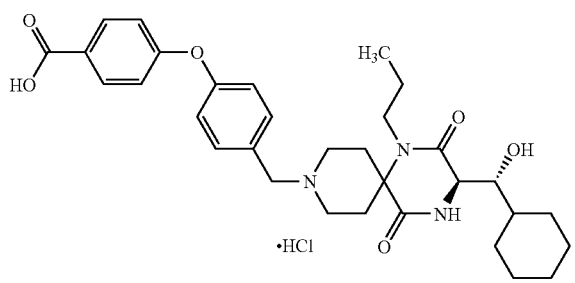

TLC: Rf 0.21 (chloroform:methanol:acetic acid=20:2:1);
NMR (CD$_3$OD): δ 8.04 (d, J=9.0 Hz, 2H), 7.62 (d, J=8.4 Hz, 2H), 7.17 (d, J=8.4 Hz, 2H), 7.07 (d, J=9.0 Hz, 2H), 4.37 (s, 2H), 4.15 (d, J=2.1 Hz, 1H), 4.01 (m, 1H), 3.75 (m, 1H), 3.55–3.38 (m, 3H), 3.30–3.09 (m, 2H), 2.55–2.26 (m, 3H), 2.18–1.88 (m, 3H), 1.83–1.60 (m, 5H), 1.57–1.10 (m, 4H), 1.04–0.80 (m, 2H), 0.93 (t, J=7.5 Hz, 3H).

EXAMPLE 14(5)

(3R)-1-propyl-2,5-dioxo-3-((1R)-1-hydroxy-1-cyclohexylmethyl)-9-(4-(4-methoxycarbonylphenyloxy)phenylmethyl)-1,4,9-triazaspiro[5.5]undecane.hydrochloride

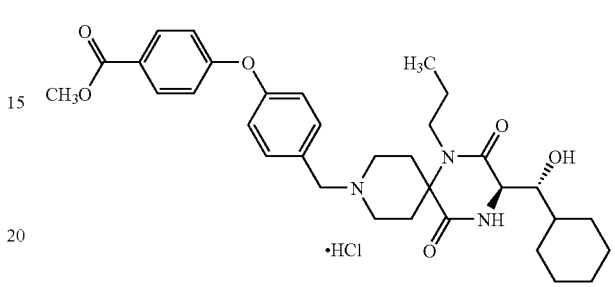

TLC: Rf 0.54 (chloroform:methanol=10:1);
NMR (CD$_3$OD): δ 8.03 (d, J=8.7 Hz, 2H), 7.62 (d, J=8.7 Hz, 2H), 7.17 (d, J=8.7 Hz, 2H), 7.07 (d, J=8.7 Hz, 2H), 4.37 (s, 2H), 4.15 (d, J=2.1 Hz, 1H), 4.00 (m, 1H), 3.88 (s, 3H), 3.75 (m, 1H), 3.54–3.41 (m, 3H), 3.30–3.10 (m, 2H), 2.58–2.27 (m, 3H), 2.18–1.87 (m, 3H), 1.84–1.61 (m, 5H), 1.56–1.08 (m, 4H), 1.04–0.80 (m, 2H), 0.94 (t, J=7.2 Hz, 3H).

EXAMPLE 15

(3R)-1-propyl-2,5-dioxo-3-(1-cyclohexylmethylidene)-9-(4-(4-carboxyphenyloxy)phenylmethyl)-1,4,9-triazaspiro[5.5]undecane.hydrochloride

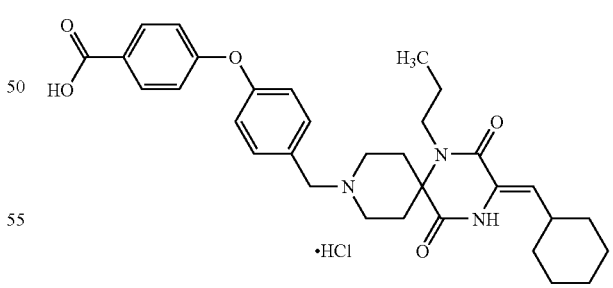

By the same procedure as described in Example 5 using the compound prepared in Example 14(5) instead of the compound prepared in Example 4(42), the title compound having the following physical data was obtained.

TLC: Rf 0.42 (chloroform:methanol=10:1);

NMR (CD₃OD): δ 8.03 (d, J=8.7 Hz, 2H), 7.62 (d, J=8.7 Hz, 2H), 7.17 (d, J=8.7 Hz, 2H), 7.07 (d, J=8.7 Hz, 2H), 5.87 (d, J=10.5 Hz, 1H), 4.37 (s, 2H), 3.78–3.62 (m, 2H), 3.58–3.38 (m, 4H), 2.54–2.36 (m, 3H), 2.27–2.15 (m, 2H), 1.80–1.51 (m, 7H), 1.50–1.08 (m, 5H), 0.93 (t, J=7.2 Hz, 3H).

EXAMPLE 16

(3S)-1-propyl-2,5-dioxo-3-(2-methylpropyl)-9-(3,5-dimethyl-1-cyclohexylpyrazol-4-ylmethyl)-1,4,9-triazaspiro[5.5]undecane.hydrochloride

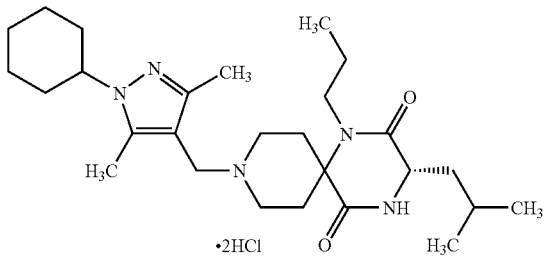

By the same procedure as described in Reference example 1→Reference example 2→Example 1→Reference example 3→Example 2 using the corresponding amino acid derivative instead of (2R,3R)-2-(t-butoxycarbonylamino)-3-hydroxy-4-methylpentanoic acid, and using the corresponding amine derivative instead of n-butylamine, and using the corresponding aldehyde derivative instead of 3-formyl-6-phenyloxypyridine, the title compound having the following physical data was obtained.

TLC: Rf 0.51 (chloroform:methanol=10:1);
NMR (CD₃OD): δ 4.39–4.27 (m, 1H), 4.28 (s, 2H), 4.01 (dd, J=7.8, 4.5 Hz, 1H), 3.92–3.68 (m, 2H), 3.61–3.50 (m, 2H), 3.47–3.38 (m, 2H), 2.68–2.50 (m, 2H), 2.49 (s, 3H), 2.45 (s, 3H), 2.25–2.05 (m, 2H), 2.03–1.20 (m, 15H), 0.98–0.89 (m, 9H).

EXAMPLE 16 (1)–16(6)

By the same procedure as described in Example 16 using the corresponding aldehyde derivatives respectively instead of 1-cyclohexyl-4-formyl-3,5-dimethylpyrazole, the following compounds having the following physical data were obtained.

EXAMPLE 16(1)

(3S)-1-propyl-2,5-dioxo-3-(2-methylpropyl)-9-(4-(4-methylsulfonylaminophenyloxy)phenylmethyl)-1,4,9-triazaspiro[5.5]undecane.hydrochloride

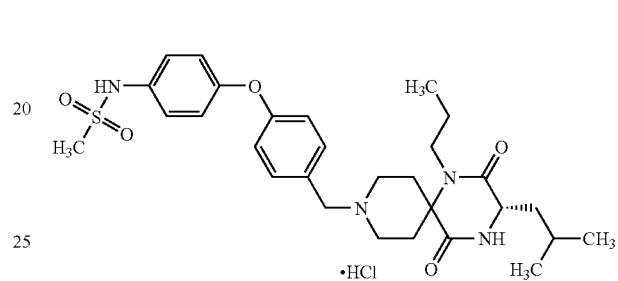

TLC: Rf 0.53 (chloroform:methanol=10:1);
NMR (CD₃OD): δ 7.53 (d, J=8.7 Hz, 2H), 7.29 (d, J=9.0 Hz, 2H), 7.07 (d, J=8.7 Hz, 2H), 7.03 (d, J=9.0 Hz, 2H), 4.34 (s, 2H), 4.01 (dd, J=7.8, 4.8 Hz, 1H), 3.90–3.69 (m, 2H), 3.55–3.43 (m, 2H), 3.39–3.30 (m, 2H), 2.95 (s, 3H), 2.48–2.29 (m, 2H), 2.28–2.09 (m, 2H), 1.90–1.44 (m, 5H), 0.94 (d, J=6.6 Hz, 3H), 0.93 (d, J=6.6 Hz, 3H), 0.93 (t, J=7.5 Hz, 3H).

EXAMPLE 16(2)

(3S)-1-propyl-2,5-dioxo-3-(2-methylpropyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane.hydrochloride

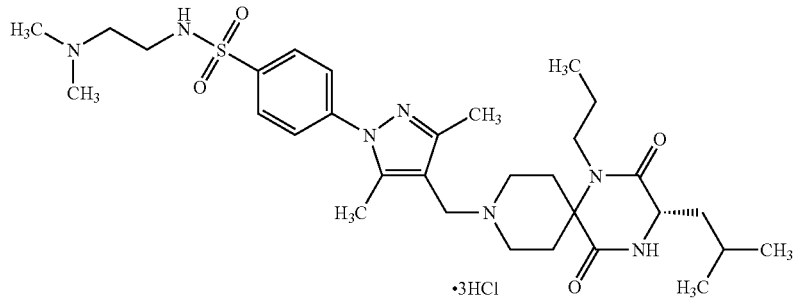

TLC: Rf 0.09 (chloroform:methanol:acetic acid=10:5:1);
NMR (CD₃OD): δ 8.07 (d, J=9.0 Hz, 2H), 7.78 (d, J=9.0 Hz, 2H), 4.31 (s, 2H), 4.02 (dd, J=7.8, 4.5 Hz, 1H), 3.95–3.73 (m, 2H), 3.66–3.56 (m, 2H), 3.50–3.40 (m, 2H), 3.35–3.20 (m, 4H), 2.95 (s, 6H), 2.72–2.53 (m, 2H), 2.49 (s, 3H), 2.41 (s, 3H), 2.30–2.08 (m, 2H), 1.92–1.45 (m, 5H), 0.99–0.89 (m, 9H).

EXAMPLE 16(3)

(3S)-1-propyl-2,5-dioxo-3-cyclohexylmethyl-9-(3,5-dimethyl-1-cyclohexylpyrazol-4-ylmethyl)-1,4,9-triazaspiro[5.5]undecane.2hydrochloride

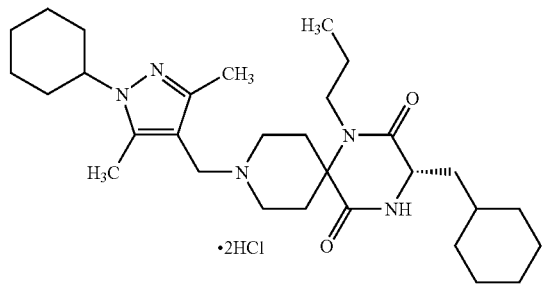

TLC: Rf 0.57 (chloroform:methanol=10:1);

NMR (CD$_3$OD): δ 4.43–4.25 (m, 1H), 4.29 (s, 2H), 4.04 (dd, J=7.8, 4.5 Hz, 1H), 3.92–3.70 (m, 2H), 3.60–3.50 (m, 2H), 3.48–3.38 (m, 2H), 2.70–2.50 (m, 2H), 2.51 (s, 3H), 2.47 (s, 3H), 2.25–2.03 (m, 2H), 2.03–1.40 (m, 19H), 1.40–1.08 (m, 4H), 1.05–0.83 (m, 2H), 0.93 (t, J=7.5 Hz, 3H).

EXAMPLE 16(4)

(3S)-1-propyl-2,5-dioxo-3-cyclohexylmethyl-9-(4-(4-methylsulfonylaminophenyloxy)phenylmethyl)-1,4,9-triazaspiro[5.5]undecane.hydrochloride

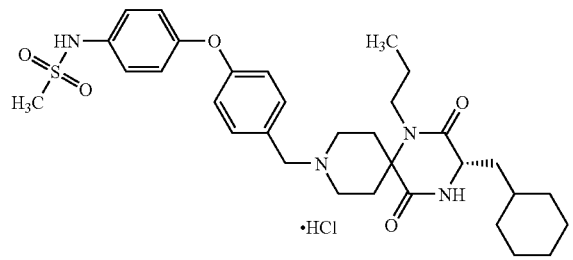

TLC: Rf 0.55 (chloroform:methanol=10:1);

NMR (CD$_3$OD): δ 7.53 (d, J=9.0 Hz, 2H), 7.29 (d, J=9.0 Hz, 2H), 7.07 (d, J=9.0 Hz, 2H), 7.03 (d, J=9.0 Hz, 2H), 4.33 (s, 2H), 4.04 (dd, J=7.5, 4.5 Hz, 1H), 3.89–3.69 (m, 2H), 3.54–3.43 (m, 2H), 3.39–3.30 (m, 2H), 2.95 (s, 3H), 2.50–2.30 (m, 2H), 2.28–2.06 (m, 2H), 1.83–1.40 (m, 10H), 1.40–1.10 (m, 3H), 1.05–0.85 (m, 2H), 0.93 (t, J=7.5 Hz, 3H).

EXAMPLE 16(5)

1-butyl-2,5-dioxo-9-(4-(4-methylsulfonylaminophenyloxy)phenylmethyl)-1,4,9-triazaspiro[5.5]undecane.hydrochloride

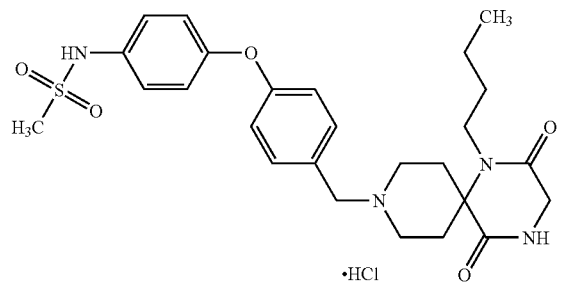

TLC: Rf 0.48 (chloroform:methanol=10:1);

NMR (CD$_3$OD): δ 7.54 (d, J=8.7 Hz, 2H), 7.29 (d, J=8.7 Hz, 2H), 7.06 (d, J=8.7 Hz, 2H), 7.03 (d, J=8.7 Hz, 2H), 4.32 (s, 2H), 3.97 (s, 2H), 3.77–3.62 (m, 2H), 3.55–3.35 (m, 4H), 2.95 (s, 3H), 2.48–2.33 (m, 2H), 2.33–2.22 (m, 2H), 1.60–1.46 (m, 2H), 1.43–1.26 (m, 2H), 0.95 (t, J=7.2 Hz, 3H).

EXAMPLE 16(6)

1-butyl-2,5-dioxo-9-(3,5-dimethyl-1-cyclohexylpyrazol-4-ylmethyl)-1,4,9-triazaspiro[5.5]undecane.2hydrochloride

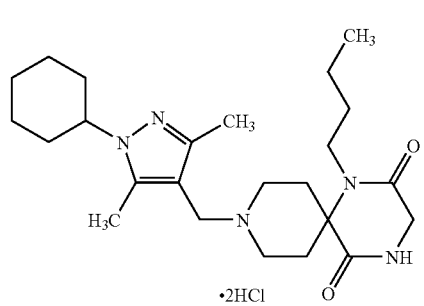

TLC: Rf 0.50 (chloroform:methanol=10:1);

NMR (CD$_3$OD): δ 4.34 (m, 1H), 4.27 (s, 2H), 3.97 (s, 2H), 3.78–3.65 (m, 2H), 3.62–3.47 (m, 4H), 2.65–2.50 (m, 2H), 2.50 (s, 3H), 2.45 (s, 3H), 2.31–2.20 (m, 2H), 2.04–1.70 (m, 6H), 1.65–1.42 (m, 4H), 1.42–1.20 (m, 4H), 0.94 (t, J=7.2 Hz, 3H).

EXAMPLE 17

(3R)-1-(2-butynyl)-2,5-dioxo-3-((1R)-1-hydroxy-1-cyclohexylmethyl)-9-(3,5-dimethyl-1-phenylpyrazol-4-ylmethyl)-1,4,9-triazaspiro[5.5]undecane.2hydrochloride

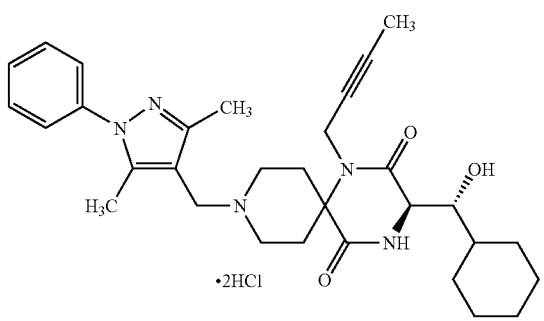

By the same procedure as described in Reference example 1→Reference example 2→Example 1 using (2R,3R)-2-(t-butoxycarbonylamino)-3-cyclohexyl-3-hydroxypropanoic acid instead of (2R,3R)-2-(t-butoxycarbonylamino)-3-hydroxy-4-methylpentanoic acid, 2-butynylamine instead of n-butylamine, N-(3,5-dimethyl-1-phenylpyrazol-4-yl)methyl-4-piperidone instead of N-benzyl-4-piperidone, and n-butylisonitrile instead of benzylisonitrile, the title compound having the following physical data was obtained.

TLC: Rf 0.45 (chloroform:methanol=10:1);

NMR (CD$_3$OD): δ 7.60–7.45 (m, 5H), 4.44–4.28 (m, 3H), 4.21 (d, J=2.1 Hz, 1H), 4.10–3.94 (m, 2H), 3.79 (m, 1H), 3.66–3.54 (m, 2H), 3.32 (m, 1H), 2.74 (m, 1H), 2.56–2.34 (m, 8H), 2.24 (m, 1H), 2.08–1.90 (m, 2H), 1.84–1.62 (m, 7H), 1.44–1.12 (m, 3H), 1.05–0.82 (m, 2H).

EXAMPLE 17(1)

(3S)-1-(2-butynyl)-2,5-dioxo-3-((1S)-1-hydroxy-1-cyclohexylmethyl)-9-(3,5-dimethyl-1-phenylpyrazol-4-ylmethyl)-1,4,9-triazaspiro[5.5]undecane.2hydrochloride

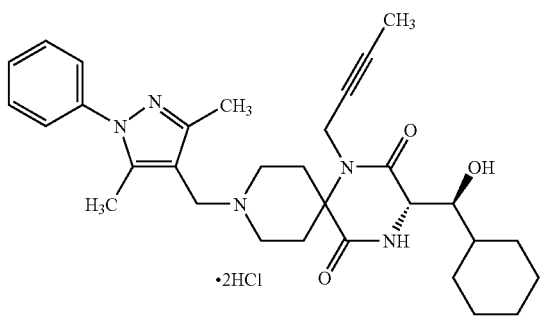

By the same procedure as described in Example 17, using (2S,3S)-2-(t-butoxycarbonylamino)-3-cyclohexyl-3-hydroxypropanoic acid instead of (2R,3R)-2-(t-butoxycarbonylamino)-3-cyclohexyl-3-hydroxypropanoic acid, the title compound having the following physical data was obtained.

TLC: Rf 0.45 (chloroform:methanol=10:1);

NMR (CD$_3$OD): δ 7.60–7.45 (m, 5H), 4.44–4.28 (m, 3H), 4.21 (d, J=2.1 Hz, 1H), 4.10–3.94 (m, 2H), 3.79 (m, 1H), 3.66–3.54 (m, 2H), 3.32 (m, 1H), 2.74 (m, 1H), 2.56–2.34 (m, 8H), 2.24 (m, 1H), 2.08–1.90 (m, 2H), 1.84–1.62 (m, 7H), 1.44–1.12 (m, 3H), 1.05–0.82 (m, 2H).

EXAMPLE 18

(3S)-1-butyl-2,5-dioxo-3-cyclohexylmethyl-9-(2-(4-phenyloxyphenyl)ethyl)-1,4,9-triazaspiro[5.5]undecane.hydrochloride

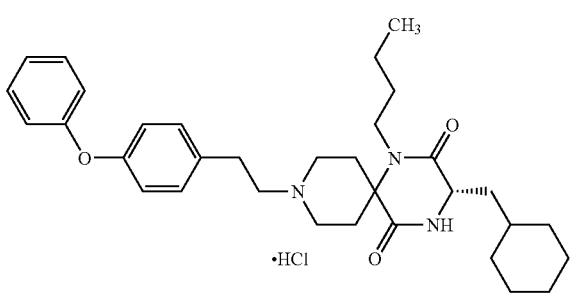

To the PS-TsCl-HL resin (brand name of Argonaut Technologies, catalog number 800366) (305 mg) was added a solution of 2-(4-phenyloxyphenyl)ethyl alcohol (112 mg) in dichloromethane (2 ml) and pyridine (2 ml). The reaction mixture was stirred for 5 hours at room temperature. The resin was washed with dichloromethane for 3 times, dimethylformamide for 5 times, dimethylformamide:water=3:1 for 5 times, tetrahydrofuran for 3 times, dichloromethane for 3 times and acetonitrile for 3 times. The obtained resin was added a solution of the compound prepared in Reference example 3(2) (116 mg) in acetonitrile (5 ml) and diisopropylethylamine (0.366 ml). The reaction mixture was stirred for 18 hours at 70° C. After cooling it, the resin was washed with acetonitrile, the obtained washings were concentrated. The obtained residue was purified by column chromatography on silica gel (ethyl acetate:methanol=20:1), and the obtained compound was treated with hydrochloric acid to give the title compound (82 mg) having the following physical data was obtained.

TLC: Rf 0.54 (ethyl acetate:methanol=10:1);

NMR (CD$_3$OD): δ 7.37–7.29 (m, 4H), 7.11 (t, J=7.2 Hz, 1H), 6.97–6.95 (m, 4H), 4.06 (d, J=7.5, 4.5 Hz, 1H), 3.88–3.77 (m, 2H), 3.65 (m, 2H), 3.46–3.36 (m, 4H), 3.13–3.07 (m, 2H), 2.48 (m, 2H), 2.28–2.14 (m, 2H), 1.80–1.21 (m, 15H), 0.98 (t, J=7.0 Hz, 3H), 0.99–0.91 (m, 2H).

EXAMPLE 18(1) AND 18(2)

By the same procedure as described in Example 18 using the corresponding alcohol derivatives respectively instead of 2-(4-phenyloxyphenyl)ethyl alcohol, and using the compound prepared in Reference example 3(1) instead of the compound prepared in Reference example 3(2), the following compounds having the following physical data were obtained.

EXAMPLE 18(1)

(3S)-1-butyl-2,5-dioxo-3-(2-methylpropyl)-9-(2-(4-phenyloxyphenyl)ethyl)-1,4,9-triazaspiro[5.5]undecane.hydrochloride

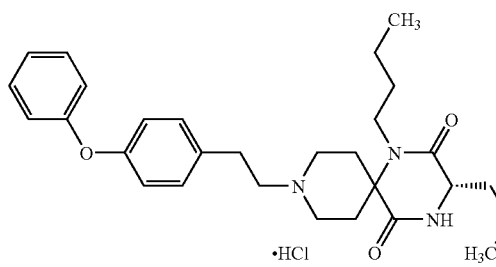

TLC: Rf 0.37 (ethyl acetate:methanol=10:1);

NMR (CD$_3$OD): δ 7.37–7.29 (m, 4H), 7.11 (t, J=7.5 Hz, 1H), 6.98–6.95 (m, 4H), 4.03 (d, J=7.5, 4.5 Hz, 1H), 3.89–3.77 (m, 2H), 3.64 (m, 2H), 3.42–3.32 (m, 4H), 3.12–3.07 (m, 2H), 2.45 (m, 2H), 2.29–2.16 (m, 2H), 1.88–1.36 (m, 7H), 0.98 (t, J=7.0 Hz, 3H), 0.95 (d, J=6.3 Hz, 3H), 0.94 (d, J=6.3 Hz, 3H).

EXAMPLE 18(2)

(3S)-1-butyl-2,5-dioxo-3-(2-methylpropyl)-9-(2-(4-methoxyphenyl)ethyl)-1,4,9-triazaspiro[5.5]undecane.hydrochloride

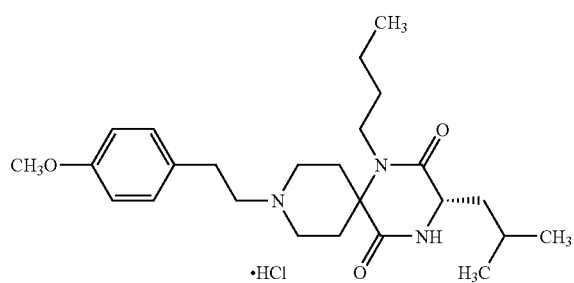

TLC: Rf 0.37 (ethyl acetate:methanol=10:1);

NMR (CD$_3$OD): δ 7.22 (d, J=9.0 Hz, 2H), 6.90 (d, J=9.0 Hz, 2H), 4.01 (d, J=7.5, 4.5 Hz, 1H), 3.87–3.77 (m, 2H), 3.77 (s, 3H), 3.63 (m, 2H), 3.43–3.32 (m, 4H), 3.03 (m, 2H), 2.44 (m, 2H), 2.28–2.15 (m, 2H), 1.85–1.36 (m, 7H), 0.97 (t, J=7.5 Hz, 3H), 0.95 (d, J=6.3 Hz, 3H), 0.94 (d, J=6.3 Hz, 3H).

EXAMPLE 19

(3S)-1-butyl-2,5-dioxo-3-cyclohexylmethyl-9-(4-ethoxycarbonylphenyl)-1,4,9-triazaspiro[5.5]undecane.hydrochloride

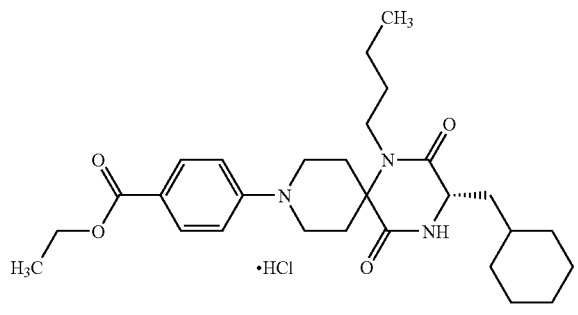

To a solution of the compound prepared in Reference example 3(2) (186 mg) in dimethylsulfoxide (3 ml) was added ethyl 4-fluorobenzoate (164 mg) and potassium carbonate (141 mg). The reaction mixture was stirred for 24 hours at 140° C. The reaction mixture was added water and t-butylmethyl ether and extracted. The extract was washed with saturated aqueous solution of sodium chloride, dried over anhydrous magnesium sulfate and concentrated. The obtained residue was purified by column chromatography on silica gel (hexane:ethyl acetate=4:1→3:1), and the obtained compound was treated with 4N hydrogen chloride/ethyl acetate to give the title compound (67 mg) having the following physical data.

TLC: Rf 0.27 (hexane:ethyl acetate=2:1);

NMR (CD$_3$OD): δ 8.13 (d, J=8.7 Hz, 2H), 7.59 (d, J=8.7 Hz, 2H), 4.37 (q, J=7.2 Hz, 2H), 4.31–4.15 (m, 2H), 4.07 (dd, J=7.5, 4.5 Hz, 1H), 3.85–3.75 (m, 2H), 3.47–3.38 (m, 2H), 2.67–2.50 (m, 2H), 2.30–2.12 (m, 2H), 1.85–1.46 (m, 10H), 1.44–1.19 (m, 5H), 1.38 (t, J=7.2 Hz, 3H), 1.05–0.88 (m, 2H), 0.95 (t, J=7.2 Hz, 3H).

REFERENCE EXAMPLE 4

(3S)-1-butyl-2,5-dioxo-3-cyclohexylmethyl-9-benzyloxycarbonyl-1,4,9-triazaspiro[5.5]undecane

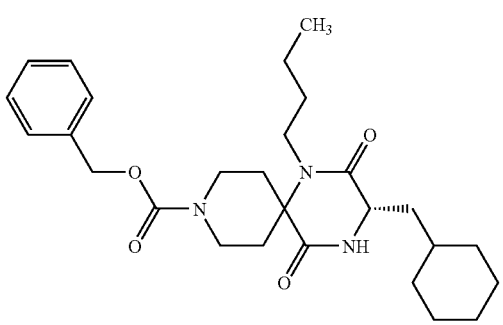

By the same procedure as described in Reference example 1→Reference example 2→Example 1 using (3S)-2-(t-butoxycarbonylamino)-3-cyclohexylpropanoic acid instead of (2R,3R)-2-(t-butoxycarbonylamino)-3-hydroxy-4-methyl-pentanoic acid, and N-benzyloxycarbonyl-4-piperidone instead of N-benzyl-4-piperidone, the title compound having the following physical data was obtained.

TLC: Rf 0.35 (hexane:ethyl acetate=1:1);

NMR (CD₃OD): δ 7.39–7.31 (m, 5H), 6.48 (brs, 1H), 5.16 (s, 2H), 4.15 (brs, 2H), 4.00 (ddd, J=9.6, 4.8, 1.5 Hz, 1H), 3.76–3.16 (m, 4H), 2.02–1.12 (m, 19H), 1.08–0.88 (m, 2H), 0.92 (t, J=7.2 Hz, 3H).

REFERENCE EXAMPLE 5

(3S)-1-butyl-2,5-dioxo-3-cyclohexylmethyl-4-methyl-9-benzyloxycarbonyl-1,4,9-triazaspiro[5.5]undecane.hydrochloride

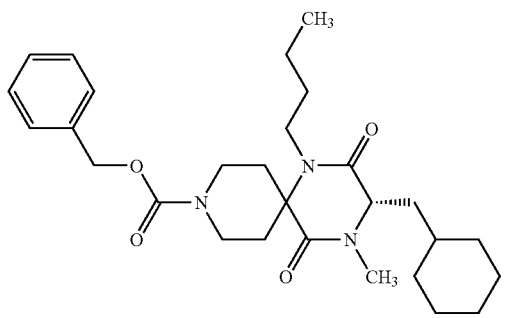

To a solution of the compound prepared in Reference example 4 (1 g) in dimethylformamide (20 ml) was added 60% sodium hydride (164 mg) under ice bath. The reaction mixture was stirred for 1 hour at room temperature. The reaction mixture was added methyl iodide (0.3 ml) under ice bath. The reaction mixture was stirred overnight at room temperature. The reaction mixture was added ice water and extracted with ethyl acetate. The extract was washed with water and saturated aqueous solution of sodium chloride, dried over anhydrous magnesium sulfate and concentrated. The obtained residue was purified by column chromatography on silica gel (hexane:ethyl acetate=2:1) to give the title compound (1 g) having the following physical data.

TLC: Rf 0.34 (hexane:ethyl acetate.1:1);

NMR (CD₃OD): δ 7.40–7.32 (m, 5H), 5.16 (s, 2H), 4.12 (brs, 2H), 3.91 (t, J=5.7 Hz, 1H), 3.88 (brs, 1H), 3.49 (m, 1H), 3.35 (m, 1H), 2.92 (s, 3H), 2.90 (m, 1H), 2.04–1.10 (m, 19H), 1.04–0.82 (m, 2H), 0.92 (t, J=7.2 Hz, 3H).

REFERENCE EXAMPLE 6

(3S)-1-butyl-2,5-dioxo-3-cyclohexylmethyl-4-methyl-1,4,9-triazaspiro[5.5]undecane.hydrochloride

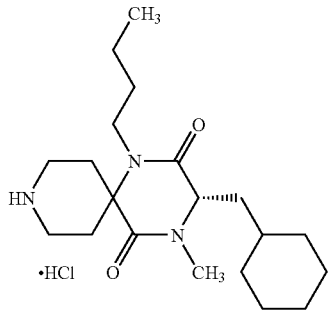

To a solution of the compound prepared in Reference example 5 (1 g) in methanol (20 ml) was added 10% palladium on carbon (60 mg). Under an atmosphere of hydrogen, the reaction mixture was stirred for 8 hours at room temperature. The reaction mixture was filtrated through Celite (brand name) and the filtrate was added 4N hydrogen chloride ethyl acetate solution and concentrated to give the title compound (799 mg) having the following physical data.

TLC: Rf 0.28 (chloroform:methanol:acetic acid=90:10:1);

NMR (CD₃OD): δ 4.05 (dd, J=7.5, 4.2 Hz, 1H), 4.01 (dt, J=4.2, 12.9 Hz, 1H), 3.59 (dt, J=3.3, 12.9 Hz, 1H), 3.51 (m, 1H), 3.40 (brd, J=5.4 Hz, 1H), 3.36 (brd, J=5.4 Hz, 1H), 3.25 (m, 1H), 2.93 (s, 3H), 2.37 (dt, J=5.4, 14.4 Hz, 1H), 2.32 (dt, J=5.4, 14.4 Hz, 1H), 2.11 (brd, J=14.4 Hz, 1H), 1.99 (brd, J=14.4 Hz, 1H), 1.86–1.14 (m, 15H), 1.07–0.87 (m, 2H), 0.97 (t, J=7.2 Hz, 3H).

EXAMPLE 20

(3S)-1-butyl-2,5-dioxo-3-cyclohexylmethyl-4-methyl-9-(4-phenyloxyphenylmethyl)-1,4,9-triazaspiro[5.5]undecane.hydrochloride

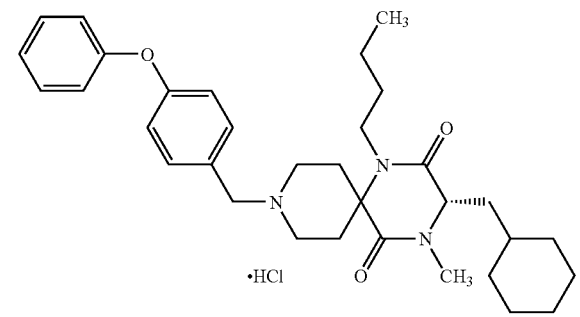

By the same procedure as described in Example 2 using the compound prepared in Reference example 6 instead of the compound prepared in Reference example 3, the title compound having the following physical data was obtained.

TLC: Rf 0.32 (ethyl acetate);

NMR (CD₃OD): δ7.53 (d, J=8.7 Hz, 2H), 7.39 (dd, J=8.7, 7.5 Hz, 2H), 7.18 (t, J=7.5 Hz, 1H), 7.09–7.01 (m, 4H), 4.34 (s, 2H), 4.05 (m, 1H), 4.04 (dd, J=7.2, 3.9 Hz, 1H), 3.68–3.43 (m, 4H), 3.27 (m, 1H), 2.93 (s, 3H), 2.48 (dd, J=14.4, 5.4 Hz, 1H), 2.39 (dd, J=14.4, 5.4 Hz, 1H), 2.16 (brd, J=14.4 Hz, 1H), 2.03 (brd, J=14.4 Hz, 1H), 1.86–1.58 (m, 8H), 1.53–1.14 (m, 7H), 1.07–0.86 (m, 2H), 0.95 (t, J=7.5 Hz, 3H).

EXAMPLE 21

(3R)-1-butyl-2,5-dioxo-3-((1R)-1-hydroxy-1-cyclohexylmethyl)-9-(4-(2-methylpropanoylamino)phenylmethyl)-1,4,9-triazaspiro[5.5]undecane.hydrochloride

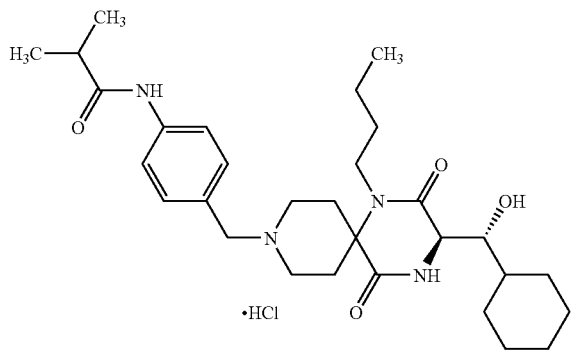

By the same procedure as described in Example 2 using the compound prepared in Reference example 3(3) instead of the compound prepared in Reference example 3, and using 4-(2-methylpropanoylamino)benzaldehyde instead of 3-formyl-6-phenyloxypyridine the title compound having the following physical data was obtained.

TLC: Rf 0.28 (chloroform:methanol=10:1);

NMR (d$_6$-DMSO): δ 10.6 (s, 1H), 10.0 (s, 1H), 8.02 (m, 1H), 7.68 (d, J=8.7 Hz, 2H), 7.52 (d, J=8.7 Hz, 2H), 5.24 (s, 1H), 4.22 (s, 2H), 3.96 (m, 1H), 3.70 (m, 1H), 3.66–3.12 (m, 6H), 2.68–2.20 (m, 4H), 2.02–1.42 (m, 8H), 1.40–1.00 (m, 6H), 1.10 (d, J=6.9 Hz, 6H), 0.98–0.64 (m, 2H), 0.88 (t, J=6.9 Hz, 3H).

EXAMPLE 21(1)–21(6)

By the same procedure as described in Example 21 using the corresponding aldehyde derivatives respectively instead of 4-(2-methylpropanoylamino)benzaldehyde, the following compounds having the following physical data were obtained.

EXAMPLE 21(1)

(3R)-1-butyl-2,5-dioxo-3-((1R)-1-hydroxy-1-cyclohexylmethyl)-9-(4-(2-methoxyacetylamino)phenylmethyl)-1,4,9-triazaspiro[5.5]undecane.hydrochloride

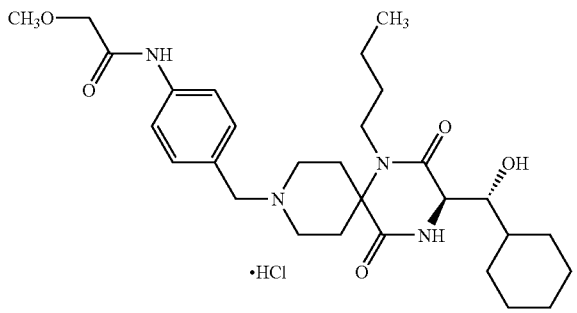

TLC: Rf 0.36 (chloroform:methanol=10:1);

NMR (d$_6$-DMSO): δ 10.5 (s, 1H), 9.95 (s, 1H), 8.02 (m, 1H), 7.75 (d, J=8.4 Hz, 2H), 7.55 (d, J=8.4 Hz, 2H), 4.26 (s, 2H), 4.02 (s, 2H), 3.96 (m, 1H), 3.80–3.10 (m, 7H), 3.38 (s, 3H), 2.60–2.18 (m, 4H), 2.02–1.44 (m, 8H), 1.40–1.00 (m, 6H), 0.98–0.64 (m, 2H), 0.88 (t, J=7.2 Hz, 3H).

EXAMPLE 21(2)

(3R)-1-butyl-2,5-dioxo-3-((1R)-1-hydroxy-1-cyclohexylmethyl)-9-(4-(2-phenylacetylamino)phenylmethyl)-1,4,9-triazaspiro[5.5]undecane.hydrochloride

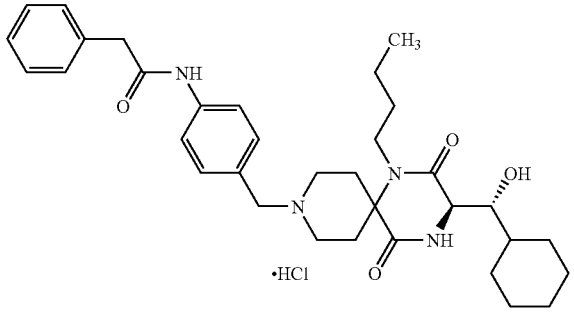

TLC: Rf 0.27 (chloroform:methanol=10:1);

NMR (d$_6$-DMSO): δ 10.6 (s, 1H), 10.4 (s, 1H), 8.01 (m, 1H), 7.67 (d, J=9.0 Hz, 2H), 7.54 (d, J=9.0 Hz, 2H), 7.40–7.18 (m, 5H), 4.24 (s, 2H), 3.96 (s, 1H), 3.84–3.10 (m, 8H), 2.62–2.18 (m, 4H), 2.04–1.42 (m, 8H), 1.40–1.00 (m, 6H), 0.98–0.64 (m, 2H), 0.88 (t, J=7.2 Hz, 3H).

EXAMPLE 21(3)

(3R)-1-butyl-2,5-dioxo-3-((1R)-1-hydroxy-1-cyclohexylmethyl)-9-(4-(2-(4-fluorophenyl)acetylamino)phenylmethyl)-1,4,9-triazaspiro[5.5]undecane.hydrochloride

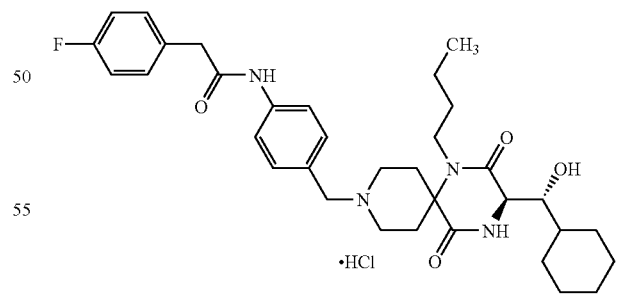

TLC: Rf 0.26 (chloroform:methanol=10:1);

NMR (d$_6$-DMSO): δ 10.8 (s, 1H), 10.4 (s, 1H), 8.01 (m, 1H), 7.66 (d, J=8.4 Hz, 2H), 7.54 (d, J=8.4 Hz, 2H), 7.37 (dd, J=8.4, 5.4 Hz, 2H), 7.14 (t, J=8.4 Hz, 2H), 4.34–3.10 (m, 8H), 4.24 (s, 2H), 3.96 (s, 1H), 2.66–2.18 (m, 4H), 2.02–1.42 (m, 8H), 1.40–1.00 (m, 6H), 0.98–0.64 (m, 2H), 0.88 (t, J=6.9 Hz, 3H).

EXAMPLE 21(4)

(3R)-1-butyl-2,5-dioxo-3-((1R)-1-hydroxy-1-cyclohexylmethyl)-9-(4-(4-methoxycarbonylphenylaminocarbonyl)phenylmethyl)-1,4,9-triazaspiro[5.5]undecane.hydrochloride

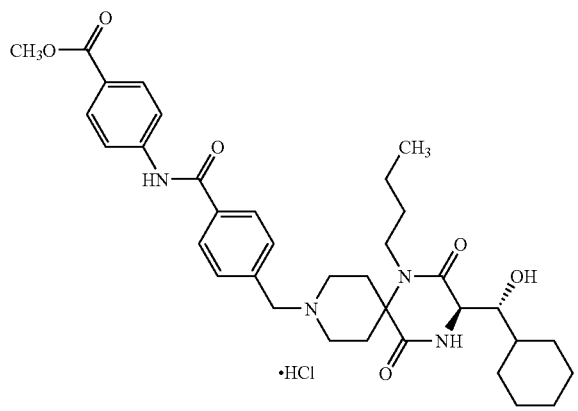

TLC: Rf 0.35 (chloroform:methanol=10:1);

NMR (d$_6$-DMSO): δ 10.90 (br.s, 1H), 10.70 (s, 1H), 8.05 (m, 1H), 8.04 (d, J=8.4 Hz, 2H), 7.97 (s, 4H), 7.83 (d, J=8.4 Hz, 2H), 5.24 (m, 1H), 4.43 (s, 2H), 3.97 (m, 1H), 3.90–3.06 (m, 7H), 3.84 (s, 3H), 2.62–2.20 (m, 3H), 2.06–1.42 (m, 8H), 1.40–1.02 (m, 6H), 0.98–0.66 (m, 2H), 0.89 (t, J=6.9 Hz, 3H).

EXAMPLE 21(5)

(3R)-1-butyl-2,5-dioxo-3-((1R)-1-hydroxy-1-cyclohexylmethyl)-9-(4-(4-methoxyphenylmethyloxycarbonyl)phenylmethyl)-1,4,9-triazaspiro[5.5]undecane.hydrochloride

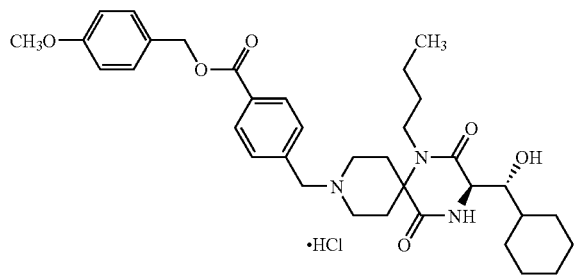

TLC: Rf 0.41 (chloroform:methanol=10:1);

NMR (d$_6$-DMSO): δ 10.6 (s, 1H), 8.03 (d, J=8.7 Hz, 2H), 8.02 (m, 1H), 7.78 (d, J=8.7 Hz, 2H), 7.42 (d, J=8.7 Hz, 2H), 6.96 (d, J=8.7 Hz, 2H), 5.30 (s, 2H), 5.24 (m, 1H), 4.42 (s, 2H), 3.96 (m, 1H), 3.86–3.10 (m, 7H), 3.76 (s, 3H), 2.64–2.20 (m, 3H), 2.02–1.42 (m, 8H), 1.40–1.00 (m, 6H), 0.96–0.68 (m, 2H), 0.88 (t, J=6.3 Hz, 3H).

EXAMPLE 21(6)

(3R)-1-butyl-2,5-dioxo-3-((1R)-1-hydroxy-1-cyclohexylmethyl)-9-(2-(4-methylaminocarbonylphenyloxy)pyridin-5-ylmethyl)-1,4,9-triazaspiro[5.5]undecane.hydrochloride

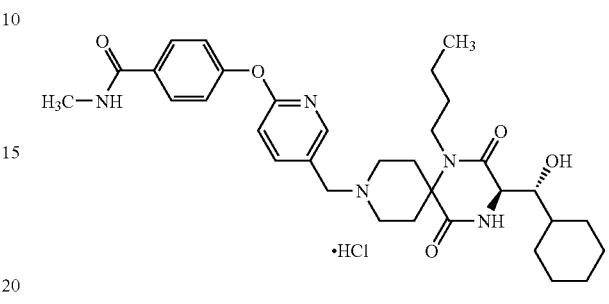

TLC: Rf 0.37 (chloroform:methanol=9:1);

NMR (CD$_3$OD): δ 8.35 (d, J=2.5 Hz, 1H), 8.15 (dd, J=8.5, 2.5 Hz, 1H), 7.89 (d, J=8.5 Hz, 2H), 7.23 (d, J=8.5 Hz, 2H), 7.14 (d, J=8.5 Hz, 1H), 4.39 (s, 2H), 4.15 (d, J=2.0 Hz, 1H), 4.00 (m, 1H), 3.75 (m, 1H), 3.57–3.45 (m, 3H), 3.30–3.22 (m, 2H), 2.92 (s, 3H), 2.56 (m, 1H), 2.50–2.39 (m, 2H), 2.14–1.91 (m, 3H), 1.80–1.60 (m, 5H), 1.50–1.10 (m, 6H), 1.00–0.87 (m, 2H), 0.95 (t, J=7.0 Hz, 3H).

EXAMPLE 22

(3S)-1-butyl-2,5-dioxo-3-((1S)-1-hydroxy-1-cyclohexylmethyl)-9-(4-(4-carboxyphenyloxy)phenylmethyl)-1,4,9-triazaspiro[5.5]undecane.hydrochloride

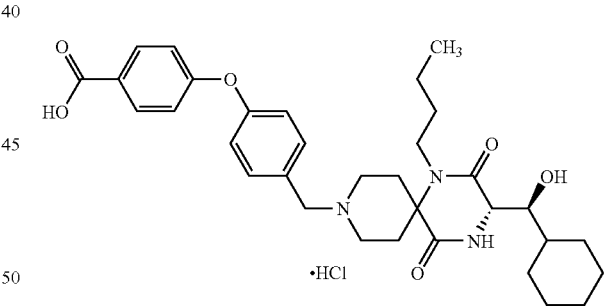

By the same procedure as described in Example 2 using the compound prepared in Reference example 3(9) instead of the compound prepared in Reference example 3, using 4-(4-carboxyphenyloxy)benzaldehyde instead of 3-formyl-6-phenyloxypyridine, the title compound having the following physical data was obtained.

TLC: Rf 0.45 (chloroform:methanol=5:1);

NMR (d$_6$-DMSO): δ 10.4 (s, 1H), 8.05 (m, 1H), 7.97 (d, J=8.7 Hz, 2H), 7.69 (d, J=8.7 Hz, 2H), 7.19 (d, J=8.7 Hz, 2H), 7.09 (d, J=8.7 Hz, 2H), 5.28 (d, J=6.9 Hz, 1H) 4.35 (s, 2H), 3.97 (m, 1H), 3.88–3.12 (m, 7H), 2.64–2.20 (m, 3H), 2.06–1.42 (m, 8H), 1.40–1.00 (m, 6H), 0.89 (t, J=6.9 Hz, 3H), 0.80 (m, 2H).

EXAMPLE 23

(3S)-1-butyl-2,5-dioxo-3-(pyridin-3-ylmethyl)-9-(4-(4-methylaminocarbonylphenyloxy)phenylmethyl)-1,4,9-triazaspiro[5.5]undecane.2hydrochloride

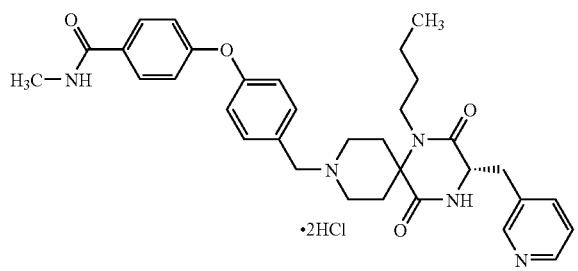

By the same procedure as described in Reference example 1→Reference example 2→Example 1 using N-t-butoxycarbonyl-3-pyridyl-L-alanine instead of (2R,3R)-2-(t-butoxycarbonylamino)-3-hydroxy-4-methylpentanoic acid, and using N-benzyl-4-piperidone-2-morpholinoethylisonitrile instead of N-(4-(4-methylaminocarobonylphenyloxy)phenylmethyl)-4-piperidone the title compound having the following physical data was obtained.

TLC: Rf 0.25 (chloroform:methanol=10:1);
NMR (CD₃OD): δ 8.82–8.76 (m, 2H), 8.55 (d, J=8.4 Hz, 1H), 8.06 (dd, J=7.8, 5.7 Hz, 1H), 7.84 (d, J=9.0 Hz, 2H), 7.63 (d, J=8.7 Hz, 2H), 7.15–7.02 (m, 4H), 4.55 (t, J=5.4 Hz, 1H), 4.33 (s, 2H), 3.80 (m, 1H), 3.68–3.28 (m, 7H), 2.91 (s, 3H), 2.56–2.40 (m, 2H), 2.20 (m, 1H), 1.70 (m, 1H), 1.50–1.20 (m, 4H), 0.92 (t, J=6.9 Hz, 3H).

EXAMPLE 23(1)–23(5)

By the same procedure as described in Example 23 using the corresponding amino acid derivatives respectively instead of N-t-butoxycarbonyl-3-pyridyl-L-alanine, the following compounds having the following physical data were obtained.

EXAMPLE 23(1)

(3S)-1-butyl-2,5-dioxo-3-phenylmethyl-9-(4-(4-methylaminocarbonylphenyloxy)phenylmethyl)-1,4,9-triazaspiro[5.5]undecane.hydrochloride

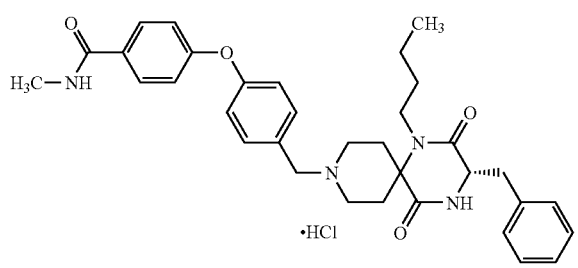

TLC: Rf 0.51 (chloroform:methanol:acetic acid=20:2:1);
NMR (CD₃OD): δ 7.84 (d, J=9.0 Hz, 2H), 7.56 (d, J=9.0 Hz, 2H), 7.30–7.04 (m, 9H), 4.36 (dd, J=4.5, 3.6 Hz, 1H), 4.25 (s, 2H), 3.78 (m, 1H), 3.50–3.02 (m, 6H), 3.00–2.84 (m, 4H), 2.38 (m, 1H), 2.02 (m, 1H), 1.86 (m, 1H), 1.60–1.24 (m, 4H), 0.93 (t, J=6.9 Hz, 3H), 0.04 (m, 1H).

EXAMPLE 23(2)

(3S)-1-butyl-2,5-dioxo-3-(pyridin-2-ylmethyl)-9-(4-(4-methylaminocarbonylphenyloxy)phenylmethyl)-1,4,9-triazaspiro[5.5]undecane.2hydrochloride

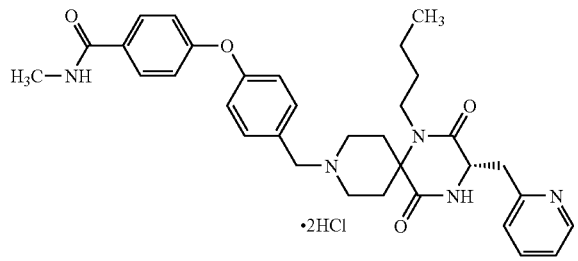

TLC: Rf 0.46 (chloroform:methanol:acetic acid=20:2:1);
NMR (CD₃OD): δ 8.78 (dd, J=7.5, 1.5 Hz, 1H), 8.57 (td, J=7.8, 1.5 Hz, 1H), 8.06 (d, J=8.4 Hz, 1H), 8.00 (m, 1H), 7.84 (d, J=8.2 Hz, 2H), 7.64 (d, J=6.6 Hz, 2H), 7.16–7.04 (m, 4H), 4.68 (dd, J=6.9, 5.7 Hz, 1H), 4.38 (s, 2H), 3.84 (m, 1H), 3.70–3.32 (m, 7H), 2.91 (s, 3H), 2.64–2.44 (m, 2H), 2.16 (m, 1H), 2.06 (m, 1H), 1.50–1.22 (m, 4H), 0.91 (t, J=6.9 Hz, 3H).

EXAMPLE 23(3)

(3S)-1-butyl-2,5-dioxo-3-hydroxymethyl-9-(4-(4-methylaminocarbonylphenyloxy)phenylmethyl)-1,4,9-triazaspiro[5.5]undecane.hydrochloride

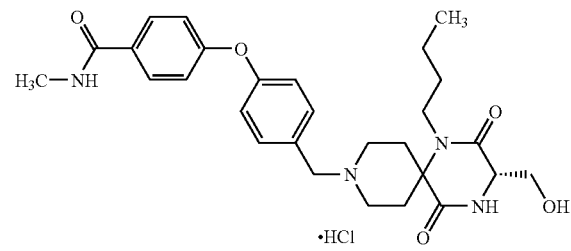

TLC: Rf 0.28 (chloroform:methanol:acetic acid=20:2:1);
NMR (CD₃OD): δ 7.84 (d, J=9.0 Hz, 2H), 7.61 (d, J=8.7 Hz, 2H), 7.14 (d, J=8.7 Hz, 2H), 7.07 (d, J=9.0 Hz, 2H), 4.36 (s, 2H), 4.02–3.88 (m, 3H), 3.80–3.44 (m, 5H), 3.30 (m, 1H), 2.91 (s, 3H), 2.60–2.36 (m, 3H), 2.18 (m, 1H), 1.64 (m, 1H), 1.50–1.26 (m, 3H), 1.02–0.90 (m, 3H).

EXAMPLE 23(4)

(3S)-1-butyl-2,5-dioxo-3-(pyridin-1-oxido-2-ylmethyl)-9-(4-(4-methylaminocarbonylphenyloxy)phenylmethyl)-1,4,9-triazaspiro[5.5]undecane.hydrochloride

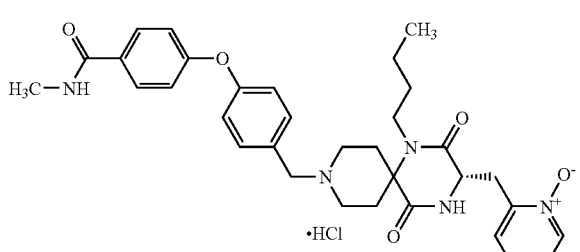

TLC: Rf 0.86 (chloroform:methanol:acetic acid=10:2:1);
NMR (CD$_3$OD): δ 8.70 (dd, J=5.4, 1.0 Hz, 1H), 8.05 (td, J=6.6, 1.2 Hz, 1H), 7.92–7.72 (m, 4H), 7.64 (d, J=9.0 Hz, 2H), 7.20–7.06 (m, 4H), 4.67 (d, J=6.3 Hz, 1H), 4.36 (s, 2H), 3.86–3.18 (m, 8H), 2.91 (s, 3H), 2.70–2.26 (m, 2H), 2.34–2.06 (m, 2H), 1.60–1.44 (m, 2H), 1.44–1.24 (m, 2H), 0.92 (t, J=7.5 Hz, 3H).

EXAMPLE 23(5)

(3S)-1-butyl-2,5-dioxo-3-(pyridin-1-oxido-3-ylmethyl)-9-(4-(4-methylaminocarbonylphenyloxy)phenylmethyl)-1,4,9-triazaspiro[5.5]undecane.hydrochloride

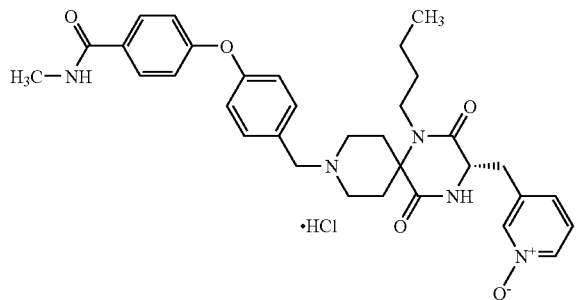

TLC: Rf 0.65 (chloroform:methanol:acetic acid=10:2:1);
NMR (CD$_3$OD): δ 8.74–8.60 (m, 2H), 8.06 (d, J=7.8 Hz, 1H), 7.88 (m, 1H), 7.84 (d, J=8.7 Hz, 2H), 7.62 (d, J=8.7 Hz, 2H), 7.12 (d, J=8.7 Hz, 2H), 7.06 (d, J=8.7 Hz, 2H), 4.52 (t, J=5.1 Hz, 1H), 4.33 (s, 2H), 4.00 (m, 1H), 3.78 (m, 1H), 3.60 (m, 1H), 3.56–3.18 (m, 5H), 2.91 (s, 3H), 2.56–2.18 (m, 2H), 2.20 (m, 1H), 1.66 (m, 1H), 1.52–1.22 (m, 4H), 0.93 (t, J=6.9 Hz, 3H).

EXAMPLE 24

(3R)-1-(4-methoxyphenylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

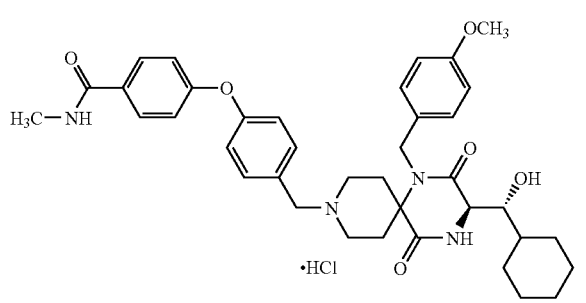

By the same procedure as described in Reference example 1→Reference example 2→Example 1 using (2R,3R)-2-(t-butoxycarbonylamino)-3-cyclohexyl-3-hydroxypropanoic acid instead of (2R,3R)-2-(t-butoxycarbonylamino)-3-hydroxy-4-methylpentanoic acid, and using 4-methoxybenzylamine instead of n-butylamine, using N-(4-(4-methylaminocarobonylphenyloxy)phenylmethyl)-4-piperidone instead of N-benzyl-4-piperidone, using 2-morpholinoethylisonitrile instead of benzylisonitrile, the title compound having the following physical data was obtained.

TLC: Rf 0.24 (chloroform:methanol=10:1);
NMR (CD$_3$OD): δ 7.84 (d, J=8.7 Hz, 2H), 7.56 (d, J=8.7 Hz, 2H), 7.18 (d, J=8.7 Hz, 2H), 7.13 (d, J=8.7 Hz, 2H), 7.07 (d, J=8.7 Hz, 2H), 6.85 (d, J=8.7 Hz, 2H), 4.48 (m, 1H), 4.33 (s, 4H), 3.96 (m, 1H), 3.75 (m, 1H), 3.75 (s, 3H), 3.58–3.18 (m, 3H), 2.92 (s, 3H), 2.66–2.28 (m, 3H), 2.16–1.58 (m, 7H), 1.40–0.82 (m, 5H).

EXAMPLE 24(1)–24(4)

By the same procedure as described in Example 24 using the corresponding amines instead of 4-methoxybenzylamine, the title compounds were obtained.

EXAMPLE 24(1)

(3R)-1-phenylmethyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

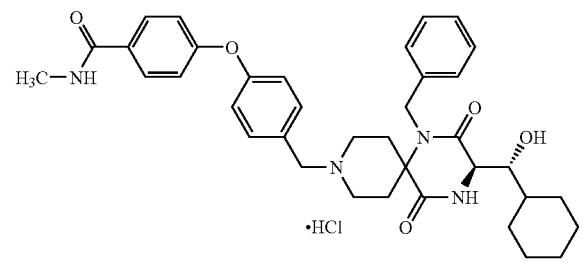

TLC: Rf 0.28 (chloroform:methanol=10:1);
NMR (CD$_3$OD): δ 7.85 (d, J=8.7 Hz, 2H), 7.56 (d, J=8.7 Hz, 2H), 7.40–7.02 (m, 5H), 7.13 (d, J=8.7 Hz, 2H), 7.06 (d, J=8.7 Hz, 2H), 4.58 (m, 1H), 4.33 (s, 4H), 3.96 (m, 1H), 3.76 (m, 1H), 3.54–3.18 (m, 3H), 2.92 (s, 3H), 2.64–2.28 (m, 3H), 2.14–1.58 (m, 7H), 1.40–0.80 (m, 5H).

EXAMPLE 24(2)

(3R)-1-(2-methoxyethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

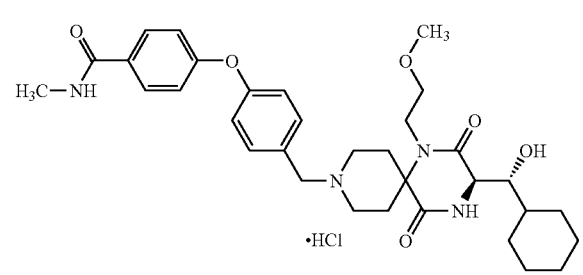

TLC: Rf 0.35 (chloroform:methanol=10:1);

NMR (CD$_3$OD): δ 7.84 (d, J=8.7 Hz, 2H), 7.57 (d, J=8.7 Hz, 2H), 7.15 (d, J=8.7 Hz, 2H), 7.07 (d, J=8.7 Hz, 2H), 4.36 (s, 2H), 4.18 (d, J=2.1 Hz, 1H), 3.98 (m, 1H), 3.86–3.18 (m, 8H), 3.31 (s, 3H), 2.91 (s, 3H), 2.60–1.58 (m, 10H), 1.42–0.80 (m, 5H).

EXAMPLE 24(3)

(3R)-1-(pyridin-2-ylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.2hydrochloride

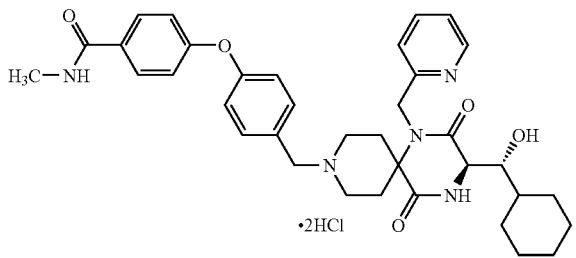

TLC: Rf 0.83 (chloroform:methanol:acetic acid=10:2:1);

NMR (CD$_3$OD): δ 8.76 (dd, J=6.6, 1.8 Hz, 1H), 8.54 (td, J=8.4, 1.8 Hz, 1H), 8.12 (d, J=8.4 Hz, 1H), 7.93 (dd, J=8.4, 6.6 Hz, 1H), 7.83 (d, J=9.0 Hz, 2H), 7.65 (d, J=8.7 Hz, 2H), 7.14–7.02 (m, 4H), 5.34–5.20 (m, 2H), 4.38 (s, 2H), 4.30 (d, J=1.8 Hz, 1H), 3.96 (m, 1H), 3.78 (m, 1H), 3.52–3.38 (m, 2H), 3.32 (m, 1H), 2.90 (s, 3H), 2.72–2.54 (m, 3H), 2.30 (m, 1H), 2.06 (m, 1H), 1.88 (m, 1H), 1.82–1.50 (m, 4H), 1.28–1.06 (m, 3H), 1.06–0.80 (m, 2H).

EXAMPLE 24(4)

(3R)-1-(pyridin-3-ylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.2hydrochloride

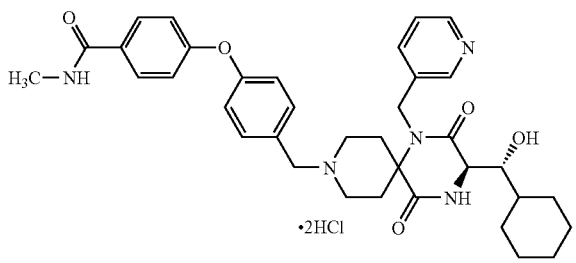

TLC: Rf 0.58 (chloroform:methanol:acetic acid=10:2:1);

NMR (CD$_3$OD): δ 8.89 (s, 1H), 8.73 (d, J=5.7 Hz, 1H), 8.64 (d, J=8.1 Hz, 1H), 8.03 (dd, J=8.1, 5.7 Hz, 1H), 7.83 (d, J=8.7 Hz, 2H), 7.65 (d, J=8.4 Hz, 2H), 7.18–7.02 (m, 4H), 5.19 (d, J=18.0 Hz, 1H), 5.11 (d, J=18.0 Hz, 1H), 4.40–4.26 (m, 3H), 3.90 (m, 1H), 3.78 (m, 1H), 3.50–3.38 (m, 2H), 3.30 (m, 1H), 2.90 (s, 3H), 2.74–2.42 (m, 3H), 2.20–1.88 (m, 3H), 1.82–1.56 (m, 4H), 1.32–1.06 (m, 3H), 1.02–0.80 (m, 2H).

REFERENCE EXAMPLE 7

(3R)-1-butyl-2,5-dioxo-3-cyclohexylmethyl-1,4,9-triazaspiro[5.5]undecane.hydrochloride

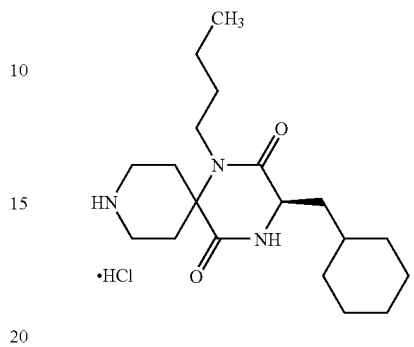

By the same procedure as described in Reference example 1→Reference example 2→Example 1→Reference example 3 using N-t-butoxycarbonyl-D-cyclohexylalanine instead of (2R,3R)-2-(t-butoxycarbonylamino)-3-hydroxy-4-methylpentanoic acid, the title compound having the following physical data was obtained.

TLC: Rf 0.59 (n-butanol:acetic acid:H$_2$O=4:2:1);

NMR (CD$_3$OD): δ 4.05 (dd, J=7.5, 4.8 Hz, 1H), 3.83–3.69 (m, 2H), 3.42–3.37 (m, 4H), 2.39–2.07 (m, 4H), 1.80–1.49 (m, 10H), 1.45–1.19 (m, 5H), 1.03–0.91 (m, 5H);

Optical rotation: [α]$_D$ +35.5 (c 1.05, methanol, 21° C.).

EXAMPLE 25

(3R)-1-butyl-2,5-dioxo-3-cyclohexylmethyl-9-(4-(4-carboxyphenyloxy)phenylmethyl)-1,4,9-triazaspiro[5.5]undecane.hydrochloride

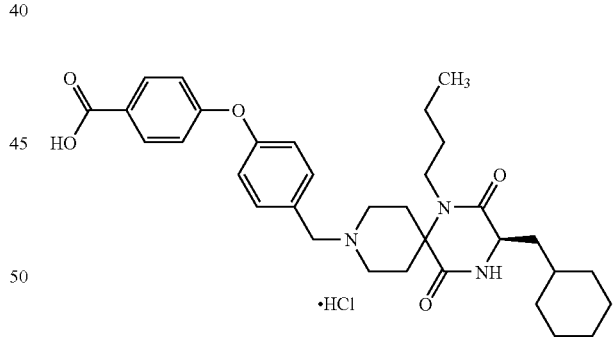

By the same procedure as described in Example 2 using the compound prepared in Reference example 7 instead of the compound prepared in Reference example 3, and using 4-(4-carboxyphenyloxy)benzaldehyde instead of 3-formyl-6-phenyloxypyridine, the title compound having the following physical data was obtained.

TLC: Rf 0.36 (chloroform:methanol=10:1);

NMR (d$_6$-DMSO): δ 10.92 (br-s, 1H), 8.41 (br-s, 1H), 7.95 (d, J=8.7 Hz, 2H), 7.69 (d, J=8.7 Hz, 2H), 7.17 (d, J=8.7 Hz, 2H), 7.07 (d, J=8.7 Hz, 2H), 4.32 (s, 2H), 3.91 (m, 1H), 3.59–3.35 (m, 6H), 2.56–2.35 (m, 2H), 2.10 (m, 1H), 1.98 (m, 1H), 1.72–1.35 (m, 10H), 1.32–1.14 (m, 5H), 0.90–0.78 (m, 5H).

EXAMPLE 26

(3S)-1-butyl-2,5-dioxo-3-(pyridin-1-oxido-2-ylmethyl)-9-(4-(4-methylaminocarbonylphenyloxy)phenylmethyl)-1,4,9-triazaspiro[5.5]undecane.9-oxide

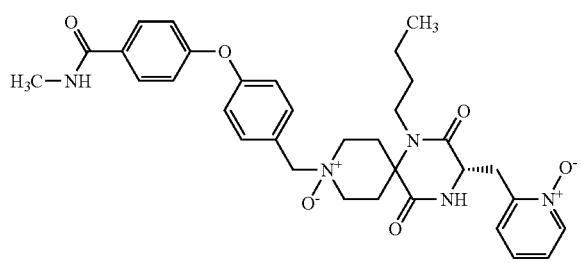

To a solution of the free form of the compound prepared in Example 23(2) (117 mg) in chloroform (10 ml) was added dropwise the solution (4 ml) of 3-chloroperbenzoic acid (114 mg). After the reaction mixture was stirred overnight at room temperature, the solvent was evaporated. The obtained residue was purified by column chromatography on silica gel (Fuji Silysia Chemical Ltd., NH-DM1020, chloroform) to give the title compound (100 mg) having the following physical data.

TLC: Rf 0.23 (chloroform:methanol:acetic acid=20:2:1);
NMR (CDCl$_3$): δ 8.81 (s, 1H), 8.28 (dd, J=6.0, 1.2 Hz, 1H), 7.77 (d, J=8.7 Hz, 2H), 7.52–7.46 (m, 3H), 7.32–7.22 (m, 2H), 7.16–6.98 (m, 4H), 6.32 (m, 1H), 4.40–4.24 (m, 4H), 3.87 (dd, J=11.0, 5.1 Hz, 1H), 3.66–3.34 (m, 4H), 3.16–2.86 (m, 4H), 3.01 (d, J=4.5 Hz, 3H), 1.84–1.20 (m, 6H), 0.90 (t, J=7.2 Hz, 3H).

REFERENCE EXAMPLE 8

1-butyl-2,5-dioxo-3-(morpholin-4-ylmethyl)-1,4,9-triazaspiro[5.5]undecane.2hydrochloride

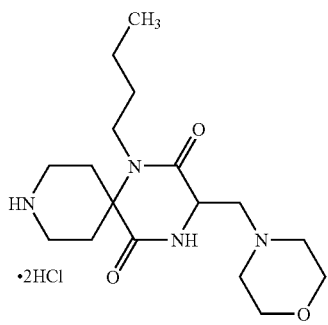

By the same procedure as described in Reference example 1→Reference example 2 →Example 1→Reference example 3 using 2-(t-butoxycarbonylamino)-3-(morpholin-4-yl)propanoic acid instead of (2R,3R)-2-(t-butoxycarbonylamino)-3-hydroxy-4-methylpentanoic acid, the title compound having the following physical data was obtained.

TLC: Rf 0.07 (chloroform:methanol=10:1);
NMR (CD$_3$OD): δ 4.76 (dd, J=8.4, 4.8 Hz, 1H), 4.05–3.82 (m, 6H), 3.71–3.40 (m, 10H), 2.41 (m, 1H), 2.31–2.21 (m, 3H), 1.98–1.54 (m, 2H), 1.46–1.36 (m, 2H), 0.97 (t, J=7.5 Hz, 3H).

EXAMPLE 27

1-butyl-2,5-dioxo-3-(morpholin-4-ylmethyl)-9-(4-(4-methylaminocarbonylphenyloxy)phenylmethyl)-1,4,9-triazaspiro[5.5]undecane.2hydrochloride

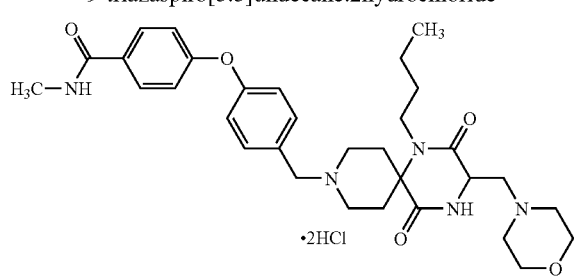

By the same procedure as described in Example 2 using the compound prepared in Reference example 8 instead of the compound prepared in Reference example 3, and using 4-(4-methylaminocarobonyl)phenyloxybenzaldehyde instead of 3-formyl-6-phenyloxypyridine, the title compound having the following physical data was obtained.

TLC: Rf 0.41 (chloroform:methanol=10:1);
NMR (CD$_3$OD): δ 7.84 (d, J=9.0 Hz, 2H), 7.63 (d, J=8.5 Hz, 2H), 7.14 (d, J=8.5 Hz, 2H), 7.07 (d, J=9.0 Hz, 2H), 4.73 (dd, J=8.1, 5.1 Hz, 1H), 4.37 (s, 2H), 4.10–3.85 (m, 5H), 3.76–3.43 (m, 9H), 3.40–3.20 (m, 2H), 2.91 (s, 3H), 2.63–2.43 (m, 2H), 2.33–2.24 (m, 2H), 1.65–1.50 (m, 2H), 1.44–1.34 (m, 2H), 0.96 (t, J=7.0 Hz, 3H).

EXAMPLE 28

(3R)-1-butyl-2,5-dioxo-3-((1R)-1-hydroxy-1-cyclohexylmethyl)-9-(4-(4-(N-hydroxycarbamoyl)phenyloxy)phenylmethyl)-1,4,9-triazaspiro[5.5]undecane-.hydrochloride

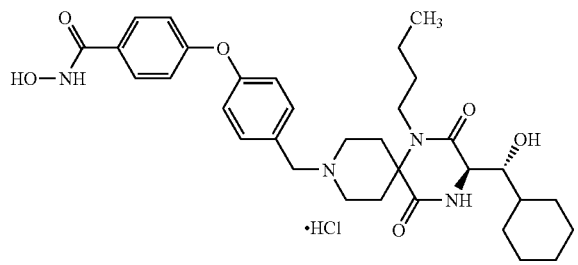

To a suspension of the compound prepared in Example 9(54) (120 mg) and (1-methoxyisopropyl)oxyamine (31 mg) in dimethylformamide (1.6 ml) was added diisopropylethylamine (68 μl), 1-ethyl-3-[3-(dimethylamino)propyl]carbodiimide.hydrochloride (56 mg) and 1-hydroxybenztriazole (40 mg). The reaction mixture was stirred for 1 hour at room temperature. The reaction mixture was added 1N hydrochloric acid (2 ml) and stirred for 15 minutes at room temperature. The reaction mixture was diluted with water and extracted with ethyl acetate. The extract was washed with water, saturated aqueous solution of sodium bicarbonate and saturated aqueous solution of sodium chloride and the obtained residue was dried over anhydrous sodium sulfate and concentrated. To a solution of the obtained residue in methanol was added 4N hydrogen chloride/ethyl acetate solution and concentrated. The obtained residue was washed with ethyl acetate to give the title compound (116 mg) having the following physical data.

TLC: Rf 0.43(chloroform:methanol:acetic acid=20:4:1);
NMR (CD$_3$OD): δ 7.79 (d, J=8.7 Hz, 2H), 7.60 (d, J=8.7 Hz, 2H), 7.14 (d, J=8.7 Hz, 2H), 7.06 (d, J=8.7 Hz, 2H), 4.36 (s, 2H), 4.15 (d, J=2.1 Hz, 1H), 4.00 (m, 1H), 3.75 (m, 1H), 3.60–3.40 (m, 3H), 3.30–3.11 (m, 2H), 2.58–2.27 (m, 3H), 2.19–1.96 (m, 3H), 1.93–1.60 (m, 5H), 1.50–1.09 (m, 6H), 1.05–0.80 (m, 2H), 0.94 (t, J=7.2 Hz, 3H).

EXAMPLE 29

(3R)-1-butyl-2,5-dioxo-3-((1R)-1-hydroxy-1-cyclohexylmethyl)-9-(4-(4-methylaminocarbonylphenyloxy)phenylcarbonyl)-1,4,9-triazaspiro[5.5]undecane

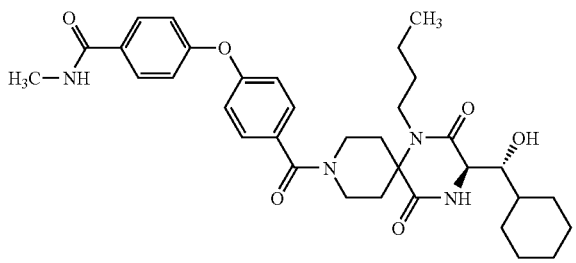

To a solution of 4-(4-methylaminocarobonylphenyloxy) benzoic acid (53.8 mg) in dimethylformamide (4 ml) was added 1-hydroxybenztriazole (34.9 mg) and 1-ethyl-3-[3-(dimethylamino)propyl]carbodiimide.hydrochloride (49.5 mg). The reaction mixture was stirred for 40 minutes at room temperature. The reaction mixture was added the compound prepared in Example 3(3) (100 mg) and stirred for 19 hours at room temperature. The reaction mixture was diluted with methylene dichloride, added water, and extracted with methylene dichloride. The extract was washed with 10% aqueous solution of citric acid and saturated aqueous solution of sodium chloride, dried over anhydrous sodium sulfate and concentrated. The obtained residue was purified by column chromatography on silica gel (ethyl acetate:methanol=10:1) and washed with diethyl ether to give the title compound (56.1 mg) having the following physical data.

TLC: Rf 0.41 (ethyl acetate:methanol=10:1);

NMR (CD$_3$OD): δ 7.84 (d, J=8.7 Hz, 2H), 7.49 (t, J=8.7 Hz, 2H), 7.13–7.06 (m, 4H), 3.70 (m, 1H), 4.16 (m, 1H), 4.12–2.98 (m, 6H), 2.91 (s, 3H), 2.42–0.80 (m, 19H), 0.96 (t, J=6.9 Hz, 3H).

EXAMPLE 30

(3R)-1-butyl-2,5-dioxo-3-((1R)-1-hydroxy-1-cyclohexylmethyl)-9-(4-(4-methylaminocarbonylphenyloxy)phenyl)-1,4,9-triazaspiro[5.5]undecane.hydrochloride

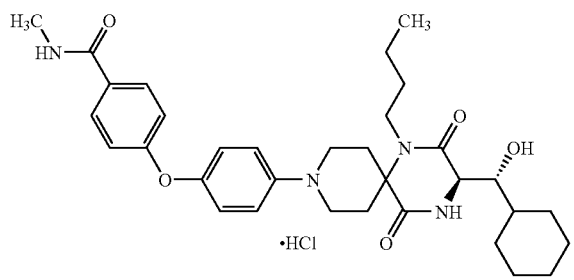

By the same procedure as described in Reference example 1→Reference example 2→Example 1 using (2R,3R)-2-(t-butoxycarbonylamino)-3-cyclohexyl-3-hydroxypropanoic acid instead of (2R,3R)-2-(t-butoxycarbonylamino)-3-hydroxy-4-methylpentanoic acid, and using N-(4-(4-methylaminocarobonylphenyloxy)phenyl)-4-piperidone instead of N-benzyl-4-piperidone, and using 2-morpholinoethylisonitrile instead of benzylisonitrile, the title compound having the following physical data was obtained.

TLC: Rf 0.40 (ethyl acetate);

NMR (CD$_3$OD): δ 7.87 (d, J=9.0 Hz, 2H), 7.78 (d, J=9.0 Hz, 2H), 7.25 (d, J=9.0 Hz, 2H), 7.10 (d, J=9.0 Hz, 2H), 4.65 (m, 1H), 4.39 (m, 1H), 4.20 (d, J=1.8 Hz, 1H), 3.73–3.65 (m, 3H), 3.43–3.27 (m, 2H), 2.91 (s, 3H), 2.90–2.52 (m, 3H), 2.25 (m, 1H), 2.10–1.90 (m, 2H), 1.85–1.60 (m, 5H), 1.60–1.10 (m, 6H), 0.99 (t, J=7.2 Hz, 3H), 1.00–0.82 (m, 2H).

FORMULATION EXAMPLE 1

The following components were admixed in a conventional manner, punched out to give 100 tablets each containing 50 mp of active ingredient.

| | |
|---|---|
| (3R)-1-butyl-2,5-dioxo-3-((1R)-1-hydroxy-2-methylpropyl)-9-(6-phenyloxypyridin-3-ylmethyl)-1,4,9-triazaspiro[5.5]undecane.2hydrochloride | 5.0 g |
| calcium carboxymethyl cellulose (disintegrant) | 0.2 g |
| magnesium stearate (lubricant) | 0.1 g |
| microcrystalline cellulose | 4.7 g |

FORMULATION EXAMPLE 2

The following components were admixed in a conventional technique. The solution was sterilized in a conventional technique, filled in ampoules 5 ml each and freeze-dried over in a conventional technique to give 100 ampoules each containing 20 mg of active ingredient.

| | |
|---|---|
| (3R)-1-butyl-2,5-dioxo-3-((1R)-1-hydroxy-2-methylpropyl)-9-(6-phenyloxypyridin-3-ylmethyl)-1,4,9-triazaspiro[5.5]undecane.2hydrochloride | 2.0 g |
| mannitol | 20 g |
| distilled water | 500 ml |

---

The invention claimed is:

1. (3R)-1-Butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane, a quaternary ammonium salt thereof, an N-oxide thereof, or a non-toxic salt thereof.

2. (3R)-1-Butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride.

3. A pharmaceutical compositon comprising (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane, a quaternary ammonium salt thereof, an N-oxide thereof, or a non-toxic salt thereof, and a pharmaceutically acceptable carrier.

4. A pharmaceutical compositon comprising (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride and a pharmaceutically acceptable carrier.

* * * * *

SEQUENCE LISTING

<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Forward primer hCCR5XbaI

```
-continued

<400> SEQUENCE: 1
agctagtcta gatccgttcc cctacaagaa actctcc                              37

<210> SEQ ID NO 2
<211> LENGTH: 37
<212> TYPE: DNA
<213> ORGANISM: Artificial Sequence
<220> FEATURE:
<223> OTHER INFORMATION: Reverse primer hCCR5XbaI

<400> SEQUENCE: 2
agctagtcta gagtgcacaa ctctgactgg gtcacca                              37
```